(12) United States Patent
Rauscher et al.

(10) Patent No.: US 12,404,307 B2
(45) Date of Patent: Sep. 2, 2025

(54) METHODS AND COMPOSITIONS FOR USE OF RECOMBINANT BACTERIAL EFFECTOR PROTEINS AS ANTI-INFLAMMATORY AGENTS

(71) Applicant: The Wistar Institute of Anatomy and Biology, Philadelphia, PA (US)

(72) Inventors: Frank J. Rauscher, Wayne, PA (US); Peter Mondics, Newtown Square, PA (US)

(73) Assignees: The Wistar Institute of Anatomy and Biology, Philadelphia, PA (US); Innate Biologics LLC, Harrisburg, PA (US)

( * ) Notice: Subject to any disclaimer, the term of this patent is extended or adjusted under 35 U.S.C. 154(b) by 0 days.

(21) Appl. No.: 17/686,110

(22) Filed: Mar. 3, 2022

(65) Prior Publication Data
US 2022/0306702 A1    Sep. 29, 2022

Related U.S. Application Data

(63) Continuation of application No. 16/964,762, filed as application No. PCT/US2019/015224 on Jan. 25, 2019, now abandoned.

(60) Provisional application No. 62/622,068, filed on Jan. 25, 2018.

(51) Int. Cl.
| C07K 14/255 | (2006.01) |
| A61K 38/00 | (2006.01) |
| C07K 14/25 | (2006.01) |

(52) U.S. Cl.
CPC ............ *C07K 14/255* (2013.01); *C07K 14/25* (2013.01); *A61K 38/00* (2013.01); *C07K 2319/03* (2013.01); *C07K 2319/30* (2013.01); *C07K 2319/70* (2013.01)

(58) Field of Classification Search
None
See application file for complete search history.

(56) References Cited

U.S. PATENT DOCUMENTS

| 5,635,497 | A | 6/1997 | Molenaar |
| 8,840,901 | B2 | 9/2014 | Ruter et al. |
| 2004/0086976 | A1 | 5/2004 | Fleer et al. |
| 2004/0147719 | A1 | 7/2004 | Cornelis |
| 2004/0208889 | A1 | 10/2004 | Sutton et al. |
| 2011/0183908 | A1 | 7/2011 | Ruter et al. |
| 2012/0064572 | A1 | 3/2012 | Finlay |

FOREIGN PATENT DOCUMENTS

| WO | WO 2001/19393 | 4/2001 |
| WO | WO 2014/076642 | 5/2014 |

OTHER PUBLICATIONS

Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Jung et al., Identification of tissue-specific targeting peptide, Journal of Computer-Aided Molecular Design, vol. 26:1267-1275, Oct. 2012.
Zakrewsky et al., Choline and Geranate Deep Eutectic Solvent as a Broad-Spectrum Antiseptic Agent for Preventative and Therapeutic Applications, Advanced Healthcare Materials, vol. 5(11):1282-1289, Jun. 2016.
Banerjee et al., Transdermal Protein Delivery Using Choline and Geranate (CAGE) Deep Eutectic Solvent, Advance Healthcare Matter, vol. 6(15):1601411, Aug. 2017.
Badenhorst et al., Pharmaceutical Strategies for the Topical Dermal Delivery of Peptides/Proteins for Cosmetic and Therapeutic Applications, Austin Journal of Pharmacology and Therapeutics, vol. 2(6): 1-100, Aug. 2014.
Cornelis, G., The Yersinia Ysc-Yop virulence apparatus, International Journal of Medical Microbiology, vol. 291(6-7):455-62, Feb. 2002.
Cataliotti et al., Oral Brain Natriuretic Peptide: A Novel Strategy for Chronic Protein Therapy for Cardiovascular Disease, Trends in Cardiovascular Medicine, vol. 17(1): 10-14, Jan. 2007.
Veronese, F., & Mero, A., The impact of PEGylation on biological therapies, BioDrugs, vol. 22(5):315-29, Aug. 2012.
Miller et al., Amphiphilic conjugates of human brain natriuretic peptide designed for oral delivery: in vitro activity screening, Bioconjugate Chemistry, vol. 17(2):267-74, Mar.-Apr. 2006.
Veronese, F., & Pasut, G., PEGylation, Successful Approach to Drug Delivery, Drug Discovery Today, vol. 10(21): 1451-8, Dec. 2005.
Wang et al., AlbuBNP, a recombinant B-type natriuretic peptide and human serum albumin fusion hormone, as a long-term therapy of congestive heart failure, Pharmaceutical Research, vol. 21(11):2105-11, Nov. 2004.
Guidotti et al., Cell-Penetrating Peptides: From Basic Research to Clinics, Trends in Pharmacological Sciences, vol. Trends in Pharmacological Sciences, vol. 38(4):406-424, Apr. 2017.
Norkowski i et al., Bacterial LPX motif-harboring virulence factors constitute a species-spanning family of cell-penetrating effectors, Cellular and Molecular Life Sciences, vol. 75(66-73):1-17, Dec. 2017.
Dixon et al., Correction for Dixon et al., Highly efficient delivery of functional cargoes by the synergistic effect of GAG binding motifs and cell-penetrating peptides, PNAS, vol. 113(3):E291-299, Jan. 2016.
Tezgel et al., Synthetic Protein Mimics for Functional Protein Delivery, Biomacromolecules, vol. 18(3):819-825, Mar. 2017.
Bolhassani et al., In vitro and in vivo delivery of therapeutic proteins using cell penetrating peptides, Peptides, vol. 87:50-63, Nov. 2016.

(Continued)

*Primary Examiner* — Brian Gangle
(74) *Attorney, Agent, or Firm* — Howson & Howson LLP; Colleen M. Schaller; Richard F. Kane

(57) ABSTRACT

Provided herein are methods and compositions comprising a set of paired peptides comprising a first bacterial effector polypeptide or fragment thereof linked to a second bacterial effector polypeptide or fragment thereof. The paired peptides can be linked to a protein transduction domain. The compositions can be formulated as pharmaceuticals. The compositions are useful for the treatment of inflammatory disorders.

12 Claims, 29 Drawing Sheets

Specification includes a Sequence Listing.

(56) References Cited

OTHER PUBLICATIONS

Yao et al., Structure and specificity of the bacterial cysteine methyltransferase effector NleE suggests a novel substrate in human DNA repair pathway, PLOS Pathogens, vol. 10(11):e1004522, Nov. 2014.
Ruter, P., 'Drugs from Bugs': bacterial effector proteins as promising biological (immune-) therapeutics, FEMS Microbiology Letters, vol. 351(2):126-132, Feb. 2014.
International Search Report and Written Opinion issued in International Patent Application No. PCT/US2019/015224, dated May 14, 2019.

* cited by examiner

FIG. 1

Cloning Strategy for YopM PTD-NleE WT (& Mutant R107

Cloning Strategy for YopM PTD-NleE WT No Linker, PAPA Linker, GSGS Linker (

MINPVTNTQGVSPINTKYAE_VVKNIYPEIK_DYFNESPNIYDK EI...Y
G...G                FV
KYIS_____VAELKQEEFVNEKARRFSYMKTMYSV_PEAFEPIS
RNEASTPEGSWLTVISGK_PMGQFSVDSLYNPDLHAL_ELPDI_
_KIFPKENNDFLYIVV_RNDSPLGEQRAN__ELYNIKRDIMQ
ELNYELPELKAVKSEMITAPEMGEIFSYMPGE_IDSYMKYIN

YopM Amino Acid Sequence (SEQ ID NO: 2)

MFINPRNVSNTFLQEPLRHSSNLTEMPVEAENVKSKTEYYNAWSEWERNA
PPGNGEQREMAVSRLRDCLDRQAHELELNNLGLSSLPELPPHLESLVASCN
SLTELPELPQSLKSLLVDNNNLKAISDLPPLLEYLGVSNNQLEKLPELQNSS
FLKIIDVDNNSIKKLPDLPPSLEFIAAGNNQLEELPELQNLPFLTAIYADNNS
LKKLPDLPLSLESIVAGNNILEELPELQNLPFLTTIYADNNLKTLPDLPPSL
EALNVRDNYLTDLPELPQSLTFLDVSENIFSGLSELPPNLYYLNASSNEIRSL
CDLPPSLEELNVSNNKLIELPALPPRLERLIASFNHLAEVPELPQNLKQLHVE
YNPLREFPDIPESVEDLRMNSERVVDPYEFAHETTDKLEDDVFE

FIG. 29

SEQUENCE LISTING

```
<160> NUMBER OF SEQ ID NOS: 93

<210> SEQ ID NO 1
<211> LENGTH: 224
<212> TYPE: PRT
<213> ORGANISM: Unknown
<220> FEATURE:
<223> OTHER INFORMATION: Description of Unknown:
      NleE sequence

<400> SEQUENCE: 1

Met Ile Asn Pro Val Thr Asn Thr Gln Gly Val Ser Pro Ile Asn Thr
1               5                   10                  15

Lys Tyr Ala Glu His Val Val Lys Asn Ile Tyr Pro Glu Ile Lys His
            20                  25                  30

Asp Tyr Phe Asn Glu Ser Pro Asn Ile Tyr Asp Lys Lys Tyr Ile Ser
        35                  40                  45

Gly Ile Thr Arg Gly Val Ala Glu Leu Lys Gln Glu Glu Phe Val Asn
    50                  55                  60

Glu Lys Ala Arg Arg Phe Ser Tyr Met Lys Thr Met Tyr Ser Val Cys
```

```
              65                  70                  75                  80
        Pro Glu Ala Phe Glu Pro Ile Ser Arg Asn Glu Ala Ser Thr Pro Glu
                             85                  90                  95

Gly Ser Trp Leu Thr Val Ile Ser Gly Lys Arg Pro Met Gly Gln Phe
                            100                 105                 110

Ser Val Asp Ser Leu Tyr Asn Pro Asp Leu His Ala Leu Cys Glu Leu
                            115                 120                 125

Pro Asp Ile Cys Cys Lys Ile Phe Pro Lys Glu Asn Asn Asp Phe Leu
                            130                 135                 140

Tyr Ile Val Val Val Tyr Arg Asn Asp Ser Pro Leu Gly Glu Gln Arg
        145                 150                 155                 160

Ala Asn Arg Phe Ile Glu Leu Tyr Asn Ile Lys Arg Asp Ile Met Gln
                            165                 170                 175

Glu Leu Asn Tyr Glu Leu Pro Glu Leu Lys Ala Val Lys Ser Glu Met
                            180                 185                 190

Ile Ile Ala Arg Glu Met Gly Glu Ile Phe Ser Tyr Met Pro Gly Glu
                            195                 200                 205

Ile Asp Ser Tyr Met Lys Tyr Ile Asn Asn Lys Leu Ser Lys Ile Glu
        210                 215                 220
```

<210> SEQ ID NO 2
<211> LENGTH: 409
<212> TYPE: PRT
<213> ORGANISM: Yersinia pestis

<400> SEQUENCE: 2

```

```
Asn Ile Leu Glu Glu Leu Pro Glu Leu Gln Asn Leu Pro Phe Leu Thr
225                 230                 235                 240

Thr Ile Tyr Ala Asp Asn Leu Leu Lys Thr Leu Pro Asp Leu Pro
            245                 250                 255

Pro Ser Leu Glu Ala Leu Asn Val Arg Asp Asn Tyr Leu Thr Asp Leu
                260                 265                 270

Pro Glu Leu Pro Gln Ser Leu Thr Phe Leu Asp Val Ser Glu Asn Ile
            275                 280                 285

Phe Ser Gly Leu Ser Glu Leu Pro Pro Asn Leu Tyr Tyr Leu Asn Ala
    290                 295                 300

Ser Ser Asn Glu Ile Arg Ser Leu Cys Asp Leu Pro Pro Ser Leu Glu
305                 310                 315                 320

Glu Leu Asn Val Ser Asn Asn Lys Leu Ile Glu Leu Pro Ala Leu Pro
                325                 330                 335

Pro Arg Leu Glu Arg Leu Ile Ala Ser Phe Asn His Leu Ala Glu Val
            340                 345                 350

Pro Glu Leu Pro Gln Asn Leu Lys Gln Leu His Val Glu Tyr Asn Pro
            355                 360                 365

Leu Arg Glu Phe Pro Asp Ile Pro Glu Ser Val Glu Asp Leu Arg Met
370                 375                 380

Asn Ser Glu Arg Val Val Asp Pro Tyr Glu Phe Ala His Glu Thr Thr
385                 390                 395                 400

Asp Lys Leu Glu Asp Asp Val Phe Glu
                405

<210> SEQ ID NO 3
<211> LENGTH: 367
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Phe Ile Thr Pro Arg Asn Val Ser Asn Thr Phe Leu Gln Glu Pro
1               5                   10                  15

Leu Arg His Ser Ser Asp Leu Thr Glu Met Pro Val Glu Ala Glu Asn
                20                  25                  30

Val Lys Ser Lys Thr Glu Tyr Tyr Asn Ala Trp Ala Val Trp Glu Arg
            35                  40                  45

Asn Ala Pro Pro Gly Asn Gly Glu Gln Arg Glu Met Ala Val Ser Arg
        50                  55                  60

Leu Arg Asp Cys Leu Asp Arg Gln Ala His Glu Leu Glu Leu Asn Asn
65                  70                  75                  80

Leu Gly Leu Ser Ser Leu Pro Glu Leu Pro Pro His Leu Glu Ser Leu
                85                  90                  95

Val Ala Ser Cys Asn Ser Leu Thr Glu Leu Pro Glu Leu Pro Gln Ser
                100                 105                 110

Leu Lys Ser Leu Gln Val Asp Asn Asn Asn Leu Lys Ala Leu Ser Asp
            115                 120                 125

Leu Pro Pro Ser Leu Glu Phe Leu Ala Ala Gly Asn Asn Gln Leu Glu
        130                 135                 140

Glu Leu Pro Glu Leu Gln Asn Ser Ser Phe Leu Lys Ile Ile Asp Val
145                 150                 155                 160

Asp Asn Asn Ser Leu Lys Lys Leu Pro Asp Leu Pro Pro Ser Leu Glu
                165                 170                 175
```

```
Phe Leu Ala Ala Gly Asn Asn Gln Leu Glu Glu Leu Ser Glu Leu Gln
                180                 185                 190

Asn Leu Pro Phe Leu Thr Glu Ile His Ala Asp Asn Asn Ser Leu Lys
            195                 200                 205

Thr Leu Pro Asp Leu Pro Pro Ser Leu Lys Thr Leu Asn Val Arg Glu
210                 215                 220

Asn Tyr Leu Thr Asp Leu Pro Glu Leu Pro Gln Ser Leu Thr Phe Leu
225                 230                 235                 240

Asp Val Ser Asp Asn Ile Phe Ser Gly Leu Ser Glu Leu Pro Pro Asn
                245                 250                 255

Leu Tyr Tyr Leu Asp Ala Ser Ser Asn Gly Ile Arg Ser Leu Cys Asp
            260                 265                 270

Leu Pro Pro Ser Leu Val Glu Leu Asp Val Arg Asp Asn Gln Leu Ile
            275                 280                 285

Glu Leu Pro Ala Leu Pro Pro His Leu Glu Arg Leu Ile Ala Ser Leu
    290                 295                 300

Asn His Leu Ala Glu Val Pro Glu Leu Pro Gln Asn Leu Lys Gln Leu
305                 310                 315                 320

His Val Glu His Asn Ala Leu Arg Glu Phe Pro Asp Ile Pro Glu Ser
                325                 330                 335

Val Glu Asp Leu Arg Met Asp Ser Glu Arg Val Thr Asp Thr Tyr Glu
            340                 345                 350

Phe Ala His Glu Thr Thr Asp Lys Leu Glu Asp Asp Val Phe Glu
            355                 360                 365

<210> SEQ ID NO 4
<211> LENGTH: 1104
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
atgtttataa ctccaagaaa tgtatctaat acttttttgc aagaaccatt acgtcattct      60
tctgatttaa ctgagatgcc ggttgaagca gaaaatgtta atctaagac tgaatattat     120 aatgcatggg cggtatggga acgaaatgcc cctccgggga atggtgaaca gagggaaatg    180
gcggtttcaa ggttacgcga ttgcctggac cgacaagccc atgagctaga actaaataat    240
ctggggctga gttctttgcc ggaattacct ccgcatttag agagtttagt ggcgtcatgt    300
aattctctta cagaattacc ggaattgccg cagagcctga atcacttca agttgataat    360 aacaatctga aggcattatc cgatttacct ccttcactgg aatttcttgc tgctggtaat    420
aatcagctgg aagaattgcc agagttgcaa aactcgtcct tcttgaaaat tattgatgtt    480
gataacaatt cactgaaaaa actacctgat ttacctcctt cactggaatt tcttgctgct    540
ggtaataatc agctggaaga attgtcagag ttacaaaact tgccattctt gactgagatt    600
catgctgata caattcact gaaaacatta cccgatttac cccttccct gaaaacactt      660 aatgtcagag aaaattattt aactgatctg ccagaattac gcagagtttt aaccttctta    720
gatgtttctg ataatatttt ttctggatta tcggaattgc caccaaactt gtattatctc    780
gatgcatcca gcaatggaat aagatcctta tgcgatttac cccttcact ggtagaactt     840 gatgtcagag ataatcagtt gatcgaactg ccagcgttac tccacactt agaacgttta     900 atcgcttcac ttaatcatct tgctgaagta cctgaattgc cgcaaaaacct gaaacagctc   960
```

```
cacgtagagc acaacgctct aagagagttt cccgatatac ctgagtcagt ggaagatctt    1020
cggatggact ctgaacgtgt aactgataca tatgaatttg ctcatgagac tacagacaaa    1080
cttgaagatg atgtatttga gtag                                           1104
```

<210> SEQ ID NO 5
<211> LENGTH: 86
<212> TYPE: PRT
<213> ORGANISM: Yersinia pestis

<400> SEQUENCE: 5

```
Met Phe Ile Asn Pro Arg Asn Val Ser Asn Thr Phe Leu Gln Glu Pro
1               5                   10                  15

Leu Arg His Ser Ser Asn Leu Thr Glu Met Pro Val Glu Ala Glu Asn
            20                  25                  30

Val Lys Ser Lys Thr Glu Tyr Tyr Asn Ala Trp Ser Glu Trp Glu Arg
        35                  40                  45

Asn Ala Pro Pro Gly Asn Gly Glu Gln Arg Glu Met Ala Val Ser Arg
    50                  55                  60

Leu Arg Asp Cys Leu Asp Arg Gln Ala His Glu Leu Glu Leu Asn Asn
65                  70                  75                  80

Leu Gly Leu Ser Ser Leu
                85
```

<210> SEQ ID NO 6
<211> LENGTH: 258
<212> TYPE: DNA
<213> ORGANISM: Yersinia pestis

<400> SEQUENCE: 6

```
atgttcatca ctccacgcaa tgtatctaac acctttctgc aggaaccgct gcgtcattct    60
agcgacctga ccgaaatgcc agttgaagcg gagaacgtga aatctaagac tgaatactac    120
aacgcgtggg cagtatggga gcgcaatgca ccaccaggta acggtgaaca gcgtgaaatg    180
gcagtaagcc gtctgcgtga ttgcctggat cgccaggctc acgagctgga gctgaacaac    240
ctgggtctgt ctagcctg                                                  258
```

<210> SEQ ID NO 7
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

```
Met Phe Ile Asn Pro Arg Asn Val Ser Asn Thr Phe Leu Gln Glu Pro
1               5                   10                  15

Leu Arg His Ser Ser Asn Leu Thr Glu Met Pro Val Glu Ala Glu Asn
            20                  25                  30

Val Lys Ser Lys Thr Glu Tyr Tyr Asn Ala Trp Ser Glu Trp Glu Arg
        35                  40                  45

Asn Ala Pro Pro Gly Asn Gly Glu Gln Arg Glu Met Ala Val Ser Arg
    50                  55                  60

Leu Arg Asp Cys Leu Asp Arg Gln Ala His Glu Leu Glu Leu Asn Asn
65                  70                  75                  80

Leu Gly Leu Ser Ser Leu Pro Glu Leu Pro Pro His Leu Glu Ser Leu
                85                  90                  95
```

Val Ala Ser Cys Asn Ser Leu Thr Glu Leu Pro Glu Leu Pro Gln Ser
                100                 105                 110

Leu Lys Ser Leu Leu Val Asp Asn Asn Leu Lys Ala Leu Ser Asp
            115                 120                 125

Leu Pro Pro
        130

<210> SEQ ID NO 8
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
atgtttatta acccgcgcaa cgtgagcaac acctttctgc aggaaccgct gcgccatagc      60 agcaaccctga ccgaaatgcc ggtggaagcg gaaaacgtga aaagcaaaac cgaatattat     120
aacgcgtgga gcgaatggga acgcaacgcg ccgccgggca acggcgaaca gcgcgaaatg     180
gcggtgagcc gcctgcgcga ttgcctggat cgccaggcgc atgaactgga actgaacaac     240
ctgggcctga gcagcctgcc ggaactgccg ccgcatctgg aaagcctggt ggcgagctgc     300
aacagcctga ccgaactgcc ggaactgccg cagagcctga aaagcctgct ggtggataac     360
aacaacctga aagcgctgag cgatctgccg ccg                                  393

<210> SEQ ID NO 9
<211> LENGTH: 390
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Phe Ile Thr Pro Arg Asn Val Ser Asn Thr Phe Leu Gln Glu Pro
1               5                   10                  15

Leu Arg His Ser Ser Asp Leu Thr Glu Met Pro Val Glu Ala Glu Asn
            20                  25                  30

Val Lys Ser Lys Thr Glu Tyr Tyr Asn Ala Trp Ala Val Trp Glu Arg
        35                  40                  45

Asn Ala Pro Pro Gly Asn Gly Glu Gln Arg Glu Met Ala Val Ser Arg
    50                  55                  60

Leu Arg Asp Cys Leu Asp Arg Gln Ala His Glu Leu Glu Leu Asn Asn
65                  70                  75                  80

Leu Gly Leu Ser Ser Leu Pro Glu Leu Pro Pro His Leu Glu Ser Leu
                85                  90                  95

Val Ala Ser Cys Asn Ser Leu Thr Glu Leu Pro Glu Leu Pro Gln Ser
                100                 105                 110

Leu Lys Ser Leu Gln Val Asp Asn Asn Leu Lys Ala Leu Ser Asp
            115                 120                 125

Leu Pro Pro Ser Leu Glu Phe Leu Ala Ala Gly Asn Asn Gln Leu Glu
        130                 135                 140

Glu Leu Pro Glu Leu Gln Asn Ser Ser Phe Leu Lys Ile Ile Asp Ile
145                 150                 155                 160

Asn Pro Val Thr Asn Thr Gln Gly Val Ser Pro Ile Asn Thr Lys Tyr
                165                 170                 175

Ala Glu His Val Val Lys Asn Ile Tyr Pro Lys Ile Lys His Asp Tyr
            180                 185                 190

Phe Asn Glu Ser Pro Asn Ile Tyr Asp Lys Lys Tyr Ile Ser Gly Ile
        195                 200                 205

Thr Arg Gly Val Ala Glu Leu Lys Gln Glu Glu Phe Val Asn Glu Lys
    210                 215                 220

Ala Arg Arg Phe Ser Tyr Met Lys Thr Met Tyr Ser Val Cys Pro Glu
225                 230                 235                 240

Ala Phe Glu Pro Ile Ser Arg Asn Glu Ala Ser Thr Pro Glu Gly Ser
                245                 250                 255

Trp Leu Thr Val Ile Ser Gly Lys Arg Pro Met Gly Gln Phe Ser Val
            260                 265                 270

Asp Ser Leu Tyr Asn Pro Asp Leu His Ala Leu Cys Glu Leu Pro Asp
        275                 280                 285

Ile Cys Cys Lys Ile Phe Pro Lys Glu Asn Asn Asp Phe Leu Tyr Ile
    290                 295                 300

Val Val Val Tyr Arg Asn Asp Ser Pro Leu Gly Glu Gln Arg Ala Asn
305                 310                 315                 320

Arg Phe Ile Glu Leu Tyr Asn Ile Lys Arg Asp Ile Met Gln Glu Leu
                325                 330                 335

Asn Tyr Glu Leu Pro Glu Leu Lys Ala Val Lys Ser Glu Met Ile Ile
            340                 345                 350

Ala Arg Glu Met Gly Glu Ile Phe Ser Tyr Met Pro Gly Glu Ile Asp
        355                 360                 365

Ser Tyr Met Lys Tyr Ile Asn Asn Lys Leu Ser Lys Ile Glu Gly Ser
    370                 375                 380

His His His His His His
385                 390

<210> SEQ ID NO 10
<211> LENGTH: 384
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Phe Ile Thr Pro Arg Asn Val Ser Asn Thr Phe Leu Gln Glu Pro
1               5                   10                  15

Leu Arg His Ser Ser Asp Leu Thr Glu Met Pro Val Glu Ala Glu Asn
            20                  25                  30

Val Lys Ser Lys Thr Glu Tyr Tyr Asn Ala Trp Ala Val Trp Glu Arg
        35                  40                  45

Asn Ala Pro Pro Gly Asn Gly Glu Gln Arg Glu Met Ala Val Ser Arg
    50                  55                  60

Leu Arg Asp Cys Leu Asp Arg Gln Ala His Glu Leu Glu Leu Asn Asn
65                  70                  75                  80

Leu Gly Leu Ser Ser Leu Pro Glu Leu Pro Pro His Leu Glu Ser Leu
                85                  90                  95

Val Ala Ser Cys Asn Ser Leu Thr Glu Leu Pro Glu Leu Pro Gln Ser
            100                 105                 110

Leu Lys Ser Leu Gln Val Asp Asn Asn Asn Leu Lys Ala Leu Ser Asp
        115                 120                 125

Leu Pro Pro Ser Leu Glu Phe Leu Ala Ala Gly Asn Asn Gln Leu Glu
    130                 135                 140

Glu Leu Pro Glu Leu Gln Asn Ser Ser Phe Leu Lys Ile Ile Asp Ile
145                 150                 155                 160

Asn Pro Val Thr Asn Thr Gln Gly Val Ser Pro Ile Asn Thr Lys Tyr
            165                 170                 175

Ala Glu His Val Val Lys Asn Ile Tyr Pro Lys Ile Lys His Asp Tyr
        180                 185                 190

Phe Asn Glu Ser Pro Asn Ile Tyr Asp Lys Lys Tyr Ile Ser Gly Ile
    195                 200                 205

Thr Arg Gly Val Ala Glu Leu Lys Gln Glu Glu Phe Val Asn Glu Lys
210                 215                 220

Ala Arg Arg Phe Ser Tyr Met Lys Thr Met Tyr Ser Val Cys Pro Glu
225                 230                 235                 240

Ala Phe Glu Pro Ile Ser Arg Asn Glu Ala Ser Thr Pro Glu Gly Ser
            245                 250                 255

Trp Leu Thr Val Ile Ser Gly Lys Arg Pro Met Gly Gln Phe Ser Val
        260                 265                 270

Asp Ser Leu Tyr Asn Pro Asp Leu His Ala Leu Cys Glu Leu Pro Asp
    275                 280                 285

Ile Cys Cys Lys Ile Phe Pro Lys Glu Asn Asn Asp Phe Leu Tyr Ile
290                 295                 300

Val Val Val Tyr Arg Asn Asp Ser Pro Leu Gly Glu Gln Arg Ala Asn
305                 310                 315                 320

Arg Phe Ile Glu Leu Tyr Asn Ile Lys Arg Asp Ile Met Gln Glu Leu
            325                 330                 335

Asn Tyr Glu Leu Pro Glu Leu Lys Ala Val Lys Ser Glu Met Ile Ile
        340                 345                 350

Ala Arg Glu Met Gly Glu Ile Phe Ser Tyr Met Pro Gly Glu Ile Asp
    355                 360                 365

Ser Tyr Met Lys Tyr Ile Asn Asn Lys Leu Ser Lys Ile Glu Gly Ser
370                 375                 380

<210> SEQ ID NO 11
<211> LENGTH: 1173
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
atgttcatca ctccacgcaa tgtatctaac acctttctgc aggaaccgct gcgtcattct      60
agcgacctga ccgaaatgcc agttgaagcg agaacgtgaa atctaagac tgaatactac     120 aacgcgtggg cagtatggga gcgcaatgca ccaccaggta acgtgaaca gcgtgaaatg     180 gcagtaagcc gtctgcgtga ttgcctggat cgccaggctc acgagctgga gctgaacaac     240
ctgggtctgt ctagcctgcc agagctccca ccacatctgg aaagcctggt ggctagctgt     300
aactctctga ctgaactgcc agagctgcca caaagcctga atccctgca ggtggacaac     360 aacaacctga agcgctgtc cgatctgcca ccgtctctgg agtttctggc agctggtaac     420
aaccaactgg aagaactgcc agagctgcag aactcctcct ttctgaagat catcgatatt     480
aatcctgtta ctaatactca gggcgtgtcc cctataaata ctaaatatgc tgaacatgtg     540
gtgaaaaata tttacccgaa aattaaacat gattacttta tgaatcacc caatatatat     600 gataagaagt atatatccgg tataaccaga ggagtagctg aactaaaaca ggaagaattt     660

```
gttaacgaga aagccagacg gttttcttat atgaagacta tgtattctgt atgtccagaa      720
gcgtttgaac ctatttccag aaatgaagcc agtacaccgg aaggaagctg gctaacagtt      780
atatccggaa aagccccaat ggggcagttt tctgtagata gtttatacaa tcctgattta      840
catgcattat gtgagcttcc ggacatttgt tgtaagatct tccctaaaga aaataatgat      900
tttttataca tagttgttgt gtacagaaat gacagccctc taggagaaca acgggcaaat      960
agatttatag aattatataa tataaaaaga gatatcatgc aggaattaaa ttatgagtta     1020
ccagagttaa aggcagtaaa atctgaaatg attatcgcac gtgaaatggg agaaatcttt     1080
agctacatgc ctggggaaat agacagttat atgaaataca taataataaa actttctaaa     1140
attgagggat ctcatcacca tcaccatcac taa                                  1173
```

<210> SEQ ID NO 12
<211> LENGTH: 406
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

```
Met Phe Ile Thr Pro Arg Asn Val Ser Asn Thr Phe Leu Gln Glu Pro
 1               5                  10                  15

Leu Arg His Ser Ser Asp Leu Thr Glu Met Pro Val Glu Ala Glu Asn
            20                  25                  30

Val Lys Ser Lys Thr Glu Tyr Tyr Asn Ala Trp Ala Val Trp Glu Arg
        35                  40                  45

Asn Ala Pro Pro Gly Asn Gly Glu Gln Arg Glu Met Ala Val Ser Arg
    50                  55                  60

Leu Arg Asp Cys Leu Asp Arg Gln Ala His Glu Leu Glu Leu Asn Asn
65                  70                  75                  80

Leu Gly Leu Ser Ser Leu Pro Glu Leu Pro Pro His Leu Glu Ser Leu
                85                  90                  95

Val Ala Ser Cys Asn Ser Leu Thr Glu Leu Pro Glu Leu Pro Gln Ser
           100                 105                 110

Leu Lys Ser Leu Gln Val Asp Asn Asn Asn Leu Lys Ala Leu Ser Asp
       115                 120                 125

Leu Pro Pro Ser Leu Glu Phe Leu Ala Ala Gly Asn Asn Gln Leu Glu
   130                 135                 140

Glu Leu Pro Glu Leu Gln Asn Ser Ser Phe Leu Lys Ile Ile Asp Pro
145                 150                 155                 160

Ala Pro Ala Pro Ala Pro Ala Pro Ala Pro Ala Pro Ala Pro Ala Ile
                165                 170                 175

Asn Pro Val Thr Asn Thr Gln Gly Val Ser Pro Ile Asn Thr Lys Tyr
           180                 185                 190

Ala Glu His Val Val Lys Asn Ile Tyr Pro Lys Ile Lys His Asp Tyr
       195                 200                 205

Phe Asn Glu Ser Pro Asn Ile Tyr Asp Lys Lys Tyr Ile Ser Gly Ile
   210                 215                 220

Thr Arg Gly Val Ala Glu Leu Lys Gln Glu Glu Phe Val Asn Glu Lys
225                 230                 235                 240

Ala Arg Arg Phe Ser Tyr Met Lys Thr Met Tyr Ser Val Cys Pro Glu
                245                 250                 255

Ala Phe Glu Pro Ile Ser Arg Asn Glu Ala Ser Thr Pro Glu Gly Ser
           260                 265                 270
```

```
Trp Leu Thr Val Ile Ser Gly Lys Arg Pro Met Gly Gln Phe Ser Val
            275                 280                 285

Asp Ser Leu Tyr Asn Pro Asp Leu His Ala Leu Cys Glu Leu Pro Asp
290                 295                 300

Ile Cys Cys Lys Ile Phe Pro Lys Glu Asn Asn Asp Phe Leu Tyr Ile
305                 310                 315                 320

Val Val Val Tyr Arg Asn Asp Ser Pro Leu Gly Glu Gln Arg Ala Asn
                325                 330                 335

Arg Phe Ile Glu Leu Tyr Asn Ile Lys Arg Asp Ile Met Gln Glu Leu
                340                 345                 350

Asn Tyr Glu Leu Pro Glu Leu Lys Ala Val Lys Ser Glu Met Ile Ile
                355                 360                 365

Ala Arg Glu Met Gly Glu Ile Phe Ser Tyr Met Pro Gly Glu Ile Asp
                370                 375                 380

Ser Tyr Met Lys Tyr Ile Asn Asn Lys Leu Ser Lys Ile Glu Gly Ser
385                 390                 395                 400

His His His His His His
                405

<210> SEQ ID NO 13
<211> LENGTH: 400
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Phe Ile Thr Pro Arg Asn Val Ser Asn Thr Phe Leu Gln Glu Pro
1               5                   10                  15

Leu Arg His Ser Ser Asp Leu Thr Glu Met Pro Val Glu Ala Glu Asn
                20                  25                  30

Val Lys Ser Lys Thr Glu Tyr Tyr Asn Ala Trp Ala Val Trp Glu Arg
                35                  40                  45

Asn Ala Pro Pro Gly Asn Gly Glu Gln Arg Glu Met Ala Val Ser Arg
50                  55                  60

Leu Arg Asp Cys Leu Asp Arg Gln Ala His Glu Leu Glu Leu Asn Asn
65                  70                  75                  80

Leu Gly Leu Ser Ser Leu Pro Glu Leu Pro Pro His Leu Glu Ser Leu
                85                  90                  95

Val Ala Ser Cys Asn Ser Leu Thr Glu Leu Pro Glu Leu Pro Gln Ser
                100                 105                 110

Leu Lys Ser Leu Gln Val Asp Asn Asn Asn Leu Lys Ala Leu Ser Asp
                115                 120                 125

Leu Pro Pro Ser Leu Glu Phe Leu Ala Ala Gly Asn Asn Gln Leu Glu
130                 135                 140

Glu Leu Pro Glu Leu Gln Asn Ser Ser Phe Leu Lys Ile Ile Asp Pro
145                 150                 155                 160

Ala Pro Ala Pro Ala Pro Ala Pro Ala Pro Ala Pro Ala Pro Ala Ile
                165                 170                 175

Asn Pro Val Thr Asn Thr Gln Gly Val Ser Pro Ile Asn Thr Lys Tyr
                180                 185                 190

Ala Glu His Val Val Lys Asn Ile Tyr Pro Lys Ile Lys His Asp Tyr
                195                 200                 205

Phe Asn Glu Ser Pro Asn Ile Tyr Asp Lys Lys Tyr Ile Ser Gly Ile
```

```
                 210                 215                 220

Thr Arg Gly Val Ala Glu Leu Lys Gln Glu Glu Phe Val Asn Glu Lys
225                 230                 235                 240

Ala Arg Arg Phe Ser Tyr Met Lys Thr Met Tyr Ser Val Cys Pro Glu
                245                 250                 255

Ala Phe Glu Pro Ile Ser Arg Asn Glu Ala Ser Thr Pro Glu Gly Ser
                260                 265                 270

Trp Leu Thr Val Ile Ser Gly Lys Arg Pro Met Gly Gln Phe Ser Val
                275                 280                 285

Asp Ser Leu Tyr Asn Pro Asp Leu His Ala Leu Cys Glu Leu Pro Asp
                290                 295                 300

Ile Cys Cys Lys Ile Phe Pro Lys Glu Asn Asn Asp Phe Leu Tyr Ile
305                 310                 315                 320

Val Val Val Tyr Arg Asn Asp Ser Pro Leu Gly Glu Gln Arg Ala Asn
                325                 330                 335

Arg Phe Ile Glu Leu Tyr Asn Ile Lys Arg Asp Ile Met Gln Glu Leu
                340                 345                 350

Asn Tyr Glu Leu Pro Glu Leu Lys Ala Val Lys Ser Glu Met Ile Ile
                355                 360                 365

Ala Arg Glu Met Gly Glu Ile Phe Ser Tyr Met Pro Gly Glu Ile Asp
                370                 375                 380

Ser Tyr Met Lys Tyr Ile Asn Asn Lys Leu Ser Lys Ile Glu Gly Ser
385                 390                 395                 400

<210> SEQ ID NO 14
<211> LENGTH: 1221
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
atgttcatca ctccacgcaa tgtatctaac acctttctgc aggaaccgct gcgtcattct      60
agcgacctga ccgaaatgcc agttgaagcg gagaacgtga atctaagac tgaatactac     120
aacgcgtggg cagtatggga gcgcaatgca ccaccaggta acggtgaaca gcgtgaaatg     180
gcagtaagcc gtctgcgtga ttgcctggat cgccaggctc acgagctgga gctgaacaac     240
ctgggtctgt ctagcctgcc agagctccca ccacatctgg aaagcctggt ggctagctgt     300
aactctctga ctgaactgcc agagctgcca caaagcctga atccctgca ggtggacaac      360
aacaacctga agcgctgtc cgatctgcca ccgtctctgg agtttctggc agctggtaac      420
aaccaactgg aagaactgcc agagctgcag aactcctcct ttctgaagat catcgatcca     480
gcaccagcac cagcaccagc accagcacca gcaccagcac cagcaattaa tcctgttact     540
aatactcagg gcgtgtcccc tataaatact aaatatgctg aacatgtggt gaaaaatatt     600
tacccgaaaa ttaaacatga ttactttaat gaatcaccca atatatatga taagaagtat     660
atatccggta taaccagagg agtagctgaa ctaaacagg aagaatttgt taacgagaaa      720
gccagacggt ttcttatat gaagactatg tattctgtat gtccagaagc gtttgaacct      780
atttccagaa atgaagccag tacaccggaa ggaagctggc taacagttat atccggaaaa     840
cgcccaatgg ggcagttttc tgtagatagt ttatacaatc ctgatttaca tgcattatgt     900
gagcttccgg acatttgttg taagatcttc cctaaagaaa ataatgattt tttatacata     960
gttgttgtgt acagaaatga cagccctcta ggagaacaac gggcaaatag atttatagaa    1020
```

```
ttatataata taaaaagaga tatcatgcag gaattaaatt atgagttacc agagttaaag    1080
gcagtaaaat ctgaaatgat tatcgcacgt gaaatgggag aaatctttag ctacatgcct    1140
ggggaaatag acagttatat gaaatacata aataataaac tttctaaaat tgagggatct    1200
catcaccatc accatcacta a                                              1221
```

```
<210> SEQ ID NO 15
<211> LENGTH: 406
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15
```

Met Phe Ile Thr Pro Arg Asn Val Ser Asn Thr Phe Leu Gln Glu Pro
1               5                   10                  15

Leu Arg His Ser Ser Asp Leu Thr Glu Met Pro Val Glu Ala Glu Asn
            20                  25                  30

Val Lys Ser Lys Thr Glu Tyr Tyr Asn Ala Trp Ala Val Trp Glu Arg
        35                  40                  45

Asn Ala Pro Pro Gly Asn Gly Glu Gln Arg Glu Met Ala Val Ser Arg
    50                  55                  60

Leu Arg Asp Cys Leu Asp Arg Gln Ala His Glu Leu Glu Leu Asn Asn
65                  70                  75                  80

Leu Gly Leu Ser Ser Leu Pro Glu Leu Pro Pro His Leu Glu Ser Leu
                85                  90                  95

Val Ala Ser Cys Asn Ser Leu Thr Glu Leu Pro Glu Leu Pro Gln Ser
            100                 105                 110

Leu Lys Ser Leu Gln Val Asp Asn Asn Leu Lys Ala Leu Ser Asp
        115                 120                 125

Leu Pro Pro Ser Leu Glu Phe Leu Ala Ala Gly Asn Asn Gln Leu Glu
    130                 135                 140

Glu Leu Pro Glu Leu Gln Asn Ser Ser Phe Leu Lys Ile Ile Asp Gly
145                 150                 155                 160

Ser Gly Ser Gly Ser Gly Ser Gly Ser Gly Ser Gly Ser Gly Ser Ile
                165                 170                 175

Asn Pro Val Thr Asn Thr Gln Gly Val Ser Pro Ile Asn Thr Lys Tyr
            180                 185                 190

Ala Glu His Val Val Lys Asn Ile Tyr Pro Lys Ile Lys His Asp Tyr
        195                 200                 205

Phe Asn Glu Ser Pro Asn Ile Tyr Asp Lys Lys Tyr Ile Ser Gly Ile
    210                 215                 220

Thr Arg Gly Val Ala Glu Leu Lys Gln Glu Glu Phe Val Asn Glu Lys
225                 230                 235                 240

Ala Arg Arg Phe Ser Tyr Met Lys Thr Met Tyr Ser Val Cys Pro Glu
                245                 250                 255

Ala Phe Glu Pro Ile Ser Arg Asn Glu Ala Ser Thr Pro Glu Gly Ser
            260                 265                 270

Trp Leu Thr Val Ile Ser Gly Lys Arg Pro Met Gly Gln Phe Ser Val
        275                 280                 285

Asp Ser Leu Tyr Asn Pro Asp Leu His Ala Leu Cys Glu Leu Pro Asp
    290                 295                 300

Ile Cys Cys Lys Ile Phe Pro Lys Glu Asn Asn Asp Phe Leu Tyr Ile
305                 310                 315                 320

```
Val Val Val Tyr Arg Asn Asp Ser Pro Leu Gly Glu Gln Arg Ala Asn
            325                 330                 335

Arg Phe Ile Glu Leu Tyr Asn Ile Lys Arg Asp Ile Met Gln Glu Leu
            340                 345                 350

Asn Tyr Glu Leu Pro Glu Leu Lys Ala Val Lys Ser Glu Met Ile Ile
            355                 360                 365

Ala Arg Glu Met Gly Glu Ile Phe Ser Tyr Met Pro Gly Glu Ile Asp
            370                 375                 380

Ser Tyr Met Lys Tyr Ile Asn Asn Lys Leu Ser Lys Ile Glu Gly Ser
385                 390                 395                 400

His His His His His His
            405

<210> SEQ ID NO 16
<211> LENGTH: 400
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Phe Ile Thr Pro Arg Asn Val Ser Asn Thr Phe Leu Gln Glu Pro
1               5                   10                  15

Leu Arg His Ser Ser Asp Leu Thr Glu Met Pro Val Glu Ala Glu Asn
            20                  25                  30

Val Lys Ser Lys Thr Glu Tyr Tyr Asn Ala Trp Ala Val Trp Glu Arg
            35                  40                  45

Asn Ala Pro Pro Gly Asn Gly Glu Gln Arg Glu Met Ala Val Ser Arg
50                  55                  60

Leu Arg Asp Cys Leu Asp Arg Gln Ala His Glu Leu Glu Leu Asn Asn
65                  70                  75                  80

Leu Gly Leu Ser Ser Leu Pro Glu Leu Pro His Leu Glu Ser Leu
            85                  90                  95

Val Ala Ser Cys Asn Ser Leu Thr Glu Leu Pro Glu Leu Pro Gln Ser
            100                 105                 110

Leu Lys Ser Leu Gln Val Asp Asn Asn Leu Lys Ala Leu Ser Asp
            115                 120                 125

Leu Pro Pro Ser Leu Glu Phe Leu Ala Ala Gly Asn Asn Gln Leu Glu
130                 135                 140

Glu Leu Pro Glu Leu Gln Asn Ser Ser Phe Leu Lys Ile Ile Asp Gly
145                 150                 155                 160

Ser Gly Ser Gly Ser Gly Ser Gly Ser Gly Ser Gly Ser Gly Ser Ile
            165                 170                 175

Asn Pro Val Thr Asn Thr Gln Gly Val Ser Pro Ile Asn Thr Lys Tyr
            180                 185                 190

Ala Glu His Val Val Lys Asn Ile Tyr Pro Lys Ile Lys His Asp Tyr
            195                 200                 205

Phe Asn Glu Ser Pro Asn Ile Tyr Asp Lys Lys Tyr Ile Ser Gly Ile
            210                 215                 220

Thr Arg Gly Val Ala Glu Leu Lys Gln Glu Phe Val Asn Glu Lys
225                 230                 235                 240

Ala Arg Arg Phe Ser Tyr Met Lys Thr Met Tyr Ser Val Cys Pro Glu
            245                 250                 255

Ala Phe Glu Pro Ile Ser Arg Asn Glu Ala Ser Thr Pro Glu Gly Ser
```

```
                260             265             270
Trp Leu Thr Val Ile Ser Gly Lys Arg Pro Met Gly Gln Phe Ser Val
            275                 280                 285
Asp Ser Leu Tyr Asn Pro Asp Leu His Ala Leu Cys Glu Leu Pro Asp
            290                 295                 300
Ile Cys Cys Lys Ile Phe Pro Lys Glu Asn Asn Asp Phe Leu Tyr Ile
305                 310                 315                 320
Val Val Val Tyr Arg Asn Asp Ser Pro Leu Gly Glu Gln Arg Ala Asn
                325                 330                 335
Arg Phe Ile Glu Leu Tyr Asn Ile Lys Arg Asp Ile Met Gln Glu Leu
            340                 345                 350
Asn Tyr Glu Leu Pro Glu Leu Lys Ala Val Lys Ser Glu Met Ile Ile
            355                 360                 365
Ala Arg Glu Met Gly Glu Ile Phe Ser Tyr Met Pro Gly Glu Ile Asp
            370                 375                 380
Ser Tyr Met Lys Tyr Ile Asn Asn Lys Leu Ser Lys Ile Glu Gly Ser
385                 390                 395                 400

<210> SEQ ID NO 17
<211> LENGTH: 1221
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
atgttcatca ctccacgcaa tgtatctaac acctttctgc aggaaccgct gcgtcattct      60
agcgacctga ccgaaatgcc agttgaagcg gagaacgtga atctaagac tgaatactac     120
aacgcgtggg cagtatggga gcgcaatgca ccaccaggta acggtgaaca gcgtgaaatg    180
gcagtaagcc gtctgcgtga ttgcctggat cgccaggctc acgagctgga gctgaacaac    240
ctgggtctgt ctagcctgcc agagctccca ccacatctgg aaagcctggt ggctagctgt    300
aactctctga ctgaactgcc agagctgcca caaagcctga atccctgca ggtggacaac    360
aacaacctga agcgctgtc cgatctgcca ccgtctctgg agtttctggc agctggtaac    420
aaccaactgg aagaactgcc agagctgcag aactcctcct ttctgaagat catcgatggt    480
agcggtagcg gtagcggtag cggtagcggt agcggtagcg gtagcattaa tcctgttact    540
aatactcagg gcgtgtcccc tataaatact aaatatgctg aacatgtggt gaaaaatatt    600
tacccgaaaa ttaaacatga ttactttaat gaatcaccca atatatga taagaagtat    660
atatccggta taaccagagg agtagctgaa ctaaaacagg aagaatttgt taacgagaaa    720
gccagacggt tttcttatat gaagactatg tattctgtat gtccagaagc gtttgaacct    780
atttccagaa atgaagccag tacaccggaa ggaagctggc taacagttat atccggaaaa    840
gccccaatgg ggcagttttc tgtagatagt ttatacaatc ctgatttaca tgcattatgt    900
gagcttccgg acatttgttg taagatcttc cctaaagaaa ataatgattt tttatacata    960
gttgttgtgt acagaaatga cagccctcta ggagaacaac gggcaaatag atttatagaa   1020
ttatataata taaaaagaga tatcatgcag gaattaaatt atgagttacc agagttaaag   1080
gcagtaaaat ctgaaatgat tatcgcacgt gaaatgggag aaatctttag ctacatgcct   1140
ggggaaatag acagttatat gaaatacata aataataaac tttctaaaat tgagggatct   1200
catcaccatc accatcacta a                                              1221
```

```
<210> SEQ ID NO 18
<211> LENGTH: 390
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Phe Ile Thr Pro Arg Asn Val Ser Asn Thr Phe Leu Gln Glu Pro
1               5                   10                  15

Leu Arg His Ser Ser Asp Leu Thr Glu Met Pro Val Glu Ala Glu Asn
            20                  25                  30

Val Lys Ser Lys Thr Glu Tyr Tyr Asn Ala Trp Ala Val Trp Glu Arg
        35                  40                  45

Asn Ala Pro Pro Gly Asn Gly Glu Gln Arg Glu Met Ala Val Ser Arg
    50                  55                  60

Leu Arg Asp Cys Leu Asp Arg Gln Ala His Glu Leu Glu Leu Asn Asn
65                  70                  75                  80

Leu Gly Leu Ser Ser Leu Pro Glu Leu Pro Pro His Leu Glu Ser Leu
                85                  90                  95

Val Ala Ser Cys Asn Ser Leu Thr Glu Leu Pro Glu Leu Pro Gln Ser
            100                 105                 110

Leu Lys Ser Leu Gln Val Asp Asn Asn Leu Lys Ala Leu Ser Asp
        115                 120                 125

Leu Pro Pro Ser Leu Glu Phe Leu Ala Ala Gly Asn Asn Gln Leu Glu
    130                 135                 140

Glu Leu Pro Glu Leu Gln Asn Ser Ser Phe Leu Lys Ile Ile Asp Ile
145                 150                 155                 160

Asn Pro Val Thr Asn Thr Gln Gly Val Ser Pro Ile Asn Thr Lys Tyr
                165                 170                 175

Ala Glu His Val Val Lys Asn Ile Tyr Pro Lys Ile Lys His Asp Tyr
            180                 185                 190

Phe Asn Glu Ser Pro Asn Ile Tyr Asp Lys Lys Tyr Ile Ser Gly Ile
        195                 200                 205

Thr Arg Gly Val Ala Glu Leu Lys Gln Glu Glu Phe Val Asn Glu Lys
    210                 215                 220

Ala Arg Arg Phe Ser Tyr Met Lys Thr Met Tyr Ser Val Cys Pro Glu
225                 230                 235                 240

Ala Phe Glu Pro Ile Ser Arg Asn Glu Ala Ser Thr Pro Glu Gly Ser
                245                 250                 255

Trp Leu Thr Val Ile Ser Gly Lys Ala Pro Met Gly Gln Phe Ser Val
            260                 265                 270

Asp Ser Leu Tyr Asn Pro Asp Leu His Ala Leu Cys Glu Leu Pro Asp
        275                 280                 285

Ile Cys Cys Lys Ile Phe Pro Lys Glu Asn Asn Asp Phe Leu Tyr Ile
    290                 295                 300

Val Val Val Tyr Arg Asn Asp Ser Pro Leu Gly Glu Gln Arg Ala Asn
305                 310                 315                 320

Arg Phe Ile Glu Leu Tyr Asn Ile Lys Arg Asp Ile Met Gln Glu Leu
                325                 330                 335

Asn Tyr Glu Leu Pro Glu Leu Lys Ala Val Lys Ser Glu Met Ile Ile
            340                 345                 350

Ala Arg Glu Met Gly Glu Ile Phe Ser Tyr Met Pro Gly Glu Ile Asp
        355                 360                 365
```

```
Ser Tyr Met Lys Tyr Ile Asn Asn Lys Leu Ser Lys Ile Glu Gly Ser
    370                 375                 380

His His His His His
385                 390

<210> SEQ ID NO 19
<211> LENGTH: 384
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Phe Ile Thr Pro Arg Asn Val Ser Asn Thr Phe Leu Gln Glu Pro
1               5                   10                  15

Leu Arg His Ser Ser Asp Leu Thr Glu Met Pro Val Glu Ala Glu Asn
                20                  25                  30

Val Lys Ser Lys Thr Glu Tyr Tyr Asn Ala Trp Ala Val Trp Glu Arg
            35                  40                  45

Asn Ala Pro Pro Gly Asn Gly Glu Gln Arg Glu Met Ala Val Ser Arg
    50                  55                  60

Leu Arg Asp Cys Leu Asp Arg Gln Ala His Glu Leu Glu Leu Asn Asn
65                  70                  75                  80

Leu Gly Leu Ser Ser Leu Pro Glu Leu Pro Pro His Leu Glu Ser Leu
                85                  90                  95

Val Ala Ser Cys Asn Ser Leu Thr Glu Leu Pro Glu Leu Pro Gln Ser
            100                 105                 110

Leu Lys Ser Leu Gln Val Asp Asn Asn Asn Leu Lys Ala Leu Ser Asp
        115                 120                 125

Leu Pro Pro Ser Leu Glu Phe Leu Ala Ala Gly Asn Asn Gln Leu Glu
    130                 135                 140

Glu Leu Pro Glu Leu Gln Asn Ser Ser Phe Leu Lys Ile Ile Asp Ile
145                 150                 155                 160

Asn Pro Val Thr Asn Thr Gln Gly Val Ser Pro Ile Asn Thr Lys Tyr
                165                 170                 175

Ala Glu His Val Val Lys Asn Ile Tyr Pro Lys Ile Lys His Asp Tyr
            180                 185                 190

Phe Asn Glu Ser Pro Asn Ile Tyr Asp Lys Lys Tyr Ile Ser Gly Ile
        195                 200                 205

Thr Arg Gly Val Ala Glu Leu Lys Gln Glu Glu Phe Val Asn Glu Lys
    210                 215                 220

Ala Arg Arg Phe Ser Tyr Met Lys Thr Met Tyr Ser Val Cys Pro Glu
225                 230                 235                 240

Ala Phe Glu Pro Ile Ser Arg Asn Glu Ala Ser Thr Pro Glu Gly Ser
                245                 250                 255

Trp Leu Thr Val Ile Ser Gly Lys Ala Pro Met Gly Gln Phe Ser Val
            260                 265                 270

Asp Ser Leu Tyr Asn Pro Asp Leu His Ala Leu Cys Glu Leu Pro Asp
        275                 280                 285

Ile Cys Cys Lys Ile Phe Pro Lys Glu Asn Asn Asp Phe Leu Tyr Ile
    290                 295                 300

Val Val Val Tyr Arg Asn Asp Ser Pro Leu Gly Glu Gln Arg Ala Asn
305                 310                 315                 320

Arg Phe Ile Glu Leu Tyr Asn Ile Lys Arg Asp Ile Met Gln Glu Leu
```

```
                    325                 330                 335
Asn Tyr Glu Leu Pro Glu Leu Lys Ala Val Lys Ser Glu Met Ile Ile
            340                 345                 350

Ala Arg Glu Met Gly Glu Ile Phe Ser Tyr Met Pro Gly Glu Ile Asp
        355                 360                 365

Ser Tyr Met Lys Tyr Ile Asn Asn Lys Leu Ser Lys Ile Glu Gly Ser
    370                 375                 380
```

<210> SEQ ID NO 20
<211> LENGTH: 1173
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 20

```
atgttcatca ctccacgcaa tgtatctaac acctttctgc aggaaccgct gcgtcattct      60
agcgacctga ccgaaatgcc agttgaagcg gagaacgtga atctaagac tgaatactac     120
aacgcgtggg cagtatggga gcgcaatgca ccaccaggta acggtgaaca gcgtgaaatg     180
gcagtaagcc gtctgcgtga ttgcctggat cgccaggctc acgagctgga gctgaacaac     240
ctgggtctgt ctagcctgcc agagctccca ccacatctgg aaagcctggt ggctagctgt     300
aactctctga ctgaactgcc agagctgcca caaagcctga atccctgca ggtggacaac     360
aacaacctga agcgctgtc cgatctgcca ccgtctctgg agtttctggc agctggtaac     420
aaccaactgg aagaactgcc agagctgcag aactcctcct ttctgaagat catcgatatt     480
aatcctgtta ctaatactca gggcgtgtcc cctataaata ctaaatatgc tgaacatgtg     540
gtgaaaaata tttacccgaa aattaaacat gattacttta tgaatcacc caatatatat     600
gataagaagt atatatccgg tataaccaga ggagtagctg aactaaaaca ggaagaattt     660
gttaacgaga aagccagacg ttttctttat atgaagacta tgtattctgt atgtccagaa     720
gcgtttgaac ctatttccag aaatgaagcc agtacaccgg aaggaagctg gctaacagtt     780
atatccggaa aagccccaat ggggcagttt tctgtagata gtttatacaa tcctgattta     840
catgcattat gtgagcttcc ggacatttgt tgtaagatct tccctaaaga aaataatgat     900
tttttataca tagttgttgt gtacagaaat gacagccctc taggagaaca acggcaaat     960
agatttatag aattatataa tataaaaaga gatatcatgc aggaattaaa ttatgagtta    1020
ccagagttaa aggcagtaaa atctgaaatg attatcgcac gtgaaatggg agaaatctt     1080
agctacatgc ctggggaaat agacagttat atgaaataca taataataa actttctaaa    1140
attgagggat ctcatcacca tcaccatcac taa                                 1173
```

<210> SEQ ID NO 21
<211> LENGTH: 406
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 21

```
Met Phe Ile Thr Pro Arg Asn Val Ser Asn Thr Phe Leu Gln Glu Pro
1               5                   10                  15

Leu Arg His Ser Ser Asp Leu Thr Glu Met Pro Val Glu Ala Glu Asn
            20                  25                  30
```

Val Lys Ser Lys Thr Glu Tyr Tyr Asn Ala Trp Ala Val Trp Glu Arg
     35                  40                  45

Asn Ala Pro Pro Gly Asn Gly Glu Gln Arg Glu Met Ala Val Ser Arg
 50                  55                  60

Leu Arg Asp Cys Leu Asp Arg Gln Ala His Glu Leu Glu Leu Asn Asn
 65                  70                  75                  80

Leu Gly Leu Ser Ser Leu Pro Glu Leu Pro Pro His Leu Glu Ser Leu
                 85                  90                  95

Val Ala Ser Cys Asn Ser Leu Thr Glu Leu Pro Glu Leu Pro Gln Ser
             100                 105                 110

Leu Lys Ser Leu Gln Val Asp Asn Asn Leu Lys Ala Leu Ser Asp
         115                 120                 125

Leu Pro Pro Ser Leu Glu Phe Leu Ala Ala Gly Asn Asn Gln Leu Glu
 130                 135                 140

Glu Leu Pro Glu Leu Gln Asn Ser Ser Phe Leu Lys Ile Ile Asp Gly
145                 150                 155                 160

Ser Gly Ser Gly Ser Gly Ser Gly Ser Gly Ser Gly Ser Ile
                 165                 170                 175

Asn Pro Val Thr Asn Thr Gln Gly Val Ser Pro Ile Asn Thr Lys Tyr
                 180                 185                 190

Ala Glu His Val Val Lys Asn Ile Tyr Pro Lys Ile Lys His Asp Tyr
             195                 200                 205

Phe Asn Glu Ser Pro Asn Ile Tyr Asp Lys Lys Tyr Ile Ser Gly Ile
 210                 215                 220

Thr Arg Gly Val Ala Glu Leu Lys Gln Glu Glu Phe Val Asn Glu Lys
225                 230                 235                 240

Ala Arg Arg Phe Ser Tyr Met Lys Thr Met Tyr Ser Val Cys Pro Glu
                 245                 250                 255

Ala Phe Glu Pro Ile Ser Arg Asn Glu Ala Ser Thr Pro Glu Gly Ser
             260                 265                 270

Trp Leu Thr Val Ile Ser Gly Lys Ala Pro Met Gly Gln Phe Ser Val
         275                 280                 285

Asp Ser Leu Tyr Asn Pro Asp Leu His Ala Leu Cys Glu Leu Pro Asp
 290                 295                 300

Ile Cys Cys Lys Ile Phe Pro Lys Glu Asn Asn Asp Phe Leu Tyr Ile
305                 310                 315                 320

Val Val Val Tyr Arg Asn Asp Ser Pro Leu Gly Glu Gln Arg Ala Asn
                 325                 330                 335

Arg Phe Ile Glu Leu Tyr Asn Ile Lys Arg Asp Ile Met Gln Glu Leu
             340                 345                 350

Asn Tyr Glu Leu Pro Glu Leu Lys Ala Val Lys Ser Glu Met Ile Ile
         355                 360                 365

Ala Arg Glu Met Gly Glu Ile Phe Ser Tyr Met Pro Gly Glu Ile Asp
 370                 375                 380

Ser Tyr Met Lys Tyr Ile Asn Asn Lys Leu Ser Lys Ile Glu Gly Ser
385                 390                 395                 400

His His His His His His
                 405

<210> SEQ ID NO 22
<211> LENGTH: 400
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 22

```
Met Phe Ile Thr Pro Arg Asn Val Ser Asn Thr Phe Leu Gln Glu Pro
1               5                   10                  15

Leu Arg His Ser Ser Asp Leu Thr Glu Met Pro Val Glu Ala Glu Asn
            20                  25                  30

Val Lys Ser Lys Thr Glu Tyr Tyr Asn Ala Trp Ala Val Trp Glu Arg
        35                  40                  45

Asn Ala Pro Pro Gly Asn Gly Glu Gln Arg Glu Met Ala Val Ser Arg
    50                  55                  60

Leu Arg Asp Cys Leu Asp Arg Gln Ala His Glu Leu Glu Leu Asn Asn
65                  70                  75                  80

Leu Gly Leu Ser Ser Leu Pro Glu Leu Pro His Leu Glu Ser Leu
                85                  90                  95

Val Ala Ser Cys Asn Ser Leu Thr Glu Leu Pro Glu Leu Pro Gln Ser
            100                 105                 110

Leu Lys Ser Leu Gln Val Asp Asn Asn Leu Lys Ala Leu Ser Asp
            115                 120                 125

Leu Pro Pro Ser Leu Glu Phe Leu Ala Ala Gly Asn Asn Gln Leu Glu
    130                 135                 140

Glu Leu Pro Glu Leu Gln Asn Ser Ser Phe Leu Lys Ile Ile Asp Gly
145                 150                 155                 160

Ser Gly Ser Gly Ser Gly Ser Gly Ser Gly Ser Gly Ser Ile
                165                 170                 175

Asn Pro Val Thr Asn Thr Gln Gly Val Ser Pro Ile Asn Thr Lys Tyr
            180                 185                 190

Ala Glu His Val Val Lys Asn Ile Tyr Pro Lys Ile Lys His Asp Tyr
        195                 200                 205

Phe Asn Glu Ser Pro Asn Ile Tyr Asp Lys Lys Tyr Ile Ser Gly Ile
    210                 215                 220

Thr Arg Gly Val Ala Glu Leu Lys Gln Glu Glu Phe Val Asn Glu Lys
225                 230                 235                 240

Ala Arg Arg Phe Ser Tyr Met Lys Thr Met Tyr Ser Val Cys Pro Glu
                245                 250                 255

Ala Phe Glu Pro Ile Ser Arg Asn Glu Ala Ser Thr Pro Glu Gly Ser
            260                 265                 270

Trp Leu Thr Val Ile Ser Gly Lys Ala Pro Met Gly Gln Phe Ser Val
        275                 280                 285

Asp Ser Leu Tyr Asn Pro Asp Leu His Ala Leu Cys Glu Leu Pro Asp
    290                 295                 300

Ile Cys Cys Lys Ile Phe Pro Lys Glu Asn Asn Asp Phe Leu Tyr Ile
305                 310                 315                 320

Val Val Val Tyr Arg Asn Asp Ser Pro Leu Gly Glu Gln Arg Ala Asn
                325                 330                 335

Arg Phe Ile Glu Leu Tyr Asn Ile Lys Arg Asp Ile Met Gln Glu Leu
            340                 345                 350

Asn Tyr Glu Leu Pro Glu Leu Lys Ala Val Lys Ser Glu Met Ile Ile
        355                 360                 365

Ala Arg Glu Met Gly Glu Ile Phe Ser Tyr Met Pro Gly Glu Ile Asp
    370                 375                 380

Ser Tyr Met Lys Tyr Ile Asn Asn Lys Leu Ser Lys Ile Glu Gly Ser
385                 390                 395                 400
```

<210> SEQ ID NO 23
<211> LENGTH: 1221
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 23

| | |
|---|---:|
| atgttcatca ctccacgcaa tgtatctaac acctttctgc aggaaccgct gcgtcattct | 60 |
| agcgacctga ccgaaatgcc agttgaagcg agaacgtga atctaagac tgaatactac | 120 |
| aacgcgtggg cagtatggga gcgcaatgca ccaccaggta acggtgaaca gcgtgaaatg | 180 |
| gcagtaagcc gtctgcgtga ttgcctggat cgccaggctc acgagctgga gctgaacaac | 240 |
| ctgggtctgt ctagcctgcc agagctccca ccacatctgg aaagcctggt ggctagctgt | 300 |
| aactctctga ctgaactgcc agagctgcca caaagcctga atccctgca ggtggacaac | 360 |
| aacaacctga agcgctgtc cgatctgcca ccgtctctgg agtttctggc agctggtaac | 420 |
| aaccaactgg aagaactgcc agagctgcag aactcctcct ttctgaagat catcgatggt | 480 |
| agcggtagcg gtagcggtag cggtagcggt agcggtagcg gtagcattaa tcctgttact | 540 |
| aatactcagg gcgtgtcccc tataaatact aaatatgctg aacatgtggt gaaaaatatt | 600 |
| tacccgaaaa ttaaacatga ttactttaat gaatcaccca atatatga taagaagtat | 660 |
| atatccggta taaccagagg agtagctgaa ctaaaacagg aagaatttgt taacgagaaa | 720 |
| gccagacggt tttcttatat gaagactatg tattctgtat gtccagaagc gtttgaacct | 780 |
| atttccagaa atgaagccag tacaccggaa ggaagctggc taacagttat atccggaaaa | 840 |
| gccccaatgg ggcagttttc tgtagatagt ttatacaatc ctgatttaca tgcattatgt | 900 |
| gagcttccgg acatttgttg taagatcttc cctaaagaaa ataatgattt tttatacata | 960 |
| gttgttgtgt acagaaatga cagccctcta ggagaacaac gggcaaatag atttatagaa | 1020 |
| ttatataata taaaaagaga tatcatgcag gaattaaatt atgagttacc agagttaaag | 1080 |
| gcagtaaaat ctgaaatgat tatcgcacgt gaaatgggag aaatctttag ctacatgcct | 1140 |
| ggggaaatag acagttatat gaaatacata ataataaac tttctaaaat tgagggatct | 1200 |
| catcaccatc accatcacta a | 1221 |

<210> SEQ ID NO 24
<211> LENGTH: 406
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

Met Phe Ile Thr Pro Arg Asn Val Ser Asn Thr Phe Leu Gln Glu Pro
1               5                   10                  15

Leu Arg His Ser Ser Asp Leu Thr Glu Met Pro Val Glu Ala Glu Asn
                20                  25                  30

Val Lys Ser Lys Thr Glu Tyr Tyr Asn Ala Trp Ala Val Trp Glu Arg
            35                  40                  45

Asn Ala Pro Pro Gly Asn Gly Glu Gln Arg Glu Met Ala Val Ser Arg
        50                  55                  60

Leu Arg Asp Cys Leu Asp Arg Gln Ala His Glu Leu Glu Leu Asn Asn
65                  70                  75                  80

Leu Gly Leu Ser Ser Leu Pro Glu Leu Pro Pro His Leu Glu Ser Leu
                85                  90                  95

Val Ala Ser Cys Asn Ser Leu Thr Glu Leu Pro Glu Leu Pro Gln Ser
            100                 105                 110

Leu Lys Ser Leu Gln Val Asp Asn Asn Leu Lys Ala Leu Ser Asp
        115                 120                 125

Leu Pro Pro Ser Leu Glu Phe Leu Ala Ala Gly Asn Asn Gln Leu Glu
    130                 135                 140

Glu Leu Pro Glu Leu Gln Asn Ser Ser Phe Leu Lys Ile Ile Asp Pro
145                 150                 155                 160

Ala Pro Ala Pro Ala Pro Ala Pro Ala Pro Ala Pro Ala Ile
                165                 170                 175

Asn Pro Val Thr Asn Thr Gln Gly Val Ser Pro Ile Asn Thr Lys Tyr
            180                 185                 190

Ala Glu His Val Val Lys Asn Ile Tyr Pro Lys Ile Lys His Asp Tyr
        195                 200                 205

Phe Asn Glu Ser Pro Asn Ile Tyr Asp Lys Lys Tyr Ile Ser Gly Ile
    210                 215                 220

Thr Arg Gly Val Ala Glu Leu Lys Gln Glu Glu Phe Val Asn Glu Lys
225                 230                 235                 240

Ala Arg Arg Phe Ser Tyr Met Lys Thr Met Tyr Ser Val Cys Pro Glu
            245                 250                 255

Ala Phe Glu Pro Ile Ser Arg Asn Glu Ala Ser Thr Pro Glu Gly Ser
        260                 265                 270

Trp Leu Thr Val Ile Ser Gly Lys Ala Pro Met Gly Gln Phe Ser Val
    275                 280                 285

Asp Ser Leu Tyr Asn Pro Asp Leu His Ala Leu Cys Glu Leu Pro Asp
290                 295                 300

Ile Cys Cys Lys Ile Phe Pro Lys Glu Asn Asn Asp Phe Leu Tyr Ile
305                 310                 315                 320

Val Val Val Tyr Arg Asn Asp Ser Pro Leu Gly Glu Gln Arg Ala Asn
            325                 330                 335

Arg Phe Ile Glu Leu Tyr Asn Ile Lys Arg Asp Ile Met Gln Glu Leu
        340                 345                 350

Asn Tyr Glu Leu Pro Glu Leu Lys Ala Val Lys Ser Glu Met Ile Ile
    355                 360                 365

Ala Arg Glu Met Gly Glu Ile Phe Ser Tyr Met Pro Gly Glu Ile Asp
        370                 375                 380

Ser Tyr Met Lys Tyr Ile Asn Asn Lys Leu Ser Lys Ile Glu Gly Ser
385                 390                 395                 400

His His His His His His
                405

<210> SEQ ID NO 25
<211> LENGTH: 400
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Phe Ile Thr Pro Arg Asn Val Ser Asn Thr Phe Leu Gln Glu Pro
1               5                   10                  15

Leu Arg His Ser Ser Asp Leu Thr Glu Met Pro Val Glu Ala Glu Asn
                20                  25                  30

Val Lys Ser Lys Thr Glu Tyr Tyr Asn Ala Trp Ala Val Trp Glu Arg
        35                  40                  45

Asn Ala Pro Pro Gly Asn Gly Glu Gln Arg Glu Met Ala Val Ser Arg
 50                  55                  60

Leu Arg Asp Cys Leu Asp Arg Gln Ala His Glu Leu Glu Leu Asn Asn
 65                  70                  75                  80

Leu Gly Leu Ser Ser Leu Pro Glu Leu Pro Pro His Leu Glu Ser Leu
                 85                  90                  95

Val Ala Ser Cys Asn Ser Leu Thr Glu Leu Pro Glu Leu Pro Gln Ser
            100                 105                 110

Leu Lys Ser Leu Gln Val Asp Asn Asn Leu Lys Ala Leu Ser Asp
        115                 120                 125

Leu Pro Pro Ser Leu Glu Phe Leu Ala Ala Gly Asn Asn Gln Leu Glu
        130                 135                 140

Glu Leu Pro Glu Leu Gln Asn Ser Ser Phe Leu Lys Ile Ile Asp Pro
145                 150                 155                 160

Ala Pro Ala Pro Ala Pro Ala Pro Ala Pro Ala Pro Ala Pro Ala Ile
                165                 170                 175

Asn Pro Val Thr Asn Thr Gln Gly Val Ser Pro Ile Asn Thr Lys Tyr
            180                 185                 190

Ala Glu His Val Val Lys Asn Ile Tyr Pro Lys Ile Lys His Asp Tyr
        195                 200                 205

Phe Asn Glu Ser Pro Asn Ile Tyr Asp Lys Lys Tyr Ile Ser Gly Ile
        210                 215                 220

Thr Arg Gly Val Ala Glu Leu Lys Gln Glu Glu Phe Val Asn Glu Lys
225                 230                 235                 240

Ala Arg Arg Phe Ser Tyr Met Lys Thr Met Tyr Ser Val Cys Pro Glu
                245                 250                 255

Ala Phe Glu Pro Ile Ser Arg Asn Glu Ala Ser Thr Pro Glu Gly Ser
            260                 265                 270

Trp Leu Thr Val Ile Ser Gly Lys Ala Pro Met Gly Gln Phe Ser Val
        275                 280                 285

Asp Ser Leu Tyr Asn Pro Asp Leu His Ala Leu Cys Glu Leu Pro Asp
        290                 295                 300

Ile Cys Cys Lys Ile Phe Pro Lys Glu Asn Asn Asp Phe Leu Tyr Ile
305                 310                 315                 320

Val Val Val Tyr Arg Asn Asp Ser Pro Leu Gly Glu Gln Arg Ala Asn
                325                 330                 335

Arg Phe Ile Glu Leu Tyr Asn Ile Lys Arg Asp Ile Met Gln Glu Leu
            340                 345                 350

Asn Tyr Glu Leu Pro Glu Leu Lys Ala Val Lys Ser Glu Met Ile Ile
        355                 360                 365

Ala Arg Glu Met Gly Glu Ile Phe Ser Tyr Met Pro Gly Glu Ile Asp
        370                 375                 380

Ser Tyr Met Lys Tyr Ile Asn Asn Lys Leu Ser Lys Ile Glu Gly Ser
385                 390                 395                 400

<210> SEQ ID NO 26
<211> LENGTH: 1221
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26

```
atgttcatca ctccacgcaa tgtatctaac acctttctgc aggaaccgct gcgtcattct      60
agcgacctga ccgaaatgcc agttgaagcg gagaacgtga atctaagac tgaatactac     120
aacgcgtggg cagtatggga gcgcaatgca ccaccaggta acggtgaaca gcgtgaaatg    180
gcagtaagcc gtctgcgtga ttgcctggat cgccaggctc acgagctgga gctgaacaac    240
ctgggtctgt ctagcctgcc agagctccca ccacatctgg aaagcctggt ggctagctgt    300
aactctctga ctgaactgcc agagctgcca caaagcctga atccctgca ggtggacaac    360
aacaacctga agcgctgtc cgatctgcca ccgtctctgg agtttctggc agctggtaac    420
aaccaactgg aagaactgcc agagctgcag aactcctcct ttctgaagat catcgatcca    480
gcaccagcac cagcaccagc accagcacca gcaccagcac cagcaattaa tcctgttact    540
aatactcagg gcgtgtcccc tataaatact aaatatgctg aacatgtggt gaaaatatt    600
tacccgaaaa ttaaacatga ttactttaat gaatcaccca atatatatga taagaagtat    660
atatccggta taaccagagg agtagctgaa ctaaaacagg aagaatttgt taacgagaaa    720
gccagacggt tttcttatat gaagactatg tattctgtat gtccagaagc gtttgaacct    780
atttccagaa atgaagccag tacaccgaaa ggaagctggc taacagttat atccggaaaa    840
gccccaatgg ggcagttttc tgtagatagt ttatacaatc ctgatttaca tgcattatgt    900
gagcttccgg acatttgttg taagatcttc cctaaagaaa ataatgattt ttatacata    960
gttgttgtgt acagaaatga cagccctcta ggagaacaac gggcaaatag atttatagaa   1020
ttatataata taaaagaga tatcatgcag gaattaaatt atgagttacc agagttaaag   1080
gcagtaaaat ctgaaatgat tatcgcacgt gaaatgggag aaatctttag ctacatgcct   1140
ggggaaatag acagttatat gaaatacata aataataaac tttctaaaat tgagggatct   1200
catcaccatc accatcacta a                                            1221
```

<210> SEQ ID NO 27
<211> LENGTH: 252
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 27

```
Gly Ser Met Arg Lys Lys Arg Arg Gln Arg Arg Ile Asn Pro Val
1               5                   10                  15

Thr Asn Thr Gln Ile Asn Pro Val Thr Asn Thr Gln Gly Val Ser Pro
            20                  25                  30

Ile Asn Thr Lys Tyr Ala Glu His Val Val Lys Asn Ile Tyr Pro Lys
        35                  40                  45

Ile Lys His Asp Tyr Phe Asn Glu Ser Pro Asn Tyr Asp Lys Lys Tyr
    50                  55                  60

Ile Ser Gly Ile Thr Arg Gly Val Ala Glu Leu Lys Gln Glu Glu Phe
65                  70                  75                  80

Val Asn Glu Lys Ala Arg Arg Phe Ser Tyr Met Lys Thr Met Tyr Ser
                85                  90                  95

Val Cys Pro Glu Ala Phe Glu Pro Ile Ser Arg Asn Glu Ala Ser Thr
            100                 105                 110

Pro Glu Gly Ser Trp Leu Thr Val Ile Ser Gly Lys Arg Pro Met Gly
        115                 120                 125
```

```
Gln Phe Ser Val Asp Ser Leu Tyr Asn Pro Asp Leu His Ala Leu Cys
            130                 135                 140

Glu Leu Pro Asp Ile Cys Cys Lys Ile Phe Pro Lys Glu Asn Asn Asp
145                 150                 155                 160

Phe Leu Tyr Ile Val Val Tyr Arg Asn Asp Ser Pro Leu Gly Glu
                    165                 170                 175

Gln Arg Ala Asn Arg Phe Ile Glu Leu Tyr Asn Ile Lys Arg Asp Ile
                180                 185                 190

Met Gln Glu Leu Asn Tyr Glu Leu Pro Glu Leu Lys Ala Val Lys Ser
            195                 200                 205

Glu Met Ile Ile Ala Arg Glu Met Gly Glu Ile Phe Ser Tyr Met Pro
210                 215                 220

Gly Glu Ile Asp Ser Tyr Met Lys Tyr Ile Asn Asn Lys Leu Ser Lys
225                 230                 235                 240

Ile Glu Gly Ser Arg Ser His His His His His
                    245                 250

<210> SEQ ID NO 28
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gly Ser Met Arg Lys Lys Arg Arg Gln Arg Arg Ile Asn Pro Val
1               5                   10                  15

Thr Asn Thr Gln Ile Asn Pro Val Thr Asn Thr Gln Gly Val Ser Pro
                20                  25                  30

Ile Asn Thr Lys Tyr Ala Glu His Val Val Lys Asn Ile Tyr Pro Lys
            35                  40                  45

Ile Lys His Asp Tyr Phe Asn Glu Ser Pro Asn Tyr Asp Lys Lys Tyr
50                  55                  60

Ile Ser Gly Ile Thr Arg Gly Val Ala Glu Leu Lys Gln Glu Glu Phe
65                  70                  75                  80

Val Asn Glu Lys Ala Arg Arg Phe Ser Tyr Met Lys Thr Met Tyr Ser
                85                  90                  95

Val Cys Pro Glu Ala Phe Glu Pro Ile Ser Arg Asn Glu Ala Ser Thr
                100                 105                 110

Pro Glu Gly Ser Trp Leu Thr Val Ile Ser Gly Lys Arg Pro Met Gly
            115                 120                 125

Gln Phe Ser Val Asp Ser Leu Tyr Asn Pro Asp Leu His Ala Leu Cys
            130                 135                 140

Glu Leu Pro Asp Ile Cys Cys Lys Ile Phe Pro Lys Glu Asn Asn Asp
145                 150                 155                 160

Phe Leu Tyr Ile Val Val Tyr Arg Asn Asp Ser Pro Leu Gly Glu
                    165                 170                 175

Gln Arg Ala Asn Arg Phe Ile Glu Leu Tyr Asn Ile Lys Arg Asp Ile
                180                 185                 190

Met Gln Glu Leu Asn Tyr Glu Leu Pro Glu Leu Lys Ala Val Lys Ser
            195                 200                 205

Glu Met Ile Ile Ala Arg Glu Met Gly Glu Ile Phe Ser Tyr Met Pro
210                 215                 220

Gly Glu Ile Asp Ser Tyr Met Lys Tyr Ile Asn Asn Lys Leu Ser Lys
225                 230                 235                 240
```

Ile Glu Gly Ser Arg Ser
            245

<210> SEQ ID NO 29
<211> LENGTH: 762
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29

```
ggatccatga ggaagaagcg gagacagcga cgaagaatta atcctgttac taatactcag      60
attaatcctg ttactaatac tcagggcgtg tcccctataa atactaaata tgctgaacat     120
gtggtgaaaa atatttaccc gaaaattaaa catgattact ttaatgaatc acccaatata     180
tatgataaga agtatatatc cggtataacc agaggagtag ctgaactaaa acaggaagaa     240
tttgttaacg agaaagccag acggttttct tatatgaaga ctatgtattc tgtatgtcca     300
gaagcgtttg aacctatttc cagaaatgaa gccagtacac cggaaggaag ctggctaaca     360
gttatatccg gaaaacgccc aatggggcag ttttctgtag atagtttata caatcctgat     420
ttacatgcat tatgtgagct tccggacatt tgttgtaaga tcttccctaa agaaaataat     480
gattttttat acatagttgt tgtgtacaga aatgacagcc ctctaggaga caacgggca      540 aatagattta tagaattata taatataaaa agagatatca tgcaggaatt aaattatgag     600
ttaccagagt taaaggcagt aaaatctgaa atgattatcg cacgtgaaat gggagaaatc     660
tttagctaca tgcctgggga aatagacagt tatatgaaat acataaataa taaactttct     720
aaaattgagg gatccagatc tcatcaccat caccatcact aa                        762
```

<210> SEQ ID NO 30
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gly Ser Met Arg Lys Lys Arg Arg Gln Arg Arg Ile Asn Pro Val
1               5                   10                  15

Thr Asn Thr Gln Ile Asn Pro Val Thr Asn Thr Gln Gly Val Ser Pro
            20                  25                  30

Ile Asn Thr Lys Tyr Ala Glu His Val Val Lys Asn Ile Tyr Pro Lys
        35                  40                  45

Ile Lys His Asp Tyr Phe Asn Glu Ser Pro Asn Tyr Asp Lys Lys Tyr
50                  55                  60

Ile Ser Gly Ile Thr Arg Gly Val Ala Glu Leu Lys Gln Glu Glu Phe
65                  70                  75                  80

Val Asn Glu Lys Ala Arg Arg Phe Ser Tyr Met Lys Thr Met Tyr Ser
                85                  90                  95

Val Cys Pro Glu Ala Phe Glu Pro Ile Ser Arg Asn Glu Ala Ser Thr
            100                 105                 110

Pro Glu Gly Ser Trp Leu Thr Val Ile Ser Gly Lys Ala Pro Met Gly
        115                 120                 125

Gln Phe Ser Val Asp Ser Leu Tyr Asn Pro Asp Leu His Ala Leu Cys
    130                 135                 140

```
Glu Leu Pro Asp Ile Cys Cys Lys Ile Phe Pro Lys Glu Asn Asn Asp
145                 150                 155                 160

Phe Leu Tyr Ile Val Val Val Tyr Arg Asn Asp Ser Pro Leu Gly Glu
                165                 170                 175

Gln Arg Ala Asn Arg Phe Ile Glu Leu Tyr Asn Ile Lys Arg Asp Ile
            180                 185                 190

Met Gln Glu Leu Asn Tyr Glu Leu Pro Glu Leu Lys Ala Val Lys Ser
        195                 200                 205

Glu Met Ile Ile Ala Arg Glu Met Gly Glu Ile Phe Ser Tyr Met Pro
    210                 215                 220

Gly Glu Ile Asp Ser Tyr Met Lys Tyr Ile Asn Asn Lys Leu Ser Lys
225                 230                 235                 240

Ile Glu Gly Ser Arg Ser His His His His His
                245                 250

<210> SEQ ID NO 31
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gly Ser Met Arg Lys Lys Arg Arg Gln Arg Arg Ile Asn Pro Val
1               5                   10                  15

Thr Asn Thr Gln Ile Asn Pro Val Thr Asn Thr Gln Gly Val Ser Pro
            20                  25                  30

Ile Asn Thr Lys Tyr Ala Glu His Val Val Lys Asn Ile Tyr Pro Lys
        35                  40                  45

Ile Lys His Asp Tyr Phe Asn Glu Ser Pro Asn Tyr Asp Lys Lys Tyr
    50                  55                  60

Ile Ser Gly Ile Thr Arg Gly Val Ala Glu Leu Lys Gln Glu Glu Phe
65                  70                  75                  80

Val Asn Glu Lys Ala Arg Arg Phe Ser Tyr Met Lys Thr Met Tyr Ser
                85                  90                  95

Val Cys Pro Glu Ala Phe Glu Pro Ile Ser Arg Asn Glu Ala Ser Thr
            100                 105                 110

Pro Glu Gly Ser Trp Leu Thr Val Ile Ser Gly Lys Ala Pro Met Gly
        115                 120                 125

Gln Phe Ser Val Asp Ser Leu Tyr Asn Pro Asp Leu His Ala Leu Cys
    130                 135                 140

Glu Leu Pro Asp Ile Cys Cys Lys Ile Phe Pro Lys Glu Asn Asn Asp
145                 150                 155                 160

Phe Leu Tyr Ile Val Val Val Tyr Arg Asn Asp Ser Pro Leu Gly Glu
                165                 170                 175

Gln Arg Ala Asn Arg Phe Ile Glu Leu Tyr Asn Ile Lys Arg Asp Ile
            180                 185                 190

Met Gln Glu Leu Asn Tyr Glu Leu Pro Glu Leu Lys Ala Val Lys Ser
        195                 200                 205

Glu Met Ile Ile Ala Arg Glu Met Gly Glu Ile Phe Ser Tyr Met Pro
    210                 215                 220

Gly Glu Ile Asp Ser Tyr Met Lys Tyr Ile Asn Asn Lys Leu Ser Lys
225                 230                 235                 240

Ile Glu Gly Ser Arg Ser
                245
```

<210> SEQ ID NO 32
<211> LENGTH: 762
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32

```
ggatccatga ggaagaagcg gagacagcga cgaagaatta atcctgttac taatactcag      60
attaatcctg ttactaatac tcagggcgtg tcccctataa atactaaata tgctgaacat     120
gtggtgaaaa atatttaccc gaaaattaaa catgattact ttaatgaatc acccaatata     180
tatgataaga agtatatatc cggtataacc agaggagtag ctgaactaaa acaggaagaa     240
tttgttaacg agaaagccag acggttttct tatatgaaga ctatgtattc tgtatgtcca     300
gaagcgtttg aacctatttc cagaaatgaa gccagtacac cggaaggaag ctggctaaca     360
gttatatccg gaaaagcccc aatggggcag ttttctgtag atagtttata caatcctgat     420
ttacatgcat tatgtgagct tccggacatt tgttgtaaga tcttccctaa agaaaataat     480
gattttttat acatagttgt tgtgtacaga aatgacagcc ctctaggaga caacgggca      540
aatagattta tagaattata taatataaaa agagatatca tgcaggaatt aaattatgag     600
ttaccagagt taaaggcagt aaaatctgaa atgattatcg cacgtgaaat gggagaaatc     660
tttagctaca tgcctgggga aatagacagt tatatgaaat acataaataa taaactttct     720
aaaattgagg gatccagatc tcatcaccat caccatcact aa                        762
```

<210> SEQ ID NO 33
<211> LENGTH: 257
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

```
Gly Ser Met Arg Lys Lys Arg Arg Gln Arg Arg Ser Ile Glu Ile
1               5                   10                  15

Lys Met Ile Ser Pro Ile Lys Asn Ile Lys Asn Val Phe Pro Ile Asn
            20                  25                  30

Thr Ala Asn Thr Glu Tyr Ile Val Arg Asn Ile Tyr Pro Arg Val Glu
        35                  40                  45

His Gly Tyr Phe Asn Glu Ser Pro Asn Ile Tyr Asp Lys Lys Tyr Ile
    50                  55                  60

Ser Gly Ile Thr Arg Ser Met Ala Gln Leu Lys Ile Glu Glu Phe Ile
65                  70                  75                  80

Asn Glu Lys Ser Arg Arg Leu Asn Tyr Met Lys Thr Met Tyr Ser Pro
                85                  90                  95

Cys Pro Glu Asp Phe Gln Pro Ile Ser Arg Asp Glu Ala Ser Thr Pro
            100                 105                 110

Glu Gly Ser Trp Leu Thr Val Ile Ser Gly Lys Arg Pro Met Gly Gln
        115                 120                 125

Phe Ser Val Asp Ser Leu Tyr His Pro Asp Leu His Ala Leu Cys Glu
    130                 135                 140

Leu Pro Glu Ile Ser Cys Lys Ile Phe Pro Lys Glu Asn Ser Asp Phe
145                 150                 155                 160
```

Leu Tyr Ile Ile Val Phe Arg Asn Asp Ser Pro Gln Gly Glu Leu
                165                 170                 175

Arg Ala Asn Arg Phe Ile Glu Leu Tyr Asp Ile Lys Arg Glu Ile Met
            180                 185                 190

Gln Val Leu Arg Asp Glu Ser Pro Glu Leu Lys Ser Ile Lys Ser Glu
        195                 200                 205

Ile Ile Ile Ala Arg Glu Met Gly Glu Leu Phe Ser Tyr Ala Ser Glu
210                 215                 220

Glu Ile Asp Ser Tyr Ile Lys Gln Met Asn Asp Arg Leu Ser Gln Ile
225                 230                 235                 240

Lys Ala Arg Met Pro Val Thr Gly Ser Arg Ser His His His His
                245                 250                 255

His

<210> SEQ ID NO 34
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gly Ser Met Arg Lys Lys Arg Gln Arg Arg Ser Ile Glu Ile
1               5                   10                  15

Lys Met Ile Ser Pro Ile Lys Asn Ile Lys Asn Val Phe Pro Ile Asn
            20                  25                  30

Thr Ala Asn Thr Glu Tyr Ile Val Arg Asn Ile Tyr Pro Arg Val Glu
        35                  40                  45

His Gly Tyr Phe Asn Glu Ser Pro Asn Ile Tyr Asp Lys Lys Tyr Ile
    50                  55                  60

Ser Gly Ile Thr Arg Ser Met Ala Gln Leu Lys Ile Glu Glu Phe Ile
65                  70                  75                  80

Asn Glu Lys Ser Arg Arg Leu Asn Tyr Met Lys Thr Met Tyr Ser Pro
                85                  90                  95

Cys Pro Glu Asp Phe Gln Pro Ile Ser Arg Asp Glu Ala Ser Thr Pro
            100                 105                 110

Glu Gly Ser Trp Leu Thr Val Ile Ser Gly Lys Arg Pro Met Gly Gln
        115                 120                 125

Phe Ser Val Asp Ser Leu Tyr His Pro Asp Leu His Ala Leu Cys Glu
130                 135                 140

Leu Pro Glu Ile Ser Cys Lys Ile Phe Pro Lys Glu Asn Ser Asp Phe
145                 150                 155                 160

Leu Tyr Ile Ile Val Phe Arg Asn Asp Ser Pro Gln Gly Glu Leu
                165                 170                 175

Arg Ala Asn Arg Phe Ile Glu Leu Tyr Asp Ile Lys Arg Glu Ile Met
            180                 185                 190

Gln Val Leu Arg Asp Glu Ser Pro Glu Leu Lys Ser Ile Lys Ser Glu
        195                 200                 205

Ile Ile Ile Ala Arg Glu Met Gly Glu Leu Phe Ser Tyr Ala Ser Glu
210                 215                 220

Glu Ile Asp Ser Tyr Ile Lys Gln Met Asn Asp Arg Leu Ser Gln Ile
225                 230                 235                 240

Lys Ala Arg Met Pro Val Thr Gly Ser Arg Ser
                245                 250

<210> SEQ ID NO 35
<211> LENGTH: 774
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 35

```
ggatccatga ggaagaagcg gagacagcga cgaagatcca tcgagatcaa gatgatctct      60
ccgatcaaga acatcaagaa cgtattcccg atcaacactg cgaataccga gtacatcgtt     120
cgcaacatct acccacgcgt agaacacggc tacttcaacg agagcccaaa catctacgac     180
aagaagtaca tcagcggtat cactcgctct atggctcaac tgaagatcga gagttcatc     240
aacgagaagt cccgtcgtct gaactacatg aagaccatgt actctccgtg tccggaagat     300
ttccaaccga tctctcgtga tgaagctagc actccagaag gcagctggct gaccgtgatc     360
tctggcaaac gtccgatggg tcagttctcc gttgactctc tgtaccatcc agacctgcac     420
gctctgtgcg aactgccaga gatttcttgc aagatctttc gaaagagaa ctctgatttc     480
ctgtacatca tcgttgtgtt ccgcaacgat tctccacaag gtgaactgcg tgctaaccgc     540
ttcatcgaac tgtacgatat caagcgtgag atcatgcagg tgctgcgcga cgagtctcca     600
gaactgaaga gcatcaaatc cgagatcatc attgcccgtg aaatgggcga actgttctct     660
tacgcatctg aagaaatcga ctcttacatc aagcagatga cgatcgtct gtcccagatc     720
aaggctcgta tgccggtaac cggatccaga tctcatcacc atcaccatca ctaa          774
```

<210> SEQ ID NO 36
<211> LENGTH: 322
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 36

```
Gly Ser Met Phe Ile Thr Pro Arg Asn Val Ser Asn Thr Phe Leu Gln
 1               5                  10                  15

Glu Pro Leu Arg His Ser Ser Asp Leu Thr Glu Met Pro Val Glu Ala
             20                  25                  30

Glu Asn Val Lys Ser Lys Thr Glu Tyr Tyr Asn Ala Trp Ala Val Trp
         35                  40                  45

Glu Arg Asn Ala Pro Pro Gly Asn Gly Glu Gln Arg Glu Met Ala Val
     50                  55                  60

Ser Arg Leu Arg Asp Cys Leu Asp Arg Gln Ala His Glu Leu Glu Leu
 65                  70                  75                  80

Asn Asn Leu Gly Leu Ser Ser Leu Met Ile Asn Pro Val Thr Asn Thr
                 85                  90                  95

Gln Gly Val Ser Pro Ile Asn Thr Lys Tyr Ala Glu His Val Val Lys
            100                 105                 110

Asn Ile Tyr Pro Lys Ile Lys His Asp Tyr Phe Asn Glu Ser Pro Asn
        115                 120                 125

Ile Tyr Asp Lys Lys Tyr Ile Ser Gly Ile Thr Arg Gly Val Ala Glu
    130                 135                 140

Leu Lys Gln Glu Glu Phe Val Asn Glu Lys Ala Arg Arg Phe Ser Tyr
145                 150                 155                 160

Met Lys Thr Met Tyr Ser Val Cys Pro Glu Ala Phe Glu Pro Ile Ser
```

```
                         165                 170                 175
Arg Asn Glu Ala Ser Thr Pro Glu Gly Ser Trp Leu Thr Val Ile Ser
                180                 185                 190

Gly Lys Arg Pro Met Gly Gln Phe Ser Val Asp Ser Leu Tyr Asn Pro
            195                 200                 205

Asp Leu His Ala Leu Cys Glu Leu Pro Asp Ile Cys Cys Lys Ile Phe
        210                 215                 220

Pro Lys Glu Asn Asn Asp Phe Leu Tyr Ile Val Val Tyr Arg Asn
225                 230                 235                 240

Asp Ser Pro Leu Gly Glu Gln Arg Ala Asn Arg Phe Ile Glu Leu Tyr
                245                 250                 255

Asn Ile Lys Arg Asp Ile Met Gln Glu Leu Asn Tyr Glu Leu Pro Glu
                260                 265                 270

Leu Lys Ala Val Lys Ser Glu Met Ile Ile Ala Arg Glu Met Gly Glu
            275                 280                 285

Ile Phe Ser Tyr Met Pro Gly Glu Ile Asp Ser Tyr Met Lys Tyr Ile
        290                 295                 300

Asn Asn Lys Leu Ser Lys Ile Glu Gly Ser Arg Ser His His His His
305                 310                 315                 320

His His

<210> SEQ ID NO 37
<211> LENGTH: 316
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gly Ser Met Phe Ile Thr Pro Arg Asn Val Ser Asn Thr Phe Leu Gln
1               5                   10                  15

Glu Pro Leu Arg His Ser Ser Asp Leu Thr Glu Met Pro Val Glu Ala
            20                  25                  30

Glu Asn Val Lys Ser Lys Thr Glu Tyr Tyr Asn Ala Trp Ala Val Trp
        35                  40                  45

Glu Arg Asn Ala Pro Pro Gly Asn Gly Glu Gln Arg Glu Met Ala Val
    50                  55                  60

Ser Arg Leu Arg Asp Cys Leu Asp Arg Gln Ala His Glu Leu Glu Leu
65                  70                  75                  80

Asn Asn Leu Gly Leu Ser Ser Leu Met Ile Asn Pro Val Thr Asn Thr
                85                  90                  95

Gln Gly Val Ser Pro Ile Asn Thr Lys Tyr Ala Glu His Val Val Lys
            100                 105                 110

Asn Ile Tyr Pro Lys Ile Lys His Asp Tyr Phe Asn Glu Ser Pro Asn
        115                 120                 125

Ile Tyr Asp Lys Lys Tyr Ile Ser Gly Ile Thr Arg Gly Val Ala Glu
    130                 135                 140

Leu Lys Gln Glu Glu Phe Val Asn Glu Lys Ala Arg Arg Phe Ser Tyr
145                 150                 155                 160

Met Lys Thr Met Tyr Ser Val Cys Pro Glu Ala Phe Glu Pro Ile Ser
                165                 170                 175

Arg Asn Glu Ala Ser Thr Pro Glu Gly Ser Trp Leu Thr Val Ile Ser
            180                 185                 190

Gly Lys Arg Pro Met Gly Gln Phe Ser Val Asp Ser Leu Tyr Asn Pro
```

```
                195                 200                 205
Asp Leu His Ala Leu Cys Glu Leu Pro Asp Ile Cys Cys Lys Ile Phe
    210                 215                 220

Pro Lys Glu Asn Asn Asp Phe Leu Tyr Ile Val Val Tyr Arg Asn
225                 230                 235                 240

Asp Ser Pro Leu Gly Glu Gln Arg Ala Asn Arg Phe Ile Glu Leu Tyr
                245                 250                 255

Asn Ile Lys Arg Asp Ile Met Gln Glu Leu Asn Tyr Glu Leu Pro Glu
            260                 265                 270

Leu Lys Ala Val Lys Ser Glu Met Ile Ile Ala Arg Glu Met Gly Glu
        275                 280                 285

Ile Phe Ser Tyr Met Pro Gly Glu Ile Asp Ser Tyr Met Lys Tyr Ile
    290                 295                 300

Asn Asn Lys Leu Ser Lys Ile Glu Gly Ser Arg Ser
305                 310                 315

<210> SEQ ID NO 38
<211> LENGTH: 969
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
ggatccatgt tcatcactcc acgcaatgta tctaacacct ttctgcagga accgctgcgt      60
cattctagcg acctgaccga atgccagtt gaagcggaga acgtgaaatc taagactgaa     120
tactacaacg cgtgggcagt atgggagcgc aatgcaccac aggtaacgg tgaacagcgt     180
gaaatggcag taagccgtct gcgtgattgc ctggatcgcc aggctcacga gctggagctg     240
aacaacctgg gtctgtctag cctgatgatt aatcctgtta ctaatactca gggcgtgtcc     300
cctataaata ctaaatatgc tgaacatgtg gtgaaaaata tttacccgaa aattaaacat     360
gattacttta atgaatcacc caatatatat gataagaagt atatatccgg tataaccaga     420
ggagtagctg aactaaaaca ggaagaattt gttaacgaga aagccagacg ttttctttat     480
atgaagacta tgtattctgt atgtccagaa gcgtttgaac ctatttccag aaatgaagcc     540
agtacaccgg aaggaagctg gctaacagtt atatccggaa aacgcccaat ggggcagttt     600
tctgtagata gtttatacaa tcctgattta catgcattat gtgagcttcc ggacatttgt     660
tgtaagatct tccctaaaga aaataatgat tttttataca tagttgttgt gtacagaaat     720
gacagccctc taggagaaca acgggcaaat agatttatag aattatataa tataaaaaga     780
gatatcatgc aggaattaaa ttatgagtta ccagagttaa aggcagtaaa atctgaaatg     840
attatcgcac gtgaaatggg agaaatcttt agctacatgc ctggggaaat agacagttat     900
atgaaataca taataataa actttctaaa attgagggat ccagatctca tcaccatcac     960
catcactaa                                                             969

<210> SEQ ID NO 39
<211> LENGTH: 322
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39
```

Gly Ser Met Phe Ile Thr Pro Arg Asn Val Ser Asn Thr Phe Leu Gln
1               5                   10                  15

Glu Pro Leu Arg His Ser Ser Asp Leu Thr Glu Met Pro Val Glu Ala
            20                  25                  30

Glu Asn Val Lys Ser Lys Thr Glu Tyr Tyr Asn Ala Trp Ala Val Trp
        35                  40                  45

Glu Arg Asn Ala Pro Pro Gly Asn Gly Glu Gln Arg Glu Met Ala Val
50                  55                  60

Ser Arg Leu Arg Asp Cys Leu Asp Arg Gln His Glu Leu Glu Leu
65                  70                  75                  80

Asn Asn Leu Gly Leu Ser Ser Leu Met Ile Asn Pro Val Thr Asn Thr
                85                  90                  95

Gln Gly Val Ser Pro Ile Asn Thr Lys Tyr Ala Glu His Val Val Lys
            100                 105                 110

Asn Ile Tyr Pro Lys Ile Lys His Asp Tyr Phe Asn Glu Ser Pro Asn
            115                 120                 125

Ile Tyr Asp Lys Lys Tyr Ile Ser Gly Ile Thr Arg Gly Val Ala Glu
            130                 135                 140

Leu Lys Gln Glu Glu Phe Val Asn Glu Lys Ala Arg Arg Phe Ser Tyr
145                 150                 155                 160

Met Lys Thr Met Tyr Ser Val Cys Pro Glu Ala Phe Glu Pro Ile Ser
                165                 170                 175

Arg Asn Glu Ala Ser Thr Pro Glu Gly Ser Trp Leu Thr Val Ile Ser
            180                 185                 190

Gly Lys Ala Pro Met Gly Gln Phe Ser Val Asp Ser Leu Tyr Asn Pro
            195                 200                 205

Asp Leu His Ala Leu Cys Glu Leu Pro Asp Ile Cys Cys Lys Ile Phe
210                 215                 220

Pro Lys Glu Asn Asn Asp Phe Leu Tyr Ile Val Val Tyr Arg Asn
225                 230                 235                 240

Asp Ser Pro Leu Gly Glu Gln Arg Ala Asn Arg Phe Ile Glu Leu Tyr
            245                 250                 255

Asn Ile Lys Arg Asp Ile Met Gln Glu Leu Asn Tyr Glu Leu Pro Glu
            260                 265                 270

Leu Lys Ala Val Lys Ser Glu Met Ile Ile Ala Arg Glu Met Gly Glu
            275                 280                 285

Ile Phe Ser Tyr Met Pro Gly Glu Ile Asp Ser Tyr Met Lys Tyr Ile
            290                 295                 300

Asn Asn Lys Leu Ser Lys Ile Glu Gly Ser Arg Ser His His His
305                 310                 315                 320

His His

<210> SEQ ID NO 40
<211> LENGTH: 316
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Gly Ser Met Phe Ile Thr Pro Arg Asn Val Ser Asn Thr Phe Leu Gln
1               5                   10                  15

Glu Pro Leu Arg His Ser Ser Asp Leu Thr Glu Met Pro Val Glu Ala
            20                  25                  30

Glu Asn Val Lys Ser Lys Thr Glu Tyr Tyr Asn Ala Trp Ala Val Trp
 35                  40                  45

Glu Arg Asn Ala Pro Pro Gly Asn Gly Glu Gln Arg Glu Met Ala Val
 50                  55                  60

Ser Arg Leu Arg Asp Cys Leu Asp Arg Gln Ala His Glu Leu Glu Leu
65                  70                  75                  80

Asn Asn Leu Gly Leu Ser Ser Leu Met Ile Asn Pro Val Thr Asn Thr
                 85                  90                  95

Gln Gly Val Ser Pro Ile Asn Thr Lys Tyr Ala Glu His Val Val Lys
             100                 105                 110

Asn Ile Tyr Pro Lys Ile Lys His Asp Tyr Phe Asn Glu Ser Pro Asn
         115                 120                 125

Ile Tyr Asp Lys Lys Tyr Ile Ser Gly Ile Thr Arg Gly Val Ala Glu
130                 135                 140

Leu Lys Gln Glu Glu Phe Val Asn Glu Lys Ala Arg Arg Phe Ser Tyr
145                 150                 155                 160

Met Lys Thr Met Tyr Ser Val Cys Pro Glu Ala Phe Glu Pro Ile Ser
                165                 170                 175

Arg Asn Glu Ala Ser Thr Pro Glu Gly Ser Trp Leu Thr Val Ile Ser
            180                 185                 190

Gly Lys Ala Pro Met Gly Gln Phe Ser Val Asp Ser Leu Tyr Asn Pro
        195                 200                 205

Asp Leu His Ala Leu Cys Glu Leu Pro Asp Ile Cys Cys Lys Ile Phe
    210                 215                 220

Pro Lys Glu Asn Asn Asp Phe Leu Tyr Ile Val Val Val Tyr Arg Asn
225                 230                 235                 240

Asp Ser Pro Leu Gly Glu Gln Arg Ala Asn Arg Phe Ile Glu Leu Tyr
                245                 250                 255

Asn Ile Lys Arg Asp Ile Met Gln Glu Leu Asn Tyr Glu Leu Pro Glu
            260                 265                 270

Leu Lys Ala Val Lys Ser Glu Met Ile Ile Ala Arg Glu Met Gly Glu
        275                 280                 285

Ile Phe Ser Tyr Met Pro Gly Glu Ile Asp Ser Tyr Met Lys Tyr Ile
    290                 295                 300

Asn Asn Lys Leu Ser Lys Ile Glu Gly Ser Arg Ser
305                 310                 315

<210> SEQ ID NO 41
<211> LENGTH: 969
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
ggatccatgt tcatcactcc acgcaatgta tctaacacct ttctgcagga accgctgcgt      60
cattctagcg acctgaccga atgccagtt gaagcggaga acgtgaaatc taagactgaa     120
tactacaacg cgtgggcagt atgggagcgc aatgcaccac caggtaacgg tgaacagcgt     180
gaaatggcag taagccgtct gcgtgattgc ctggatcgcc aggctcacga gctggagctg     240
aacaacctgg gtctgtctag cctgatgatt aatcctgtta ctaatactca gggcgtgtcc     300
cctataaata ctaaatatgc tgaacatgtg gtgaaaaata tttacccgaa aattaaacat     360
gattacttta atgaatcacc caatatatat gataagaagt atatatccgg tataaccaga     420

```
ggagtagctg aactaaaaca ggaagaattt gttaacgaga aagccagacg gttttcttat    480
atgaagacta tgtattctgt atgtccagaa gcgtttgaac ctatttccag aaatgaagcc    540
agtacaccgg aaggaagctg ctaacagtt atatccggaa aagccccaat ggggcagttt    600
tctgtagata gtttatacaa tcctgattta catgcattat gtgagcttcc ggacatttgt    660
tgtaagatct tccctaaaga aaataatgat tttttataca tagttgttgt gtacagaaat    720
gacagccctc taggagaaca acgggcaaat agatttatag aattatataa tataaaaga    780 gatatcatgc aggaattaaa ttatgagtta ccagagttaa aggcagtaaa atctgaaatg    840
attatcgcac gtgaaatggg agaaatcttt agctacatgc ctggggaaat agacagttat    900
atgaaataca taaataataa actttctaaa attgagggat ccagatctca tcaccatcac    960
catcactaa                                                            969
```

<210> SEQ ID NO 42
<211> LENGTH: 240
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 42

Met Thr Lys Ile Thr Leu Ser Pro Gln Asn Phe Arg Ile Gln Lys Gln
1               5                   10                  15

Glu Thr Thr Leu Leu Lys Glu Lys Ser Thr Glu Lys Asn Ser Leu Ala
            20                  25                  30

Lys Ser Ile Leu Ala Val Lys Asn His Phe Ile Glu Leu Arg Ser Lys
        35                  40                  45

Leu Ser Glu Arg Phe Ile Ser His Lys Asn Thr Glu Ser Ser Ala Thr
    50                  55                  60

His Phe His Arg Gly Ser Ala Ser Glu Gly Arg Ala Val Leu Thr Asn
65                  70                  75                  80

Lys Val Val Lys Asp Phe Met Leu Gln Thr Leu Asn Asp Ile Asp Ile
                85                  90                  95

Arg Gly Ser Ala Ser Lys Asp Pro Ala Tyr Ala Ser Gln Thr Arg Glu
            100                 105                 110

Ala Ile Leu Ser Ala Val Tyr Ser Lys Asn Lys Asp Gln Cys Cys Asn
        115                 120                 125

Leu Leu Ile Ser Lys Gly Ile Asn Ile Ala Pro Phe Leu Gln Glu Ile
    130                 135                 140

Gly Glu Ala Ala Lys Asn Ala Gly Leu Pro Gly Thr Thr Lys Asn Asp
145                 150                 155                 160

Val Phe Thr Pro Ser Gly Ala Gly Ala Asn Pro Phe Ile Thr Pro Leu
                165                 170                 175

Ile Ser Ser Ala Asn Ser Lys Tyr Pro Arg Met Phe Ile Asn Gln His
            180                 185                 190

Gln Gln Ala Ser Phe Lys Ile Tyr Ala Glu Lys Ile Ile Met Thr Glu
        195                 200                 205

Val Ala Pro Leu Phe Asn Glu Cys Ala Met Pro Thr Pro Gln Gln Phe
    210                 215                 220

Gln Leu Ile Leu Glu Asn Ile Ala Asn Lys Tyr Ile Gln Asn Thr Pro
225                 230                 235                 240

<210> SEQ ID NO 43
<211> LENGTH: 1011

<212> TYPE: DNA
<213> ORGANISM: Artificial Sequence
<220> FEATURE:
<223> OTHER INFORMATION: Description of Artificial Sequence: Synthetic
   polynucleotide

<400> SEQUENCE: 43

```
tttctaattc atcaatcaga tggacatagc atttgctata aaaataaaa gtattcctgc        60
tatctatata taaatgagtt atgtacatat aaaaggagca ttaccgtgac aaaaataact      120
ttatttcccc ataactttag aatccaaaaa caggaagcca caccactaaa agaaaaatca     180
accgagaaaa attctttagc aaaaagtatt ctcgcagtaa aaaatcactt catcaaatta     240
aattcaaaat tatcggaacg ttttatttcg cataagaaca ctgaatcttc tgcaacacac     300
tttcaccgag gaagcgcatc tgagggccgg gcagtgttga caaataaagt cgttaaaaac    360
tttatgcttc aaacgctcca tgatatagat attagaggta gcgcgagtaa agaccccgca    420
tacgccagcc agaccgtgaa agctatacta tcggcagttt acagcaagta taaagatcag    480
tattgtaact tgctcatcag caaaggaatc gacatagcgc cttttcttaa ggaaattggc    540
gaggctgcgc aaaatgcagg tctgcccgga gcaaccaaga atgacgtttt tagcccaagc    600
ggcgcaggag ccaatccttt tataactccg ttgattacat cagcatacag taagtatcca    660
catatgttta ccagtcaaca tcagaaggca tcctttaaca tctatgcgga gaagatcatt    720
atgacagaag ttgtaccgct gtttaatgag tgtgctatgc cgactccaca gcaattccaa    780
caaatactag aaaacattgc taataaatat atccaaaaca ctccctgaac acagaaacac    840
caaaaaatat gcgagcctct tcctgattaa tatgaaccaa tagtatccat aattttttccc   900
aggaactaac tctggagcta aaccgtcatt taccagtgct aaaattatac actcaaccat    960
caaaataata gccattgctg ctatataaca tatagcagca atctctacta c             1011
```

<210> SEQ ID NO 44
<211> LENGTH: 561
<212> TYPE: PRT
<213> ORGANISM: Artificial Sequence
<220> FEATURE:
<223> OTHER INFORMATION: Description of Artificial Sequence: Synthetic
   polypeptide

<400> SEQUENCE: 44

```
Met Gln Ile Gln Ser Phe Tyr His Ser Ala Ser Leu Lys Thr Gln Glu
1               5                   10                  15

Ala Phe Lys Ser Leu Gln Lys Thr Leu Tyr Asn Gly Met Gln Ile Leu
            20                  25                  30

Ser Gly Gln Gly Lys Ala Pro Ala Lys Ala Pro Asp Ala Arg Pro Glu
        35                  40                  45

Ile Ile Val Leu Arg Glu Pro Gly Ala Thr Trp Gly Asn Tyr Leu Gln
    50                  55                  60

His Gln Lys Ala Ser Asn His Ser Leu His Asn Leu Tyr Asn Leu Gln
65                  70                  75                  80

Arg Asp Leu Leu Thr Val Ala Ala Thr Val Leu Gly Lys Gln Asp Pro
                85                  90                  95

Val Leu Thr Ser Met Ala Asn Gln Met Glu Leu Ala Lys Val Lys Ala
            100                 105                 110

Asp Arg Pro Ala Thr Lys Gln Glu Glu Ala Ala Lys Ala Leu Lys
        115                 120                 125

Lys Asn Leu Ile Glu Leu Ile Ala Ala Arg Thr Gln Gln Gln Asp Gly
    130                 135                 140
```

```
Leu Pro Ala Lys Glu Ala His Arg Phe Ala Val Ala Phe Arg Asp
145                 150                 155                 160

Ala Gln Val Lys Gln Leu Asn Asn Gln Pro Trp Gln Thr Ile Lys Asn
            165                 170                 175

Thr Leu Thr His Asn Gly His His Tyr Thr Asn Thr Gln Leu Pro Ala
            180                 185                 190

Ala Glu Met Lys Ile Gly Ala Lys Asp Ile Phe Pro Ser Ala Tyr Glu
            195                 200                 205

Gly Lys Gly Val Cys Ser Trp Asp Thr Lys Asn Ile His His Ala Asn
210                 215                 220

Asn Leu Trp Met Ser Thr Val Ser Val His Glu Asp Gly Lys Asp Lys
225                 230                 235                 240

Thr Leu Phe Cys Gly Ile Arg His Gly Val Leu Ser Pro Tyr His Glu
            245                 250                 255

Lys Asp Pro Leu Leu Arg His Val Gly Ala Glu Asn Lys Ala Lys Glu
            260                 265                 270

Val Leu Thr Ala Ala Leu Phe Ser Lys Pro Glu Leu Leu Asn Lys Ala
            275                 280                 285

Leu Ala Gly Glu Ala Val Ser Leu Lys Leu Val Ser Val Gly Leu Leu
290                 295                 300

Thr Ala Ser Asn Ile Phe Gly Lys Gly Thr Met Val Glu Asp Gln
305                 310                 315                 320

Met Arg Ala Trp Gln Ser Leu Thr Gln Pro Gly Lys Met Ile His Leu
            325                 330                 335

Lys Ile Arg Asn Lys Asp Gly Asp Leu Gln Thr Val Lys Ile Lys Pro
            340                 345                 350

Asp Val Ala Ala Phe Asn Val Gly Val Asn Glu Leu Ala Leu Lys Leu
            355                 360                 365

Gly Phe Gly Leu Lys Ala Ser Asp Ser Tyr Asn Ala Glu Ala Leu His
370                 375                 380

Gln Leu Leu Gly Asn Asp Leu Arg Pro Glu Ala Arg Pro Gly Gly Trp
385                 390                 395                 400

Val Gly Glu Trp Leu Ala Gln Tyr Pro Asp Asn Tyr Glu Val Val Asn
            405                 410                 415

Thr Leu Ala Arg Gln Ile Lys Asp Ile Trp Lys Asn Asn Gln His His
            420                 425                 430

Lys Asp Gly Gly Glu Pro Tyr Lys Leu Ala Gln Arg Leu Ala Met Leu
            435                 440                 445

Ala His Glu Ile Asp Ala Val Pro Ala Trp Asn Cys Lys Ser Gly Lys
            450                 455                 460

Asp Arg Thr Gly Met Met Asp Ser Glu Ile Lys Arg Glu Ile Ile Ser
465                 470                 475                 480

Leu His Gln Thr His Met Leu Ser Ala Pro Gly Ser Leu Pro Asp Ser
            485                 490                 495

Gly Gly Gln Lys Ile Phe Gln Lys Val Leu Leu Asn Ser Gly Asn Leu
            500                 505                 510

Glu Ile Gln Lys Gln Asn Thr Gly Gly Ala Gly Asn Lys Val Met Lys
            515                 520                 525

Asn Leu Ser Pro Glu Val Leu Asn Leu Ser Tyr Gln Lys Arg Val Gly
            530                 535                 540

Asp Glu Asn Ile Trp Gln Ser Val Lys Gly Ile Ser Ser Leu Ile Thr
545                 550                 555                 560
```

Ser

<210> SEQ ID NO 45
<211> LENGTH: 1253
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45

```
tgcctgcaaa ggaggctcgc cgccttgcgg cagcagattt taagagtgcc caggtcaagc      60
agcttaataa tcaaccgtgg cagaccataa aaatacact aacgcataat gggcatcaat      120
ataccagcac gcaggttcct gccgcagaga tgaaaatcgg cgcacaggat atttttccta     180
aagcctatca gggaaagggc gtatgcagtt gggataccca aaatattcat cacgctacta     240
acctgtggat gtccacaata agtgtacatg aggacggtga agataaaacg cttttagtg      300
ggatacgtca tggcgtgctt tcaccctatc atgtggaaga tccgcttctg cgtcagaccg     360
gcgctgaaag cagagccaaa gaagtattaa ctgcagcgct ctttagtaaa cctgagttgc     420
ttaccagggc cttaaaggac gaagcggtaa gcctgaaact ggtatctgtc tgtttactca     480
ccgcgtcgaa tgttctaggc caggagggaa caatggtcaa ggagcaaatg agagcatggc     540
aatcgttgac ccagccggga aaaatgattc atttaaaaat ccgcaatgac gatggcgaac     600
tacagacggt aaaaataaag ccggaagtcg ccgcgttcaa tgtgggtgtc aatgagttag     660
cactcaagtt cggctttggc cttaaggcat ctgatagtta taatatcgag gcgctacagc     720
agttattagg caatgattta cgccctgagg ccagaccagg cggttgggtt ggcgagtggc     780
tggcgcgata tccggataac gatgaaagcg taaatacatt agcacgccag attaaagata     840
tctggcaaaa taagctgcat cacaaagatg gcggcgaacc ctataaatta gcacaacgcc     900
ttgcaatgtt agccaatgaa atcgatgtgg tacccgcctg gaattgtaaa gcggcaaag     960
atcgcacagg aatgatggac tcagaaacca agcgagaagc catttcttc catcagaccc     1020
atactttgag ttctccaggc agccttccgg atcgcagcgg acagcaaatc ttccaaaaag    1080
tattacttaa tagcggaaac ctggaaattc aaaaacaaaa tacaagcggg gcgggaaaca    1140
aagtaataaa aaacttgtcg ccagaagtgc ttaatctttc ctatcataaa cgaattggag    1200
atgaaaatac ctggcaatcg gtaaagggaa tttctacatt aatcatttct tga           1253
```

<210> SEQ ID NO 46
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Met Thr Asn Ile Thr Leu Ser Thr Gln His Tyr Arg Ile His Arg Ser
1               5                   10                  15

Asp Val Glu Pro Val Lys Glu Lys Thr Thr Glu Lys Asp Ile Phe Ala
            20                  25                  30

Lys Ser Ile Thr Ala Val Arg Asn Ser Phe Ile Ser Leu Ser Thr Ser
        35                  40                  45

Leu Ser Asp Arg Phe Ser Leu His Gln Gln Thr Asp Ile Pro Thr Thr
    50                  55                  60

His Phe His Arg Gly Asn Ala Ser Glu Gly Arg Ala Val Leu Thr Ser

```
                65                  70                  75                  80
Lys Thr Val Lys Asp Phe Met Leu Gln Lys Leu Asn Ser Leu Asp Ile
                    85                  90                  95

Lys Gly Asn Ala Ser Lys Asp Pro Ala Tyr Ala Arg Gln Thr Cys Glu
                100                 105                 110

Ala Ile Leu Ser Ala Val Tyr Ser Asn Asn Lys Asp Gln Cys Cys Lys
                115                 120                 125

Leu Leu Ile Ser Lys Gly Val Ser Ile Thr Pro Phe Leu Lys Glu Ile
            130                 135                 140

Gly Glu Ala Ala Gln Asn Ala Gly Leu Pro Gly Glu Ile Lys Asn Gly
145                 150                 155                 160

Val Phe Thr Pro Gly Gly Ala Gly Ala Asn Pro Phe Val Val Pro Leu
                165                 170                 175

Ile Ala Ser Ala Ser Ile Lys Tyr Pro His Met Phe Ile Asn His Asn
                180                 185                 190

Gln Gln Val Ser Phe Lys Ala Tyr Ala Glu Lys Ile Val Met Lys Glu
                195                 200                 205

Val Thr Pro Leu Phe Asn Lys Gly Thr Met Pro Thr Pro Gln Gln Phe
            210                 215                 220

Gln Leu Thr Ile Glu Asn Ile Ala Asn Lys Tyr Leu Gln Asn Ala Ser
225                 230                 235                 240

<210> SEQ ID NO 47
<211> LENGTH: 1316
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
taagtgacag aagaacaaaa tccatcagga aaataaaatt tataaatatc aatgagtaaa      60
aatggttgtg gagaaggtgg ctattttttg aaagcaagaa atataaacaa agtgtagcta     120
tgcatagtta tctaaaagga gaactaccgt gactaacata acactatcca cccagcacta     180
cagaatccat agaagtgacg ttgaaccagt aaaagaaaaa acaacggaga aggacatttt     240
tgcaaaaagt attactgccg ttagaaatag ctttatcagc ctgtcgacga gtctgtcaga     300
tcgttttagc ctgcatcaac aaacagacat accgactacc catttttcatc gtgggaacgc     360 ttctgagggt agggcggtat taaccagtaa aactgttaaa gattttatgc tgcaaaagct     420
caatagtctg gatatcaaag gtaatgcgag taaagatccg gcctatgctc gtcagacatg     480
cgaagccata ttatcagccg tgtacagtaa taataaagat caatgttgta aattactcat     540
cagtaaaggg gtcagtatta cccccttttt gaaagagata ggagaggctg cgcagaatgc     600
ggggctacct ggggagataa aaatggcgt atttactcca ggtgggcag gggcgaatcc     660 ttttgtcgtc ccctcattg cttccgcgag tattaaaatat ccgcatatgt ttataaatca     720
taatcagcag gtatctttta aagcgtatgc tgagaaaatc gttatgaaag aggttacgcc     780
gctgtttaat aaggggacga tgccaacgcc acaacaattt cagttaacta gaaaaatat     840 tgcgaataag tatcttcaga atgcctcctg atggtagtaa atacaatact gctattaacc     900
atatgaatta atagcagatt ttctgaaact atatattcgt ttttatggcg acgcttttaa     960
caaaacgtcg tcatctttat tttaatataa aaatcaaatg gataacctta aaacttaaaa    1020
taattgttat tactctaaat acctgcacaa ccagacagct ttttttgtaa cgctgcgtgt    1080
```

```
tgttaagtct atgatacccg cgcacggatg atgtctcgat aaggattaat ggtctgttaa    1140
ctgtcaggag aggttatgcc gcctttaaaa aaaattgtgc tgcgcctgtt tgtgggggcg    1200
atggtcgcca cggtaacgac acctgcattg gcgctggttt gccttgagga tcactccgct    1260
aaagagtgtg ctatatcgtg tgctgaggtg atgtggttta tgtctcgaga tcggat       1316
```

<210> SEQ ID NO 48
<211> LENGTH: 900
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 48

```
Met Pro Met Trp Ala Gly Gly Val Gly Ser Pro Arg Arg Gly Met Ala
1               5                   10                  15

Pro Ala Ser Thr Asp Asp Leu Phe Ala Arg Lys Leu Arg Gln Pro Ala
            20                  25                  30

Arg Pro Pro Leu Thr Pro His Thr Phe Glu Pro Arg Pro Val Arg Gly
        35                  40                  45

Pro Leu Leu Arg Ser Gly Ser Asp Ala Gly Glu Ala Arg Pro Pro Thr
    50                  55                  60

Pro Ala Ser Pro Arg Ala Arg Ala His Ser His Glu Glu Ala Ser Arg
65                  70                  75                  80

Pro Ala Ala Thr Ser Thr Arg Leu Phe Thr Asp Pro Leu Ala Leu Leu
                85                  90                  95

Gly Leu Pro Ala Glu Glu Pro Glu Pro Ala Phe Pro Pro Val Leu Glu
            100                 105                 110

Pro Arg Trp Phe Ala His Tyr Asp Val Gln Ser Leu Leu Phe Asp Trp
        115                 120                 125

Ala Pro Arg Ser Gln Gly Met Gly Ser His Ser Glu Ala Ser Ser Gly
    130                 135                 140

Thr Leu Ala Ser Ala Glu Asp Gln Ala Ala Ser Ser Asp Leu Leu His
145                 150                 155                 160

Gly Ala Pro Gly Phe Val Cys Glu Leu Gly Gly Glu Gly Glu Leu Gly
                165                 170                 175

Leu Gly Gly Pro Ala Ser Pro Pro Val Pro Pro Ala Leu Pro Asn Ala
            180                 185                 190

Ala Val Ser Ile Leu Glu Glu Pro Gln Asn Arg Thr Ser Ala Tyr Ser
        195                 200                 205

Leu Glu His Ala Asp Leu Gly Ala Gly Tyr Tyr Arg Lys Tyr Phe Tyr
    210                 215                 220

Gly Lys Glu His Gln Asn Phe Phe Gly Met Asp Glu Ser Leu Gly Pro
225                 230                 235                 240

Val Ala Val Ser Leu Arg Arg Glu Glu Lys Glu Gly Ser Gly Gly Gly
                245                 250                 255

Thr Leu His Ser Tyr Arg Val Ile Val Arg Thr Thr Gln Leu Arg Thr
            260                 265                 270

Leu Arg Gly Thr Ile Ser Glu Asp Ala Leu Pro Pro Gly Pro Pro Arg
        275                 280                 285

Gly Leu Ser Pro Arg Lys Leu Leu Glu His Val Ala Pro Gln Leu Ser
    290                 295                 300

Pro Ser Cys Leu Arg Leu Gly Ser Ala Ser Pro Lys Val Pro Arg Thr
305                 310                 315                 320
```

```
Leu Leu Thr Leu Asp Glu Gln Val Leu Ser Phe Gln Arg Lys Val Gly
              325                 330                 335
Ile Leu Tyr Cys Arg Ala Gly Gln Gly Ser Glu Glu Met Tyr Asn
          340                 345                 350
Asn Gln Glu Ala Gly Pro Ala Phe Met Gln Phe Leu Thr Leu Leu Gly
              355                 360                 365
Asp Val Val Arg Leu Lys Gly Phe Glu Ser Tyr Arg Ala Gln Leu Asp
          370                 375                 380
Thr Lys Thr Asp Ser Thr Gly Thr His Ser Leu Tyr Thr Thr Tyr Gln
385                 390                 395                 400
Asp His Glu Ile Met Phe His Val Ser Thr Met Leu Pro Tyr Thr Pro
              405                 410                 415
Asn Asn Gln Gln Gln Leu Leu Arg Lys Arg His Ile Gly Asn Asp Ile
              420                 425                 430
Val Thr Ile Val Phe Gln Glu Pro Gly Ser Lys Pro Phe Cys Pro Thr
          435                 440                 445
Thr Ile Arg Ser His Phe Gln His Val Phe Leu Val Val Arg Ala His
          450                 455                 460
Thr Pro Cys Thr Pro His Thr Thr Tyr Arg Val Ala Val Ser Arg Thr
465                 470                 475                 480
Gln Asp Thr Pro Ala Phe Gly Pro Ala Leu Pro Ala Gly Gly Pro
              485                 490                 495
Phe Ala Ala Asn Ala Asp Phe Arg Ala Phe Leu Leu Ala Lys Ala Leu
              500                 505                 510
Asn Gly Glu Gln Ala Ala Gly His Ala Arg Gln Phe His Ala Met Ala
          515                 520                 525
Thr Arg Thr Arg Gln Gln Tyr Leu Gln Asp Leu Ala Thr Asn Glu Val
          530                 535                 540
Thr Thr Thr Ser Leu Asp Ser Ala Ser Arg Phe Gly Leu Pro Ser Leu
545                 550                 555                 560
Gly Gly Arg Arg Arg Ala Ala Pro Arg Gly Pro Gly Ala Glu Leu Gln
              565                 570                 575
Ala Ala Gly Ser Leu Val Trp Gly Val Arg Ala Ala Pro Gly Ala Arg
          580                 585                 590
Val Ala Ala Gly Ala Gln Ala Ser Gly Pro Glu Gly Ile Glu Val Pro
          595                 600                 605
Cys Leu Leu Gly Ile Ser Ala Glu Ala Leu Val Leu Val Ala Pro Arg
          610                 615                 620
Asp Gly Arg Val Val Phe Asn Cys Ala Cys Arg Asp Val Leu Ala Trp
625                 630                 635                 640
Thr Phe Ser Glu Gln Gln Leu Asp Leu Tyr His Gly Arg Gly Glu Ala
              645                 650                 655
Ile Thr Leu Arg Phe Asp Gly Ser Pro Gly Gln Ala Val Gly Glu Val
          660                 665                 670
Val Ala Arg Leu Gln Leu Val Ser Arg Gly Cys Glu Thr Arg Glu Leu
          675                 680                 685
Ala Leu Pro Arg Asp Gly Gln Gly Arg Leu Gly Phe Glu Val Asp Ala
          690                 695                 700
Glu Gly Phe Val Thr His Val Glu Arg Phe Thr Phe Ala Glu Thr Ala
705                 710                 715                 720
Gly Leu Arg Pro Gly Ala Arg Leu Leu Arg Val Cys Gly Gln Thr Leu
              725                 730                 735
Pro Ser Leu Arg Pro Glu Ala Ala Ala Gln Leu Leu Arg Ser Ala Pro
```

Lys Val Cys Val Thr Val Leu Pro Pro Asp Glu Ser Gly Arg Pro Arg
        740                 745                 750
                755                 760                 765

Arg Ser Phe Ser Glu Leu Tyr Thr Leu Ser Leu Gln Glu Pro Ser Arg
                770                 775                 780

Arg Gly Ala Pro Asp Pro Val Gln Asp Glu Val Gln Gly Val Thr Leu
785                 790                 795                 800

Leu Pro Thr Thr Lys Gln Leu Leu His Leu Cys Leu Gln Asp Gly Gly
                805                 810                 815

Ser Pro Pro Gly Pro Gly Asp Leu Ala Glu Glu Arg Thr Glu Phe Leu
                820                 825                 830

His Ser Gln Asn Ser Leu Ser Pro Arg Ser Ser Leu Ser Asp Glu Ala
                835                 840                 845

Pro Val Leu Pro Asn Thr Thr Pro Asp Leu Leu Leu Ala Thr Thr Ala
                850                 855                 860

Lys Pro Ser Val Pro Ser Ala Asp Ser Glu Thr Pro Leu Thr Gln Asp
865                 870                 875                 880

Arg Pro Gly Ser Pro Ser Gly Ser Glu Asp Lys Gly Asn Pro Ala Pro
                885                 890                 895

Glu Leu Arg Ala
        900

<210> SEQ ID NO 49
<211> LENGTH: 720
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
atggttacaa gtgtaaggac tcagccccccc gtcataatgc caggtatgca gaccgagatc    60
aaaacgcagg ccacgaatct tgcggcgaat ctttccgcag tcagagaaag tgccacaacg   120
acgctgtcag gggaaattaa aggcccgcaa ctggaagatt ttcccgcgct gatcaaacag   180
gcgagtctgg atgcattgtt taaatgcggg aaagacgctg aggcgttaaa agaagttttt   240
accaattcaa ataatgtcgc cggtaagaaa gcgataatgg agtttgccgg gctctttcgt   300
tcagcgctca acgccaccag tgattctcct gaggcgaaga cgctactgat gaaggtgggg   360
gcagagtata ccgcgcaaat cataaaagat ggcctgaaag aaaagtcagc ttttgggcca   420
tggctgccag aaacaaagaa agcggaagcg aagctgaaaa acctggaaaa gcagctgtta   480
gatattatca aaataacac tggtggtgaa ttaagtaaat tatcgacgaa tcttgttatg   540
caggaggtga tgccctatat tgccagctgc attgaacata actttggctg tacgttagat   600 ccgttaacccc gcagcaatct tacgcacctt gttgacaaag cggcggcgaa ggcggttgag   660
gcgcttgata tgtgccacca aaaattaacg caagagcagg gtaccagcgt aggacgggaa   720

<210> SEQ ID NO 50
<211> LENGTH: 907
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Met Trp Asn Val Ser Lys Ser Ser Asn Asn Leu Gly Ala Tyr Lys Leu

-continued

```
1               5                   10                  15
Pro Leu Glu Ala Gln Thr Pro Glu Lys Ile Ser Pro Phe Asp Ala
                20                  25                  30
Met Ser Ala Ala Gln Pro Glu Gly Lys Ala Pro His Asp Gln Leu Gln
                35                  40                  45
Asn Asp Gln Tyr Pro Ile Gln Gln Ala Glu Asp Arg Gly His Leu
    50                  55                  60
Val Glu Gln Ala Glu Ile Gln Ala His Val Gln His Cys His Ser Lys
65                  70                  75                  80
Ala Pro Glu Ile Gly Asp Ala Thr Lys Thr Gln Ser Val Ser Glu Lys
                85                  90                  95
Leu Gly Thr Ala Lys Asn Ser Ser Cys Asp Ala Ser Gln Ile Leu Ile
                100                 105                 110
Gly Ser Lys Asn Asp Asp Phe His Lys Asn Lys Ala Gly Ser Asn Gly
                115                 120                 125
Asp Ile Asn Lys Ser Ser Asp Pro Ser Ala Leu Arg Cys Ser Leu Ser
    130                 135                 140
Pro Ala Pro Arg Arg Val Pro Lys Ser Lys Ser Tyr Gly Ala Ala
145                 150                 155                 160
Thr Ile Gly Gly Lys Val Tyr His Pro His Glu Lys Thr Asp Ser Thr
                165                 170                 175
Ile Ala Asp Phe Leu Ser Arg Ser Leu Ser Asn Asn Ala Tyr Arg Ser
                180                 185                 190
Glu Arg His Leu Arg Lys Arg Ala Leu Ala Tyr Leu Asn His Ile Ser
                195                 200                 205
Ala Glu Lys Glu Ile Thr Ser Asn Ala Cys Phe Ala Met Lys Asp Val
    210                 215                 220
Asn Ser Phe Ala His Lys Gln Ser Glu Trp Leu Cys His Leu Glu Arg
225                 230                 235                 240
Ser Leu Trp Arg Asp Glu Pro Ala Leu Gln Phe His Asp Arg Gln Gln
                245                 250                 255
Leu Gly Asn Glu Val Leu Gly Leu Lys Lys Pro Asp Asp Gln Ser Pro
                260                 265                 270
Tyr Phe Lys Pro Arg Ala Trp Lys Ile Ser Asp Glu Ala Ala Ser Ala
                275                 280                 285
Phe Ala Met Met Leu Lys Gly Glu Ser Gly Pro Phe Thr Gln Asp Gln
    290                 295                 300
Val Lys Val Gly Phe Glu Ile Cys Gln Glu Gly Glu Leu Leu Ala Gly
305                 310                 315                 320
Arg Leu Lys Ile Gln Pro Arg Met Ala Phe Arg Leu Lys Asn Arg His
                325                 330                 335
Asp Ala Asn Arg Ser Gly Thr His Ser Val Lys Ser Leu Ser Gly Leu
                340                 345                 350
Asp Leu Ser Ala Asp Val Gly Thr Asp Ile Arg Glu Phe Phe Gln Val
    355                 360                 365
Pro Val Met Ser Gly Thr Ser Gly Thr Ser Ser Asp Val Val Ile Ala
    370                 375                 380
Ala Arg Tyr Ala Ala Met His Ala Gly Leu Lys Trp Ser Ala Pro Glu
385                 390                 395                 400
Leu Thr Ile Asp Gln Ala Lys His Ala Leu Ile Asp Leu Ser Met Asp
                405                 410                 415
Phe Phe Arg Arg Asn Gly Pro Ala Val Val Met Ala Leu Arg Met Asn
                420                 425                 430
```

-continued

```
Ser Leu Arg Lys Asn Gln Gly Leu Pro Tyr Lys Glu Val Asp Arg Cys
        435                 440                 445

Glu Val Phe Thr His Ser Tyr Ala Glu Ile His Gly Ala Ile Ser Leu
    450                 455                 460

Thr Ile Asp Gly Val Asp Pro Ala Asp Lys Val Glu Val Lys Asn Arg
465                 470                 475                 480

Leu Tyr Gly Tyr Thr Leu Asp Ala Lys Ala Thr Leu Met Lys Ile Ala
                    485                 490                 495

Asp Arg Ser Ile Arg Arg Gly Val Arg Ser Lys Val Asp Ile Arg Ser
                500                 505                 510

Thr Ser Thr Ser Leu Gln Thr Pro Gln Leu Arg Arg Val Leu Glu Lys
            515                 520                 525

Lys Lys Ile Val Gln Lys Val Ala Glu Leu Tyr Ser Glu Met Gly Lys
        530                 535                 540

Ala Gly Asn Ser Ala Thr Leu Lys Glu Ala Ile Thr Lys Ser Ser Val
545                 550                 555                 560

Lys Glu Leu Leu Val Asn Asp Lys Pro Val Ser Arg Asp Tyr Ala
                    565                 570                 575

Leu Gly Glu Pro Leu Met Val Arg Ser Leu Arg Phe Ser His Asp His
                580                 585                 590

Glu Ala Thr Ser Ser Phe Gly Ser Ala Gly Lys Thr Pro Ala Lys Arg
            595                 600                 605

Glu Val Asp Thr Leu Cys Asp Asn Ser Thr Ala Phe Asp Ile Val Met
        610                 615                 620

Thr Pro Phe Ser Val Ile Asn Ala Lys Ala Lys Gly Asp Thr Ile Ser
625                 630                 635                 640

Glu Met Lys Val Pro His Arg Pro Lys Trp Lys Gly Leu Pro Ser Val
                    645                 650                 655

Leu Tyr Lys Val Thr Ala Ser Val Asp Leu Pro Glu Tyr Ala Val Ala
                660                 665                 670

Arg Pro Gly Phe Gly Asp Ile His Ser Phe Asn Ser Asn Lys Ala Phe
            675                 680                 685

Ser Ser Glu Phe Ser Ser Val Arg Asn Ser Leu Ser His Ala Glu Lys
        690                 695                 700

Met Gly Phe Ile Glu Asn Ser Leu Lys Pro Tyr Ile Lys His Asp Pro
705                 710                 715                 720

Asp Arg Glu Ser Phe Asp Phe Lys His Ser Ile Asp Glu Leu Ala Asp
                    725                 730                 735

Ala Gln Cys Met Leu Gln Ser Arg Lys Pro Asn Ser Thr Leu Arg His
                740                 745                 750

Asn Glu Tyr Cys Ala Lys Leu Glu Leu Trp Asp Ala Lys Ala Ile Glu
            755                 760                 765

Val Gly Met Ser Arg Pro Val Ala Val Ala Thr Leu Ile Glu Phe Asn
        770                 775                 780

Leu Glu Met Leu Ser Ala Ala Arg Tyr Ile Glu Asp Glu Gly Tyr Asp
785                 790                 795                 800

Gly Lys Leu Ile Thr Asn Phe Leu Glu Arg Gln Leu Ser Trp Phe Gly
                    805                 810                 815

Gln Asn Ala Ala Leu Asn Lys Glu Val Thr Leu Lys Lys Leu Trp Gly
                820                 825                 830

Leu Pro Phe Asp Glu Arg Lys Ala Val Ala Glu Lys Val Cys Glu Ala
            835                 840                 845
```

```
Leu Arg Gln Gly Val Ser Leu Cys Val Tyr Glu Lys Asn Val Glu Gly
        850                 855                 860

Ser Arg Ile Arg Glu Leu Ser Leu Leu Asn Phe Asn Ala Tyr Asp Ile
865                 870                 875                 880

Met Arg Gly Ile Glu Leu Phe Leu Ser Ser Lys Leu Leu Gln Pro Pro
                885                 890                 895

Thr Gly Ala Gly Pro Thr Val Lys Ser Arg Leu
                900                 905
```

<210> SEQ ID NO 51
<211> LENGTH: 1080
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51

```
accgctatcg ctgttccggg gactgaaact agacgcgcat ttacagcgca ctgcttttgc      60
acataaccct gctgtacctg acgataattg cgcgttaccg attgcggtag gaatgaatta     120
aaatattttt tatcatttat gaccatgtgt tgagcttta ttataaaaaa gattttttga     180
gtagtaattc ttatatataa tcatccggag gtggttggta gcctggctca atcattgagg     240
catattttg caggcaatat attgaatctg aaaagttaaa gatgatattt tcggtgcagg     300
agctatcatg tggagggaaa agtatgctaa gtcctacgac tcgtaatatg ggggcgagtt     360
tatcgcctca gcctgacgtc agcggggagc taaacaccga agcattgacc tgtattgttg     420
agcgtctgga aagtgaaatt atagatggca gctggattca tatcagttac gaggaaaccg     480
atctcgaaat gatgcctttt cttgttgcac aggccaataa gaagtatcca gagttaaatc     540
ttaaatttgt tatgtcagtc catgagcttg tttcctctat aaaggagacc agaatggaag     600
gcgttgaatc tgcccgattt ctcgtaaata tgggaagttc aggtatccat atttcagtcg     660
tcgattttag agttatggac ggaaagacat cggtgatttt gttcgaacca gcagcgtgta     720
gcgcttttgg acctgcactg gcgttgagga ccaaagcagc tcttgaacgt gaacaactgc     780
ctgattgtta ttttgctatg gtcgagctgg acattcaacg aagctcttct gaatgcggta     840
tttttagcct ggcgctcgcc aaaaaacttc agcttgaatt tatgaactta gtaaaaattc     900
atgaagataa tatttgtgaa cgtctgtgtg gtgaagaacc ttttctcccg tccgataaag     960
cagaccgcta tctgccggtg agtttttaca aacatactca aggcgcacaa cgattaaatg    1020
aatatgtgga ggccaatccg gcggcgggaa gcagtatagt aaacaaaaag aatgaaacgc    1080
```

<210> SEQ ID NO 52
<211> LENGTH: 700
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

```
Met Phe Asn Ile Arg Asn Thr Gln Pro Ser Val Ser Met Gln Ala Ile
1               5                   10                  15

Ala Gly Ala Ala Ala Pro Glu Ala Ser Pro Glu Glu Ile Val Trp Glu
                20                  25                  30

Lys Ile Gln Val Phe Phe Pro Gln Glu Asn Tyr Glu Glu Ala Gln Gln
            35                  40                  45
```

```
Cys Leu Ala Glu Leu Cys His Pro Ala Arg Gly Met Leu Pro Asp His
 50                  55                  60

Ile Ser Ser Gln Phe Ala Arg Leu Lys Ala Leu Thr Phe Pro Ala Trp
 65                  70                  75                  80

Glu Glu Asn Ile Gln Cys Asn Arg Asp Gly Ile Asn Gln Phe Cys Ile
                 85                  90                  95

Leu Asp Ala Gly Ser Lys Glu Ile Leu Ser Ile Thr Leu Asp Asp Ala
            100                 105                 110

Gly Asn Tyr Thr Val Asn Cys Gln Gly Tyr Ser Glu Ala His Asp Phe
            115                 120                 125

Ile Met Asp Thr Glu Pro Gly Glu Glu Cys Thr Glu Phe Ala Glu Gly
130                 135                 140

Ala Ser Gly Thr Ser Leu Arg Pro Ala Thr Thr Val Ser Gln Lys Ala
145                 150                 155                 160

Ala Glu Tyr Asp Ala Val Trp Ser Lys Trp Glu Arg Asp Ala Pro Ala
                165                 170                 175

Gly Glu Ser Pro Gly Arg Ala Ala Val Val Gln Glu Met Arg Asp Cys
            180                 185                 190

Leu Asn Asn Gly Asn Pro Val Leu Asn Val Gly Ala Ser Gly Leu Thr
            195                 200                 205

Thr Leu Pro Asp Arg Leu Pro Pro His Ile Thr Thr Leu Val Ile Pro
210                 215                 220

Asp Asn Asn Leu Thr Ser Leu Pro Glu Leu Pro Glu Gly Leu Arg Glu
225                 230                 235                 240

Leu Glu Val Ser Gly Asn Leu Gln Leu Thr Ser Leu Pro Ser Leu Pro
                245                 250                 255

Gln Gly Leu Gln Lys Leu Trp Ala Tyr Asn Asn Trp Leu Ala Ser Leu
            260                 265                 270

Pro Thr Leu Pro Pro Gly Leu Gly Asp Leu Ala Val Ser Asn Asn Gln
            275                 280                 285

Leu Thr Ser Leu Pro Glu Met Pro Pro Ala Leu Arg Glu Leu Arg Val
290                 295                 300

Ser Gly Asn Asn Leu Thr Ser Leu Pro Ala Leu Pro Ser Gly Leu Gln
305                 310                 315                 320

Lys Leu Trp Ala Tyr Asn Asn Arg Leu Thr Ser Leu Pro Glu Met Ser
                325                 330                 335

Pro Gly Leu Gln Glu Leu Asp Val Ser His Asn Gln Leu Thr Arg Leu
            340                 345                 350

Pro Gln Ser Leu Thr Gly Leu Ser Ser Ala Ala Arg Val Tyr Leu Asp
            355                 360                 365

Gly Asn Pro Leu Ser Val Arg Thr Leu Gln Ala Leu Arg Asp Ile Ile
            370                 375                 380

Gly His Ser Gly Ile Arg Ile His Phe Asp Met Ala Gly Pro Ser Val
385                 390                 395                 400

Pro Arg Glu Ala Arg Ala Leu His Leu Ala Val Ala Asp Trp Leu Thr
                405                 410                 415

Ser Ala Arg Glu Gly Glu Ala Ala Gln Ala Asp Arg Trp Gln Ala Phe
            420                 425                 430

Gly Leu Glu Asp Asn Ala Ala Phe Ser Leu Val Leu Asp Arg Leu
            435                 440                 445

Arg Glu Thr Glu Asn Phe Lys Lys Asp Ala Gly Phe Lys Ala Gln Ile
450                 455                 460

Ser Ser Trp Leu Thr Gln Leu Ala Glu Asp Ala Ala Leu Arg Ala Lys
```

```
            465                 470                 475                 480
Thr Phe Ala Met Ala Thr Glu Ala Thr Ser Thr Cys Glu Asp Arg Val
                485                 490                 495
Thr His Ala Leu His Gln Met Asn Asn Val Gln Leu Val His Asn Ala
            500                 505                 510
Glu Lys Gly Glu Tyr Asp Asn Asn Leu Gln Gly Leu Val Ser Thr Gly
        515                 520                 525
Arg Glu Met Phe Arg Leu Ala Thr Leu Glu Gln Ile Ala Arg Glu Lys
    530                 535                 540
Ala Gly Thr Leu Ala Leu Val Asp Asp Val Glu Val Tyr Leu Ala Phe
545                 550                 555                 560
Gln Asn Lys Leu Lys Glu Ser Leu Glu Leu Thr Ser Val Thr Ser Glu
                565                 570                 575
Met Arg Phe Phe Asp Val Ser Gly Val Thr Val Ser Asp Leu Gln Ala
            580                 585                 590
Ala Glu Leu Gln Val Lys Thr Ala Glu Asn Ser Gly Phe Ser Lys Trp
        595                 600                 605
Ile Leu Gln Trp Gly Pro Leu His Ser Val Leu Glu Arg Lys Val Pro
    610                 615                 620
Glu Arg Phe Asn Ala Leu Arg Glu Lys Gln Ile Ser Asp Tyr Glu Asp
625                 630                 635                 640
Thr Tyr Arg Lys Leu Tyr Asp Glu Val Leu Lys Ser Ser Gly Leu Val
                645                 650                 655
Asp Asp Thr Asp Ala Glu Arg Thr Ile Gly Val Ser Ala Met Asp Ser
            660                 665                 670
Ala Lys Lys Glu Phe Leu Asp Gly Leu Arg Ala Leu Val Asp Glu Val
        675                 680                 685
Leu Gly Ser Tyr Leu Thr Ala Arg Trp Arg Leu Asn
    690                 695                 700
```

<210> SEQ ID NO 53
<211> LENGTH: 2091
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 53

```
gccggaacgc tttaacgcgc ttcgtgaaaa gcaaatatcg gattatgaag acacgtaccg    60
gaagctgtat gacgaagtgc tgaaatcgtc cgggctggtc gacgataccg atgcagaacg   120
tactatcgga gtaagtgcga tggatagtgc gaaaaaagaa tttctggatg gcctgcgcgc   180
tcttgtggat gaggtgctgg gtagctatct gacagcccgg tggcgtctta actgagcacg   240
atattcaccg caccaggcga atgtggtgcg gtgaacaaag atattcctgg acaaacaaca   300
tcagacagca ctgatgatgc acaggtgaaa caggggagac ttcttcagtc agggcgtagc   360
gcaactcaac cttttcgacg ataacgcgcc gcgcgccgat agtgcgaagt tgatggaagt   420
actggaccat cttaatgcaa agacgggaa ggggacgctg tacttcgccg ggtaggggat   480
gtcgcaacag tgggctatga agcgagaaat gctttcacct cggtatacga ccagattttc   540
cgatctgcca atagtcaggt aacgggtttg atcagctctt ccccttgatt tttcacattg   600
ccaacggcgc gcttcacggc gtgccaggta aatttatctg tcggcacggc accatcagta   660
attatctcct ctacctcctt cccgcttatg ccctggcgca tccattttcg cgcggtgcca   720
```

```
ggtgacagaa cgagaggacg acggtcgtga atgtctacca gacctttatc agctgcggag    780
gtaacaatca ggaatccctc tgcgtcatcg ccgcgctcaa acgtgtact gccaatggca    840
gccatgaata tcggcttccc gtcctttctg tgaatgaaat acggctgttt cttgtcgcct    900
tccttcttcc actcaaacca accatcagca aacacgatag ctcggccatg ttgccatagc    960
ggtttaaaca ttctgctggt ggccgcagtc tcaacccgtg cattaatcag cggtggttta   1020
tcccaccatc cgggcgcaaa tccccagaat accggatcca gatgcagttg ctcgtcgcgt   1080
tcactgagca gcagaacttt ggtaccgggc gccacgttgt accggcctat aggttcaggg   1140
tcataagcga tatcgcgctc ggcttcatcg gccagatatg ccaggtattc ttcgcgggtc   1200
tgtgcttgtg caaagcgtcc acacatatga acctccagt cggtcagact gaaagtatag    1260
aagaggatat gcgagtggct gttccggtgt tcttcgagc gacctcaacc aatgtagaag    1320
cttcactatt gggggttgcc actagtagca tcatgttgaa tgtactggcg tgaaaaaatt   1380
ggaatcttga agaaaactct tccccaaaac tataatcaac gttttgataa tcaatgagtt   1440
gtaaaagaca gttactggat ttttttgata gtaggaagaa tgataatttc aactttatca   1500
aatggttgat atgttttttgg caatgtaatg ctgcgccaca tgcagtggtt cgaagccgca   1560
gacctgattg ttaaaggtat ggaaggcgcg attgccgcga agaccgtgac ctatgacttt   1620
gaacgcctga tggaaggcgc taagctgctg aaatgtagtg agtttggtga cgcgattatc   1680
gcgaatatgt aataacgata attgttaaaa acaaaaacgg ggacttaacg tccccgtttt   1740
tattattagt attcgaacgg ttatcaaaac tttatcaaaa ctccctcaat tcagaccgca   1800
atagtagttc atcctttacc ccgatcgtca tgataacctg agaccccct gaaagctgat    1860
agttaccgat tttgattgta gtggttttct taataatgtg tgatttggct attttttgaa   1920
agtgccttac cagattttatt gttattatca ggagaatttt ttaataaaaa gtgatggttt   1980
attgactaca atagtgggta ggttaagtat tttataaaat tattagcatg ctttatttgc   2040
tcttctacaa ggctgctaag aagtgttgaa atatcagcct gataaagaat a             2091
```

<210> SEQ ID NO 54
<211> LENGTH: 340
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Met Asn Ile Cys Val Asn Ser Leu Tyr Arg Leu Ser Ile Pro Gln Phe
1               5                   10                  15

His Ser Leu Tyr Thr Glu Glu Val Ser Asp Glu Ala Leu Thr Leu Leu
            20                  25                  30

Phe Ser Ala Val Glu Asn Gly Asp Gln Asn Cys Ile Asp Leu Leu Cys
        35                  40                  45

Asn Leu Ala Leu Arg Asn Asp Asp Leu Gly His Arg Val Glu Lys Phe
    50                  55                  60

Leu Phe Asp Leu Phe Ser Gly Lys Arg Thr Gly Ser Ser Asp Ile Asp
65                  70                  75                  80

Lys Lys Ile Asn Gln Ala Cys Leu Val Leu His Gln Ile Ala Asn Asn
                85                  90                  95

Asp Ile Thr Lys Asp Asn Thr Glu Trp Lys Lys Leu His Ala Pro Ser
            100                 105                 110

Arg Leu Leu Tyr Met Ala Gly Ser Ala Thr Thr Asp Leu Ser Lys Lys

|   |   |   |   |   | 115 |   |   |   |   | 120 |   |   |   |   | 125 |   |   |
|---|---|---|---|---|---|---|---|---|---|---|---|---|---|---|---|---|---|

Ile Gly Ile Ala His Lys Ile Met Gly Asp Gln Phe Ala Gln Thr Asp
    130                 135                 140

Gln Glu Gln Val Gly Val Glu Asn Leu Trp Cys Gly Ala Arg Met Leu
145                 150                 155                 160

Ser Ser Asp Glu Leu Ala Ala Thr Gln Gly Leu Val Gln Glu Ser
            165                 170                 175

Pro Leu Leu Ser Val Asn Tyr Pro Ile Gly Leu Ile His Pro Thr Thr
            180                 185                 190

Lys Glu Asn Ile Leu Ser Thr Gln Leu Leu Glu Lys Ile Ala Gln Ser
            195                 200                 205

Gly Leu Ser His Asn Glu Val Phe Leu Val Asn Thr Gly Asp His Trp
    210                 215                 220

Leu Leu Cys Leu Phe Tyr Lys Leu Ala Glu Lys Ile Lys Cys Leu Ile
225                 230                 235                 240

Phe Asn Thr Tyr Tyr Asp Leu Asn Glu Asn Thr Lys Gln Glu Ile Ile
                245                 250                 255

Glu Ala Ala Lys Ile Ala Gly Ile Ser Glu Ser Asp Glu Val Asn Phe
            260                 265                 270

Ile Glu Met Asn Leu Gln Asn Asn Val Pro Asn Gly Cys Gly Leu Phe
            275                 280                 285

Cys Tyr His Thr Ile Gln Leu Leu Ser Asn Ala Gly Gln Asn Asp Pro
    290                 295                 300

Ala Thr Thr Leu Arg Glu Phe Ala Glu Asn Phe Leu Thr Leu Ser Val
305                 310                 315                 320

Glu Glu Gln Ala Leu Phe Asn Thr Gln Thr Arg Arg Gln Ile Tyr Glu
                325                 330                 335

Tyr Ser Leu Gln
        340

<210> SEQ ID NO 55
<211> LENGTH: 954
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55

```
gtgagcgatg agacgcttgc gttgttgttt agcgccgtag agaacggtga tcagaattgt      60
attgatctgt tatgcaatct tgcgttacac aatgataacc tgggacatag agttgagaaa     120 tttcttttg aactctttag cggaaaaaga tcgggctcac cagatataga taaaaaaatc      180
aatcaggctt gccttgtatt acatcaaatt gccaataacg atataacaaa aataatact      240 gagtggaaaa agctacatac cccttccaga ttactttata tggccggttc cgcgacaacc     300
gacctttcta aaaaatag aaatagcacat aaaattatgg caaccagtt cgctcagaca      360 gataaagaac aggttggagt tgaaaatctt tggtgtggtg tgcgaatgat gtcgtcagat     420
gagctggcag ctgcaacgca aggtctggtt caagaatcac cttttctctc ggtaaactat     480
cccattggac ttattcatcc taccaccaaa gaaatatat aagcactca gctacttgaa      540 aagattgctc aatcaggatt atgtgaaaat gaatctttc tgataaatac aggagatcac     600
tggcttctct gtttattta aaacttgca gaaaaaataa aatgtctcat atttaacagt      660
tatcatgatt taaatgaaaa tactaagcaa gagattatag aagcagcaaa gattgcaggt     720
```

```
atatcagaaa gcgatgaggt taattttatc gaaattaatt tacagaataa tgtacccaac     780
ggctgtggtc tattttgtta ccatgcaatt caactcttat cgaatgccgg gcaaaacgat     840
cctgttacca cactacgaga atttgcggaa aatttcttaa cgcttccagt agaggaacaa     900
acactattta acacccaaac ccggcgacaa atatatgaat acagtctcca gtaa           954
```

<210> SEQ ID NO 56
<211> LENGTH: 189
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

```
Met Pro Gly Thr Ile Ser Ser Ser Gly Phe Gly Phe Ser Ile Ala Lys
1               5                   10                  15

Gln Pro His Ser Ser Gly Gln Lys Thr Val Ile Asp Gly Phe Phe Leu
            20                  25                  30

Gly Thr Arg Lys Ile Ser Phe Ser Tyr Leu Arg Leu Glu Ser Glu Leu
        35                  40                  45

Met Gln Cys Ile Asn Leu Lys Asn Glu Gly Lys Met Asn Glu Trp Met
    50                  55                  60

Arg Glu Glu Cys Ile Cys Phe Val Ser Arg Asp Val Asn Lys Gln Leu
65                  70                  75                  80

Asp Ile Phe Ala Lys Asn Asn Gln Thr Thr Ile Pro Gly Cys Val Arg
                85                  90                  95

Glu Arg Val Phe Gln Arg Ala Ser Phe His Cys Gly Phe Ser Leu Asp
            100                 105                 110

Val Arg Cys Ala Gln Thr Ser Thr His His Met Ile Leu Asn Ser Leu
        115                 120                 125

Tyr Phe Gln Lys Lys Met Asp Thr Leu Phe Gly Ser Ala Asp Val Glu
    130                 135                 140

Val Arg Asn Gln Cys Val Arg Thr Ala Leu Ser Ser Leu Ala Asp Ile
145                 150                 155                 160

Phe Phe Glu Arg Asn Val Asn Ser Ile Asp Met Asn Lys Phe Arg Asp
                165                 170                 175

Lys Val Tyr Asp Ala Ile Val Gln Glu Ala Gln Arg Thr
            180                 185
```

<210> SEQ ID NO 57
<211> LENGTH: 551
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57

```
acagtaaact cctgtggttt tggatttagc attacaaaag cccctattc ttccggacaa      60 aaaccattta tagatggttt cttttaggc gcgaggaaaa tctcattctc ttatcctcga     120
ctggaaagcg agttaataca gtgcattaac ctgaaaaatg aaggaaaaaa gaatgagtgg    180
atgaaggagg agggtatttg ttttgtttcg cgggatgtca ataaactcct ggatatgttt    240
gctaaaaaca accagacaaa catacctgag ggggtccggg agcgggtttt tcagctcgca    300
agttttattt gcggtttctc gttggatgca agatgcgccc agacatccac tcatcacatg    360 atttttaaata gtcagtattt tcagaaaaaa atggatactc ttttgacttc agtagatata    420
```

```
aatgtcagaa atcagtgtgt ccgtacagcg ctaagtagtc tagcggatac tttttttgag      480
aataatgtta acaatataga tatgaataaa ttccgtgaca gggttcataa cactattgta      540
caggaggttc a                                                          551
```

<210> SEQ ID NO 58
<211> LENGTH: 293
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 58

```
Met Leu Ser Pro Tyr Ser Val Asn Leu Gly Cys Ser Trp Asn Ser Leu
1               5                   10                  15

Thr Arg Asn Leu Thr Ser Pro Asp Asn Arg Val Leu Ser Ser Val Arg
            20                  25                  30

Asp Ala Ala Val His Ser Asp Asn Gly Ala Gln Val Lys Val Gly Asn
        35                  40                  45

Arg Thr Tyr Arg Val Val Ala Thr Asp Asn Lys Phe Cys Val Thr Arg
50                  55                  60

Glu Ser His Ser Gly Cys Phe Thr Asn Leu Leu His Arg Leu Gly Trp
65                  70                  75                  80

Pro Lys Gly Glu Ile Ser Arg Lys Ile Glu Val Met Leu Asn Ala Ser
                85                  90                  95

Pro Val Ser Ala Ala Met Glu Arg Gly Ile Val His Ser Asn Arg Pro
            100                 105                 110

Asp Leu Pro Pro Val Asp Tyr Ala Pro Pro Glu Leu Pro Ser Val Asp
        115                 120                 125

Tyr Asn Arg Leu Ser Val Pro Gly Asn Val Ile Gly Lys Gly Gly Asn
130                 135                 140

Ala Val Val Tyr Glu Asp Ala Glu Asp Ala Thr Lys Val Leu Lys Met
145                 150                 155                 160

Phe Thr Thr Ser Gln Ser Asn Glu Glu Val Thr Ser Glu Val Arg Cys
                165                 170                 175

Phe Asn Gln Tyr Tyr Gly Ala Gly Ser Ala Glu Lys Ile Tyr Gly Asn
            180                 185                 190

Asn Gly Asp Ile Ile Gly Ile Arg Met Asp Lys Ile Asn Gly Glu Ser
        195                 200                 205

Leu Leu Asn Ile Ser Ser Leu Pro Ala Gln Ala Glu His Ala Ile Tyr
210                 215                 220

Asp Met Phe Asp Arg Leu Glu Gln Lys Gly Ile Leu Phe Val Asp Thr
225                 230                 235                 240

Thr Glu Thr Asn Ile Leu Tyr Asp Arg Ala Lys Asn Glu Phe Asn Pro
                245                 250                 255

Ile Asp Ile Ser Ser Tyr Asn Val Ser Asp Arg Ser Trp Ser Glu Ser
            260                 265                 270

Gln Ile Met Gln Ser Tyr His Gly Gly Lys Gln Asp Leu Ile Ser Val
        275                 280                 285

Val Leu Ser Lys Ile
    290
```

<210> SEQ ID NO 59
<211> LENGTH: 795
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 59

```
atgctgagcc cgtatagcgt gaacctgggc tgcagctgga acagcctgac ccgcaacctg      60
accagcccgg ataaccgcgt gctgagcagc gtgcgcgatg cggcggtgca tagcgataac     120
ggcgcgcagg tgaaagtggg caaccgcacc tatcgcgtgg tggcgaccga taacaaattt     180
tgcgtgaccc gcgaaagcca tagcggctgc tttaccaacc tgctgcatcg cctgggctgg     240
ccgaaaggcg aaattagccg caaaattgaa gtgatgctga cgcgagccc ggtgagcgcg      300
gcgatggaac gcggcattgt gcatagcaac cgcccggatc tgccgccggt ggattatgcg     360
ccgccggaac tgccgagcgt ggattataac cgcctgagcg tgccgggcaa cgtgattggc     420
aaaggcggca acgcggtggt gtatgaagat gcggaagatg cgaccaaagt gctgaaaatg     480
tttaccacca gccagagcaa cgaagaagtg accagcgaag tgcgctgctt taaccagtat     540
tatggcgcgg gcagcgcgga aaaaatttat ggcaacaacg gcgatattat tggcattcgc     600
atggataaaa ttaacggcga aagcctgctg aacattagca gcctgccggc gcaggcggaa     660
catgcgattt atgatatgtt tgatcgcctg aacagaaag gcattctgtt tgtggatacc      720
accgaaacca acattctgta tgatcgcgcg catggcggca acaggatct gattagcgtg      780
gtgctgagca aaatt                                                      795
```

<210> SEQ ID NO 60
<211> LENGTH: 336
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 60

```
Met Ile Pro Pro Leu Asn Arg Tyr Val Pro Ala Leu Ser Lys Asn Glu
1               5                   10                  15

Leu Val Lys Thr Val Thr Asn Arg Asp Ile Gln Phe Thr Ser Phe Asn
            20                  25                  30

Gly Lys Asp Tyr Pro Leu Cys Phe Leu Asp Glu Lys Thr Pro Leu Leu
        35                  40                  45

Phe Gln Trp Phe Glu Arg Asn Pro Ala Arg Phe Gly Lys Asn Asp Ile
    50                  55                  60

Pro Ile Ile Asn Thr Glu Lys Asn Pro Tyr Leu Asn Asn Ile Ile Lys
65                  70                  75                  80

Ala Ala Thr Ile Glu Lys Glu Arg Leu Ile Gly Ile Phe Val Asp Gly
                85                  90                  95

Asp Phe Phe Pro Gly Gln Lys Asp Ala Phe Ser Lys Leu Glu Tyr Asp
            100                 105                 110

Tyr Glu Asn Ile Lys Val Ile Tyr Arg Asn Asp Ile Asp Phe Ser Met
        115                 120                 125

Tyr Asp Lys Lys Leu Ser Glu Ile Tyr Met Glu Asn Ile Ser Lys Gln
    130                 135                 140

Glu Ser Met Pro Glu Glu Lys Arg Asp Cys His Leu Leu Gln Leu Leu
145                 150                 155                 160

Lys Lys Glu Leu Ser Asp Ile Gln Glu Gly Asn Asp Ser Leu Ile Lys
                165                 170                 175
```

Ser Tyr Leu Leu Asp Lys Gly His Gly Trp Phe Asp Phe Tyr Arg Asn
            180                 185                 190

Met Ala Met Leu Lys Ala Gly Gln Leu Phe Leu Glu Ala Asp Lys Val
        195                 200                 205

Gly Cys Tyr Asp Leu Ser Thr Asn Ser Gly Cys Ile Tyr Leu Asp Ala
    210                 215                 220

Asp Met Ile Ile Thr Glu Lys Leu Gly Gly Ile Tyr Ile Pro Asp Gly
225                 230                 235                 240

Ile Ala Val His Val Glu Arg Ile Asp Gly Arg Ala Ser Met Glu Asn
                245                 250                 255

Gly Ile Ile Ala Val Asp Arg Asn Asn His Pro Ala Leu Leu Ala Gly
            260                 265                 270

Leu Glu Ile Met His Thr Lys Phe Asp Ala Asp Pro Tyr Ser Asp Gly
        275                 280                 285

Val Cys Asn Gly Ile Arg Lys His Phe Asn Tyr Ser Leu Asn Glu Asp
    290                 295                 300

Tyr Asn Ser Phe Cys Asp Phe Ile Glu Phe Lys His Asp Asn Ile Ile
305                 310                 315                 320

Met Asn Thr Ser Gln Phe Thr Gln Ser Ser Trp Ala Arg His Val Gln
                325                 330                 335

<210> SEQ ID NO 61
<211> LENGTH: 540
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
atgttatctc cattaaatgt tcttcaattt aatttcagag gagagaccgc tttatcagat    60
agtgctcctc tccagactgt ttcctttgct ggaaaagatt attctatgga acccattgat   120
gaaaaaacac ccattctttt tcagtggttt gaagcaaggc cagagcgata cggaaaaggt   180
gaagtaccga tattgaatac caaagagcat ccgtatttga gcaatattat aaatgctgca   240
aaaatagaaa atgagcgcgt aataggagta ctggtagacg gagactttac ttatgagcaa   300
agaaaagaat ttctcagtct tgaagatgaa catcaaaata taagataat atatcgggaa    360 aatgttgatt tcagtatgta tgataaaaaa ctgtctgata tttatcttga aaatattcat   420
gaacaagaat catatccagc gagtgagaga gataattatc tgttaggctt attaagagaa   480
gagttaaaaa atattccata cggaaaggac tctttgattg aatcatatgc agaaaaaaga   540

<210> SEQ ID NO 62
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Met Lys Ile Pro Ser Leu Gln Ser Asn Phe Asn Phe Ser Ala Pro Ala
1               5                   10                  15

Gly Tyr Ser Ala Pro Ile Ala Pro Asn Arg Ala Glu Asn Ala Tyr Ala
            20                  25                  30

Asp Tyr Val Leu Asp Ile Gly Lys Arg Ile Pro Leu Ser Ala Ala Asp
        35                  40                  45

```
Leu Ser Asn Val Tyr Glu Ser Val Ile Arg Ala Val His Asp Ser Arg
    50                  55                  60

Ser Arg Leu Ile Asp Gln His Thr Val Asp Met Ile Gly Asn Thr Val
 65                  70                  75                  80

Leu Asp Ala Leu Ser Arg Ser Gln Thr Phe Arg Asp Ala Val Ser Tyr
                 85                  90                  95

Gly Ile His Asn Glu Lys Val His Ile Gly Cys Ile Lys Tyr Arg Asn
                100                 105                 110

Glu Tyr Glu Leu Asn Glu Glu Ser Val Lys Ile Asp Asp Ile Gln
                115                 120                 125

Ser Leu Thr Cys Asn Glu Leu Tyr Glu Tyr Asp Val Gly Gln Glu Pro
    130                 135                 140

Ile Phe Pro Ile Cys Glu Ala Gly Glu Asn Asp Asn Glu Glu Pro Tyr
145                 150                 155                 160

Val Ser Phe Ser Val Ala Pro Asp Thr Asp Ser Tyr Glu Met Pro Ser
                165                 170                 175

Trp Gln Glu Gly Leu Ile His Glu Ile Ile His Val Thr Gly Ser
                180                 185                 190

Ser Asp Pro Ser Gly Asp Ser Asn Ile Glu Leu Gly Pro Thr Glu Ile
    195                 200                 205

Leu Ala Arg Arg Val Ala Gln Glu Leu Gly Trp Ser Val Pro Asp Phe
210                 215                 220

Lys Gly Tyr Ala Glu Pro Glu Arg Glu Ala His Leu Arg Leu Arg Asn
225                 230                 235                 240

Leu Asn Ala Leu Arg Gln Ala Ala Met Arg His Glu Glu Asn Glu Arg
                245                 250                 255

Ala Phe Phe Glu Arg Leu Gly Thr Ile Ser Asp Arg Tyr Glu Ala Ser
                260                 265                 270

Pro Asp Phe Thr Glu Tyr Ser Ala Val Ser Asn Ile Gly Tyr Gly Phe
                275                 280                 285

Ile Gln Gln His Asp Phe Pro Gly Leu Ala Ile Asn Asp Asn Leu Gln
            290                 295                 300

Asp Ala Asn Gln Ile Gln Leu Tyr His Gly Ala Pro Tyr Ile Phe Thr
305                 310                 315                 320

Phe Gly Asp Val Asp Lys His Asn Gln Arg
                325                 330

<210> SEQ ID NO 63
<211> LENGTH: 1464
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63
gaattcatcc ggtcaaacgg cttcttttg caggaaagga atatgagtta aggtcattg      60 atgaaaaaac gcctattatc ctgctctact tgagggattg tcttttatgc acagaagagt   120
agatgctcat ccatattatg atggtttagg taaagggata agaaatatatt ttgattttac   180 tcaattacat gattacaatc attttatga ctttattgag tttaaacatc caaatattat    240
tatgaacaca gtcagtata caggcagttc atggtaaatg gtttttacat agtttattct    300
gttgtaataa atgattagca tggtattagg tatcaacatg aaaattccct cactccagcc    360
cagcttcaac ttttcgccc cagcaggata ctctgctgcc gttgctccca atcgttcgga    420
```

```
caatgcctat gctgattacg tattggatat aggcaagcga ataccacttt ccgcggaaga    480
tttaggcaac ctatatgaaa atgtcattcg cgccgttcgt gacagccgta gcaagctcat    540
agatcagcat acggtcgata tgattggtaa cactatactt gatgctttga gccgatcaca    600
aacctttcgt gatgccgtaa gctatggcat tcataataag gaggtacaca ttggttgcat    660
taaatacaga aacgaatacg agctcaacgg agaatccccc gtcaaagttg atgatattca    720
atcactaacc tgtaccgaat tatatgaata cgatgtcggg caagaaccaa ttttacccat    780
ttgcgaggca ggagaaaacg ataacgaaga gccttatgtc agttttagtg ttgcgccaga    840
tactgactct tatgagatgc catcgtggca ggaagggctg attcacgaga ttattcatca    900
tgtgactgga gctagcgatc cgtctggaga tagtaatata gagctaggac ccacggagat    960
tctcgcacgt cgtgtcgctc aagagctggg atggactgtc cccgacttca taggatatgc   1020
agagccagat cgtgaagctc atcttagggg acgtaacctg aatgcccttc gacaggcggc   1080
catgcgacat gaagataatg agaggacttt cttcgaaagg ctgggtatga tcagtgatcg   1140
atatgaggcg agtcctgatt tcacagagta ttccgctgtg tctaacatag aatatggatt   1200
tatccagcaa catgattttc ccgggttggc tatcgacgat aatttacagg atgcaaatca   1260
gatccaactc tatcatggag caccttatat ctttacattc ggggatgtgg acaaacacaa   1320
tcagcgctga cgcgtctttg cagcgacaca aggctactac tcttgcattt taacggagtt   1380
gatgatggaa aatcgtgcaa ccttgtatgt aaaggcgaaa aaccaaattt tacggtagta   1440
agtgagcctg gcgggaatgg tacc                                          1464
```

<210> SEQ ID NO 64
<211> LENGTH: 558
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 64

```
Met Pro Ile Gly Asn Leu Gly His Asn Pro Asn Val Asn Asn Ser Ile
1               5                   10                  15

Pro Pro Ala Pro Pro Leu Pro Ser Gln Thr Asp Gly Ala Gly Gly Arg
            20                  25                  30

Gly Gln Leu Ile Asn Ser Thr Gly Pro Leu Gly Ser Arg Ala Leu Phe
        35                  40                  45

Thr Pro Val Arg Asn Ser Met Ala Asp Ser Gly Asp Asn Arg Ala Ser
    50                  55                  60

Asp Val Pro Gly Leu Pro Val Asn Pro Met Arg Leu Ala Ala Ser Glu
65                  70                  75                  80

Ile Thr Leu Asn Asp Gly Phe Glu Val Leu His Asp His Gly Pro Leu
                85                  90                  95

Asp Thr Leu Asn Arg Gln Ile Gly Ser Ser Val Phe Arg Val Glu Thr
            100                 105                 110

Gln Glu Asp Gly Lys His Ile Ala Val Gly Gln Arg Asn Gly Val Glu
        115                 120                 125

Thr Ser Val Val Leu Ser Asp Gln Glu Tyr Ala Arg Leu Gln Ser Ile
    130                 135                 140

Asp Pro Glu Gly Lys Asp Lys Phe Val Phe Thr Gly Arg Gly Gly Gly
145                 150                 155                 160

Ala Gly His Ala Met Val Thr Val Ala Ser Asp Ile Thr Glu Ala Arg
                165                 170                 175
```

Gln Arg Ile Leu Glu Leu Leu Glu Pro Lys Gly Thr Gly Glu Ser Lys
                180                 185                 190

Gly Ala Gly Glu Ser Lys Gly Val Gly Glu Leu Arg Glu Ser Asn Ser
            195                 200                 205

Gly Ala Glu Asn Thr Thr Glu Thr Gln Thr Ser Thr Ser Thr Ser Ser
        210                 215                 220

Leu Arg Ser Asp Pro Lys Leu Trp Leu Ala Leu Gly Thr Val Ala Thr
225                 230                 235                 240

Gly Leu Ile Gly Leu Ala Ala Thr Gly Ile Val Gln Ala Leu Ala Leu
                245                 250                 255

Thr Pro Glu Pro Asp Ser Pro Thr Thr Thr Asp Pro Asp Ala Ala Ala
            260                 265                 270

Ser Ala Thr Glu Thr Ala Thr Arg Asp Gln Leu Thr Lys Glu Ala Phe
        275                 280                 285

Gln Asn Pro Asp Asn Gln Lys Val Asn Ile Asp Glu Leu Gly Asn Ala
    290                 295                 300

Ile Pro Ser Gly Val Leu Lys Asp Asp Val Val Ala Asn Ile Glu Glu
305                 310                 315                 320

Gln Ala Lys Ala Ala Gly Glu Glu Ala Lys Gln Gln Ala Ile Glu Asn
                325                 330                 335

Asn Ala Gln Ala Gln Lys Lys Tyr Asp Glu Gln Gln Ala Lys Arg Gln
            340                 345                 350

Glu Glu Leu Lys Val Ser Ser Gly Ala Gly Tyr Gly Leu Ser Gly Ala
        355                 360                 365

Leu Ile Leu Gly Gly Gly Ile Gly Val Ala Val Thr Ala Ala Leu His
    370                 375                 380

Arg Lys Asn Gln Pro Val Glu Gln Thr Thr Thr Thr Thr Thr Thr Thr
385                 390                 395                 400

Thr Thr Thr Ser Ala Arg Thr Val Glu Asn Lys Pro Ala Asn Asn Thr
                405                 410                 415

Pro Ala Gln Gly Asn Val Asp Thr Pro Gly Ser Glu Asp Thr Met Glu
            420                 425                 430

Ser Arg Arg Ser Ser Met Ala Ser Thr Ser Ser Thr Phe Phe Asp Thr
        435                 440                 445

Ser Ser Ile Gly Thr Val Gln Asn Pro Tyr Ala Asp Val Lys Thr Ser
    450                 455                 460

Leu His Asp Ser Gln Val Pro Thr Ser Asn Ser Asn Thr Ser Val Gln
465                 470                 475                 480

Asn Met Gly Asn Thr Asp Ser Val Val Tyr Ser Thr Ile Gln His Pro
                485                 490                 495

Pro Arg Asp Thr Thr Asp Asn Gly Ala Arg Leu Leu Gly Asn Pro Ser
            500                 505                 510

Ala Gly Ile Gln Ser Thr Tyr Ala Arg Leu Ala Leu Ser Gly Gly Leu
        515                 520                 525

Arg His Asp Met Gly Gly Leu Thr Gly Gly Ser Asn Ser Ala Val Asn
    530                 535                 540

Thr Ser Asn Asn Pro Pro Ala Pro Gly Ser His Arg Phe Val
545                 550                 555

<210> SEQ ID NO 65
<211> LENGTH: 1689
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 65

```
taaataaaag gatatatgta tgcctattgg taaccttggt aataatgtaa atagcaatca      60
tttaattccc cctgcgccgc cactaccttc acaaacagac ggcgcggcac ggggaggaac     120
tggtcatcta attagctcta caggagcatt aggatctcgt tcattgtttt ctcccctgag     180
aaattctgtg gctgattctg tcgattccag agatattcca ggacttcctg caaacccatc     240
gaggcttgct gcagctacat ctgagacatg cttgcttgga ggatttgaag ttctccatga     300
taagggccca cttgatactc ttaatcagca aattggaccc tctgcatttc gtgttgaagc     360
gcaggcagat ggtactcatg ccgctattgg agaaaaaaat ggtttggagg ttagcgttgc     420
attaagtcct caagaattgc aaagcttgca atcattgat attgagggga aaacagatt      480
tgttttacc gggggacgtg gcggtagtgg gcatccgatg gtcactgtcg catcagatat     540
cgcggaagct cgtatgaaaa tactggccaa attagaccca gacaatcatg gaggacgtca     600
acccaaggac gttgatacgc gttctgttgg tgttggcagc gcttcgggaa tagatgatgg     660
cgttgttagc gaaacccata cttcaacaac aaattccagc gttcgctcag atcctaaatt     720
ctgggttct gtcggcgcaa ttgctgctgg tttagcggga ctggcggcaa ctggtattgc     780
acaggcgttg gcttttgacac cggaaccgga tgatcctaca accaccgatc ctgatcaggc     840
cgcaaatgct gcagaaagtg caacaaaaga tcagttaacg caagaagcat tcaagaaccc     900
tgagaaccag aaagttaaca tcgatgcgaa cggaaatgct attccgtctg ggaattaaa     960
agatgatatt gttgagcaaa tagcacaaca agctaaagag gctggtgagg tggccagaca    1020
gcaggctgtt gaaagcaatg cacaggcgca gcagcgatat gaggatcagt atgccagacg    1080
tcaggaggaa ttacagcttt catcgggtat tggttacggc ctcagcagtg cattgattgg    1140
tgctggggga attggtgctg gtgtaacgac tgcgctccat agacgaaatc agccggcaga    1200
acagacaact actacaacaa cacatacggt agtgcagcag cagaccggag ggaataccc     1260
agcacaaggt ggcactgatg ccacaagagc agaagatgct tctctgaata acgtgattc     1320
gcaggggagt gttgcatcga cacactggtc agattcctct agcgaagtgg ttaatccata    1380
tgctgaagtt ggggagcctc ggaatagtct atcgactcgt cagcaagaag agcatattta    1440
cgatgaggtc gctgcagatc ctgtttatag cgtcattcag aattttttcac ggaatgctcc    1500
agttaccgga aggttaatgg gaagcccagg gcaaggtatc caaagtactt atgcgcttct    1560
ggcaaacagc gctggattgc gtttaggtat gggaggatta acggggagtg gcgagagcgc    1620
agtaaatact gcaaatgcaa atgccgcacc aacgccggga ccagtacgtt tcgtttaaat    1680
atatctgtg                                                            1689
```

<210> SEQ ID NO 66
<211> LENGTH: 358
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 66

```
Met Gln Asn Lys Ile Lys Gln Leu Lys Asn Tyr Ala Val Tyr Asp Asp
1               5                   10                  15

Ile Glu Gly Phe Leu Ile Asn Lys Asp Ile Arg Ser Ser Ser Gly Asn
            20                  25                  30
```

```
Ser Asn Tyr Met Met Pro Ser Ser Thr Arg Arg Val Ser Asn Thr Arg
        35                  40                  45

Lys Asn Tyr Glu Gly Asp Ile Lys Gln Phe Phe Ser Val Ile Lys Gly
 50                  55                  60

Lys Asp Val Lys Ser Leu Val Pro Asp Asp Leu Val Val Ser Lys Ser
65                  70                  75                  80

Glu Leu Ser Asn Tyr Val Lys Tyr Leu Gln Glu Lys Gly Leu Val Asn
                85                  90                  95

Asn Ser Ile Asn Arg Lys Met Thr Ser Leu Lys Met Leu Tyr Thr Tyr
            100                 105                 110

Leu Glu His Asp Tyr Lys Asp Tyr Ile Asp Leu Ser Val Phe Asn Thr
        115                 120                 125

Val Glu Arg Leu Lys Thr Val Thr Lys Asn Trp Asp Lys Thr Thr Gln
    130                 135                 140

Thr Glu Ala Glu Arg Ile Ala Gln Asp Met Tyr Ile Asn Glu Arg Gln
145                 150                 155                 160

Lys Pro Leu Met Lys Lys Leu Phe Val Lys Phe Ala Ile Arg Thr Ser
                165                 170                 175

Phe Arg Val Ser Ala Ile Leu Arg Val Arg Trp Lys Asp Ile Gln Leu
            180                 185                 190

Asp Glu Ser Thr Gly His Tyr Ile Val Thr Val Ile Asp Lys Gly Ser
        195                 200                 205

Gln Val Val Ser Thr Gly Ile Asn Gln Val Phe Tyr Glu Glu Leu Leu
    210                 215                 220

Gln Leu Lys Glu Glu Asp Ser Glu Thr Glu Leu Val Phe Gln Gly
225                 230                 235                 240

Leu Ser Glu Gln Ser Leu Arg His Ser Leu Lys Arg Ser Lys Lys Arg
                245                 250                 255

Leu Gly Ile Pro Pro Glu Arg Glu Leu Val Leu His Ser Phe Lys Gly
            260                 265                 270

Val Gly Ile Asp Tyr Val Tyr Glu Asn Ser Gly His Asp Leu Leu Ala
        275                 280                 285

Ala Lys Glu Gln Gly Asn His Lys Asn Thr Leu Thr Thr Glu Arg Tyr
    290                 295                 300

Met Ser Arg Lys Ile Asn Ile Ala Asn Ser Ala Gly Val Thr Met Asp
305                 310                 315                 320

Glu Lys Ile Asp Leu Asn Pro Leu Tyr Glu Ala Thr Gln Glu Asp Phe
                325                 330                 335

Ile Ser Phe Phe Glu Asn Ala Asp Leu Val Thr Leu Lys Lys Phe Ile
            340                 345                 350

Lys His Val Asn Glu Arg
        355

<210> SEQ ID NO 67
<211> LENGTH: 867
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67
atgattgggc caatatcaca ataaacagc ttcggtggct tatcagaaaa agagacccgt      60
tctttaatca gtaatgaaga gcttaaaaat atcataatac agttggaaac tgatatagcg    120
```

```
gatggatcct ggttccataa aaattattca cgcctggata tagaagtcat gcccgcatta    180
gtaattcagg cgaacaataa atatccggaa atgaatctta attttgttac atctccccag    240
gacctttcga tagaaataaa aaatgtcata gaaaatggag ttggatcttc ccgcttcata    300
attaacatgg gggagggtgg aatacatttc agtgtaattg attacaaaca tataaatggg    360
aaaacatctc tgatattatt tgaaccagta aactttaata gtatggggcc agcgatactg    420
gcaataagta caaaaacggc cattgaacgt tatcaattac ctgattgcca ttttccatg     480
gtggaaatgg atattcagcg aagctcatct gaatgtggta tttttagttt ggcactggca    540
aaaaaacttt acaccgagag agatagcctg ttgaaaatac atgaagataa tataaaaggt    600
atattaagtg atagtgaaaa tcctttaccc cacaataagt tggatccgta tctcccggta    660
acttttaca aacatactca aggtaaaaaa cgtcttaatg aatatttaaa tactaacccg     720
cagggagttg gtactgttgt taacaaaaaa aatgaaacca tctttaatag gtttgataac    780
aataaatcca ttatagatgg aaaggaatta tcagtttcgg tacataaaaa gagaatagct    840
gaatataaaa cacttctcaa agtataa                                         867
```

<210> SEQ ID NO 68
<211> LENGTH: 288
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

```
Met Ile Gly Pro Ile Ser Gln Ile Asn Ile Ser Gly Gly Leu Ser Glu
1               5                   10                  15

Lys Glu Thr Ser Ser Leu Ile Ser Asn Glu Glu Leu Lys Asn Ile Ile
            20                  25                  30

Thr Gln Leu Glu Thr Asp Ile Ser Asp Gly Ser Trp Phe His Lys Asn
        35                  40                  45

Tyr Ser Arg Met Asp Val Glu Val Met Pro Ala Leu Val Ile Gln Ala
    50                  55                  60

Asn Asn Lys Tyr Pro Glu Met Asn Leu Asn Leu Val Thr Ser Pro Leu
65                  70                  75                  80

Asp Leu Ser Ile Glu Ile Lys Asn Val Ile Glu Asn Gly Val Arg Ser
                85                  90                  95

Ser Arg Phe Ile Ile Asn Met Gly Glu Gly Ile His Phe Ser Val
            100                 105                 110

Ile Asp Tyr Lys His Ile Asn Gly Lys Thr Ser Leu Ile Leu Phe Glu
        115                 120                 125

Pro Ala Asn Phe Asn Ser Met Gly Pro Ala Met Leu Ala Ile Arg Thr
    130                 135                 140

Lys Thr Ala Ile Glu Arg Tyr Gln Leu Pro Asp Cys His Phe Ser Met
145                 150                 155                 160

Val Glu Met Asp Ile Gln Arg Ser Ser Glu Cys Gly Ile Phe Ser
                165                 170                 175

Phe Ala Leu Ala Lys Lys Leu Tyr Ile Glu Arg Asp Ser Leu Leu Lys
            180                 185                 190

Ile His Glu Asp Asn Ile Lys Gly Ile Leu Ser Asp Gly Glu Asn Pro
        195                 200                 205

Leu Pro His Asp Lys Leu Asp Pro Tyr Leu Pro Val Thr Phe Tyr Lys
    210                 215                 220
```

```
His Thr Gln Gly Lys Lys Arg Leu Asn Glu Tyr Leu Asn Thr Asn Pro
225                 230                 235                 240

Gln Gly Val Gly Thr Val Val Asn Lys Lys Asn Glu Thr Ile Val Asn
            245                 250                 255

Arg Phe Asp Asn Asn Lys Ser Ile Val Asp Gly Lys Glu Leu Ser Val
        260                 265                 270

Ser Val His Lys Lys Arg Ile Ala Glu Tyr Lys Thr Leu Leu Lys Val
        275                 280                 285
```

<210> SEQ ID NO 69
<211> LENGTH: 867
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 69

```
atgatcggac caatatcaca aataaatatc tccggtggct tatcagaaaa agagaccagt      60
tctttaatca gtaatgaaga gcttaaaaat atcataacac agttggaaac tgatatatcg     120
gatggatcct ggttccataa aaattattca cgtatggatg tagaagtcat gcccgcattg     180
gtaatccagg cgaacaataa atatccggaa atgaatctta atcttgttac atctccattg     240
gacctttcaa tagaaataaa aaacgtcata gaaatggag ttagatcttc ccgcttcata      300
attaacatgg gggaaggtgg aatacatttc agtgtaattg attacaaaca tataaatggg     360
aaaacatctc tgatattgtt tgaaccagca aactttaaca gtatgggggcc agcgatgctg    420
gcaataagga caaaaacggc tattgaacgt tatcaattac ctgattgcca tttctccatg     480
gtggaaatgg atattcagcg aagctcatct gaatgtggta tttttagttt tgcactggca     540
aaaaaacttt acatcgagag agatagcctg ttgaaaatac atgaagataa tataaaaggt     600
atattaagtg atggtgaaaa tccttttaccc cacgataagt tggacccgta tctcccggta     660
acttttttaca acatactca aggtaaaaaa cgtcttaatg aatatttaaa tactaacccg     720
cagggagttg gtactgttgt taacaaaaaa aatgaaacca tcgttaatag atttgataac     780
aataaatcca ttgtagatgg aaaggaatta tcagtttcgg tacataaaaa agagaatagct    840
gaatatataaa cacttctcaa agtataa                                        867
```

<210> SEQ ID NO 70
<211> LENGTH: 219
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 70

```
Met Lys Ile Ser Ser Phe Ile Ser Thr Ser Leu Pro Leu Pro Ala Ser
1               5                   10                  15

Val Ser Gly Ser Ser Val Gly Glu Met Ser Gly Arg Ser Val Ser
            20                  25                  30

Gln Gln Lys Ser Asp Gln Tyr Ala Asn Asn Leu Ala Gly Arg Thr Glu
        35                  40                  45

Ser Pro Gln Gly Ser Ser Leu Ala Ser Arg Ile Ile Glu Arg Leu Ser
    50                  55                  60

Ser Met Ala His Ser Val Ile Gly Phe Ile Gln Arg Met Phe Ser Glu
65                  70                  75                  80
```

Gly Ser His Lys Pro Val Val Thr Pro Ala Leu Thr Pro Ala Gln Met
            85                  90                  95

Pro Ser Pro Thr Ser Phe Ser Asp Ser Ile Lys Gln Leu Ala Ala Glu
        100                 105                 110

Thr Leu Pro Lys Tyr Met Gln Gln Leu Ser Ser Leu Asp Ala Glu Thr
        115                 120                 125

Leu Gln Lys Asn His Asp Gln Phe Ala Thr Gly Ser Gly Pro Leu Arg
    130                 135                 140

Gly Ser Ile Thr Gln Cys Gln Gly Leu Met Gln Phe Cys Gly Gly Glu
145                 150                 155                 160

Leu Gln Ala Glu Ala Ser Ala Ile Leu Asn Thr Pro Val Cys Gly Ile
                165                 170                 175

Pro Phe Ser Gln Trp Gly Thr Val Gly Gly Ala Ala Ser Ala Tyr Val
            180                 185                 190

Ala Ser Gly Val Asp Leu Thr Gln Ala Ala Asn Glu Ile Lys Gly Leu
        195                 200                 205

Gly Gln Gln Met Gln Gln Leu Leu Ser Leu Met
    210                 215

<210> SEQ ID NO 71
<211> LENGTH: 1152
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71
gaattcccca actttgacac cgataaccgg ttcaatagta tctggaatag acagcgaaag      60
ttgttgaaat aattgagtga tagcttgttc aaatgaatac atttgatctc ctaatagtta    120
gataaaatat caacttaacc aaagcactct cggcagacca tcaattttag cctataattt    180
ttagttttta ttttgtctaa tataacaaca aaaacagcag cggttttta tataaccacc     240 ggctatttc ccactaagat aaccttgttt aatagccaa gggaataaat agtcatgaaa      300
atatcatcat ttatttctac atcactgccc ctgccggcat cagtgtcagg atctagcagc    360
gtaggagaaa tgtctgggcg ctcagtctca cagcaaaaaa gtgatcaata tgcaaacaat    420
ctggccgggc gcactgaaag ccctcagggt tccagcttag ccagccgtat cattgagagg    480
ttatcatcaa tggcccactc tgtgattgga tttatccaac gcatgttctc ggaggggagc    540
cataaaccgg tggtgacacc agcactcacg cctgcacaaa tgccaagccc tacgtctttc    600
agtgatagta tcaagcaact gctgctgag acgctgccaa atacatgca gcagttgagt      660 agcttggatg cagagacgct gcagaaaaat catgaccagt tcgccacggg cagcggccct    720
cttcgtggca gtatcactca atgccaaggg ctgatgcagt tttgtggtgg ggaattgcaa    780
gctgaggcca gtgccatttt aaacacgcct gtttgtggta ttcccttctc gcagtgggga    840
actgttggtg gggcggccag cgcgtacgtc gccagtggcg ttgatctaac gcaggcagca    900
aatgagatca aagggctggg gcaacagatg cagcaattac tgtcattgat gtgatatgga    960
taaaaacaag gggtagtgt ttccccctt ttctatcaat attgcgaata tcttcgtccc     1020
tgatctttca ggggcgaatc gttttttagc atgctcattg ttagaatttc tgacttatct   1080
ctcttctgta ttactactca tactctggaa aatcctgagc atttatatct atggattgat   1140
gcagcactcg ag                                                        1152

```
<210> SEQ ID NO 72
<211> LENGTH: 545
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Met Leu Pro Ile Asn Asn Phe Ser Leu Pro Gln Asn Ser Phe Tyr
1               5                   10                  15

Asn Thr Ile Ser Gly Thr Tyr Ala Asp Tyr Phe Ser Ala Trp Asp Lys
            20                  25                  30

Trp Glu Lys Gln Ala Leu Pro Gly Glu Glu Arg Asp Glu Ala Val Ser
        35                  40                  45

Arg Leu Lys Glu Cys Leu Ile Asn Asn Ser Asp Glu Leu Arg Leu Asp
    50                  55                  60

Arg Leu Asn Leu Ser Ser Leu Pro Asp Asn Leu Pro Ala Gln Ile Thr
65                  70                  75                  80

Leu Leu Asn Val Ser Tyr Asn Gln Leu Thr Asn Leu Pro Glu Leu Pro
                85                  90                  95

Val Thr Leu Lys Lys Leu Tyr Ser Ala Ser Asn Lys Leu Ser Glu Leu
            100                 105                 110

Pro Val Leu Pro Pro Ala Leu Glu Ser Leu Gln Val Gln His Asn Glu
        115                 120                 125

Leu Glu Asn Leu Pro Ala Leu Pro Asp Ser Leu Leu Thr Met Asn Ile
    130                 135                 140

Ser Tyr Asn Glu Ile Val Ser Leu Pro Ser Leu Pro Gln Ala Leu Lys
145                 150                 155                 160

Asn Leu Arg Ala Thr Arg Asn Phe Leu Thr Glu Leu Pro Ala Phe Ser
                165                 170                 175

Glu Gly Asn Asn Pro Val Val Arg Glu Tyr Phe Phe Asp Arg Asn Gln
            180                 185                 190

Ile Ser His Ile Pro Glu Ser Ile Leu Asn Leu Arg Asn Glu Cys Ser
        195                 200                 205

Ile His Ile Ser Asp Asn Pro Leu Ser Ser His Ala Leu Pro Ala Leu
    210                 215                 220

Gln Arg Leu Thr Ser Ser Pro Asp Tyr His Gly Pro Arg Ile Tyr Phe
225                 230                 235                 240

Ser Met Ser Asp Gly Gln Gln Asn Thr Leu His Arg Pro Leu Ala Asp
                245                 250                 255

Ala Val Thr Ala Trp Phe Pro Glu Asn Lys Gln Ser Asp Val Ser Gln
            260                 265                 270

Ile Trp His Ala Phe Glu His Glu His Ala Asn Thr Phe Ser Ala
        275                 280                 285

Phe Leu Asp Arg Leu Ser Asp Thr Val Ser Ala Arg Asn Thr Ser Gly
    290                 295                 300

Phe Arg Glu Gln Val Ala Ala Trp Leu Glu Lys Leu Ser Ala Ser Ala
305                 310                 315                 320

Glu Leu Arg Gln Gln Ser Phe Ala Val Ala Ala Asp Ala Thr Glu Ser
                325                 330                 335

Cys Glu Asp Arg Val Ala Leu Thr Trp Asn Asn Leu Arg Lys Thr Leu
            340                 345                 350

Leu Val His Gln Ala Ser Glu Gly Leu Phe Asp Asn Asp Thr Gly Ala
        355                 360                 365
```

```
Leu Leu Ser Leu Gly Arg Glu Met Phe Arg Leu Glu Ile Leu Glu Asp
    370                 375                 380

Ile Ala Arg Asp Lys Val Arg Thr Leu His Phe Val Asp Glu Ile Glu
385                 390                 395                 400

Val Tyr Leu Ala Phe Gln Thr Met Leu Ala Glu Lys Leu Gln Leu Ser
                405                 410                 415

Thr Ala Val Lys Glu Met Arg Phe Tyr Gly Val Ser Gly Val Thr Ala
            420                 425                 430

Asn Asp Leu Arg Thr Ala Glu Ala Met Val Arg Ser Arg Glu Glu Asn
        435                 440                 445

Glu Phe Thr Asp Trp Phe Ser Leu Trp Gly Pro Trp His Ala Val Leu
    450                 455                 460

Lys Arg Thr Glu Ala Asp Arg Trp Ala Gln Ala Glu Glu Gln Lys Tyr
465                 470                 475                 480

Glu Met Leu Glu Asn Glu Tyr Pro Gln Arg Val Ala Asp Arg Leu Lys
                485                 490                 495

Ala Ser Gly Leu Ser Gly Asp Ala Asp Ala Glu Arg Glu Ala Gly Ala
            500                 505                 510

Gln Val Met Arg Glu Thr Glu Gln Gln Ile Tyr Arg Gln Leu Thr Asp
        515                 520                 525

Glu Val Leu Ala Leu Arg Leu Pro Glu Asn Gly Ser Gln Leu His His
    530                 535                 540

Ser
545

<210> SEQ ID NO 73
<211> LENGTH: 1635
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73
atgctgccga ttaacaacaa cttttagcctg ccgcagaaca gcttttataa caccattagc    60
ggcacctatg cggattattt tagcgcgtgg gataaatggg aaaaacaggc gctgccgggc   120
gaagaacgcg atgaagcggt gagccgcctg aaagaatgcc tgattaacaa cagcgatgaa   180
ctgcgcctgg atcgcctgaa cctgagcagc ctgccggata acctgccggc gcagattacc   240
ctgctgaacg tgagctataa ccagctgacc aacctgccgg aactgccggt gaccctgaaa   300
aaactgtata gcgcgagcaa caaactgagc gaactgccgg tgctgccgcc ggcgctggaa   360
agcctgcagg tgcagcataa cgaactggaa acctgccgg cgctgccgga tagcctgctg   420
accatgaaca ttagctataa cgaaattgtg agcctgccga gcctgccgca ggcgctgaaa   480
aacctgcgcg cgacccgcaa ctttctgacc gaactgccgg cgtttagcga aggcaacaac   540
ccggtggtgc gcgaatattt ttttgatcgc aaccagatta gccatattcc ggaaagcatt   600
ctgaacctgc gcaacgaatg cagcattcat attagcgata cccgctgag cagccatgcg   660 ctgccggcgc tgcagcgcct gaccagcagc ccggattatc atggcccgcg catttatttt   720
agcatgagcg atggccagca gaaacccctg catcgcccgc tggcggatgc ggtgaccgcg   780
tggtttccgg aaaacaaaca gagcgatgtg agccagattt ggcatgcgtt tgaacatgaa   840
gaacatgcga acacctttag cgcgtttctg atcgcctga gcgataccgt gagcgcgcgc   900
aacaccagcg cgctttcgcga acaggtggcg gcgtggctgg aaaaactgag cgcgagcgcg   960
```

```
gaactgcgcc agcagagctt tgcggtggcg gcggatgcga ccgaaagctg cgaagatcgc    1020
gtggcgctga cctggaacaa cctgcgcaaa accctgctgg tgcatcaggc gagcgaaggc    1080
ctgtttgata cgataccggc gcgctgctg agcctgggcc gcgaaatgtt tcgcctggaa    1140
attctggaag atattgcgcg cgataaagtg cgcaccctgc attttgtgga tgaaattgaa    1200
gtgtatctgg cgtttcagac catgctggcg gaaaaactgc agctgagcac cgcggtgaaa    1260
gaaatgcgct tttatggcgt gagcggcgtg accgcgaacg atctgcgcac cgcggaagcg    1320
atggtgcgca gccgcgaaga aaacgaattt accgattggt ttagcctgtg gggcccgtgg    1380
catgcggtgc tgaaacgcac cgaagcggat cgctgggcgc aggcggaaga acagaaatat    1440
gaaatgctgg aaaacgaata tccgcagcgc gtggcggatc gcctgaaagc gagcggcctg    1500
agcggcgatg cggatgcgga acgcgaagcg ggcgcgcagg tgatgcgcga aaccgaacag    1560
cagatttatc gccagctgac cgatgaagtg ctggcgctgc gcctgccgga aaacggcagc    1620
cagctgcatc atagc                                                    1635
```

<210> SEQ ID NO 74
<211> LENGTH: 196
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 74

```
Met Lys Ile Thr Ser Thr Ile Ile Gln Thr Pro Phe Pro Phe Glu Asn
1               5                   10                  15

Asn Asn Ser His Ala Gly Ile Val Thr Glu Pro Ile Leu Gly Lys Leu
            20                  25                  30

Ile Gly Gln Gly Ser Thr Ala Glu Ile Phe Glu Asp Val Asn Asp Ser
        35                  40                  45

Ser Ala Leu Tyr Lys Lys Tyr Asp Leu Ile Gly Asn Gln Tyr Asn Glu
    50                  55                  60

Ile Leu Glu Met Ala Trp Gln Glu Ser Glu Leu Phe Asn Ala Phe Tyr
65                  70                  75                  80

Gly Asp Glu Ala Ser Val Val Ile Gln Tyr Gly Gly Asp Val Tyr Leu
                85                  90                  95

Arg Met Leu Arg Val Pro Gly Thr Pro Leu Ser Asp Ile Asp Thr Ala
            100                 105                 110

Asp Ile Pro Asp Asn Ile Glu Ser Leu Tyr Leu Gln Leu Ile Cys Lys
        115                 120                 125

Leu Asn Glu Leu Ser Ile Ile His Tyr Asp Leu Asn Thr Gly Asn Met
    130                 135                 140

Leu Tyr Asp Lys Glu Ser Glu Ser Leu Phe Pro Ile Asp Phe Arg Asn
145                 150                 155                 160

Ile Tyr Ala Glu Tyr Tyr Ala Ala Thr Lys Lys Asp Lys Glu Ile Ile
                165                 170                 175

Asp Arg Arg Leu Gln Met Arg Thr Asn Asp Phe Tyr Ser Leu Leu Asn
            180                 185                 190

Arg Lys Tyr Leu
            195
```

<210> SEQ ID NO 75
<211> LENGTH: 588
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75

```
atgaaaatta ccagcaccat tattcagacc ccgtttccgt ttgaaaacaa caacagccat      60
gcgggcattg tgaccgaacc gattctgggc aaactgattg gccagggcag caccgcggaa     120
attttgaag atgtgaacga tagcagcgcg ctgtataaaa aatatgatct gattggcaac      180
cagtataacg aaattctgga atggcgtgg caggaaagcg aactgtttaa cgcgttttat      240
ggcgatgaag cgagcgtggt gattcagtat ggcggcgatg tgtatctgcg catgctgcgc     300
gtgccgggca ccccgctgag cgatattgat accgcggata ttccggataa cattgaaagc     360
ctgtatctgc agctgatttg caaactgaac gaactgagca ttattcatta tgatctgaac     420
accggcaaca tgctgtatga taaagaaagc gaaagcctgt ttccgattga ttttcgcaac     480
atttatgcgg aatattatgc ggcgaccaaa aagataaag aaattattga tcgccgcctg      540
cagatgcgca ccaacgattt ttatagcctg ctgaaccgca atatctg                   588
```

<210> SEQ ID NO 76
<211> LENGTH: 462
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220
```

-continued

Gly Ser Met Ser Ile Glu Ile Lys Met Ile Ser Pro Ile Lys Asn Ile
225                 230                 235                 240

Lys Asn Val Phe Pro Ile Asn Thr Ala Asn Thr Glu Tyr Ile Val Arg
            245                 250                 255

Asn Ile Tyr Pro Arg Val Glu His Gly Tyr Phe Asn Glu Ser Pro Asn
        260                 265                 270

Ile Tyr Asp Lys Lys Tyr Ile Ser Gly Ile Thr Arg Ser Met Ala Gln
    275                 280                 285

Leu Lys Ile Glu Glu Phe Ile Asn Glu Lys Ser Arg Arg Leu Asn Tyr
290                 295                 300

Met Lys Thr Met Tyr Ser Pro Cys Pro Glu Asp Phe Gln Pro Ile Ser
305                 310                 315                 320

Arg Asp Glu Ala Ser Thr Pro Glu Gly Ser Trp Leu Thr Val Ile Ser
            325                 330                 335

Gly Lys Arg Pro Met Gly Gln Phe Ser Val Asp Ser Leu Tyr His Pro
        340                 345                 350

Asp Leu His Ala Leu Cys Glu Leu Pro Glu Ile Ser Cys Lys Ile Phe
    355                 360                 365

Pro Lys Glu Asn Ser Asp Phe Leu Tyr Ile Ile Val Val Phe Arg Asn
370                 375                 380

Asp Ser Pro Gln Gly Glu Leu Arg Ala Asn Arg Phe Ile Glu Leu Tyr
385                 390                 395                 400

Asp Ile Lys Arg Glu Ile Met Gln Val Leu Arg Asp Glu Ser Pro Glu
            405                 410                 415

Leu Lys Ser Ile Lys Ser Glu Ile Ile Ala Arg Glu Met Gly Glu
        420                 425                 430

Leu Phe Ser Tyr Ala Ser Glu Glu Ile Asp Ser Tyr Ile Lys Gln Met
    435                 440                 445

Asn Asp Arg Leu Ser Gln Ile Lys Ala Arg Met Pro Val Thr
450                 455                 460

<210> SEQ ID NO 77
<211> LENGTH: 1386
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77
atgagcccga ttctgggcta ttggaaaatt aaaggcctgg tgcagccgac ccgcctgctg      60
ctggaatatc tggaagaaaa atatgaagaa catctgtatg aacgcgatga aggcgataaa     120 tgcgcaaca aaaaatttga actgggcctg gaatttccga acctgccgta ttatattgat      180
ggcgatgtga aactgaccca gagcatggcg attattcgct atattgcgga taaacataac     240
atgctgggcg gctgcccgaa agaacgcgcg gaaattagca tgctggaagg cgcggtgctg     300
gatattcgct atggcgtgag ccgcattgcg tatagcaaag attttgaaac cctgaaagtg     360
gattttctga gcaaactgcc ggaaatgctg aaaatgtttg aagatcgcct gtgccataaa     420
acctatctga acggcgatca tgtgacccat ccggatttta tgctgtatga tgcgctggat     480
gtggtgctgt atatggatcc gatgtgcctg atgcgtttc cgaaactggt gtgctttaaa     540
aaacgcattg aagcgattcc gcagattgat aaatatctga aaagcagcaa atatattgcg     600
tggccgctgc agggctggca ggcgaccttt ggcggcggcg atcatccgcc gaaaagcgat     660
ctggtgccgc gcggcagcat gagcattgaa attaaaatga ttagcccgat taaaaacatt     720

```
aaaaacgtgt ttccgattaa caccgcgaac accgaatata ttgtgcgcaa catttatccg    780
cgcgtggaac atggctattt taacgaaagc ccgaacattt atgataaaaa atatattagc    840
ggcattaccc gcagcatggc gcagctgaaa attgaagaat ttattaacga aaaaagccgc    900
cgcctgaact atatgaaaac catgtatagc ccgtgcccgg aagattttca gccgattagc    960
cgcgatgaag cgagcacccc ggaaggcagc tggctgaccg tgattagcgg caaacgcccg   1020
atgggccagt ttagcgtgga tagcctgtat catccggatc tgcatgcgct gtgcgaactg   1080
ccggaaatta gctgcaaaat ttttccgaaa gaaaacagcg attttctgta tattattgtg   1140
gtgtttcgca acgatagccc gcagggcgaa ctgcgcgcga accgctttat tgaactgtat   1200
gatattaaac gcgaaattat gcaggtgctg cgcgatgaaa gcccggaact gaaaagcatt   1260
aaaagcgaaa ttattattgc gcgcgaaatg ggcgaactgt ttagctatgc gagcgaagaa   1320
attgatagct atattaaaca gatgaacgat cgcctgagcc agattaaagc gcgcatgccg   1380
gtgacc                                                              1386
```

<210> SEQ ID NO 78
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

```
Met Ile Asn Gly Val Ser Leu Gln Gly Thr Ala Gly Tyr Glu Ala His
1               5                   10                  15

Thr Glu Gly Asn Val Asn Val Lys Lys Leu Leu Glu Ser Leu Asn
            20                  25                  30

Ser Lys Ser Leu Gly Asp Met Asp Lys Asp Ser Glu Leu Ala Ala Thr
        35                  40                  45

Leu Gln Lys Met Ile Asn Pro Ser Gly Gly Asp Gly Asn Cys Ser Gly
    50                  55                  60

Cys Ala Leu His Ala Cys Met Ala Met Leu Gly Tyr Gly Val Arg Glu
65                  70                  75                  80

Ala Pro Val Pro Asn Glu Ile Ser Glu Tyr Met Thr Gly Phe Phe His
                85                  90                  95

Arg His Leu Glu Gln Ile Asp Ser Glu Gly Ile Val Ser His Pro Asn
            100                 105                 110

Glu Thr Tyr Ser Lys Phe Arg Glu Arg Ile Ala Glu Asn Ile Leu Gln
        115                 120                 125

Asn Thr Ser Lys Gly Ser Val Val Met Ile Ser Ile Glu Gln Ala Thr
    130                 135                 140

His Trp Ile Ala Gly Phe Asn Asp Gly Glu Lys Ile Met Phe Leu Asp
145                 150                 155                 160

Val Gln Thr Gly Lys Gly Phe Asn Leu Tyr Asp Pro Val Glu Lys Ser
                165                 170                 175

Pro Asp Ala Phe Val Asp Glu Asn Ser Ser Val Gln Val Ile His Val
            180                 185                 190

Ser Asp Gln Glu Phe Asp His Tyr Ala Asn Ser Ser Trp Lys Ser
        195                 200                 205

Lys Arg Leu Cys
    210
```

<210> SEQ ID NO 79
<211> LENGTH: 636
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 79

```
atgattaacg gcgtgagcct gcagggcacc gcgggctatg aagcgcatac cgaagaaggc      60
aacgtgaacg tgaaaaaact gctggaaagc ctgaacagca aaagcctggg cgatatggat     120
aaagatagcg aactggcggc gaccctgcag aaaatgatta acccgagcgg cggcgatggc     180
aactgcagcg gctgcgcgct gcatgcgtgc atggcgatgc tgggctatgg cgtgcgcgaa     240
gcgccggtgc cgaacgaaat tagcgaatat atgaccggct tttttcatcg ccatctggaa     300
cagattgata gcgaaggcat tgtgagccat ccgaacgaaa cctatagcaa atttcgcgaa     360
cgcattgcgg aaaacattct gcagaacacc agcaaaggca gcgtggtgat gattagcatt     420
gaacaggcga cccattggat tgcgggcttt aacgatggcg aaaaaattat gtttctggat     480
gtgcagaccg gcaaaggctt taacctgtat gatccggtgg aaaaaagccc ggatgcgttt     540
gtggatgaaa acagcagcgt gcaggtgatt catgtgagcg atcaggaatt tgatcattat     600
gcgaacagca gcagctggaa aagcaaacgc ctgtgc                                636
```

<210> SEQ ID NO 80
<211> LENGTH: 298
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 80

```
Pro Glu Leu Pro Pro His Leu Glu Ser Leu Val Ala Ser Cys Asn Ser
1               5                   10                  15

Leu Thr Glu Leu Pro Glu Leu Pro Gln Ser Leu Lys Ser Leu Gln Val
            20                  25                  30

Asp Asn Asn Asn Leu Lys Ala Leu Ser Asp Leu Pro Pro Ser Leu Glu
        35                  40                  45

Phe Leu Ala Ala Gly Asn Asn Gln Leu Glu Glu Leu Pro Glu Leu Gln
    50                  55                  60

Asn Ser Ser Phe Leu Lys Ile Ile Asp Ile Asn Pro Val Thr Asn Thr
65                  70                  75                  80

Gln Gly Val Ser Pro Ile Asn Thr Lys Tyr Ala Glu His Val Val Lys
                85                  90                  95

Asn Ile Tyr Pro Lys Ile Lys His Asp Tyr Phe Asn Glu Ser Pro Asn
            100                 105                 110

Ile Tyr Asp Lys Lys Tyr Ile Ser Gly Ile Thr Arg Gly Val Ala Glu
        115                 120                 125

Leu Lys Gln Glu Glu Phe Val Asn Glu Lys Ala Arg Arg Phe Ser Tyr
    130                 135                 140

Met Lys Thr Met Tyr Ser Val Cys Pro Glu Ala Phe Glu Pro Ile Ser
145                 150                 155                 160

Arg Asn Glu Ala Ser Thr Pro Glu Gly Ser Trp Leu Thr Val Ile Ser
                165                 170                 175

Gly Lys Arg Pro Met Gly Gln Phe Ser Val Asp Ser Leu Tyr Asn Pro
            180                 185                 190
```

```
Asp Leu His Ala Leu Cys Glu Leu Pro Asp Ile Cys Cys Lys Ile Phe
            195                 200                 205

Pro Lys Glu Asn Asn Asp Phe Leu Tyr Ile Val Val Tyr Arg Asn
210                 215                 220

Asp Ser Pro Leu Gly Glu Gln Arg Ala Asn Arg Phe Ile Glu Leu Tyr
225                 230                 235                 240

Asn Ile Lys Arg Asp Ile Met Gln Glu Leu Asn Tyr Glu Leu Pro Glu
                245                 250                 255

Leu Lys Ala Val Lys Ser Glu Met Ile Ala Arg Glu Met Gly Glu
            260                 265                 270

Ile Phe Ser Tyr Met Pro Gly Leu Ile Asp Ser Tyr Met Lys Tyr Ile
            275                 280                 285

Asn Asn Lys Leu Ser Lys Ile Glu Gly Ser
290                 295

<210> SEQ ID NO 81
<211> LENGTH: 315
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Pro Glu Leu Pro Pro His Leu Glu Ser Leu Val Ala Ser Cys Asn Ser
1               5                   10                  15

Leu Thr Glu Leu Pro Glu Leu Pro Gln Ser Leu Lys Ser Leu Gln Val
            20                  25                  30

Asp Asn Asn Asn Leu Lys Ala Leu Ser Asp Leu Pro Pro Ser Leu Glu
        35                  40                  45

Phe Leu Ala Ala Gly Asn Asn Gln Leu Glu Glu Leu Pro Glu Leu Gln
50                  55                  60

Asn Ser Ser Phe Leu Lys Ile Ile Asp Pro Ala Pro Ala Pro Ala Pro
65                  70                  75                  80

Ala Pro Ala Pro Ala Pro Pro Ala Ile Asn Pro Val Thr Asn
            85                  90                  95

Thr Gln Gly Val Ser Pro Ile Asn Thr Lys Tyr Ala Glu His Val Val
                100                 105                 110

Lys Asn Ile Tyr Pro Lys Ile Lys His Asp Tyr Phe Asn Glu Ser Pro
            115                 120                 125

Asn Ile Tyr Asp Lys Lys Tyr Ile Ser Gly Ile Thr Arg Gly Val Ala
130                 135                 140

Glu Leu Lys Gln Glu Glu Phe Val Asn Glu Lys Ala Arg Arg Phe Ser
145                 150                 155                 160

Tyr Met Lys Thr Met Tyr Ser Val Cys Pro Glu Ala Phe Glu Pro Ile
                165                 170                 175

Ser Arg Asn Glu Ala Ser Thr Pro Glu Gly Ser Trp Leu Thr Val Ile
            180                 185                 190

Ser Gly Lys Arg Pro Met Gly Gln Phe Ser Val Asp Ser Leu Tyr Asn
        195                 200                 205

Pro Asp Leu His Ala Leu Cys Glu Leu Pro Asp Ile Cys Cys Lys Ile
210                 215                 220

Phe Pro Lys Glu Asn Asn Asp Phe Leu Tyr Ile Val Val Tyr Arg
225                 230                 235                 240

Asn Asp Ser Pro Leu Gly Glu Gln Arg Ala Asn Arg Phe Ile Glu Leu
                245                 250                 255
```

Tyr Asn Ile Lys Arg Asp Ile Met Gln Glu Leu Asn Tyr Glu Leu Pro
            260                 265                 270

Glu Leu Lys Ala Val Lys Ser Glu Met Ile Ile Ala Arg Glu Met Gly
        275                 280                 285

Glu Ile Phe Ser Tyr Met Pro Gly Ile Asp Ser Tyr Met Lys Tyr
290                 295                 300

Ile Asn Asn Lys Leu Ser Lys Ile Glu Gly Ser
305                 310                 315

<210> SEQ ID NO 82
<211> LENGTH: 314
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Pro Glu Leu Pro Pro His Leu Glu Ser Leu Val Ala Ser Cys Asn Ser
1               5                   10                  15

Leu Thr Glu Leu Pro Glu Leu Pro Gln Ser Leu Lys Ser Leu Gln Val
            20                  25                  30

Asp Asn Asn Asn Leu Lys Ala Leu Ser Asp Leu Pro Pro Ser Leu Glu
        35                  40                  45

Phe Leu Ala Ala Gly Asn Asn Gln Leu Glu Glu Leu Pro Glu Leu Gln
    50                  55                  60

Asn Ser Ser Phe Leu Lys Ile Ile Asp Gly Ser Gly Ser Gly Ser Gly
65                  70                  75                  80

Ser Gly Ser Gly Ser Gly Ser Gly Ser Ile Asn Pro Val Thr Asn Thr
                85                  90                  95

Gln Gly Val Ser Pro Ile Asn Thr Lys Tyr Ala Glu His Val Val Lys
            100                 105                 110

Asn Ile Tyr Pro Lys Ile Lys His Asp Tyr Phe Asn Glu Ser Pro Asn
        115                 120                 125

Ile Tyr Asp Lys Lys Tyr Ile Ser Gly Ile Thr Arg Gly Val Ala Glu
130                 135                 140

Leu Lys Gln Glu Glu Phe Val Asn Glu Lys Ala Arg Arg Phe Ser Tyr
145                 150                 155                 160

Met Lys Thr Met Tyr Ser Val Cys Pro Glu Ala Phe Glu Pro Ile Ser
                165                 170                 175

Arg Asn Glu Ala Ser Thr Pro Glu Gly Ser Trp Leu Thr Val Ile Ser
            180                 185                 190

Gly Lys Arg Pro Met Gly Gln Phe Ser Val Asp Ser Leu Tyr Asn Pro
        195                 200                 205

Asp Leu His Ala Leu Cys Glu Leu Pro Asp Ile Cys Cys Lys Ile Phe
210                 215                 220

Pro Lys Glu Asn Asn Asp Phe Leu Tyr Ile Val Val Val Tyr Arg Asn
225                 230                 235                 240

Asp Ser Pro Leu Gly Glu Gln Arg Ala Asn Arg Phe Ile Glu Leu Tyr
                245                 250                 255

Asn Ile Lys Arg Asp Ile Met Gln Glu Leu Asn Tyr Glu Leu Pro Glu
            260                 265                 270

Leu Lys Ala Val Lys Ser Glu Met Ile Ile Ala Arg Glu Met Gly Glu
        275                 280                 285

Ile Phe Ser Tyr Met Pro Gly Glu Ile Asp Ser Tyr Met Lys Tyr Ile

```
                   290                 295                 300
Asn Asn Lys Leu Ser Lys Ile Glu Gly Ser
305                 310

<210> SEQ ID NO 83
<211> LENGTH: 298
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Pro Glu Leu Pro Pro His Leu Glu Ser Leu Val Ala Ser Cys Asn Ser
1               5                   10                  15

Leu Thr Glu Leu Pro Glu Leu Pro Gln Ser Leu Lys Ser Leu Gln Val
                20                  25                  30

Asp Asn Asn Asn Leu Lys Ala Leu Ser Asp Leu Pro Pro Ser Leu Glu
            35                  40                  45

Phe Leu Ala Ala Gly Asn Asn Gln Leu Glu Glu Leu Pro Glu Leu Gln
    50                  55                  60

Asn Ser Ser Phe Leu Lys Ile Ile Asp Ile Asn Pro Val Thr Asn Thr
65                  70                  75                  80

Gln Gly Val Ser Pro Ile Asn Thr Lys Tyr Ala Glu His Val Val Lys
                85                  90                  95

Asn Ile Tyr Pro Lys Ile Lys His Asp Tyr Phe Asn Glu Ser Pro Asn
            100                 105                 110

Ile Tyr Asp Lys Lys Tyr Ile Ser Gly Ile Thr Arg Gly Val Ala Glu
    115                 120                 125

Leu Lys Gln Glu Glu Phe Val Asn Glu Lys Ala Arg Arg Phe Ser Tyr
130                 135                 140

Met Lys Thr Met Tyr Ser Val Cys Pro Glu Ala Phe Glu Pro Ile Ser
145                 150                 155                 160

Arg Asn Glu Ala Ser Thr Pro Glu Gly Ser Trp Leu Thr Val Ile Ser
                165                 170                 175

Gly Lys Ala Pro Met Gly Gln Phe Ser Val Asp Ser Leu Tyr Asn Pro
            180                 185                 190

Asp Leu His Ala Leu Cys Glu Leu Pro Asp Ile Cys Cys Lys Ile Phe
    195                 200                 205

Pro Lys Glu Asn Asn Asp Phe Leu Tyr Ile Val Val Tyr Arg Asn
210                 215                 220

Asp Ser Pro Leu Gly Glu Gln Arg Ala Asn Arg Phe Ile Glu Leu Tyr
225                 230                 235                 240

Asn Ile Lys Arg Asp Ile Met Gln Glu Leu Asn Tyr Glu Leu Pro Glu
                245                 250                 255

Leu Lys Ala Val Lys Ser Glu Met Ile Ile Ala Arg Glu Met Gly Glu
            260                 265                 270

Ile Phe Ser Tyr Met Pro Gly Glu Ile Asp Ser Tyr Met Lys Tyr Ile
    275                 280                 285

Asn Asn Lys Leu Ser Lys Ile Glu Gly Ser
    290                 295

<210> SEQ ID NO 84
<211> LENGTH: 315
<212> TYPE: PRT
<213> ORGANISM: Artificial Sequence
<220> FEATURE:
```

<223> OTHER INFORMATION: Description of Artificial Sequence: Synthetic
polypeptide

<400> SEQUENCE: 84

Pro Glu Leu Pro Pro His Leu Glu Ser Leu Val Ala Ser Cys Asn Ser
1               5                   10                  15

Leu Thr Glu Leu Pro Glu Leu Pro Gln Ser Leu Lys Ser Leu Gln Val
            20                  25                  30

Asp Asn Asn Leu Lys Ala Leu Ser Asp Leu Pro Pro Ser Leu Glu
        35                  40                  45

Phe Leu Ala Ala Gly Asn Asn Gln Leu Glu Glu Leu Pro Glu Leu Gln
    50                  55                  60

Asn Ser Ser Phe Leu Lys Ile Ile Asp Pro Ala Pro Ala Pro Ala Pro
65              70                  75                  80

Ala Pro Ala Pro Ala Pro Ala Pro Pro Ala Ile Asn Pro Val Thr Asn
                85                  90                  95

Thr Gln Gly Val Ser Pro Ile Asn Thr Lys Tyr Ala Glu His Val Val
            100                 105                 110

Lys Asn Ile Tyr Pro Lys Ile Lys His Asp Tyr Phe Asn Glu Ser Pro
        115                 120                 125

Asn Ile Tyr Asp Lys Lys Tyr Ile Ser Gly Ile Thr Arg Gly Val Ala
    130                 135                 140

Glu Leu Lys Gln Glu Glu Phe Val Asn Glu Lys Ala Arg Arg Phe Ser
145                 150                 155                 160

Tyr Met Lys Thr Met Tyr Ser Val Cys Pro Glu Ala Phe Glu Pro Ile
                165                 170                 175

Ser Arg Asn Glu Ala Ser Thr Pro Glu Gly Ser Trp Leu Thr Val Ile
            180                 185                 190

Ser Gly Lys Ala Pro Met Gly Gln Phe Ser Val Asp Ser Leu Tyr Asn
        195                 200                 205

Pro Asp Leu His Ala Leu Cys Glu Leu Pro Asp Ile Cys Cys Lys Ile
    210                 215                 220

Phe Pro Lys Glu Asn Asn Asp Phe Leu Tyr Ile Val Val Tyr Arg
225                 230                 235                 240

Asn Asp Ser Pro Leu Gly Glu Gln Arg Ala Asn Arg Phe Ile Glu Leu
                245                 250                 255

Tyr Asn Ile Lys Arg Asp Ile Met Gln Glu Leu Asn Tyr Glu Leu Pro
            260                 265                 270

Glu Leu Lys Ala Val Lys Ser Glu Met Ile Ile Ala Arg Glu Met Gly
        275                 280                 285

Glu Ile Phe Ser Tyr Met Pro Gly Glu Ile Asp Ser Tyr Met Lys Tyr
    290                 295                 300

Ile Asn Asn Lys Leu Ser Lys Ile Glu Gly Ser
305                 310                 315

<210> SEQ ID NO 85
<211> LENGTH: 314
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Pro Glu Leu Pro Pro His Leu Glu Ser Leu Val Ala Ser Cys Asn Ser
1               5                   10                  15

```
Leu Thr Glu Leu Pro Glu Leu Pro Gln Ser Leu Lys Ser Leu Gln Val
            20                  25                  30

Asp Asn Asn Asn Leu Lys Ala Leu Ser Asp Leu Pro Pro Ser Leu Glu
        35                  40                  45

Phe Leu Ala Ala Gly Asn Asn Gln Leu Glu Glu Leu Pro Glu Leu Gln
 50                  55                  60

Asn Ser Ser Phe Leu Lys Ile Ile Asp Gly Ser Gly Ser Gly Ser Gly
 65                  70                  75                  80

Ser Gly Ser Gly Ser Gly Ser Gly Ser Ile Asn Pro Val Thr Asn Thr
                85                  90                  95

Gln Gly Val Ser Pro Ile Asn Thr Lys Tyr Ala Glu His Val Val Lys
            100                 105                 110

Asn Ile Tyr Pro Lys Ile Lys His Asp Tyr Phe Asn Glu Ser Pro Asn
        115                 120                 125

Ile Tyr Asp Lys Lys Tyr Ile Ser Gly Ile Thr Arg Gly Val Ala Glu
130                 135                 140

Leu Lys Gln Glu Glu Phe Val Asn Glu Lys Ala Arg Arg Phe Ser Tyr
145                 150                 155                 160

Met Lys Thr Met Tyr Ser Val Cys Pro Glu Ala Phe Glu Pro Ile Ser
                165                 170                 175

Arg Asn Glu Ala Ser Thr Pro Glu Gly Ser Trp Leu Thr Val Ile Ser
            180                 185                 190

Gly Lys Ala Pro Met Gly Gln Phe Ser Val Asp Ser Leu Tyr Asn Pro
        195                 200                 205

Asp Leu His Ala Leu Cys Glu Leu Pro Asp Ile Cys Cys Lys Ile Phe
210                 215                 220

Pro Lys Glu Asn Asn Asp Phe Leu Tyr Ile Val Val Tyr Arg Asn
225                 230                 235                 240

Asp Ser Pro Leu Gly Glu Gln Arg Ala Asn Arg Phe Ile Glu Leu Tyr
                245                 250                 255

Asn Ile Lys Arg Asp Ile Met Gln Glu Leu Asn Tyr Glu Leu Pro Glu
            260                 265                 270

Leu Lys Ala Val Lys Ser Glu Met Ile Ile Ala Arg Glu Met Gly Glu
        275                 280                 285

Ile Phe Ser Tyr Met Pro Gly Glu Ile Asp Ser Tyr Met Lys Tyr Ile
290                 295                 300

Asn Asn Lys Leu Ser Lys Ile Glu Gly Ser
305                 310

<210> SEQ ID NO 86
<211> LENGTH: 292
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Pro Glu Leu Pro Pro His Leu Glu Ser Leu Val Ala Ser Cys Asn Ser
1               5                   10                  15

Leu Thr Glu Leu Pro Glu Leu Pro Gln Ser Leu Lys Ser Leu Gln Val
            20                  25                  30

Asp Asn Asn Asn Leu Lys Ala Leu Ser Asp Leu Pro Pro Ser Leu Glu
        35                  40                  45

Phe Leu Ala Ala Gly Asn Asn Gln Leu Glu Glu Leu Pro Glu Leu Gln
 50                  55                  60
```

```
Asn Ser Ser Phe Leu Lys Ile Ile Asp Ile Asn Pro Val Thr Asn Thr
 65                  70                  75                  80

Gln Gly Val Ser Pro Ile Asn Thr Lys Tyr Ala Glu His Val Val Lys
                 85                  90                  95

Asn Ile Tyr Pro Lys Ile Lys His Asp Tyr Phe Asn Glu Ser Pro Asn
            100                 105                 110

Ile Tyr Asp Lys Lys Tyr Ile Ser Gly Ile Thr Arg Gly Val Ala Glu
            115                 120                 125

Leu Lys Gln Glu Glu Phe Val Asn Glu Lys Ala Arg Arg Phe Ser Tyr
130                 135                 140

Met Lys Thr Met Tyr Ser Val Cys Pro Glu Ala Phe Glu Pro Ile Ser
145                 150                 155                 160

Arg Asn Glu Ala Ser Thr Pro Glu Gly Ser Trp Leu Thr Val Ile Ser
                165                 170                 175

Gly Lys Arg Pro Met Gly Gln Phe Ser Val Asp Ser Leu Tyr Asn Pro
            180                 185                 190

Asp Leu His Ala Leu Cys Glu Leu Pro Asp Ile Cys Cys Lys Ile Phe
            195                 200                 205

Pro Lys Glu Asn Asn Asp Phe Leu Tyr Ile Val Val Tyr Arg Asn
210                 215                 220

Asp Ser Pro Leu Gly Glu Gln Arg Ala Asn Arg Phe Ile Glu Leu Tyr
225                 230                 235                 240

Asn Ile Lys Arg Asp Ile Met Gln Glu Leu Asn Tyr Glu Leu Pro Glu
                245                 250                 255

Leu Lys Ala Val Lys Ser Glu Met Ile Ile Ala Arg Glu Met Gly Glu
            260                 265                 270

Ile Phe Ser Tyr Met Pro Gly Glu Ile Asp Ser Tyr Met Lys Tyr Ile
            275                 280                 285

Asn Asn Lys Leu
    290

<210> SEQ ID NO 87
<211> LENGTH: 309
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Pro Glu Leu Pro Pro His Leu Glu Ser Leu Val Ala Ser Cys Asn Ser
1               5                   10                  15

Leu Thr Glu Leu Pro Glu Leu Pro Gln Ser Leu Lys Ser Leu Gln Val
            20                  25                  30

Asp Asn Asn Asn Leu Lys Ala Leu Ser Asp Leu Pro Pro Ser Leu Glu
        35                  40                  45

Phe Leu Ala Ala Gly Asn Asn Gln Leu Glu Gly Leu Pro Glu Leu Gln
    50                  55                  60

Asn Ser Ser Phe Leu Lys Ile Ile Asp Pro Ala Pro Ala Pro Ala
 65                  70                  75                  80

Ala Pro Ala Pro Ala Pro Ala Pro Ala Ile Asn Pro Val Thr Asn
                 85                  90                  95

Thr Gln Gly Val Ser Pro Ile Asn Thr Lys Tyr Ala Glu His Val Val
            100                 105                 110

Lys Asn Ile Tyr Pro Lys Ile Lys His Asp Tyr Phe Asn Glu Ser Pro
```

```
                115                 120                 125
Asn Ile Tyr Asp Lys Lys Tyr Ile Ser Gly Ile Thr Arg Gly Val Ala
            130                 135                 140
Glu Leu Lys Gln Glu Glu Phe Val Asn Glu Lys Ala Arg Arg Phe Ser
145                 150                 155                 160
Tyr Met Lys Thr Met Tyr Ser Val Cys Pro Glu Ala Phe Glu Pro Ile
                165                 170                 175
Ser Arg Asn Glu Ala Ser Thr Pro Glu Gly Ser Trp Leu Thr Val Ile
            180                 185                 190
Ser Gly Lys Arg Pro Met Gly Gln Phe Ser Val Asp Ser Leu Tyr Asn
                195                 200                 205
Pro Asp Leu His Ala Leu Cys Glu Leu Pro Asp Ile Cys Cys Lys Ile
            210                 215                 220
Phe Pro Lys Glu Asn Asn Asp Phe Leu Tyr Ile Val Val Tyr Arg
225                 230                 235                 240
Asn Asp Ser Pro Leu Gly Glu Gln Arg Ala Asn Arg Phe Ile Glu Leu
                245                 250                 255
Tyr Asn Ile Lys Arg Asp Ile Met Gln Glu Leu Asn Tyr Glu Leu Pro
            260                 265                 270
Glu Leu Lys Ala Val Lys Ser Glu Met Ile Ile Ala Arg Glu Met Gly
                275                 280                 285
Glu Ile Phe Ser Tyr Met Pro Gly Glu Ile Asp Ser Tyr Met Lys Tyr
            290                 295                 300
Ile Asn Asn Lys Leu
305

<210> SEQ ID NO 88
<211> LENGTH: 308
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Pro Glu Leu Pro Pro His Leu Glu Ser Leu Val Ala Ser Cys Asn Ser
1               5                   10                  15
Leu Thr Glu Leu Pro Glu Leu Pro Gln Ser Leu Lys Ser Leu Gln Val
            20                  25                  30
Asp Asn Asn Asn Leu Lys Ala Leu Ser Asp Leu Pro Pro Ser Leu Glu
        35                  40                  45
Phe Leu Ala Ala Gly Asn Asn Gln Leu Glu Glu Leu Pro Glu Leu Gln
50                  55                  60
Asn Ser Ser Phe Leu Lys Ile Ile Asp Gly Ser Gly Ser Gly Ser Gly
65                  70                  75                  80
Ser Gly Ser Gly Ser Gly Ser Gly Ser Ile Asn Pro Val Thr Asn Thr
                85                  90                  95
Gln Gly Val Ser Pro Ile Asn Thr Lys Tyr Ala Glu His Val Val Lys
            100                 105                 110
Asn Ile Tyr Pro Lys Ile Lys His Asp Tyr Phe Asn Glu Ser Pro Asn
        115                 120                 125
Ile Tyr Asp Lys Lys Tyr Ile Ser Gly Ile Thr Arg Gly Val Ala Glu
            130                 135                 140
Leu Lys Gln Glu Glu Phe Val Asn Glu Lys Ala Arg Arg Phe Ser Tyr
145                 150                 155                 160
```

```
Met Lys Thr Met Tyr Ser Val Cys Pro Glu Ala Phe Glu Pro Ile Ser
                165                 170                 175

Arg Asn Glu Ala Ser Thr Pro Glu Gly Ser Trp Leu Thr Val Ile Ser
            180                 185                 190

Gly Lys Arg Pro Met Gly Gln Phe Ser Val Asp Ser Leu Tyr Asn Pro
        195                 200                 205

Asp Leu His Ala Leu Cys Glu Leu Pro Asp Ile Cys Cys Lys Ile Phe
    210                 215                 220

Pro Lys Glu Asn Asn Asp Phe Leu Tyr Ile Val Val Tyr Arg Asn
225                 230                 235                 240

Asp Ser Pro Leu Gly Glu Gln Arg Ala Asn Arg Phe Ile Glu Leu Tyr
            245                 250                 255

Asn Ile Lys Arg Asp Ile Met Gln Glu Leu Asn Tyr Glu Leu Pro Glu
        260                 265                 270

Leu Lys Ala Val Lys Ser Glu Met Ile Ile Ala Arg Glu Met Gly Glu
    275                 280                 285

Ile Phe Ser Tyr Met Pro Gly Glu Ile Asp Ser Tyr Met Lys Tyr Ile
    290                 295                 300

Asn Asn Lys Leu
305

<210> SEQ ID NO 89
<211> LENGTH: 224
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Asn Pro Val Thr Asn Thr Gln Gly Val Ser Pro Ile Asn Thr Lys Tyr
1               5                   10                  15

Ala Glu His Val Val Lys Asn Ile Tyr Pro Lys Ile Lys His Asp Tyr
            20                  25                  30

Phe Asn Glu Ser Pro Asn Ile Tyr Asp Lys Lys Tyr Ile Ser Gly Ile
        35                  40                  45

Thr Arg Gly Val Ala Glu Leu Lys Gln Glu Glu Phe Val Asn Glu Lys
    50                  55                  60

Ala Arg Arg Phe Ser Tyr Met Lys Thr Met Tyr Ser Val Cys Pro Glu
65                  70                  75                  80

Ala Phe Glu Pro Ile Ser Arg Asn Glu Ala Ser Thr Pro Glu Gly Ser
                85                  90                  95

Trp Leu Thr Val Ile Ser Gly Lys Arg Pro Met Gly Gln Phe Ser Val
            100                 105                 110

Asp Ser Leu Tyr Asn Pro Asp Leu His Ala Leu Cys Glu Leu Pro Asp
        115                 120                 125

Ile Cys Cys Lys Ile Phe Pro Lys Glu Asn Asn Asp Phe Leu Tyr Ile
    130                 135                 140

Val Val Val Tyr Arg Asn Asp Ser Pro Leu Gly Glu Gln Arg Ala Asn
145                 150                 155                 160

Arg Phe Ile Glu Leu Tyr Asn Ile Lys Arg Asp Ile Met Gln Glu Leu
                165                 170                 175

Asn Tyr Glu Leu Pro Glu Leu Lys Ala Val Lys Ser Glu Met Ile Ile
            180                 185                 190

Ala Arg Glu Met Gly Glu Ile Phe Ser Tyr Met Pro Gly Glu Ile Asp
        195                 200                 205
```

Ser Tyr Met Lys Tyr Ile Asn Asn Lys Leu Ser Lys Ile Glu Gly Ser
    210                 215                 220

<210> SEQ ID NO 90
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 90

His His His His His His
1               5

<210> SEQ ID NO 91
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Pro Ala Pro Ala
1

<210> SEQ ID NO 92
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gly Ser Gly Ser
1

<210> SEQ ID NO 93
<211> LENGTH: 672
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93
atgattaatc ctgttactaa tactcagggc gtgtcccta taaatactaa atatgctgaa      60
catgtggtga aaatatttta cccgaaaatt aaacatgatt actttaatga atcacccaat     120
atatatgata agaagtatat atccggtata accagaggag tagctgaact aaaacaggaa     180
gaatttgtta acgagaaagc cagacggttt tcttatatga agactatgta ttctgtatgt     240
ccagaagcgt ttgaacctat ttccagaaat gaagccagta caccggaagg aagctggcta     300
acagttatat ccggaaaacg cccaatgggg cagttttctg tagatagttt atacaatcct     360

-continued

```
gatttacatg cattatgtga gcttccggac atttgttgta agatcttccc taaagaaaat    420
aatgattttt tatacatagt tgttgtgtac agaaatgaca gccctctagg agaacaacgg    480
gcaaatagat ttatagaatt atataatata aaaagagata tcatgcagga attaaattat    540
gagttaccag agttaaaggc agtaaaatct gaaatgatta tcgcacgtga aatgggagaa    600
atctttagct acatgcctgg ggaaatagac agttatatga aatacataaa taataaactt    660
tctaaaattg ag                                                        672
```

METHODS AND COMPOSITIONS FOR USE OF RECOMBINANT BACTERIAL EFFECTOR PROTEINS AS ANTI-INFLAMMATORY AGENTS

CROSS-REFERENCE TO RELATED APPLICATIONS

This application is a continuation of pending U.S. patent application Ser. No. 16/964,762, filed Jul. 24, 2020, which is a national stage of International Patent Application No. PCT/US2019/015224, filed Jan. 25, 2019, which claims the benefit of the priority of U.S. Provisional Patent Application No. 62/622,068, filed Jan. 25, 2018, which applications are incorporated herein by reference.

INCORPORATION-BY-REFERENCE OF MATERIAL SUBMITTED IN ELECTRONIC FORM

Applicant hereby incorporates by reference the Sequence Listing material filed in electronic form herewith. This file is labeled "WST171USC1_SeqList.txt", created Jul. 24, 2020, and having 223 KB.

FIELD OF THE INVENTION

The present invention relates to methods and compositions for treating inflammatory disorders.

BACKGROUND OF THE INVENTION

Most treatments for acute inflammation, such as skin inflammatory conditions, only treat the symptoms (swelling, redness, pain, heat) by using non-specific drugs like corticosteroids and emollients/skin softeners. None of these non-specific drugs affect the underlying mechanism of activation of the inflammatory pathway, e.g., NFkB/JNK/p38. Moreover, normal aging processes chronically activate ectopically these three signal transduction pathways, resulting in inflammation. The inflammation makes these pathways a target for inhibition as part of an anti-aging/wellness program.

To date, the cosmeceutical industry's approach to reducing skin inflammation has many flaws. The "Active Compounds" contained in most cremes and topicals do not have defined, specific targets in the inflamed cell/tissue the cell and are extremely complex mixtures/extracts/serums containing millions of ingredients with no defined targets, or ingredients which are not absorbed by skin and have no effect at all. Because these compositions do not target the actual pathways which are causing inflammation, they have the potential to alter many processes non-specifically leading to toxic side effects.

A continuing need in the art exists for new and effective tools and methods for treating the causes of inflammation.

SUMMARY OF THE INVENTION

Disclosed herein are compositions of paired peptides comprising a first bacterial effector polypeptide linked to a second bacterial effector polypeptide that are useful for treating an inflammatory disorder. Accordingly, disclosed are compositions that include a set of paired peptides, wherein the set of paired peptides is linked to a protein transduction domain, and wherein the set of paired peptides comprises a first bacterial effector polypeptide or fragment thereof linked to a second bacterial effector polypeptide or fragment thereof. The first and second bacterial effector polypeptides can be different, that is they can recognize a different molecular targets or modulate different inflammatory pathways. In an embodiment, the protein transduction domain and the set of paired peptides can be a fusion protein. The fusion protein can include one or more linkers. The protein transduction domain can be a YopM protein transduction domain, an SspH1 protein transduction domain, or an IpaH protein transduction domain. The first bacterial effector polypeptide or fragment thereof can be a polypeptide selected from the group consisting of NleE, NleC, NleD, NleB, NleH, YopM, YopE, YopH, YopJ, YopP, SspH1, OspG, OspF, IpaH9.8, IpaH1.4, IpaH2.5, IpaH4.5, IpaH7.8 and SlrP, and the second bacterial effector polypeptide or fragment thereof can be a polypeptide selected from the group consisting of NleE, NleC, NleD, NleB, NleH, YopM, YopE, YopH, YopJ, YopP, SspH1, OspG, OspF, IpaH9.8, IpaH1.4, IpaH2.5, IpaH4.5, IpaH7.8 and SlrP. In some embodiments, the first bacterial effector polypeptide or fragment thereof can be a polypeptide having 90% sequence identity to an amino acid sequence set forth in the group consisting of SEQ ID NOs 3, 89, 42, 44, 46, 48, 50, 52, 54, 56, 58, 60, 62, 64, 66, 68, 70, 72, 74, 76, 78, and 79 and the second bacterial effector polypeptide or fragment thereof can be a polypeptide having 90% sequence identity to an amino acid sequence set forth in the group consisting of SEQ ID NOs.3, 89, 42, 44, 46, 48, 50, 52, 54, 56, 58, 60, 62, 64, 66, 68, 70, 72, 74, 76, 78, and 79. In some embodiments, the first bacterial effector polypeptide or fragment thereof can be a YopM polypeptide or a fragment thereof and the second bacterial effector polypeptide or fragment thereof can be an NLeE polypeptide or a fragment thereof. In some embodiments, the fusion protein can have an amino acid sequence forth in SEQ ID NO. 10, 13, 16, 19, 22, or 24.

Also provided¶ are fusion proteins comprising a set of paired peptides wherein the set of paired peptides comprises a first bacterial effector polypeptide or fragment thereof linked to a second bacterial effector polypeptide or fragment thereof. The first and second bacterial effector polypeptides can be different, that is they can recognize a different molecular targets or modulate different inflammatory pathways. The fusion protein can include one or more linkers. The first bacterial effector polypeptide or fragment thereof can be a polypeptide selected from the group consisting of NleE, NleC, NleD, NleB, NleH, YopM, YopE, YopH, YopJ, YopP, SspH1, OspG, OspF, IpaH9.8, IpaH1.4, IpaH2.5, IpaH4.5, IpaH7.8 and SlrP, and the second bacterial effector polypeptide or fragment thereof can be a polypeptide selected from the group consisting of NleE, NleC, NleD, NleB, NleH, YopM, YopE, YopH, YopJ, YopP, SspH1, OspG, OspF, IpaH9.8, IpaH1.4, IpaH2.5, IpaH4.5, IpaH7.8 and SlrP. In some embodiments, the first bacterial effector polypeptide or fragment thereof can be a polypeptide having 90% sequence identity to an amino acid sequence set forth in the group consisting of SEQ ID NOs 3, 89, 42, 44, 46, 48, 50, 52, 54, 56, 58, 60, 62, 64, 66, 68, 70, 72, 74, 76, 78, and 79 and the second bacterial effector polypeptide or fragment thereof can be a polypeptide having 90% sequence identity to an amino acid sequence set forth in the group consisting of SEQ ID NOs.3, 89, 42, 44, 46, 48, 50, 52, 54, 56, 58, 60, 62, 64, 66, 68, 70, 72, 74, 76, 78, and 79. In some embodiments, the first bacterial effector polypeptide or fragment thereof can be a YopM polypeptide or a fragment thereof and the second bacterial effector polypeptide or fragment thereof can be an NLeE polypeptide or a fragment thereof. In some embodiments, the fusion protein comprising a set of paired peptides can have an amino acid sequence as set forth in SEQ ID NO. 80, 81, 82, 83, 84, 85, 86, 87, or 88.

Also provided are nucleic acids encoding a set of paired peptides, wherein the set of paired peptides is linked to a protein transduction domain, and wherein the set of paired peptides comprises a first bacterial effector polypeptide or fragment thereof linked to a second bacterial effector polypeptide or fragment thereof. Also provided are nucleic acids encoding fusion proteins comprising a set of paired peptides wherein the set of paired peptides comprises a first bacterial effector polypeptide or fragment thereof linked to a second bacterial effector polypeptide or fragment thereof. The nucleic acids can be contained within a vector, which can be expressed in a host cell. In one aspect, the compositions comprising a set of paired peptides can be formulated as pharmaceutical compositions.

Also provided are methods of treating a subject having or at risk for an inflammatory disorder, by administering to the subject a therapeutically effective amount of a pharmaceutical composition comprising the set of paired peptides. The inflammatory disorder can be a gastrointestinal disorder including inflammatory bowel disease, Crohn's disease and the ileocolitis, ileocecal, jeunoileitis, and gastroduodenal subtypes of-Crohn's disease, and ulcerative colitis. The inflammatory disorder can also be a skin disorder.

Also provided are articles of manufacture, e.g., a kit. The kit can include measured amount of one or more of the compositions of the paired peptides and one or more items selected from the group consisting of packaging material, a package insert comprising instructions for use, a sterile fluid, and a sterile container.

In one aspect, a composition comprises in a pharmaceutically acceptable carrier or excipient or formulation a first construct comprising a selected immunomodulatory effector protein or functional equivalent thereof that targets a first functional domain, optionally linked covalently or non-covalently to a selected protein transduction domain (PTD) or penetrating peptide (CPP). In one embodiment, the composition further comprises an additional construct comprising a different effector protein or a functional equivalent thereof that targets an additional functional domain, optionally linked to the same PTD or CPP or to an additional PTD or CPP. In one embodiment, a composition comprises multiple first and additional constructs. In another embodiment, the constructs are further associated with targeting moieties directing delivery of the constructs to a selected cell or tissue.

In another aspect, a recombinant polypeptide comprises a first construct comprising a selected immunomodulatory effector protein or functional equivalent thereof that targets a first functional domain, optionally linked covalently or non-covalently to a selected protein transduction domain (PTD) or penetrating peptide (CPP) and an additional construct comprising a different effector protein or a functional equivalent thereof that targets an additional functional domain, optionally linked to the same PTD or CPP or to an additional PTD or CPP. The first construct is linked covalently or non-covalently to one or more of the additional constructs in a single polypeptide. In another embodiment, the polypeptide comprises an optional linker amino acid sequence interposed between each first and additional construct. In another embodiment, the polypeptide is further associated with targeting moieties directing delivery of the polypeptide to a selected cell or tissue.

In another aspect, a recombinant nucleic acid molecule is provided which encodes one of the constructs or polypeptides described herein. These nucleic acid molecules can be further associated with regulatory sequences for expressing the constructs in vivo or in vitro.

In a further aspect, a pharmaceutical or cosmeceutical composition comprises as an active agent a polypeptide as described above, or a mixture of constructs as described above in a formulation suitable for delivery of the active agent into and through the layers of the skin. In one embodiment, the formulation contains a CAGE solvent (defined below) or other components suitable for topical administration.

In yet another aspect, a pharmaceutical or cosmeceutical composition comprises as an active agent a polypeptide as described above, or a mixture of constructs as described above in a formulation suitable for delivery to a selected cell or tissue.

In still other aspects, methods for making the compositions, constructs, polypeptides and nucleic acid molecules are provided.

In yet a further aspect, a method for treating or ameliorating or suppressing an inflammatory response comprises administering to a subject in need thereof a composition, construct, polypeptide or nucleic acid molecule described herein.

Still other aspects and advantages of these compositions and methods are described further in the following detailed description of the preferred embodiments thereof.

BRIEF DESCRIPTION OF THE DRAWINGS

These and other features and advantages of the present invention will be more fully disclosed in, or rendered obvious by, the following detailed description of the preferred embodiment of the invention, which is to be considered together with the accompanying drawings wherein like numbers refer to like parts and further wherein:

FIG. 1 is a schematic of bacterial effector constructs.

FIG. 6 is a schematic of the cloning strategy for YopM PTD-NleE VVT No Linker, PAPA Linker, GSGS Linker and for Mutant R107A.

FIG. 28 shows the amino acid sequence of NleE SEQ ID NO: 1.

FIG. 29 shows the publicly available UniProt P17778 amino acid sequence of YopM SEQ ID NO: 2.

DETAILED DESCRIPTION OF THE PREFERRED EMBODIMENT

Figure 2:
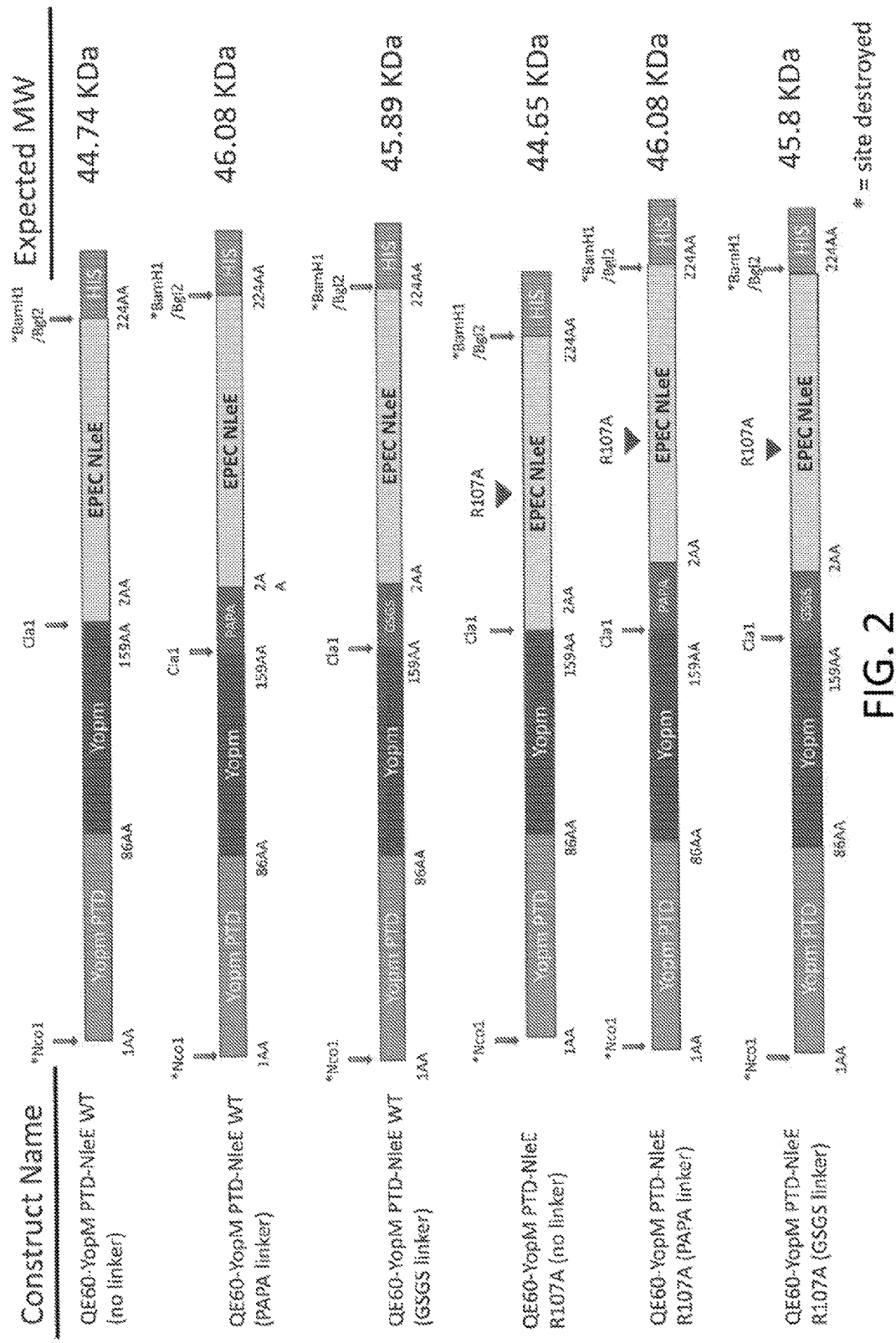
FIG. 2 is a schematic of bacterial effector constructs.

This description of preferred embodiments is intended to be read in connection with the accompanying drawings, which are to be considered part of the entire written description of this invention. The drawing figures are not necessarily to scale and certain features of the invention may be shown exaggerated in scale or in somewhat schematic form in the interest of clarity and conciseness. In the description, relative terms such as “horizontal,” “vertical,” “up,” “down,” “top” and “bottom” as well as derivatives thereof (e.g., “horizontally,” “downwardly,” “upwardly,” etc.) should be construed to refer to the orientation as then described or as shown in the drawing figure under discussion. These relative terms are for convenience of description and normally are not intended to require a particular orientation. Terms including “inwardly” versus “outwardly,” “longitudinal” versus “lateral” and the like are to be interpreted relative to one another or relative to an axis of elongation, or an axis or center of rotation, as appropriate. Terms concerning attachments, coupling and the like, such as “connected” and “interconnected,” refer to a relationship wherein structures are secured or attached to one another either directly or indirectly through intervening structures, as well as both movable or rigid attachments or relationships, unless expressly described otherwise. The term “operatively connected” is such an attachment, coupling or connection that allows the pertinent structures to operate as intended by virtue of that relationship. When only a single machine is illustrated, the term “machine” shall also be taken to include any collection of machines that individually or jointly execute a set (or multiple sets) of instructions to perform any one or more of the methodologies discussed herein. In the claims, means-plus-function clauses, if used, are intended to cover the structures described, suggested, or rendered obvious by the written description or drawings for performing the recited function, including not only structural equivalents but also equivalent structures.

Technical and scientific terms used herein have the same meaning as commonly understood by one of ordinary skill in the art to which this invention belongs and by reference to published texts, which provide one skilled in the art with a general guide to many of the terms used in the present application. The definitions contained in this specification are provided for clarity in describing the components and compositions herein and are not intended to limit the claimed invention.

The present invention is based in part on the inventors' finding that combinations of bacterial effector polypeptides can have synergistic immunomodulatory activity. Many bacterial pathogens, including enteropathogenic *Escherichia coli* (EPEC), enterohemorrhagic *E. coli*, and *Shigella*, utilize a type III secretion system (T3SS) to deliver multiple virulence proteins directly into host cells. These virulence proteins, also referred to as effector proteins, are produced by bacteria during the infection of a eukaryotic host. The effector proteins down-regulate the host's immune system, typically at the site of the infection. Thus, effector proteins that target specific inflammatory pathways can function as immunomodulators, for example, in the treatment of inflammatory disorders. The inventors have found that combinations of effector proteins that target multiple inflammatory pathways produced augmented immunomodulatory effects.

Accordingly, the invention features compositions and methods that are useful for the treatment of inflammatory disorders. The compositions can include fusion proteins comprising bacterial effector polypeptides or a fragment of a bacterial effector polypeptide. More specifically, the compositions can include a set of paired peptides configured as a first bacterial effector polypeptide or a fragment thereof and a second bacterial effector polypeptides or a fragment thereof. For ease of reading, we will not repeat the phrase “or a fragment thereof” on every occasion. It is to be understood that where we refer to a first bacterial effector polypeptide, we refer to the first bacterial like and effector polypeptide or a fragment thereof. Similarly, it is to be understood that where we refer to a second bacterial effector polypeptide, we refer to the second bacterial effector polypeptide or a fragment thereof. Also featured are compositions comprising a set of paired peptides configured as a first bacterial effector polypeptide or a fragment thereof and a second bacterial effector polypeptides or a fragment thereof, and linked to a protein transduction domain. The methods can include a method of treating a subject at risk for or having an inflammatory disorder.

The compositions and methods described herein deliver a combinatorial construct of small recombinant protein effectors that directly target cellular pathways involved in inflammation, e.g., the NFKB pathway activated in skin inflammation. As described in detail below, the delivery of a recombinant construct comprising one or multiple effector proteins linked or fused to a PTD or CPP is useful to treat inflammation. Still other embodiments include the association of an optional targeting moiety, directing the construct to a specific cell or tissue type, with the effector protein and/or formulation in a topical carrier. While these compositions and methods of treatment have a number of advantages, a significant advantage is that the protein effectors used are not able to enter into the circulation. In one embodiment, as discussed in detail below, the compositions and methods involve the use of NleE incorporated into a cream or oil formulation that reduces skin inflammation and may be widely used for many applications, both as a cosmetic beauty crème to reduce redness and irritation and as a treatment of a disease or cause of skin irritation.

The present compositions and methods using multiple e.g., NFkB/MAPK inhibitors, for treatment of inflammatory responses (e.g., pain, redness, swelling, heat) is based upon the fact that inflammation caused by infection, injury, autoimmunity, sunburn, aging, etc is detected at the cell membrane. Signals that are received by the skin cell are funneled thru the NFKB (sometimes MAPK) pathway. This is a relay mechanism in the cell that must be highly regulated. Shutting off the NFKB pathway is the key to controlling skin inflammation. Naturally occurring bacterial effector proteins (e.g., NleE, YopM, SSPH1) are very potent inhibitors of the NFKB system. Their sole target and purpose is to dampen the inflammatory response.

As described herein, when these bacterial proteins are recombinantly engineered into a selected polypeptide and delivered to inflamed skin via fusion with a PTD/CPP and optional targeting moiety, they abolish the inflammatory response. The combination of two or more effector proteins, each with a different substrate in the cell, may be combinatorially fused together in a single polypeptide. In some embodiments, such combination achieves a synergistic effect, which is a significant improvement in activity beyond that accomplished by delivery of a single effector.

The bacterial effector, NleE, is characterized by specificity, potency and efficiency in shutting down NFkB and hence inflammatory reactions. The presence of NleE and/or a combination with other bacterial effectors in an anti-inflammatory formulation has a number of advantages. Among the advantages are extremely high substrate specificity, which results in only a very low, if any, chance of off-target effects and toxicity for therapeutic use. In one embodiment, fusing PTDs to NleE and its related effectors is useful to deliver the effector to sites of inflammation. We and others have shown that a number of recombinant effector proteins, when fused to PTDs can indeed cross the cell and tissue boundary and be taken up by cells resulting in NFkB/JNK/p38 pathway inhibition The methods and compositions described below provide combinations of multiple effectors, or single or multiple effector(s) fused with a PTD, or single or multiple effector(s) fused with a targeting moiety, or single or multiple effector(s) fused with a PTD and a targeting moiety, in a chimeric recombinant protein, along with an emollient compound (such as CAGE) for use as a topical anti-inflammatory crème for many different ailments.

Compositions

Provided herein are compositions comprising engineered bacterial effector polypeptides for use in the treatment of inflammation. The engineered bacterial effector polypeptides can be configured as a set of paired peptides. More specifically, a set of paired peptides can be a construct comprising a first bacterial effector polypeptide or a fragment thereof and a second bacterial effector polypeptides or a fragment thereof. The set of paired peptides can be linked to one or more polypeptide sequences that facilitate intracellular delivery of the paired peptides, for example, a protein transduction domain (PTD) or a cell penetrating peptide (CPP).

Bacterial effector polypeptides. The first bacterial effector polypeptide and the second bacterial effector polypeptide can be a bacterial effector polypeptide selected from the exemplary bacterial effector polypeptides from a variety of bacteria as shown in Tables 1 and 2. Their enzymatic activity and host targets are also shown in Tables 1 and 2. Representative Uniprot or Genbank references for the polypeptides are shown in Tables 3 and 4. Additional amino acid sequences for, and nucleic acid sequences encoding, these bacterial effector polypeptides can be identified from databases such as UniProt, NCBI, GenBank and publications extant in the art.

TABLE 1

BACTERIAL T3SS EFFECTORS

| Effector | Bacteria | Intracellular Activity | Host Target |
|---|---|---|---|
| OspF | Shigella flexneri | Phosphothreonine lyase | ERK, p38 MAPKs |
| OspG | Shigella flexneri | Serine/threonine kinase | E2 ubiquitin ligases |
| NleH1 | EPEC-EHEC | Serine/threonine kinase | RPS3 |
| NleE/OspZ | EPEC-EHEC/ Shigella | Cysteine methylase | TAB2/NfKB |
| NleB | EPEC-EHEC | O-GlcNAc transferase | FADD, GAPDH, RIPK1, TRADD |
| NleC | EPEC-EHEC | Zinc metalloprotease | NFkB |
| YopH | Yersinia | Phosphotyrosine phosphatase | Akt/FAK |
| YopE | Yersinia | Rho GAP | Rho GTPases/ caspases |
| YopP/YopJ | Yersinia | Acetyltransferase | MAPKs |
| YopM | Yersinia | LRR motif | PKN/RSK |

TABLE 2

BACTERIAL T3SS E3 UBIQUITIN LIGASE EFFECTORS

| Type/ Family | E3 Ligase Factor | Bacteria | Intracellular Activity | Host Target |
|---|---|---|---|---|
| HECT | SopA | Salmonella typhimurium | Regulation of host inflammation | TRIM65/56 |
| | NleL | EPEC/EHEC | Formation of actin pedestal | Unknown |
| RING U-Box | NleG | EPEC/EHEC | Unknown | Unknown |
| | LubX | Legionella pneumophila | Regulation of another effector function | Cdh1, SidH |
| | Gob X | L. pneumophila | Unknown | Unknown |
| NEL | IpaH1A | Shigella flexneri | Inhibition of NF-Kb activation | HOIP |
| | IpaH2.5 | S. flexneri | Inhibition of NF-kB activation | HOIP |
| | IaH4.5 | S. flexneri | Inhibition of NF-kB and I-IFN activation | p65, TBK1 |
| | IpaH7.8 | S. flexneri | Induction of pyroptosis | GLMN |
| | IpaH9.8 | S. flexneri | Inhibition of NF-kB activation | NEMO |
| | IpaH0722 | S. flexneri | Inhibition of NF-kB activation | TRAF2 |
| | SspH1 | S. typhimurium | Inhibition of androgen receptor | PKN1 |
| | SspH2 | S. typhimurium | Promotion of IL-8 secretion | Nod1, SGT1 |
| | SlrP | S. typhimurium | Induction of host cell death | Trx |
| SidE family | SidC (SdcA) | L. pneumophila | Unknown | Unknown |

TABLE 3

Representative Amino Acid Sequences of Bacterial T3SS Effectors

| Effector | Bacteria | Host Target | UniProt or Genbank Reference ID |
|---|---|---|---|
| OspF | Shigella flexneri | ERK, p38 MAPKs | Q8VSP9 (OSPF_SHIFL) |
| OspG | Shigella flexneri | E2 ubiquitin ligases | Q99PZ6 (OSPG_SHIFL) |
| NleH1 | EPEC-EHEC | RPS3 | Q8X831 (Q8X831_ECO57) |
| NleE/OspZ | EPEC-EHEC/ Shigella | TAB2/NfKB | Q7DBA6 (Q7DBA6_ECO57) |
| NleB | EPEC-EHEC | FADD, GAPDH, RIPK1, TRADD | VEC94465.1 (Genbank) |
| NleC | EPEC-EHEC | NFkB | CBG88408.1 (Genbank) |
| YopH | Yersinia | Akt/FAK | P15273 (YOPH_YEREN) |
| YopE | Yersinia | Rho GTPases/caspases | P31492 (YOPE_YEREN) |
| YopP/YopJ | Yersinia | MAPKs | O34336 (YOPP_BACSU) |
| YopM | Yersinia | PKN/RSK | P17778 (YOPM_YERPE) |

TABLE 4

Representative Amino Acid Sequences of Bacterial T3ss E3 Ubiquitin Ligase Effectors

| E3 Ligase Factor | | | | |
|---|---|---|---|---|
| Type/ Family | Factor | Bacteria | Host Target | UniProt or Genbank Reference ID |
| HECT | SopA | Salmonella typhimurium | TRIM65/ 56 | Q8ZNR3 (SOPA_SALTY) |
| | NleL | EPEC/EHEC | Unknown | A0A0D6ZN92 (A0A0D6ZN92_ ECOLX) |
| RING | NleG | EPEC/EHEC | Unknown | A0A023YUN6 (A0A023YUN6_ ECOLX) |
| U-Box | LubX | Legionella pneumophila | Cdh1, SidH | Q5ZRQ0 (LUBX_LEGPH) |
| | Gob X | L. pneumophila | Unknown | |
| NEL | IpaH1.4 | Shigella flexneri | HOIP | A0A380D0I4 (A0A380D0I4_SHIFL) |
| | IpaH2.5 | S. flexneri | HOIP | Q99Q42 (Q99Q42_SHIFL) |
| | IaH4.5 | S. flexneri | p65, TBK1 | P18009 (IPA4_SHIFL) |
| | IpaH7.8 | S. flexneri | GLMN | P18014 (IPA7_SHIFL) |
| | IpaH9.8 | S. flexneri | NEMO | Q8VSC3 (IPA9_SHIFL) |
| | IpaH0722 | S. flexneri | TRAF2 | |
| | SspH1 | S. typhimurium | PKN1 | D0ZVG2 (SSPH1_SALT1) |
| | SspH2 | S. typhimurium | Nod1, SGT1 | P0CE12 (SSPH2_SALTY) |
| | SlrP | S. typhimurium | Trx | Q8ZQQ2 (SLRP_SALTY) |
| SidE family | SidC (SdcA) | L. pneumophila | Unknown | Q6RCR3 (Q6RCR3_LEGPN) |

Thus a bacterial effector peptide can be an SspH1; SspH2; SlrP, IpaH1.4, IpaH2.5, IpaH3, IpaH4.5, IpaH7.8, IpaH9.8, NleE, NleC; NleD; NleB; NleH, NleH1, YopM; YopE; YopH; YopJ; YopP; OspG; OspF; OspZ; OspI, SopE; SopB; SopE2; SipA; AvrA; SseL; EspT; or a TiR polypeptide.

In some embodiments, the bacterial effector polypeptide can have an amino acid sequence at least 90% identical to an amino acid sequence set forth in any of SEQ ID NOs. 3, 89, 42, 44, 46, 48, 50, 52, 54, 56, 58, 60, 62, 64, 66, 68, 70, 72, 74, 76, 78, and 79. In some embodiments, the bacterial effector polypeptide have an amino acid sequence as set forth in any of SEQ ID NOs. 3, 89, 42, 44, 46, 48, 50, 52, 54, 56, 58, 60, 62, 64, 66, 68, 70, 72, 74, 76, 78, and 79.

The term "type III secretion system or T3SS" refers to a highly specialized molecular needle construct containing a Yersiniae injectisome spanning the bacterial membranes, Yersinia outer protein (Yop) effectors and Yop translocators needed to deliver the effectors across the membrane (Camelis G R., Int J Med Microbial. 2002 February; 291(6-7): 455-62). Pathogenic Yersiniae require this T3SS to survive and replicate extracellularly within lymphoid tissues of their animal or human hosts. See, also, U.S. Pat. No. 8,840,901.

The term "immodulatory effector protein" refers to small proteins, generally bacterial in origin, that suppress the human innate immune system during infection. These effector proteins activate the NFkB, JNK, and p38 signaling pathways during infection. These effector proteins are often secreted into the cells targeted for infection by T3SS. Once inside the cell, each effector protein targets a single host protein required for innate immunity, which it inactivates using a myriad of mechanisms including acetylation, methylation, action of phosphatases on P04 proteins, induced protein degradation etc.

All T3SS bacterial effector proteins are very small, globular, highly stable, highly catalytic, have high substrate specificity, bind co-factors very tightly, and can be injected into the cell in denatured form. They modify every substrate molecule in the cell. For instance, the EPEC effector NleE is a cysteine methyltransferase which has a single target in the cell, i.e., the TAB2 scaffold protein in the NFkB pathway. EPEC are mildly infective gut bacteria that attach to colon cells and directly inject virulence proteins thru a T3SS to control innate immune pathways as a survival strategy. During EPEC infection, the injected NleE protein methylates every molecule of cellular TAB2; thereby completely shutting off NFkB signaling, as described in Yao, Q. et al., Structure and Specificity of the Bacterial Cysteine Methyltransferase Effector NleE Suggests a Novel Substrate in Human DNA Repair Pathway., PLoS Pathogens (November 2014) 10(11):e1004522; doi:10.1371/journal.ppat.1004522.

Still another effector protein is YopM, discussed in U.S. Pat. No. 8,840,901 and Rüter, C & Hardwidge, P R, 'Drugs from Bugs': bacterial effector proteins as promising biological (immune-) therapeutics. FEMS Microbiol Lett 351 (December 2013/January 2014) 126-132.

In some embodiments, the first and second bacterial effector polypeptides are different. For example, they can have different amino acid sequences, different structures, different functions, different molecular targets, or have non-overlapping redundant roles in inhibiting an inflammatory pathway, for example, the NFkB, JNK, p38, and STING pathways.

Also included as effectors or effector proteins of the compositions and methods described herein are functional equivalents of the proteins described above. By the term "functional equivalent" is meant any amino acid sequence or modification thereof that has the same targeting and immune suppressing function of the naturally occurring effector protein. In one embodiment, such functional equivalents can have modifications of one or more amino acids from the known sequences. In one embodiment, such functional equivalents can be a smaller fragment of the known sequences. In one embodiment, such functional equivalents can be a derivative of the naturally occurring sequences or be derived from other than human sources. In one embodiment, such functional equivalents can be altered by chemical modification or be altered by recombinant production to be associated with sequences with which the effector proteins are not associated in nature. Similarly, chemical or structural changes or fragments of the nucleic acid sequences that encode the effector proteins are also considered functional equivalents herein.

The paired peptides can be joined by a linker. A linker can be any reagent, molecule or macromolecule that connects the first and second bacterial effector polypeptides such that the linker does not substantially alter the physiological activity of the effector polypeptides. A linker can be a peptide bond. That is, the first and second bacterial effector polypeptides or fragments thereof can be a fusion polypeptide comprising one or more amino acid segments from the first bacterial effector polypeptide and one or more amino acid segments from second bacterial effector polypeptide. The term "amino acid segment" as used herein refers to a contiguous stretch of amino acids within a polypeptide. For example, the amino acid residues 30 to 40 within a 100 amino acid polypeptide would be considered an amino acid segment. An amino acid segment can be a length greater than eight amino acid residues (e.g., greater than about nine, ten, 15, 20, 25, 30, 40, 50, 75, 100, 150, 200, 500, 1000, or more amino acid residues). In some embodiments, an amino acid segment can have a length less than 1000 amino acid residues (e.g., less than 500, less than 400, less than 350, less than 300, less than 200, or less than 100 amino acid residues). In other embodiments, an amino acid segment can have a length from about 20 to about 200 amino acid residues (e.g., about 30 to about 180 amino acid residues, or about 40 to about 150 amino acid residues).

The amino acid segments of the first bacterial effector polypeptide can be contiguous with the amino acid segments of the second or they can be separated by amino acids inserted as a structural spacer. A spacer segment can be one or more amino acids. The one or more amino acids can include amino acids that are the same or that are different. For example, a spacer can be a repeating series of a neutral amino acid (e.g., glycine, alanine, valine, isoleucine or leucine) ranging in number from 1 to 10 or more (e.g., 1, 2, 3, 4, 5, 6, 7, 8, 9, 10 or more). Another example of a spacer configuration can be a series of interspersed amino acids that may be neutral (e.g., glycine-alanine-glycine-alanine-glycine- alanine, or glycine-glycine-glycine-valine-valine-valine) or charged amino acids (e.g., glutamate- glutamate-glutamate-arginine-arginine-arginine, or aspartate-lysine-aspartate-lysine-aspartate-lysine) or amino acids with other functional groups (e.g., proline-proline-proline-serine-serine-serine or tyrosine-glutamine-cysteine-methionine-tryptophan) ranging in number from 1 to 10 or more (e.g., 1, 2, 3, 4, 5, 6, 7, 8, 9, 10 or more). In another embodiment, a spacer configuration can be a sequence of amino acids derived from a naturally occurring protein such as the hinge region joining the heavy chain CHI and CH2 domains of immunoglobulin G. In some embodiments, the linker can be a GSGS linker (SEQ ID NO. 92) or a PAPA linker (SEQ ID NO. 91). In some embodiments, the fusion protein comprising a set of paired peptides can exclude a linker.

A fusion protein can be produced in vitro by continuous peptide synthesis according to standard chemical methods know to those in the art. Synthetic polypeptides can also be purchased from commercial sources. A fusion protein can also be produced by recombinant DNA techniques. Nucleic acid segments encoding the first bacterial effector polypeptide can be operably linked in the same open reading frame to nucleic acid sequences encoding the second bacterial effector polypeptide in a vector that includes the requisite regulatory elements, e.g., promoter sequences, transcription initiation sequences, and enhancer sequences, for expression in prokaryotic or eukaryotic cells.

The paired peptide constructs can include a combination of any of an SspH1; SspH2; SlrP; IpaH1.4; IpaH2.5; IpaH3; IpaH4.5, IpaH7.8; IpaH9.8, NleE, NleC; NleD; NleB; NleH, NleH1; YopM; YopE; YopH; YopJ; YopP; OspG; OspF; OspZ; OspI; SopE; SopB; SopE2; SipA; AvrA; SseL; EspT; or a TiR polypeptide. Thus, the first bacterial effector polypeptide can be a polypeptide selected from the group consisting of NleE, NleC, NleD, NleB, NleH, YopM, YopE, YopH, YopJ, YopP, SspH1, OspG, OspF, IpaH9.8, IpaH1.4, IpaH2.5, IpaH4.5, IpaH7.8 and SlrP, and the second bacterial effector polypeptide can be a polypeptide selected from the group consisting of NleE, NleC, NleD, NleB, NleH, YopM, YopE, YopH, YopJ, YopP, SspH1, OspG, OspF, IpaH9.8, IpaH1.4, IpaH2.5, IpaH4.5, IpaH7.8 and SlrP.

In some embodiments, the paired peptide construct can include a first bacterial effector polypeptide or fragment thereof is a YopM polypeptide or a fragment thereof or an NLeE polypeptide or a fragment thereof and a second bacterial effector polypeptide or fragment thereof is a YopM polypeptide or a fragment thereof or an NLeE polypeptide or a fragment thereof. In some embodiments, the first bacterial effector polypeptide or fragment thereof is a YopM polypeptide or a fragment thereof and the second bacterial effector polypeptide or fragment thereof is an NLeE polypeptide or a fragment thereof.

In some embodiments, the paired peptide constructs can be configured as summarized in Table 5 below.

TABLE 5

Paired Peptide Fusion Constructs

| Construct name | Effector 1 | Linker | Effector 2 | SEQ ID NO |
|---|---|---|---|---|
| YopM PTD-NleE (No linker) | YopM (L-rich) | — | EPEC NLeE | 80 |
| YopM PTD-NleE (GSGS linker) | YopM (L-rich) | GSGS | EPEC NLeE | 82 |
| YopM PTD-NleE (PAPA linker) | YopM (L-rich) | PAPA | EPEC NLeE | 81 |

In some embodiments, paired peptide fusion protein can have an amino acid sequence is at least 85% identical to the sequence set forth in SEQ ID NO. 80, 81, 82, 83, 84, 85, 86, 87, or 88. In some embodiments, paired peptide fusion protein can have an amino acid sequence is at least 90% identical to the sequence set forth in SEQ ID NO. 80, 81, 82, 83, 84, 85, 86, 87, or 88. In some embodiments, paired peptide fusion protein can have an amino acid sequence is at least 95% identical to the sequence set forth in SEQ ID NO. 80, 81, 82, 83, 84, 85, 86, 87, or 88. In some embodiments, paired peptide fusion protein can have an amino acid sequence is at least 99% identical to the sequence set forth in SEQ ID NO. 80, 81, 82, 83, 84, 85, 86, 87, or 88. In some embodiments, the paired peptide fusion protein can have an amino acid sequence as set forth in SEQ ID NOs. 80, 81, 82, 83, 84, 85, 86, 87, or 88.

Protein transduction domains. The set of paired peptides can be linked to one or more polypeptide sequences that facilitate intracellular delivery of the paired peptide. The terms "protein transduction domain (PTDs)" and/or "cell-penetrating peptide (CPPs)" refers to powerful sequences that allow intracellular delivery of conjugated cargoes to modify cell behavior. These small peptides can transport a wide variety of biologically active conjugates into the cell. Heterologous CPP coding sequences are added to effectors or effector-fusions to facilitate cellular uptake of the proteins into cells and tissues, including use of endogenous CPPs encoded in native effector proteins. This includes addition of CPP sequences or modules to the effector via chemical crosslinking, attachment to a nano-particle or other scaffold chemically or via PPIs for the purpose of transporting the effector across tissue and cell membranes. Among useful PTD or CPPs for the present methods and compositions are those known and identified in the art, including, without limitation, HIV Tat protein basic domain, (HIV Tat amino acids 48-60 or 49-57), poly-Arg or polyLys, penetratin, MPG, Pep-1, MAP, and transportan. See, e.g., Table 1 of Guidotti, G. et al, Trends in Pharmacological Sciences (April 2017), 38(4):406-424, which includes additional examples of CPPs and sequences origins and properties. Other CPPs are described in Norkowski, S. et al, Bacterial LPX motif-harboring virulence factors constitute a species-spanning family of cell-penetrating effectors, Cellular and Molecular Life Sciences (December 2017) doi.org/10.1007/s00018-017-2733-4, which described prototypes of such bacteria-derived cell-penetrating effectors (CPEs) including the *Yersinia enterocolitica*-derived YopM, the *Salmonella typhimurium* effector SspH1, and the *Shigella* IpaH proteins. Still other protein transporter molecules include those previously described in Dixon, J E et al, Proc. Natl Acad Sci, (January 2016), E291-299; as well as synthetic protein mimics described by Tezgel, A O et al BioMacromolecules (2017) 16:819-825. See, also, Bolhassani, A. et al, In vitro and in vivo delivery of therapeutic proteins using cell penetrating peptides. Peptides (November 2016), 87:50-63, which discusses useful CPPs for the present compositions and methods, including without limitation, covalent bonded CPPs, such as Poly-Arg peptides, Tat and VP22, df Tat, Cyclic CPPs, IMT-P8 (particularly useful for transdermal delivery), seven arginine (R7) and Streptolysin O (SLO)-mediated systems and elastin like polypeptide, CPP-adaptor system, 1,2-Benzisothiazolin-3-one (BIT) and Tat, activatable cell-penetrating peptides, LDP12, M918, BR2, peptide for ocular delivery (POD), native protein independent of R11-CPP, Poly-arginine/Tat and Tat-PTD among others. Also identified are non-covalent bonded CPPs such as Pep-1, CADY-2, R8 and azo-R8, Penetratin, HR9 and IR9 peptides and pVEC. All of these documents are incorporated by reference herein for detailed descriptions of known CPPs and PTDs. It is also anticipated that novel PTD/CPPs will prove useful with the compositions described herein.

Exemplary protein transduction domains include a YopM protein transduction domain, an SspH1 protein transduction domain, or an IpaH protein transduction domain. A useful YopM protein transduction domain can have an amino acid sequence as set forth in SEQ ID NO 5.

In some embodiments, a fusion protein comprising a set of paired peptides linked to a protein transduction domain can have an amino acid sequence is at least 85% identical to the sequence set forth in SEQ ID NO. 10, 13, 16, 19, 22, or 24. In some embodiments, paired peptide fusion protein can have an amino acid sequence is at least 90% identical to the sequence set forth in SEQ ID NO. 10, 13, 16, 19, 22, or 24. In some embodiments, paired peptide fusion protein can have an amino acid sequence is at least 95% identical to the sequence set forth in SEQ ID NO. 10, 13, 16, 19, 22, or 24. In some embodiments, paired peptide fusion protein can have an amino acid sequence is at least 99% identical to the sequence set forth in SEQ ID NO. 10, 13, 16, 19, 22, or 24. In some embodiments, the paired peptide fusion protein can have an amino acid sequence as set forth in SEQ ID NOs. 10, 13, 16, 19, 22, or 24.

Polypeptides. We tend to use the term "protein" to refer to longer or larger amino acid polymers, and we tend to use the term "polypeptide" to refer to shorter sequences or to a chain of amino acid residues within a larger molecule (e.g., within a fusion protein) or complex. Both terms, however, are meant to describe an entity of two or more subunit amino acids, amino acid analogs, or other peptidomimetics, regardless of post-translational modification (e.g., amidation, phosphorylation or glycosylation). The subunits can be linked by peptide bonds or other bonds such as, for example, dicysteine, ester or ether bonds. The terms "amino acid" and "amino acid residue" refer to natural and/or unnatural or synthetic amino acids, which may be D- or L-form optical isomers. Full-length proteins, analogs, mutants, and fragments thereof are encompassed by this definition.

The amino acid sequence of the bacterial effector polypeptides disclosed herein can be identical to the wild-type sequences of appropriate components. Alternatively, any of the components can contain mutations such as deletions, additions, or substitutions. All that is required is that the variant bacterial effector polypeptide have at least 5% (e.g., 10%, 20%, 30%, 40%, 50%, 60%, 70%, 80%, 90%, 95%, 99%, 100%, or even more) of the ability of the bacterial effector polypeptide containing only wild-type sequences to specifically bind the target. Substitutions will preferably be conservative substitutions. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine.

Variant bacterial effector polypeptides, e.g., those having one or more amino acid substitutions relative to a native bacterial effector polypeptide amino acid sequence, can be prepared and modified as described herein. Amino acid substitutions can be made, in some cases, by selecting substitutions that do not differ significantly in their effect on maintaining (a) the structure of the peptide backbone in the area of the substitution, (b) the charge or hydrophobicity of the molecule at the target site, or (c) the bulk of the side chain. For example, naturally occurring residues can be divided into groups based on side-chain properties: (1) hydrophobic amino acids (norleucine, methionine, alanine, valine, leucine, and isoleucine); (2) neutral hydrophilic amino acids (cysteine, serine, and threonine); (3) acidic amino acids (aspartic acid and glutamic acid); (4) basic amino acids (asparagine, glutamine, histidine, lysine, and arginine); (5) amino acids that influence chain orientation (glycine and proline); and (6) aromatic amino acids (tryptophan, tyrosine, and phenylalanine) Substitutions made within these groups can be considered conservative substitutions. Non-limiting examples of useful substitutions include, without limitation, substitution of valine for alanine, lysine for arginine, glutamine for asparagine, glutamic acid for aspartic acid, serine for cysteine, asparagine for glutamine, aspartic acid for glutamic acid, proline for glycine, arginine for histidine, leucine for isoleucine, isoleucine for leucine, arginine for lysine, leucine for methionine, leucine for phenylalanine, glycine for proline, threonine for serine, serine for threonine, tyrosine for tryptophan, phenylalanine for tyrosine, and/or leucine for valine. Variant bacterial effector polypeptides having conservative and/or non-conservative substitutions (e.g., with respect to any of SEQ ID NOS: 3, 89, 42, 44, 46, 48, 50, 52, 54, 56, 58, 60, 62, 64, 66, 68, 70, 72, 74, 76, 78, 79, 10, 13, 16, 19, 22, or 24), as well as fragments of any of SEQ ID NOS: 3, 89, 42, 44, 46, 48, 50, 52, 54, 56, 58, 60, 62, 64, 66, 68, 70, 72, 74, 76, 78, 79, 10, 13, 16, 19, 22, or 24, 80, 81, 82, 83, 84, 85, 86, 87, or 88, fragments of variants of any of SEQ ID NOS: 3, 89, 42, 44, 46, 48, 50, 52, 54, 56, 58, 60, 62, 64, 66, 68, 70, 72, 74, 76, 78, and 79. 10, 13, 16, 19, 22, or 24, 80, 81, 82, 83, 84, 85, 86, 87, or 88 and polypeptides comprising any of SEQ ID NOS: 3, 89, 42, 44, 46, 48, 50, 52, 54, 56, 58, 60, 62, 64, 66, 68, 70, 72, 74, 76, 78, and 79, 10, 13, 16, 19, 22, or 24, 80, 81, 82, 83, 84, 85, 86, 87, or 88, variants or fragments of any of SEQ ID NOS: 3, 89, 42, 44, 46, 48, 50, 52, 54, 56, 58, 60, 62, 64, 66, 68, 70, 72, 74, 76, 78, and 79, 10, 13, 16, 19, 22, or 24, 80, 81, 82, 83, 84, 85, 86, 87, or 88, or fragments of variants of any of SEQ ID NOS: 3, 89, 42, 44, 46, 48, 50, 52, 54, 56, 58, 60, 62, 64, 66, 68, 70, 72, 74, 76, 78, and 79, 10, 13, 16, 19, 22, or 24, 80, 81, 82, 83, 84, 85, 86, 87, or 88, can be screened for biological activity using suitable assays, including those described herein. For example, the activity of a bacterial effector polypeptide, for example, NLeE or a mutant or fragment thereof, can be evaluated in vitro by assaying for methylase activity or in cell based systems to characterize its effect on cytokine release.

In some embodiments, a bacterial effector polypeptide can comprise an amino acid sequence as set forth in SEQ ID NOS: 3, 89, 42, 44, 46, 48, 50, 52, 54, 56, 58, 60, 62, 64, 66, 68, 70, 72, 74, 76, 78, and 79, 10, 13, 16, 19, 22, or 24, 80, 81, 82, 83, 84, 85, 86, 87, or 88, but with a particular number of amino acid substitutions. For example, a bacterial effector polypeptides can have the amino acid sequence of any one of SEQ ID NOS: 3, 89, 42, 44, 46, 48, 50, 52, 54, 56, 58, 60, 62, 64, 66, 68, 70, 72, 74, 76, 78, 79, 10, 13, 16, 19, 22, or 24, 80, 81, 82, 83, 84, 85, 86, 87, or 88, but with one, two, three, four, or five amino acid substitutions.

In some embodiments, a bacterial effector polypeptide as provided herein can include an amino acid sequence with at least 85% (e.g., 85%, 86%, 87%, 88%, 89%, 90%, 91%, 92%, 93%, 94%, 95%, 96%, 97%, 97.5%, 98%, 98.5%, 99.0%, 99.5%, 99.6%, 99.7%, 99.8%, 99.9%, or 100%) sequence identity to a region of a reference bacterial effector polypeptide sequence (e.g., SEQ ID NOS: 3, 89, 42, 44, 46, 48, 50, 52, 54, 56, 58, 60, 62, 64, 66, 68, 70, 72, 74, 76, 78, 79, 10, 13, 16, 19, 22, or 24, 80, 81, 82, 83, 84, 85, 86, 87, or 88). Methods of determining percent sequence identity are discussed below.

In some embodiments, a polypeptide provided herein can be a substantially pure polypeptide. As used herein, the term "substantially pure" with reference to a polypeptide means that the polypeptide is substantially free of other polypeptides, lipids, carbohydrates, and nucleic acid with which it is naturally associated. Thus, a substantially pure polypeptide is any polypeptide that is removed from its natural environment and is at least 60 percent pure or is any chemically synthesized polypeptide. A substantially pure polypeptide can be at least about 60, 65, 70, 75, 80, 85, 90, 95, or 99 percent pure. Typically, a substantially pure polypeptide will yield a single major band on a non-reducing polyacrylamide gel.

A variety of methods can be used to make a polypeptide including, for example, expression by prokaryotic systems, expression by eukaryotic systems, and chemical synthesis techniques. Exemplary methods for polypeptide purification purificinclude, without limitation, fractionation, centrifugation, and chromatography, e.g., gel filtration, ion exchange chromatography, reverse-phase HPLC and immunoaffinity purification.

A polypeptide can be modified by linkage to a polymer such as polyethylene glycol (PEG), or by fusion to another polypeptide such as albumin, for example. For example, one or more PEG moieties can be conjugated to a bacterial effector polypeptide or fusion protein via lysine residues. Linkage to PEG or another suitable polymer, or fusion to albumin or another suitable polypeptide can result in a modified bacterial effector polypeptide or fusion protein having an increased half life as compared to an unmodified bacterial effector polypeptide or fusion protein. Without being bound by a particular mechanism, an increased serum half life can result from reduced proteolytic degradation, immune recognition, or cell scavenging of the modified bacterial effector polypeptide or fusion protein. Methods for modifying a polypeptide by linkage to PEG (also referred to as "PEGylation") or other polymers include those set forth in U.S. Pat. No. 6,884,780; Cataliotti et al. ((2007) Trends Cardiovasc. Med. 17:10-14; Veronese and Mero (2008) BioDrugs 22:315-329; Miller et al. (2006) Bioconjugate Chem. 17:267-274; and Veronese and Pasut (2005) Drug Discov. Today 10:1451-1458, all of which are incorporated herein by reference in their entirety. Methods for modifying a polypeptide by fusion to albumin include those set forth in U.S. Patent Publication No. 20040086976, and Wang et al. (2004) Pharm. Res. 21:2105-2111, both of which are incorporated herein by reference in their entirety.

Nucleic acids. We may use the terms "nucleic acid" and "polynucleotide" interchangeably to refer to both RNA and DNA, including cDNA, genomic DNA, synthetic DNA, and DNA (or RNA) containing nucleic acid analogs, any of which may encode a polypeptide of the invention and all of which are encompassed by the invention. Polynucleotides can have essentially any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA) and portions thereof, transfer RNA, ribosomal RNA, siRNA, micro-RNA, ribozymes, cDNA, recombinant polynucleotides, branched polynucleotides, plasmids, vectors, isolated DNA of any sequence, isolated RNA of any sequence, nucleic acid probes, and primers, as well as nucleic acid analogs. In the context of the present invention, nucleic acids can encode a bacterial effector polypeptide, paired peptide fusion protein, or construct comprising a paired peptide fusion protein linked to a protein transduction domain.

An "isolated" nucleic acid can be, for example, a naturally-occurring DNA molecule or a fragment thereof, provided that at least one of the nucleic acid sequences normally found immediately flanking that DNA molecule in a naturally-occurring genome is removed or absent. Thus, an isolated nucleic acid includes, without limitation, a DNA molecule that exists as a separate molecule, independent of other sequences (e.g., a chemically synthesized nucleic acid, or a cDNA or genomic DNA fragment produced by the polymerase chain reaction (PCR) or restriction endonuclease treatment). An isolated nucleic acid also refers to a DNA molecule that is incorporated into a vector, an autonomously replicating plasmid, a virus, or into the genomic DNA of a prokaryote or eukaryote. In addition, an isolated nucleic acid can include an engineered nucleic acid such as a DNA molecule that is part of a hybrid or fusion nucleic acid. A nucleic acid existing among many (e.g., dozens, or hundreds to millions) of other nucleic acids within, for example, cDNA libraries or genomic libraries, or gel slices containing a genomic DNA restriction digest, is not an isolated nucleic acid.

Isolated nucleic acid molecules can be produced by in several ways. For example, polymerase chain reaction (PCR) techniques can be used to obtain an isolated nucleic acid containing a nucleotide sequence described herein, including nucleotide sequences encoding a polypeptide described herein. PCR can be used to amplify specific sequences from DNA as well as RNA, including sequences from total genomic DNA or total cellular RNA. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid.

Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >50-100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector.

Two nucleic acids or the polypeptides they encode may be described as having a certain degree of identity to one another. For example, a bacterial effector polypeptide and a biologically active variant thereof may be described as exhibiting a certain degree of identity. Alignments may be assembled by locating short sequences in the Protein Information Research (PIR) site (http://pir.georgetown.edu), followed by analysis with the "short nearly identical sequences" Basic Local Alignment Search Tool (BLAST) algorithm on the NCBI website (http://www.ncbi.nlm.nih.gov/blast).

As used herein, the term "percent sequence identity" refers to the degree of identity between any given query sequence and a subject sequence. For example, a bacterial effector polypeptide disclosed herein can be the query sequence and a fragment of a bacterial effector polypeptide can be the subject sequence. Similarly, a fragment of bacterial effector polypeptide can be the query sequence and a biologically active variant thereof can be the subject sequence.

To determine sequence identity, a query nucleic acid or amino acid sequence can be aligned to one or more subject nucleic acid or amino acid sequences, respectively, using the computer program ClustalW (version 1.83, default parameters), which allows alignments of nucleic acid or protein sequences to be carried out across their entire length (global alignment).

ClustalW calculates the best match between a query and one or more subject sequences and aligns them so that identities, similarities and differences can be determined. Gaps of one or more residues can be inserted into a query sequence, a subject sequence, or both, to maximize sequence alignments. For fast pair wise alignment of nucleic acid sequences, the following default parameters are used: word size: 2; window size: 4; scoring method: percentage; number of top diagonals: 4; and gap penalty: 5. For multiple alignments of nucleic acid sequences, the following parameters are used: gap opening penalty: 10.0; gap extension penalty: 5.0; and weight transitions: yes. For fast pair wise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The output is a sequence alignment that reflects the relationship between sequences. ClustalW can be run, for example, at the Baylor College of Medicine Search Launcher site (searchlauncher.bcm.tmc.edu/multi-align/multi-align.html) and at the European Bioinformatics Institute site on the World Wide Web (ebi.ac.uk/clustalw).

To determine a percent identity between a query sequence and a subject sequence, ClustalW divides the number of identities in the best alignment by the number of residues compared (gap positions are excluded), and multiplies the result by 100. The output is the percent identity of the subject sequence with respect to the query sequence. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

The nucleic acids and polypeptides described herein may be referred to as "exogenous". The term "exogenous" indicates that the nucleic acid or polypeptide is part of, or encoded by, a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found.

Nucleic acids of the invention, that is, nucleic acids having a nucleotide sequence of any paired peptides fusion proteins and constructs disclosed herein, can include nucleic acids sequences that are at least about 70%, at least about 75%, at least about 80%, at least about 85%, at least about 90%, at least about 95%, at least about 99% identical to the reference sequences disclosed herein.

A nucleic acid, i.e., an oligonucleotide (e.g., a probe or a primer) that is specific for a target nucleic acid will hybridize to the target nucleic acid under suitable conditions. We may refer to hybridization or hybridizing as the process by which an oligonucleotide single strand anneals with a complementary strand through base pairing under defined hybridization conditions. It is a specific, i.e., non-random, interaction between two complementary polynucleotides. Hybridization and the strength of hybridization (i.e., the strength of the association between the nucleic acids) is influenced by such factors as the degree of complementary between the nucleic acids, stringency of the conditions involved, and the melting temperature (Tm) of the formed hybrid. The hybridization products can be duplexes or triplexes formed with targets in solution or on solid supports.

Vectors. Vectors containing nucleic acids such as those described herein also are provided. A "vector" is a replicon, such as a plasmid, phage, or cosmid, into which another DNA segment may be inserted so as to bring about the replication of the inserted segment. Generally, a vector is capable of replication when associated with the proper control elements. Suitable vector backbones include, for example, those routinely used in the art such as plasmids, viruses, artificial chromosomes, BACs, YACs, or PACs. The term "vector" includes cloning and expression vectors, as well as viral vectors and integrating vectors. An "expression vector" is a vector that includes a regulatory region. A wide variety of host/expression vector combinations may be used to express the nucleic acid sequences described herein. Suitable expression vectors include, without limitation, plasmids and viral vectors derived from, for example, bacteriophage, baculoviruses, and retroviruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

The vectors provided herein also can include, for example, origins of replication, scaffold attachment regions (SARs), and/or markers. A marker gene can confer a selectable phenotype on a host cell. For example, a marker can confer biocide resistance, such as resistance to an antibiotic (e.g., kanamycin, G418, bleomycin, or hygromycin). As noted above, an expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin, or Flag™ tag sequences typically are expressed as a fusion with the encoded polypeptide. Such tags can be inserted anywhere within the polypeptide, including at either the carboxyl or amino terminus.

Additional expression vectors also can include, for example, segments of chromosomal, non-chromosomal and synthetic DNA sequences. Suitable vectors include derivatives of SV40 and known bacterial plasmids, e.g., E. coli plasmids col E1, pCR1, pBR322, pMal-C2, pET, pGEX, pMB9 and their derivatives, plasmids such as RP4; phage DNAs, e.g., the numerous derivatives of phage 1, e.g., NM989, and other phage DNA, e.g., M13 and filamentous single stranded phage DNA; yeast plasmids such as the 2p plasmid or derivatives thereof, vectors useful in eukaryotic cells, such as vectors useful in insect or mammalian cells; vectors derived from combinations of plasmids and phage DNAs, such as plasmids that have been modified to employ phage DNA or other expression control sequences.

Yeast expression systems can also be used. For example, the non-fusion pYES2 vector (XbaI, SphI, ShoI, NotI, GstXI, EcoRI, BstXI, BamH1, SacI, KpnI, and HindIII cloning sites; Invitrogen) or the fusion pYESHisA, B, C (XbaI, SphI, ShoI, NotI, BstXI, EcoRI, BamH1, SacI, KpnI, and HindIII cloning sites.

The vector can also include a regulatory region. The term "regulatory region" refers to nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, nuclear localization signals, and introns.

As used herein, the term "operably linked" refers to positioning of a regulatory region and a sequence to be transcribed in a nucleic acid so as to influence transcription or translation of such a sequence. For example, to bring a coding sequence under the control of a promoter, the translation initiation site of the translational reading frame of the polypeptide is typically positioned between one and about fifty nucleotides downstream of the promoter. A promoter can, however, be positioned as much as about 5,000 nucleotides upstream of the translation initiation site or about 2,000 nucleotides upstream of the transcription start site. A promoter typically comprises at least a core (basal) promoter. A promoter also may include at least one control element, such as an enhancer sequence, an upstream element or an upstream activation region (UAR). The choice of promoters to be included depends upon several factors, including, but not limited to, efficiency, selectability, inducibility, desired expression level, and cell- or tissue-preferential expression.

Vectors include, for example, viral vectors (such as adenoviruses ("Ad"), adeno-associated viruses (AAV), and vesicular stomatitis virus (VSV) and retroviruses), liposomes and other lipid-containing complexes, and other macromolecular complexes capable of mediating delivery of a polynucleotide to a host cell. Vectors can also comprise other components or functionalities that further modulate gene delivery and/or gene expression, or that otherwise provide beneficial properties to the targeted cells.

A "recombinant viral vector" refers to a viral vector comprising one or more heterologous gene products or sequences. Since many viral vectors exhibit size-constraints associated with packaging, the heterologous gene products or sequences are typically introduced by replacing one or more portions of the viral genome. Such viruses may become replication-defective, requiring the deleted function(s) to be provided in trans during viral replication and encapsidation (by using, e.g., a helper virus or a packaging cell line carrying gene products necessary for replication and/or encapsidation).

Suitable nucleic acid delivery systems include recombinant viral vector, typically sequence from at least one of an adenovirus, adenovirus-associated virus (AAV), helper-dependent adenovirus, retrovirus, or hemagglutinating virus of Japan-liposome (HVJ) complex. In such cases, the viral vector comprises a strong eukaryotic promoter operably linked to the polynucleotide e.g., a cytomegalovirus (CMV) promoter. The recombinant viral vector can include one or more of the polynucleotides therein, preferably about one polynucleotide. In some embodiments, the viral vector used in the invention methods has a pfu (plague forming units) of from about $10^8$ to about $5 \times 10^{10}$ pfu. In embodiments in which the polynucleotide is to be administered with a non-viral vector, use of between from about 0.1 nanograms to about 4000 micrograms will often be useful e.g., about 1 nanogram to about 100 micrograms.

Additional vectors include retroviral vectors such as Moloney murine leukemia viruses and HIV-based viruses. One HIV-based viral vector comprises at least two vectors wherein the gag and pol genes are from an HIV genome and the env gene is from another virus. DNA viral vectors include pox vectors such as orthopox or avipox vectors, herpesvirus vectors such as a herpes simplex I virus (HSV) vector.

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors may be an indication for some invention embodiments. The adenovirus vector results in a shorter term expression (e.g., less than about a month) than adeno-associated virus, in some embodiments, may exhibit much longer expression. The particular vector chosen will depend upon the target cell and the condition being treated. The selection of appropriate promoters can readily be accomplished. An example of a suitable promoter is the 763-base-pair cytomegalovirus (CMV) promoter. Other suitable promoters which may be used for gene expression include, but are not limited to, the Rous sarcoma virus (RSV), the SV40 early promoter region, the herpes thymidine kinase promoter, the regulatory sequences of the metallothionein (MMT) gene, prokaryotic expression vectors such as the β-lactamase promoter, the tac promoter, promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells, insulin gene control region which is active in pancreatic beta cells, immunoglobulin gene control region which is active in lymphoid cells, mouse mammary tumor virus control region which is active in testicular, breast, lymphoid and mast cells, albumin gene control region which is active in liver, alpha-fetoprotein gene control region which is active in liver, alpha 1-antitrypsin gene control region which is active in the liver, beta-globin gene control region which is active in myeloid cells, myelin basic protein gene control region which is active in oligodendrocyte cells in the brain, myosin light chain-2 gene control region which is active in skeletal muscle, and gonadotropic releasing hormone gene control region which is active in the hypothalamus. Certain proteins can expressed using their native promoter. Other elements that can enhance expression can also be included such as an enhancer or a system that results in high levels of expression such as a tat gene and tar element. This cassette can then be inserted into a vector, e.g., a plasmid vector such as, pUC19, pUC118, pBR322, or other known plasmid vectors, that includes, for example, an *E. coli* origin of replication. The plasmid vector may also include a selectable marker such as the β-lactamase gene for ampicillin resistance, provided that the marker polypeptide does not adversely affect the metabolism of the organism being treated.

Pharmaceutical carriers. The compositions also include a pharmaceutically acceptable carrier. We use the terms "pharmaceutically acceptable" (or "pharmacologically acceptable") to refer to molecular entities and compositions that do not produce an adverse, allergic or other untoward reaction when administered to an animal or a human, as appropriate. The term "pharmaceutically acceptable carrier," as used herein, includes any and all solvents, dispersion media, coatings, antibacterial, isotonic and absorption delaying agents, buffers, excipients, binders, lubricants, gels, surfactants and the like, that may be used as media for a pharmaceutically acceptable substance.

Thus, the invention also includes pharmaceutical compositions which contain, as the active ingredient, a fusion protein comprising a set of paired peptides or a fusion protein comprising a set of paired peptides linked a protein transduction domain, in combination with one or more pharmaceutically acceptable carriers. An active ingredient can be a composition comprising a set of paired peptides linked to a protein transduction domain and wherein prepared peptides comprise a first bacterial effector polypeptide linked to a second bacterial effector polypeptide. In some embodiments, the polypeptide compositions can be sterilized using conventional sterilization techniques before or after it is combined with the pharmaceutically acceptable carrier. In making the compositions of the invention, the polypeptide compositions are typically mixed with an excipient, diluted by an excipient or enclosed within such a carrier in the form of, for example, a capsule, tablet, sachet, paper, or other container. When the excipient serves as a diluent, it can be a solid, semisolid, or liquid material (e.g., normal saline), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders. As is known in the art, the type of diluent can vary depending upon the intended route of administration. The resulting compositions can include additional agents, such as preservatives. The excipient or carrier is selected on the basis of the mode and route of administration. Suitable pharmaceutical carriers, as well as pharmaceutical necessities for use in pharmaceutical formulations, are described in Remington's Pharmaceutical Sciences (E. W. Martin), a well-known reference text in this field, and in the USP/NF (United States Pharmacopeia and the National Formulary). Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The pharmaceutical compositions can also be formulated so as to provide quick, sustained or delayed release of the active ingredient after administration to the patient.

Pharmaceutically acceptable compositions for use in the present methods, including those in which the polypeptides are entrapped in a colloid for oral delivery, can be prepared according to standard techniques. The polypeptides can be dried and compacted by grinding or pulverizing and inserted into a capsule for oral administration. In some embodiments, the polypeptides can be combined one or more excipients, for example, a disintegrant, a filler, a glidant, or a preservative. Suitable capsules include both hard shell capsules or soft-shelled capsules. Any lipid-based or polymer-based colloid may be used to form the capsule. Exemplary polymers useful for colloid preparations include gelatin, plant polysaccharides or their derivatives such as carrageenans and modified forms of starch and cellulose, e.g., hypromellose. Optionally, other ingredients may be added to the gelling agent solution, for example plasticizers such as glycerin and/or sorbitol to decrease the capsule's hardness, coloring agents, preservatives, disintegrants, lubricants and surface treatment. In some embodiments, the capsule does not include gelatin. In other embodiments, the capsule does not include plant polysaccharides or their derivatives.

Regardless of their original source or the manner in which they are obtained, the polypeptides of the invention can be formulated in accordance with their use. These compositions can be prepared in a manner well known in the pharmaceutical art, and can be administered by a variety of routes, depending upon whether local or systemic treatment is desired and upon the area to be treated. Administration may be oral or topical (including ophthalmic and to mucous membranes including intranasal, vaginal and rectal delivery). In some embodiments, administration can be pulmonary (e.g., by inhalation or insufflation of powders or aerosols, including by nebulizer; intratracheal, intranasal, epidermal and transdermal) or ocular. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids, powders, and the like. Conventional pharmaceutical carriers, aqueous, powder or oily bases, thickeners and the like may be necessary or desirable.

The compositions can be formulated in a unit dosage form, each dosage containing, for example, from about 0.005 mg to about 2000 mg of polypeptides per daily dose. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.005 mg to about 1000 mg of the compositions of the present invention.

The compositions can be formulated in a unit dosage form, each dosage containing, for example, from about 0.1 mg to about 50 mg, from about 0.1 mg to about 40 mg, from about 0.1 mg to about 20 mg, from about 0.1 mg to about 10 mg, from about 0.2 mg to about 20 mg, from about 0.3 mg to about 15 mg, from about 0.4 mg to about 10 mg, from about 0.5 mg to about 1 mg; from about 0.5 mg to about 100 mg, from about 0.5 mg to about 50 mg, from about 0.5 mg to about 30 mg, from about 0.5 mg to about 20 mg, from about 0.5 mg to about 10 mg, from about 0.5 mg to about 5 mg; from about 1 mg from to about 50 mg, from about 1 mg to about 30 mg, from about 1 mg to about 20 mg, from about 1 mg to about 10 mg, from about 1 mg to about 5 mg; from about 5 mg to about 50 mg, from about 5 mg to about 20 mg, from about 5 mg to about 10 mg; from about 10 mg to about 100 mg, from about 20 mg to about 200 mg, from about 30 mg to about 150 mg, from about 40 mg to about 100 mg, from about 50 mg to about 100 mg of the active ingredient.

In some embodiments, tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

The proportion or concentration of the compositions of the invention in a pharmaceutical composition can vary depending upon a number of factors including dosage, chemical characteristics (e.g., hydrophobicity), and the route of administration.

Methods of Treatment

The compositions disclosed herein are generally and variously useful for treatment of inflammatory disorders and conditions. Inflammatory disorders and conditions encompass a wide range of disorders covering many different systems and organs, including the gastrointestinal tract, the skin, the lungs, and the musculoskeletal system. Exemplary inflammatory disorders include inflammatory bowel disease, rheumatoid arthritis, allergy, asthma, autoimmune diseases, coeliac disease, glomerulonephritis, hepatitis, preperfusion injury and transplant rejection. An inflammatory disorder can be a gastrointestinal disorder, for example, inflammatory bowel disease, Crohn's disease, and the ileocolitis, ileocecal, jeunoileitis, and gastroduodenal subtypes of-Crohn's disease, and ulcerative colitis and subtypes of ulcerative colitis.

A subject is effectively treated whenever a clinically beneficial result ensues. This may mean, for example, a complete resolution of the symptoms associated with an inflammatory disorder, a decrease in the severity of the symptoms associated with an inflammatory disorder, or a slowing of the progression of symptoms associated with an inflammatory disorder. These methods can further include the steps of a) identifying a subject (e.g., a patient and, more specifically, a human patient) who has an inflammatory disorder; and b) providing to the subject a composition comprising a paired peptide composition disclosed herein in a physiologically acceptable carrier. An amount of such a composition provided to the subject that results in a complete resolution of the symptoms associated with an inflammatory disorder, a decrease in the severity of the symptoms associated with an inflammatory disorder, or a slowing of the progression of symptoms associated with an inflammatory disorder considered a therapeutically effective amount. The present methods may also include a monitoring step to help optimize dosing and scheduling as well as predict outcome.

The methods disclosed herein can be applied to a wide range of species, e.g., humans, non-human primates (e.g., monkeys), horses, pigs, cows or other livestock, dogs, cats or other mammals kept as pets, rats, mice, or other laboratory animals. The compositions described herein are useful in therapeutic compositions and regimens or for the manufacture of a medicament for use in treatment of conditions as described herein (e.g., inflammatory disorders and conditions.)

When formulated as pharmaceuticals, the compositions can be administered to any part of the host's body for subsequent delivery to a target cell. A composition can be delivered to, without limitation, the brain, the cerebrospinal fluid, joints, nasal mucosa, blood, lungs, intestines, muscle tissues, skin, or the peritoneal cavity of a mammal. In terms of routes of delivery, a composition can be administered by intravenous, intracranial, intraperitoneal, intramuscular, subcutaneous, intramuscular, intrarectal, intravaginal, intrathecal, intratracheal, intradermal, or transdermal injection, by oral or nasal administration, or by gradual perfusion over time. In a further example, an aerosol preparation of a composition can be given to a host by inhalation.

Regardless of how the compositions are formulated, the dosage required will depend on the route of administration, the nature of the formulation, the nature of the subject's condition, e.g., a gastrointestinal disorder or a skin disorder, the subject's size, weight, surface area, age, and sex, other drugs being administered, and the judgment of the attending clinicians. Suitable dosages are in the range of 0.01-1,000 mg/kg. Some typical dose ranges are from about 1 µg/kg to about 1 g/kg of body weight per day. In some embodiments, the dose range is from about 0.01 mg/kg to about 100 mg/kg of body weight per day. In some embodiments, the dose can be, for example, 1 mg/kg, 2 mg/kg, 5 mg/kg, 10 mg/kg, 20 mg/kg, 50 mg/kg or 100 mg/kg. The dosage is likely to depend on such variables as the type and extent of progression of the disease or disorder, the overall health status of the particular patient, the relative biological efficacy of the compound selected, formulation of the excipient, and its route of administration.

Effective doses can be extrapolated from dose-response curves derived from in vitro or animal model test systems. For example, in vitro analysis of cytokine production by peripheral blood mononuclear cells (PBMCs) can be a useful for assaying pro- and anti-inflammatory responses, e.g., secretion of IL-1beta, IL-12, IL-4 or IL-10, IL-6, IL-23, and TNF-alpha. Compositions can also be analyzed for effects in animal models, for example, IgA production, cytokine production by explants of Peyer's patches, and dendritic cell and T-cell responses.

Wide variations in the needed dosage are to be expected in view of the variety of cellular targets and the differing efficiencies of various routes of administration. Variations in these dosage levels can be adjusted using standard empirical routines for optimization, as is well understood in the art. Administrations can be single or multiple (e.g., 2- or 3-, 4-, 6-, 8-, 10-, 20-, 50-, 100-, 150-, or more fold). Encapsulation of the compounds in a suitable delivery vehicle (e.g., polymeric microparticles or implantable devices) may increase the efficiency of delivery.

The duration of treatment with any composition provided herein can be any length of time from as short as one day to as long as the life span of the host (e.g., many years). For example, a composition can be administered once a week (for, for example, 4 weeks to many months or years); once a month (for example, three to twelve months or for many years); or once a year for a period of 5 years, ten years, or longer. It is also noted that the frequency of treatment can be variable. For example, the present compositions can be administered once (or twice, three times, etc.) daily, weekly, monthly, or yearly.

Any method known to those in the art can be used to determine if a particular response is induced. Clinical methods that can assess the degree of a particular disease state can be used to determine if a response is induced. For example, a subject can be monitored for symptomatic relief, e.g., relief from colic, diarrhea, constipation, nausea, vomiting, abdominal pain, cramping, heartburn, abdominal distention, flatulence, or incontinence, dermatitis, redness, pain, swelling. Alternatively or in addition, serum markers, imaging techniques, e.g., ultrasound, x-rays, and endoscopic methods can be used.

The compositions may also be administered in conjunction with other therapeutic modalities. Other therapeutic modalities will vary according to the particular disorder, but can include, for example, anti-inflammatory agents, antibiotics and other dietary treatments, anti-diarrhea medications, anti-emetics, anti-cholinergic agents, Concurrent administration of two or more therapeutic agents does not require that the agents be administered at the same time or by the same route, as long as there is an overlap in the time period during which the agents are exerting their therapeutic effect. Simultaneous or sequential administration is contemplated, as is administration on different days or weeks.

Articles of Manufacture

The invention also features kits for administering the compositions. Accordingly, packaged products (e.g., sterile containers containing one or more of the compositions described herein and packaged for storage, shipment, or sale at concentrated or ready-to-use concentrations) and kits, are also within the scope of the invention. A product can include a container (e.g., a vial, jar, bottle, bag, microplate or beads) containing one or more compositions of the invention. In addition, an article of manufacture further may include, for example, packaging materials, instructions for use, syringes, delivery devices, buffers or other control reagents.

For example, the kit can include a measured amount of a composition comprising a set of paired peptides wherein the set of paired peptides comprises a first bacterial effect or polypeptide went to a second bacterial effector polypeptide and a protein transduction domain. The compounds, agents, and/or reagents can be packaged in a suitable container. The kit can further comprise instructions for administering the compositions. For example, the kit can include: a fusion protein comprising a protein transduction domain and a set of paired peptides. The kit can also include a buffering agent, a preservative, and/or a protein stabilizing agent. Each component of the kit can be enclosed within an individual container and all of the various containers can be within a single package. The product may also include a legend (e.g., a printed label or insert or other medium describing the product's use (e.g., an audio- or videotape or computer readable medium)). The legend can be associated with the container (e.g., affixed to the container) and can describe the manner in which the reagents can be used. The reagents can be ready for use (e.g., present in appropriate units), and may include one or more additional adjuvants, carriers or other diluents.

Also included as effectors or effector proteins of the compositions and methods described herein are functional equivalents of the proteins described above. By the term "functional equivalent" is meant any amino acid sequence or modification thereof that has the same targeting and immune suppressing function of the naturally occurring effector protein. In one embodiment, such functional equivalents can have modifications of one or more amino acids from the known sequences. In one embodiment, such functional equivalents can be a smaller fragment of the known sequences. In one embodiment, such functional equivalents can be a derivative of the naturally occurring sequences or be derived from other than human sources. In one embodiment, such functional equivalents can be altered by chemical modification or be altered by recombinant production to be associated with sequences with which the effector proteins are not associated in nature. Similarly, chemical or structural changes or fragments of the nucleic acid sequences that encode the effector proteins are also considered functional equivalents herein.

As used herein, the term "construct" as described herein refers to a chemically synthesized or genetically engineered assemblage that comprises one or more PTD/CPP associated with one or more effector proteins and further optionally associated with one or more targeting moieties. The construct can be in the form of a polypeptide or a nucleic acid molecule encoding the polypeptide.

As used herein the term(s) "cosmeceutically or pharmaceutically acceptable carrier, excipient or formulation" refer to the components of a composition that provide a vehicle for delivery. For example, where the cosmeceutical or pharmaceutical product is a topical composition, the carrier or formulation can contain typical components such as cremes, saline, vitamins, oils that are normally found in cosmetic or pharmaceutical preparations for skin. See, for example, U.S. Pat. No. 5,635,497 which discloses an oil-in-water, fatty cream composition for topical administration comprising from 60 to 80 percent by weight of fatty components, from 1.5 to 5 percent by weight of at least one non-ionic, hydrophilic surfactant having an HLB of at least 14, about 6% of fatty alcohols and esters, a therapeutically effective amount of at least one topically active therapeutic agent, and water, provided the topically active therapeutic agent is not dithranol or its derivatives. See, also International Patent Publication No. WO2014/076642. Pharmaceutically or cosmetically acceptable excipients suitable for the compositions described herein can be selected from plasticizers, disintegrants, glidants, coloring agents, lubricants, stabilizers, adsorbents, preservatives, delivery retarders and mixtures thereof. Such a composition may contain a transepidermal or transdermal carrier agent consisting of acidic electrolyzed water having a pH of 1.0 to 4.0 and comprise clusters of water having 5 to 10 molecules of water per cluster, and a polyacrylate. Other suitable formulations may include oils, emollients, lotions for topical and transdermal applications along with buffered/aqueous and saline solutions. See, also, texts such as Topical Drug Delivery Formulation (eds. Osborne and Amann), 2000, publishers Taylor & Francis, Drugs and the Pharmaceutical Sciences Series #42.

The term "CAGE" as used herein refers to deep eutectic synthetic solvent, a choline-based oil that has antimicrobial activity, which has been shown to penetrate deep into the dermis. CAGE is described by Zakrewsky, M. et al, Adv. Healthcare Mater. (March 2016), 5, 1282-1289, incorporated by reference herein. CAGE has been shown to be useful in transdermal protein delivery, wherein the protein is carried 15-20 cell layers into model skin preparations. See, e.g., Banerjee, A. et al, Adv. Healthcare Mater. 2017, 1601411 DOI: 10.1002/adhm.201601411, incorporated by reference herein.

Still other pharmaceutical strategies to enhance dermal delivery of peptides or proteins including carrier peptides, signaling peptides neurotransmitter-inhibiting peptides and enzyme-inhibiting peptides, include chemical and physical penetration enhancers, such as listed in Table 2 of Badenhorst, T. et al, Pharmaceutical Strategies for the Topical Dermal Delivery of Peptides/Proteins for Cosmetic and Therapeutic Applications. Austin Journal of Pharmacology and Therapeutics (2014), 2(6):10. Also as discussed in this document are coupling with lipophilic moiety, such as lauric, palmitic and other acids, using CPP conjugates, formulation with microemulsions, encapsulation in liposomal vesicles and use of lipid particles, as well as combinations of these formulations.

The term "targeting moiety" refers to constructs useful in fusion with the effector proteins and/or PTD/CPPs described herein to direct the fusion protein or a nucleic acid sequence encoding it to a specific cell or tissue type within the body. Alterations to the fusion constructs described by the addition of amino acid segments to naturally occurring effector or fusion effector sequence, which enables the protein to bind and to specifically target cells, tissues or other target or physiologic compartment in the human body create "targeted-effectors" and "targeted effector fusions". Such targeting moieties include amino acid segments that enhance the efficacy of the preparation by its ability to be activated due to conditions in a specific compartment of the body could be cleaved, for instance by proteolytic cleavage, addition of post-translational modifications, or forming of PPIs with cell and tissue specific host proteins. Examples of tissue-specific targeting peptides for this use include those described in Jung, E. et al., Identification of tissue-specific targeting peptide. J Comput Aided Mol Des (October 2012) 26:1267-1275, incorporated by reference herein. Targeting moieties can also be antibodies, antibody fragments, aptamers, amino acid sequences, nucleic acid sequences that are complementary to or capable of binding a complementary sequence on a cell or tissue or chemical moieties that have a three-dimensional structure that can fit into a three-dimensional pocket on the targeted cell or tissue. For example, a targeting sequence can be a hormone, or fragment thereof, that targets or binds its naturally occurring cell surface receptor, or tissue specific markers, etc.

The term "polypeptide," when used in singular or plural form, generally refers to a polymer of amino acids joined together by peptide bonds and may include unmodified or naturally occurring amino acids or modified or unnatural amino acids. In certain embodiment, the term polypeptide refers to a construct formed by multiple shorter peptides joined directly, or indirectly via linkers, to form a single peptide. In one embodiment, as described herein, a polypeptide is formed by the fusion of a PTD or CPP and an effector protein. In another embodiment, as described herein, a polypeptide is formed by the fusion of a PTD attached to an effector protein, wherein the effector protein is further attached to another effector protein (with or without its own PTD). In still another embodiment, the polypeptide of this invention is formed by the covalent association of a first PTD fused to a first effector protein, a linker followed by an additional (e.g., second, third, fourth, etc) effector protein. The term "first" is used only to distinguish among the effectors. In yet another embodiment, each effector protein of the polypeptide is associated with its own PTD or CPP. In yet another embodiment, only one PTD/CPP is present. In another embodiment, the single PTD/CPP is located at the N terminus of the polypeptide. In yet another embodiment, multiple PTD/CPP are present in the polypeptide, each located at the N terminus of its associated effector protein. In another embodiment, each PTD/CPP is separated from its effector protein by a linker. In another embodiment, each effector protein is separated from each additional effector protein by a linker. The first and additional effector constructs in a single polypeptide may occur in any order.

In still another embodiment of a polypeptide as described herein, the PTD/CPP are fused directly to the effector protein and each effector protein is fused to each additional effector protein. In certain embodiments, the polypeptides contain two or more different effector proteins, each having its own target. In certain embodiments, the polypeptides contain two or more different effector proteins, each targeting related targets. In still further embodiments, each polypeptide is further associated with a targeting moiety to target the polypeptide to a specific tissue or cell type, e.g., skin, epidermis, dermis.

By "homologous protein" is meant a protein having a percent sequence similarity or identity of greater than 80%, greater than 85%, greater than 90%, greater than 95%, greater than 97%, or greater than 99% and sharing the same function as the effector protein.

As used herein, the term "polynucleotide," when used in singular or plural form, generally refers to any polyribonucleotide or polydeoxribonucleotide, which may be unmodified RNA or DNA or modified RNA or DNA that encode any of the polypeptide constructs as described above. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The term "polynucleotide" specifically includes cDNAs. The term includes DNAs (including cDNAs) and RNAs that contain one or more modified bases. In general, the term "polynucleotide" embraces all chemically, enzymatically and/or metabolically modified forms of unmodified polynucleotides, as well as the chemical forms of DNA and RNA characteristic of viruses and cells, including simple and complex cells.

By "nucleic acid molecule" as used herein is meant the nucleic acid sequence that encodes a construct or polypeptide as described above. The nucleic acid molecule can include other operative components, such as regulatory sequences directing expression of the construct or polypeptide in a cell in vivo or in vitro. The nucleic acid molecule can be in a vector.

By "vector" is meant an entity that delivers the nucleic acid molecule to cells, for therapeutic or cosmetic purposes. As used herein, a vector may include any genetic element including, without limitation, naked DNA, a phage, transposon, cosmid, episome, plasmid, or a virus. Vectors are generated using the techniques and sequences provided herein, in conjunction with techniques known to those of skill in the art. Such techniques include conventional cloning techniques of cDNA such as those described in texts such as Sambrook et al, Molecular Cloning: A Laboratory Manual, 3rd edition, 2001 Cold Spring Harbor Press, Cold Spring Harbor, N.Y., and current editions thereof, use of overlapping oligonucleotide sequences of the adenovirus genomes, polymerase chain reaction, CRISPR, gene editing, and any suitable method which provides the desired nucleotide sequence.

By the term "attachment" or "attach" as used herein to describe the interaction between the components of the constructs is meant covalent attachments or a variety of non-covalent types of attachment. Still another useful attachment mechanism involves via "affinity interactions", i.e., one domain fused to an antibody fragment that recognizes an epitope on the second domain to be used instead of the two domains fused together. Other attachment chemistries useful in assembling the constructs described herein include, but are not limited to, thiol-maleimide, thiol-haloacetate, amine-NHS, amine-isothiocyanate, azide-alkyne (CuAAC), tetrazole-cyclooctene (iEDDA).

The "linker" refers to any moiety used to attach or associate different elements of the polypeptide//polynucleotide sequence components of the constructs (i.e., the effector, the PTD, the targeting moiety) to each other. Thus in one embodiment, the linker is a covalent bond. In another embodiment, the linker is a non-covalent bond. In an embodiment of a polynucleotide described herein, the linker is composed of at least one to about 20 nucleic acids. Thus, in various embodiments, the linker is formed of a sequence of at least 3, 6, 9, 12, 15, 18, 21, 24, 27, 30, 33, 36, 39, 42, 45, 48, 51, 54, 57 up to about 60 nucleic acids. In yet another embodiment of a polypeptide as described herein, the linker refers to at least one to about 20 amino acids. Thus, in various embodiments, the linker is formed of a sequence of at least 2, 3, 4, 5, 6, 7, 8, 9, 10, 11, 12, 13, 14, 15, 16, 17, 18, 19, or about 20 amino acids. In still other embodiments, the linker can be a larger compound or two or more compounds that associate covalently or non-covalently. In still other embodiment, the linker can be a combination of the linkers defined herein. The linkers used in the constructs of the compositions and methods are in one embodiment chemically or enzymatically cleavable, such as by redox, pH, and the like. The linkers used in the constructs of the compositions and methods are in one embodiment non-cleavable.

The term "nucleic acid molecule" refers to a recombinant assembled nucleic acid sequence encoding a construct or polypeptide described herein. The nucleic acid molecule may be naked DNA or RNA. Alternatively the nucleic acid molecule may be associated operatively with regulatory sequences permitting expression of the construct or polypeptide in vivo or in vitro. The nucleic acid molecule may be a vector, plasmid vector, or be presented in a viral vector for delivery to the subject. Generation of such nucleic acid molecules with resort to the teachings of this specification can utilize known recombinant and genetic engineering techniques. See, e.g., "Inflammatory conditions" as used herein refer, in one aspect to inflammatory skin diseases, which are the most common problem in dermatology and cause pain, redness, swelling and the sensation of heat. Such inflammatory skin conditions include, without limitation, non-specific rashes accompanied by skin itching and redness, sunburn, dermatitis, eczema, rosacea, seborrheic dermatitis, psoriasis, infection, skin injury or wounds, autoimmunity or aging effects. Other inflammatory conditions (non-skin) include, without limitation, autoimmune conditions, asthma, chronic peptic ulcer, tuberculosis, rheumatoid arthritis, periodontitis, ulcerative colitis and Crohn's disease, sinusitis, active hepatitis, gut dysbiosis syndromes and any other disease caused by NFkB/JNK/p38 pathway activation.

"Patient" or "subject" as used herein means a mammalian animal, including a human, a veterinary or farm animal, a domestic animal or pet, and animals normally used for clinical research. In one embodiment, the subject of these methods and compositions is a human.

The terms "a" or "an" refers to one or more. For example, "an expression cassette" is understood to represent one or more such cassettes. As such, the terms "a" (or "an"), "one or more," and "at least one" are used interchangeably herein.

As used herein, the term "about" means a variability of plus or minus 10% from the reference given, unless otherwise specified.

The words "comprise", "comprises", and "comprising" are to be interpreted inclusively rather than exclusively, i.e., to include other unspecified components or process steps. The words "consist", "consisting", and its variants, are to be interpreted exclusively, rather than inclusively, i.e., to exclude components or steps not specifically recited.

With resort to the definitions of the components above, in one aspect, the inventors provide a composition comprising a first construct comprising a selected immunomodulatory effector protein or its functional equivalent thereof that targets a first functional domain optionally linked covalently or non-covalently to a selected protein transduction domain (PTD) or penetrating peptide (CPP); an additional construct comprising a different effector protein or a functional equivalent thereof that targets an additional functional domain, optionally linked to the same PTD or CPP of (a) or to an additional PTD or CPP, or a combination of a first and one or more additional constructs.

In one embodiment, the first and additional constructs are further linked with a targeting moiety to direct activity of the composition to a specific cell or tissue, e.g., skin. In another embodiment, the constructs are admixed in a pharmaceutically or cosmeceutically acceptable carrier or excipient or formulation, such as a formulation suitable for topical administration to the skin.

One embodiment of such a composition is a single polypeptide comprising a fusion of two or more effectors. Another embodiment is a single polypeptide comprising a first effector-PTD fused construct linked covalently or non-covalently to one or more of additional constructs. The polypeptide in a further embodiment contains one or more optional linker amino acid sequences interposed between each construct of the polypeptide. In one embodiment, the polypeptide contains fused to the first construct and/or additional construct, a targeting moiety to direct the polypeptide to a specific cell or tissue. In a further embodiment, the single polypeptide is in a pharmaceutically or cosmeceutically acceptable carrier or excipient or formulation.

Whether the constructs are admixed in a composition or present in one or more polypeptides, the effector can be one or more of the effectors identified above, particularly in Tables 1 or 2. In one embodiment of the admixture or polypeptide, the first effector protein is NleE or a functional equivalent thereof. In yet other embodiment, the additional effector protein is one or more of NleC, NleD, NleB, NleH, YopM, YopE, YopH, YopJ, YopP, SspH1, OspG, OspF, IpaH9.8, IpaH1.4, IpaH2.5, IpaH4.5, IpaH7.8 and SlrP. In other embodiments, the admixture of constructs in the composition or present in the single polypeptide can be selected from the following embodiments. In one embodiment, the first effector is NleE and the additional effector is NleC. In another embodiment, the first effector is NleE and the additional effector is NleD. In another embodiment, the first effector is NleE and the additional effector is NleB. In another embodiment, the first effector is NleE and the additional effector is NleH. In another embodiment, the first effector is NleE and the additional effector is YopB. In another embodiment, the first effector is NleE and the additional effector is YopH. In another embodiment, the first effector is NleE and the additional effector is YopJ. In another embodiment, the first effector is NleE and the additional effector is YopP. In still another embodiment, the first effector is NleE and the additional effector is SspH1. In a further embodiment, the first effector is NleE and the additional effector is OspG. In another embodiment, the first effector is NleE and the additional effector is OspF. In another embodiment, the first effector is NleE and the additional effector is IpaH9.8. In still a further embodiment, the first effector is NleE and the additional effector is IpaH1.4. In another embodiment, the first effector is NleE and the additional effector is IpaH2.5. In another embodiment, the first effector is NleE and the additional effector is IpaH4.5. In another embodiment, the first effector is NleE and the additional effector is IpaH7.8. In yet a further embodiment, the first effector is NleE and the additional effector is SlrP. In still other embodiments of the constructs or polypeptides, three or more effectors can be delivered in a single mixture of constructs or single polypeptide. The first and additional effectors or effector constructs may occur in any order in the fusions or in the polypeptides described herein.

In the above-listed constructs and polypeptides, a suitable PTD or CPP linked to the first construct and optionally to each additional construct or polypeptide is the naturally occurring PTD of the selected effector protein, e.g., the YopM PTD (SEQ ID NO: 2; amino acids 1-50 of YopM). See U.S. Pat. No. 8,840,901.

The PTD/CPP can also be a functional equivalent, e.g., a mutated or modified version of a naturally occurring PTD, such as the naturally occurring PTD sequence of SspH1, or of *Shigella* IpaH protein or any other of the effectors. The PTD useful in the constructs and polypeptides of the compositions can be a completely novel sequence which is developed to transport the construct or polypeptide or composition across cell membranes.

In one specific embodiment, the first construct is the YopM PTD fused to NleE. In another specific embodiment, the first construct is the SspH1 PTD fused to NleE. In still another specific embodiment, the first construct is the IpaH PTD fused to NleE. In still other embodiments, the additional construct comprises YopM, optionally associated with the YopM PTD. In still other embodiments of the single polypeptide, the polypeptide further contains at least one linker sequence as defined above interposed between the first and the one or more additional constructs. In still other embodiments of the constructs and single polypeptide, each construct or polypeptide can further contain a fused targeting moiety, such as a skin cell targeting peptide or other cell or tissue targeting peptide. Given the number of effectors, PTD/CPPs, linkers and targeting moieties identified herein and in the cited publications, any number of constructs or polypeptides may be prepared according to the teachings contained herein.

In still other embodiments of the above-listed constructs and polypeptides, the admixture of protein constructs or constructs contained on the single polypeptide is such that the targeted functional domain of each effector protein in the construct is expressed in the same cell. In another embodiment, each construct in admixture or in the single polypeptide has a non-overlapping redundant role in inhibiting NFkB, JNK and p38 pathways when present in a mammalian cell.

As described above, any of the compositions described herein, whether a mixture of constructs, a single polypeptide or nucleic acid molecules encoding them, can be prepared in a formulation comprises ingredients suitable for application to, and absorption through, the cells of the skin. One such formulation employs the above-described CAGE solvent. Other suitable formulations may include oils, emollients, lotions for topical and transdermal applications along with buffered/aqueous and saline solutions.

In yet another aspect, the compositions described herein include nucleic acid molecules comprising a nucleic acid sequence encoding a first construct, an additional construct, or the single polypeptide of any one of the above-described embodiments. Such nucleic acid molecules can also comprise operatively associated regulatory sequences, such as promoters, enhancer, etc (see, e.g., Sambrook et al) necessary to express the construct or polypeptide in a suitable cell. In certain embodiments, the nucleic acid molecule is naked DNA or RNA. In certain embodiments, the molecule is part of a plasmid or contained in a recombinant vector or virus. Methods for generating such nucleic acid molecules are within the skill of the art given the teachings herein. The nucleic acid molecules may also be delivered in a cosmeceutically or pharmaceutically acceptable carrier or excipient or formulation. Such formulations are described in detail in available texts as described above.

These constructs and/or polypeptides may be formulation into a wide variety of cosmeceutically or pharmaceutically acceptable carrier or excipient or formulation for many different uses and routes of administration. While topical administration is preferred for uses on skin inflammation, it is contemplated that other conventional routes of administration will be used for treating other inflammatory conditions. In some embodiments, routes of administration include transdermal (including patch formulation), intradermal injection (including infusion and subcutaneous injection). Other pharmaceutically acceptable routes of administration include, but are not limited to, systemic routes, such as intraperitoneal, intravenous, intranasal, intramuscular, intratracheal, subcutaneous, epidural, and oral routes and other parenteral routes of administration or intratumoral or intranodal administration. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent. Routes of administration may be combined, if desired.

Other methods of delivery of the effectors include via an attenuated bacterial strain which expresses a functional Type-Three Secretion System (TTSS)-expressing microorganism and is engineered to contain nucleic acid sequences encoding at least one of the effector immuno-modulatory proteins or fusions or polypeptide, wherein amino acid sequences also code for functional TTSS secretion signal sequences. These include attenuated bacteria engineered or induced to shed outer membrane vesicles (OMV) or other type of exosome-like, bacterial or cell-derived vesicle containing the proteins described herein.

In still other embodiments, the compositions, constructs, fusions and polypeptides and nucleic acid molecules described herein may be further manipulated by encapsulation in liposomes, micro particles, microcapsules, or in recombinant cells capable of expressing the compound, receptor-mediated endocytosis construction of a nucleic acid as part of a retroviral or other vector, etc.

Still other embodiments of compositions are provided herein. In certain embodiments, a composition of single effectors, or fusions of multiple effectors, or fusions of single effector-PTD, or fusions of multiple effectors and one or more PTD, or single/multiple effector(s)-PTD-targeting moiety fusions are prepared. The polypeptide linker regions and other non-native peptide sequences are engineered into fusion-effectors and can contain active segments which can lead to their enhanced ability to be purified in active form. In another embodiment, the effector fusions can be modified recombinantly or chemically, or by e.g., editing methodologies to provide altered subcellular localization, altered stability, or altered ability to participate in protein-protein interactions. In one embodiment, the effector fusions are modified to include amino acid segments normally used as tags for efficient purification of proteins from complex mixtures (e.g., 6HIS, GST, and Maltose BP).

In still a further specific embodiment, each individual effector protein or multiple effector fusion has an amino acid sequence that is deliberately altered by designed site directed mutagenesis. In one embodiment, such mutagenesis alters the activity of the effector in terms of its potency as an anti-inflammatory effector. In another embodiment, the altered effector amino acid sequence alters the effector's specificity for a target, catalytic activity, antigenicity, stability, ability to bind substrate, and/or ability to work with other effectors in a preparation. Such mutagenic techniques can alter any other common property of an effector protein for the benefit of the efficacy of the resulting therapeutic preparation.

In another aspect, the compositions containing the effector fusions can lead to the inhibition of at least one or more of an NF-κB, JNK and p38 mediated signal transduction pathway protein in selected cells and tissues. Such inhibition provides an anti-inflammatory response, an anti-apoptotic effect or a pro-apoptotic effect in a target cell.

Still other embodiments of compositions can be obtained by selection of the components as taught herein resulting in a pharmaceutical/cosmeceutical preparation, containing active and therapeutic levels of the effector fusions and constructs as described herein for use in preventing, treating, or ameliorating an immune-related disorder whose pathology stems from aberrant activation of the NFkB, JNK or P38 pathways.

In still other aspects, methods for designing the various constructs and polypeptides described herein can be made using techniques well-known in the art of recombinant genetic engineering and manipulation of the nucleic acid techniques. Suitable techniques are known to those of skill in the art, and as provided by many of the publications incorporated by reference herein. Selection of the appropriate techniques to create the various embodiments will depend upon the effectors, PTDs, linkers, targeting moieties and other components as set out above. Molecular biology strategies to alter the proteins to make them more stable, specific, catalytic and robust are known. Further such known techniques can be used to optimize the design, construction and delivery of effector fusions based upon knowledge of the specific pathways and enzymes used by the cell in a selected inflammatory stimulus.

For example, in one embodiment the selected effectors are subject to random, high throughput mutagenesis in the catalytic active sites or the sites of substrate binding. Selection of effectors of these mutagenized populations for variants with novel substrate specificities, rates of catalysis and their combination with other known or mutagenized effectors in the fusions, constructs and polypeptides described herein can result in compositions with novel signal transduction inhibition functions.

Still other known and available methods can be employed for creating recombinant fusion effector genes/proteins and for their expression, purification, stabilization as single effectors or fusion effectors. Such methods include producing/expressing the effector protein or effector fusion proteins from cloned genes in any suitable cell based systems, including, without limitation, bacteria, yeast, insect, or mammalian cells. Methods for purification of the resulting fusion constructs resulting in highly active, stable proteins which retain the ability to target their native substrate also employ known techniques. Additional techniques for producing compositions of this invention include, without limitation, optimization of the effector preparation by incorporation into liposomes, PEGylation of the effector constructs or fusions or polypeptides. The effector constructs may be subjected to chemical derivatization to associate or conjugate the construct physically or in admixture with additional entities. Such entities include without limitation, lipids, liposomes, other drugs, and cargo molecules including nucleic acids, polypeptides, organic molecules, small organic molecules, metals, nano-particles, viruses, modified viruses, viral vectors, antibodies and/or plasmids as targets for conjugation.

Yet further aspects provide a variety of methods of using the compositions, fusions, constructs and polypeptides described above in methods for treating cosmetic conditions, such as inflammation or irritation due to normal skin agent, to the treatment of other inflammatory conditions, such as cancer, gut dysbiosis syndromes, and other conditions identified herein caused by NFkB/JNK/p38 pathway activation. For example one therapeutic use is to ameliorate the inflammation in the tumor microenvironment (TME) in any malignant or non-malignant condition that involves activation of the NFkB/JNK/p38 pathway.

The various compositions defined above may be employed therapeutically in the down regulation/normalization of the immune response elicited by the ectopic or pathologic activation of NFkB, JNK and P38 pathways. In one embodiment, such methods of treating or suppressing pathway activation can occur in subjects suffering from the consequences of normal, naturally occurring conditions such as aging associated inflammation. In yet another method, the compositions are administered for treatment of numerous conditions wherein the three pathways are aberrantly activated resulting in an inflammatory response. Such aberrant responses include without limitation, infection, wound healing, reactive dermatitis, auto-immune disease, and malignant or non-malignant proliferative disorder. These diseases, conditions and syndromes wherein the three pathways are aberrantly activated also include, but are not limited to diseases caused by autoimmunity of the patient, topical inflammation, chronic inflammation, gastroenteritis, chronic gastritis, inflammatory bowel diseases (IBD), colitis ulcerosa, psoriasis, allergic reactions, Crohns disease, dysbiosis syndromes, cancer (including gliobastoma) rheumatoid arthritis related bone diseases characterized by changes in bone resorption, reduction and relief of the signs and symptoms associated with treating inflammation, and/or suppression of the immune system.

These methods involve administering via a suitable route of administration (as described above) an amount of the composition (i.e., the effector fusions, effector-PTD fusions, effector-PTD-Targeting fusions, and the other embodiments described above) in an amount sufficient to reduce activation of the desired pathway.

Desirably, the methods further involve, in one aspect, administering a suitable dose or doses of the fusion construct(s) in a therapeutic regimen to the subject in need thereof. In one embodiment, such administration can occur once or more prior to, simultaneously with, or after any conventional additional treatment for the conditions. In one embodiment, where the condition is an infection, the additional component is an antibiotic. In another embodiment, wherein the condition is a cancer, the additional component is radiation or chemotherapy. Still other known "additional components" may be selected by one of skill in the art or the attending physician depending on the condition being treated and the physical status of the subject.

Methods for determining the timing of frequency of administration will include an assessment of subject's response to the first administration of the composition. The dose is generally the lowest dose of the composition that is effective to suppress activation of the NFKB, JNK/p38 pathway. In still other embodiments, a suboptimal dose is delivered in a continuous infusion or a slow release formulation. The dosage required will depend primarily on factors such as the condition being treated, the age, weight and health of the patient, and may thus vary among patients. In one embodiment, where the composition comprises an admixture of peptide constructs or the single polypeptide, one such dose is about 1 to 25 µM protein/polypeptide. In another embodiment, the dose is less than 10 µM protein/polypeptide. In still another embodiment, the dose is between 1 µM and 5 µM protein/polypeptide. In another embodiment, the suboptimal dose is less than 1 µM protein/polypeptide.

When the composition is in the form of a nucleic acid or vector or nucleic acid molecule, it is administered in sufficient amounts to transduce the targeted cells and to provide sufficient levels of gene transfer and expression to reduce or inhibit activation of the NFKB, JNK/p38 pathway and provide a therapeutic benefit without undue adverse or with medically acceptable physiological effects, which can be determined by those skilled in the medical arts. Dosages of these therapeutic compositions will depend primarily on factors such as the condition being treated, the age, weight and health of the patient, and may thus vary among patients. For example, a therapeutically effective adult dosage of a viral vector or siRNA nanoparticle is generally in the range of from about 100 µL to about 100 mL of a carrier containing concentrations of from about $1 \times 10^5$ to about $1 \times 10^{15}$ particles, about $1 \times 10^{11}$ to $1 \times 10^{13}$ particles, or about $1 \times 10^9$ to $1 \times 10^{12}$ virus particles.

In still another aspect, methods for use of the compositions described herein involve veterinary use for the treatment of inflammatory conditions in animals, e.g., for auto-immune diseases, reactive dermatitis, pruritis, alopecia and any other skin ailment for which the underlying pathogenesis involves alteration of NFKB, JNK/p38 pathway. Selection of administration routes, dosages and therapeutic regimens may be selected by a veterinarian.

In one aspect, a composition in a pharmaceutically acceptable carrier or excipient or formulation is provided. The composition includes: (a) a first construct comprising a selected immunomodulatory effector protein or functional equivalent thereof that targets a first functional domain optionally linked covalently or non-covalently or by affinity to a selected protein transduction domain (PTD) or penetrating peptide (CPP); (b) an additional construct comprising a different effector protein or a functional equivalent thereof that targets an additional functional domain, optionally linked to the same PTD or CPP of (a) or to an additional PTD or CPP, or (c) a combination of constructs (a) and (b) in any order.

In one embodiment of the composition, the first construct is linked covalently or non-covalently to one or more of the additional constructs in a single polypeptide. Additionally, the composition further includes an optional linker amino acid sequence interposed between each construct.

In one embodiment, the functional equivalent includes a chemically or recombinantly modified amino acid sequence of the effector protein, or a fragment of the naturally-occurring effector amino acid sequence, or of the derivative of said chemically or recombinantly modified amino acid sequence of the effector protein that shares the functional activity of the effector protein.

In one embodiment, the first effector protein is NleE or a functional equivalent thereof.

In one embodiment, the additional effector protein is one or more of NleC, NleD, NleB, NleH, YopM, YopE, YopH, YopJ, YopP, SspH1, OspG, OspF, IpaH9.8, IpaH1.4, IpaH2.5, IpaH4.5, IpaH7.8 and SlrP. In one embodiment, the PTD or CPP is the naturally occurring PTD of the selected effector protein. In one embodiment, the PTD is a sequence of YopM, of SspH1, or of *Shigella* IpaH protein. In one embodiment, the PTD is amino acids 1-50 SEQ ID NO: 2.

In one embodiment, the PTD or CPP is one or more of Poly-Arg, Tat and VP22, df Tat, a cyclic CPPs, IMT-P8, seven arginine (R7) and Streptolysin O (SLO)-mediated systems, elastin like polypeptide, CPP-adaptor system, 1,2-Benzisothiazolin-3-one (BIT) and Tat, activatable cell-penetrating peptides, LDP12, M918, BR2, POD, native protein independent of R11-CPP, Poly-arginine/Tat and Tat-PTD, Pep-1, CADY-2, R8, azo-R8, Penetratin, HR9 and IR9 peptides, or pVEC.

Figure 3:
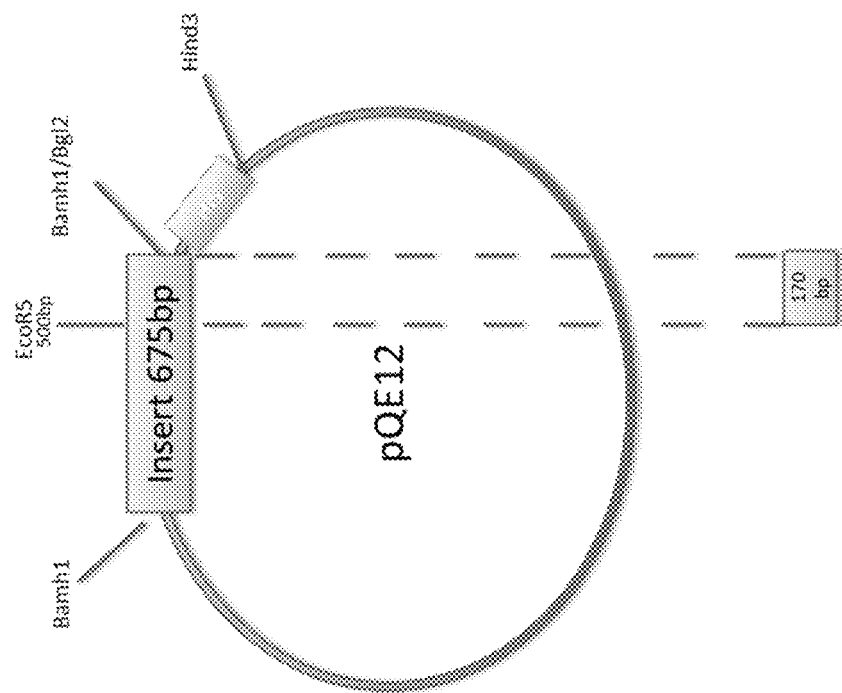
FIG. 3 is a schematic of the cloning strategy for TAT-NleE WT and Mutant R107A.

In one embodiment, each targeted functional domain of each effector protein in the construct is expressed in the same cell. In one embodiment, each construct has a non-overlapping redundant role in inhibiting NFkB, JNK and p38 pathways when present in a mammalian cell. In one embodiment, the formulation comprises ingredients suitable for application to, and absorption through, the cells of the skin. In one embodiment, the formulation comprises CAGE solvent. In one embodiment, the first construct is the YopM PTD fused to NleE or the SspH1 PTD fused to NleE or the IpaH PTD fused to NleE. In one embodiment, the additional construct comprises YopM, optionally associated with the YopM PTD. In one embodiment, the composition further includes at least one linker between the first and additional constructs.

In one embodiment, the first effector is NleE and the additional effector is NleC. In another embodiment, the first effector is NleE and the additional effector is NleD. In another embodiment, the first effector is NleE and the additional effector is NleB. In another embodiment, the first effector is NleE and the additional effector is NleH. In another embodiment, the first effector is NleE and the additional effector is YopB. In another embodiment, the first effector is NleE and the additional effector is YopH. In another embodiment, the first effector is NleE and the additional effector is YopJ. In another embodiment, the first effector is NleE and the additional effector is YopP. In another embodiment, the first effector is NleE and the additional effector is SspH1. In another embodiment, the first effector is NleE and the additional effector is OspG. In another embodiment, the first effector is NleE and the additional effector is OspF. In another embodiment, the first effector is NleE and the additional effector is IpaH9.8. In another embodiment, the first effector is NleE and the additional effector is IpaH1.4. In another embodiment, the first effector is NleE and the additional effector is IpaH2.5. In another embodiment, the first effector is NleE and the additional effector is IpaH4.5. In another embodiment, the first effector is NleE and the additional effector is IpaH7.8. In another embodiment, the first effector is NleE and the additional effector is SlrP. In any of the embodiments above, the constructs may be in any order.

In one embodiment, the composition further includes a skin cell targeting peptide.

In another aspect, a nucleic acid construct is provided. The nucleic acid sequence includes a nucleic acid sequence encoding the polypeptide of any of the compositions described above.

In one embodiment, the nucleic acid construct further includes regulatory sequences necessary to express the polypeptide in a suitable cell.

In one embodiment, the nucleic acid construct is a DNA, RNA, a plasmid or a recombinant vector or virus.

In one embodiment, the nucleic acid construct is in a pharmaceutically acceptable carrier or excipient or formulation.

In another aspect, a method is provided for treating, preventing or ameliorating an NFkB, JNK or p38 mediated inflammatory disorder in a subject, or a subject at risk from developing such disorder. The method includes administering to the subject any of the compositions or nucleic acid constructs described above.

In one embodiment of the method, the composition is administered in an amount sufficient to down-regulate the innate inflammatory response in a targeted cell or tissue of the subject mediated by the pathologic or non-pathologic activation of intracellular NFkB, JNK or P38 signal transduction pathway.

In one embodiment, the method reduces symptoms, and inhibits progression, of damage to the subject's cells or tissue caused by inflammation.

In one embodiment of the method, a composition containing multiple constructs targets multiple targeted functional domains that are expressed in the same cell and each construct plays multiple, non-overlapping redundant roles in inhibiting NFkB, JNK and p38 pathways.

In one embodiment of the method, the presence of multiple constructs in the compositions produces a synergistic therapeutic effect.

EXAMPLES

Example 1: Preparation of Recombinant Constructs

Sequences. The native YopM, NleE, OSPZ, and IpA7.8 nucleotide sequences were codon optimized for efficient bacterial expression of the encoded polypeptides. The optimized nucleotide sequences were synthesized de novo as long single stranded nucleotide chains. The overlapping and complementary single strand DNA sequences were annealed and the mixture subject to polymerize chain reaction (PCR) to generate full-length double-stranded (ds) DNA. The ds DNA was gel isolated and cloned into plasmid pQE60. The sequence of the inserted DNA was confirmed by nucleotide sequence analysis.

TAT-NleE wild type and NleE Mutant R107A. Both Vector and Amplicon were digested using BamH1 restriction enzyme overnight at 37° C. The Vector was then phosphatase treated for 1 hour then heat inactivated prior to ligation. All material was run through agarose gels and gene cleaned using a Qiagen gel extraction kit. Ligation reaction was performed at 16° C. overnight, and half of the volume was used to transform the DNA into XL-1 blue competent cells. Colonies from the subsequent transformation were picked and mini-preps were performed using a Qiagen Mini-Prep Kit. Resulting DNA was digested using BamH1 for 1 hr at 37° C. to test for the presence of the insert. 675 bp Positive clones were then digested using EcoR5 (internal to the insert) and external Hind3 site for 1 hr at 37° C. to test the orientation of the insert. Positive orientation yielded a drop-out that was 175 bp in size. Positive clones were then transformed into S9-competent cells to test protein expression rates by mini-induction. A clone was chosen from that group, and used for future maxi-induction purifications under native conditions. A schematic of the construct (based upon the backbone plasmid pQE60 available from Qiagen Inc, Catalogue number: #32903) is shown in FIG. 3.

Figure 4:
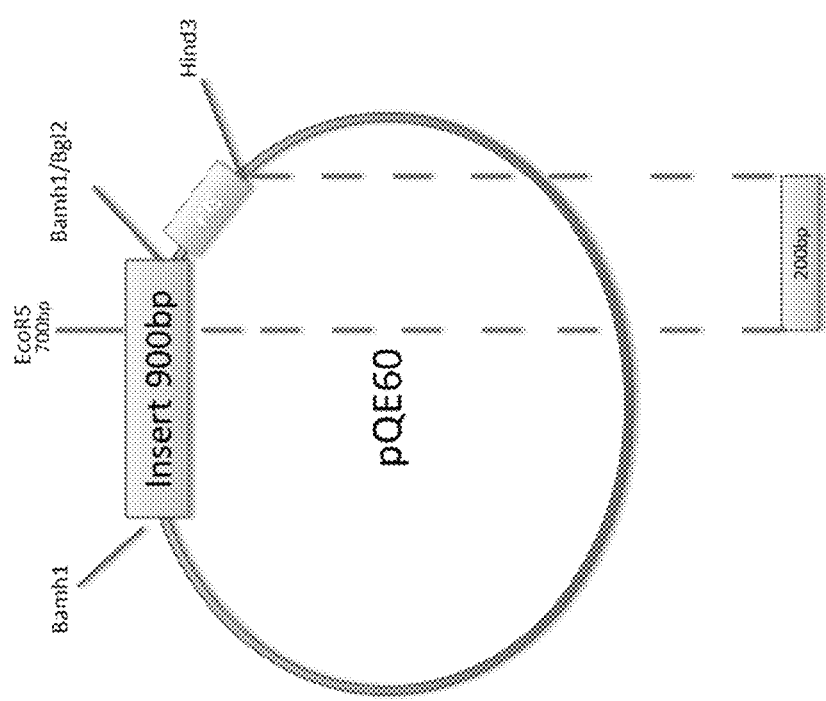
FIG. 4 is a schematic of the cloning strategy for TAT-*Shigella* OSPZ.

TAT-*Shigella* OSPZ. Both Vector and Amplicon were digested using BamH1 restriction enzyme overnight at 37*C. The Vector was then phosphatase treated for 1 hr then the enzyme was heat inactivated prior to ligation. All material was electrophoresed through agarose gels and the DNA isolated from the gel using a Qiagen DNA gel extraction kit. Ligation reaction was performed at 16*C overnight, and half of the volume was used to transform the DNA into XL-1 blue competent cells. Colonies from the subsequent transformation were picked and mini-preps were performed using a Qiagen Mini-Prep Kit. Resulting DNA was digested using BamH1 37*C for 1 hr to test for the presence of the 900 bp insert. Positive clones were then digested using EcoR5 (internal to the insert) and Hind3 located after the HIS-tag 37*C 1 hr to test the orientation of the insert. Positive orientation yielded a drop-out DNA fragment that was 200 bp in size. Positive clones were then transformed into S9-competent cells to test protein expression rates by mini-induction. A clone was chosen from that group, and used for future maxi-induction of proteins and purification of protein under native conditions. A schematic of the construct is shown in FIG. 4.

Figure 5:
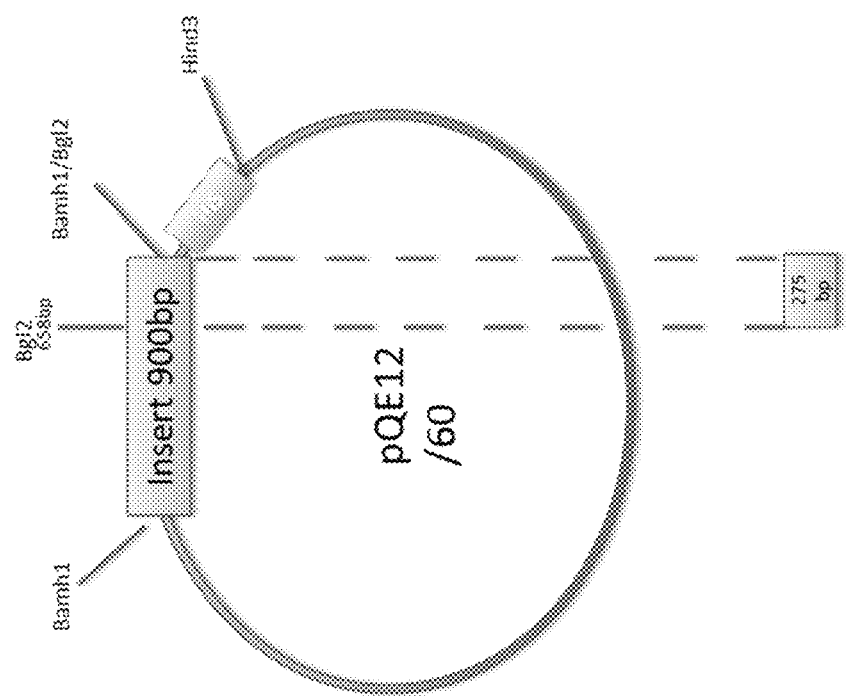
FIG. 5 is a schematic of the cloning strategy for YopM PTD-NleE WT and Mutant R107A.

YopM PTD-NleE wild type and Mutant R107A. Both Vector and Amplicon were digested using BamH1 restriction enzyme overnight at 37*C. The Vector was then phosphatase treated for 1 hr and heat inactivated prior to ligation. All material was run through agarose gels and gene cleaned using a Qiagen gel extraction kit. Ligation reaction was performed at 16*C overnight, and half of the volume was used to transform the DNA into XL-1 blue competent cells. Colonies from the subsequent transformation were picked and mini-preps were performed using a Qiagen Mini-Prep Kit. Resulting DNA was digested using BamH1 at 37*C for 1 hr to test for the presence of the insert. Positive clones were then digested using Bgl2 (internal to the insert) and Bgl2 at 37*C for 1 hr to test the orientation of the insert. Positive orientation yielded a drop-out that was 275 bp in size. Positive clones were then transformed into S9-competent cells to test protein expression rates by mini-induction. A clone was chosen from that group, and used for future maxi-induction purifications under native conditions. A schematic of the construct is shown in FIG. 5.

YopM PTD-NleE wild type and Mutant R107A, No Linker, PAPA Linker, and GSGS Linker. A QE60 vector containing a codon optimized YopM sequence was purchased from Epoch Life Science Inc. The plasmid was digested using Cla1 (internal to YopM) and Bgl2 (located outside of the cloning site). NleE was then digested using Cla1 and BamH1. Note that after ligation, the BamH1/Bgl2 site on the vector was lost. Because the vector was opened at a site that was internal to YopM, the ligation of NleE (along with its mutant R107A counterpart) lead to the fusion of the two inserts. This site is located downstream to the PTD, thus leaving it intact. Variations of this construct were made using either PAPA or GSGS linkers. These were added to the beginning of NleE during PCR by having the bridges be part of the forward primer sequence. Screening of these various constructs were done via PCR of mini-preps using NleE Cla1 FOR and TNHis Bam REV primers designed for NleE. Positive clones were then sent for sequencing to verify the clones prior to transformation into S9-cells for protein expression. A schematic of the construct is shown in FIG. 6.

Figure 1:
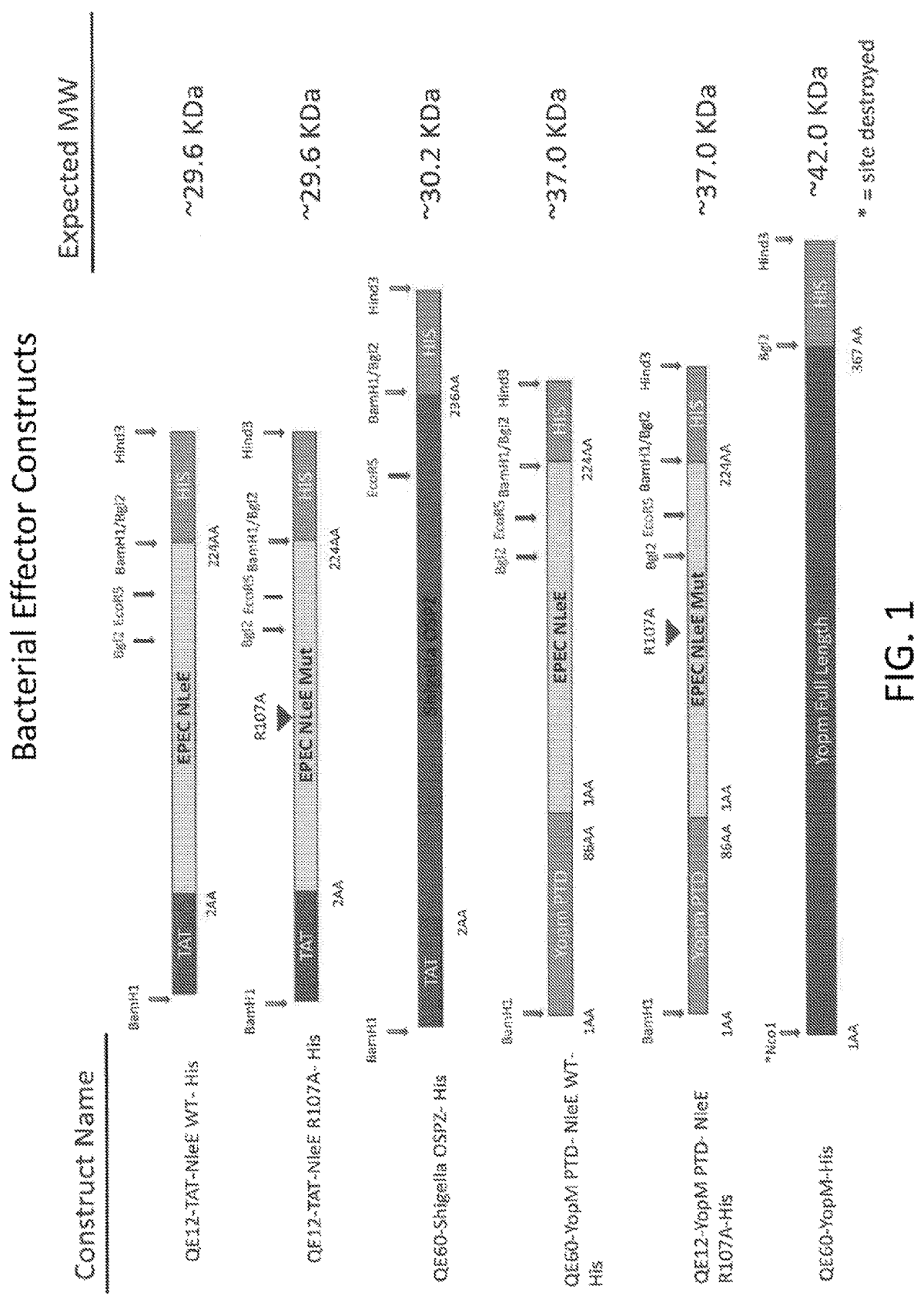

Schematics of the constructs used are shown in FIG. 1 and FIG. 2.

Purification of recombinant polypeptides. The transformed SG13009 [pREP4] were plated on an agar plate containing both ampicillin and kanamycin. A single colony was used to inoculate a 200 mL culture, shaking at 200 RPM at 37° C. overnight. A volume of the overnight culture was added to 1 L of 2YT medium containing ampicillin and kanamycin and grown as described above in an incubator shaker at 200 RPM 37° C. to an OD 600 nm of 0.6-0.8. Then, 1 mL of 1M Isopropyl β-D-1-thiogalactopyranoside (IPTG) was added to the culture and growth was continued overnight with shaking at 200 RPM at 20° C. The following morning, cells were collected by centrifugation at 6,000 RPM at 4° C. The pelleted cells were resuspended in 40 mL Sonication Buffer and sonicated on ice for two cycles of 4-5 minutes each. The sonification buffer had a pH of 7.5 and 1 L of sonification buffer included one bottle of PBS, 300 mM NaCl, 10% Glycerol, 5 mM Imidazole. The remainder of the volume was filled with ddH$_2$O. The buffer was then filtered and 1 ml 0.1M PMSF and 1 ml (2 mg/ml) each of Aprotinin, Leupeptine, and Pepstatin were added fresh. The sonicate was centrifuged 12,000 RPM at 4° C. for 30 minutes to separate lysed cells from soluble protein.

The supernatant was collected and incubated with pre-equilibrated Ni-NTA beads (available from BioRad) for 1 hour at 4° C. by rotation. The binding capacity of polypeptides for Ni-NTA beads was about 5-10 mg/ml. Following the binding step, bound materials were centrifuged 4,000 RPM 4° C. for 10 minutes to pellet the Ni-NTA beads and separate from unwanted materials or "flow-through". Beads were then washed twice in 40 mL wash buffer by rotation in 4° C. for 30 minutes per wash cycle. The was buffer had a pH of 7.5 and 1 L of wash buffer included one bottle of PBS, 300 mM NaCl, 10% Glycerol, and 20 mM Imidazole. The remainder of the volume was filled with ddH$_2$O In addition, 1 ml 0.1 M PMSF was added fresh. The washed Ni-Beads were loaded on to a disposable gravity drip column and washed with residual Wash Buffer.

Bound proteins were eluted with elution buffer, using 2× elution buffer per 1 mL of packed volume of beads, i.e., 2 ml elution buffer for 1 ml of Ni-NTA beads. The elution buffer had a pH of 7.5 and 100 ml of elution buffer contained one bottle of PBS, 300 mM NaCl, 10% Glycerol, and 500 mM Imidazole. The remainder of the volume was filled with ddH$_2$O. The elution buffer was filtered before use. Eluate was collected in 2 mL fractions. The protein content of the fractions was analyzed using Bradford reagent. Individual fractions were dialyzed overnight in dialysis buffer at 4° C. The dialysis buffer had a pH of 7.5 and 4 L of elution buffer included one bottle of PBS, 300 mM NaCl, and 10% Glycerol. The remainder of the volume was then filled with ddH$_2$O. The following were freshly added to the elution buffer: 1 ml 0.1 M PMSF and 1 ml 1 M DTT. In the morning, the dialysis buffer was discarded and replaced with fresh buffer and dialysis was continued for an additional 3 hours. After dialysis, the individual fractions were pooled and centrifuged at 12,000 RPM at 4° C. for 20 minutes to remove any precipitation. The soluble protein was concentrated in the final concentration was determined using Bradford reagent.

Figure 7:
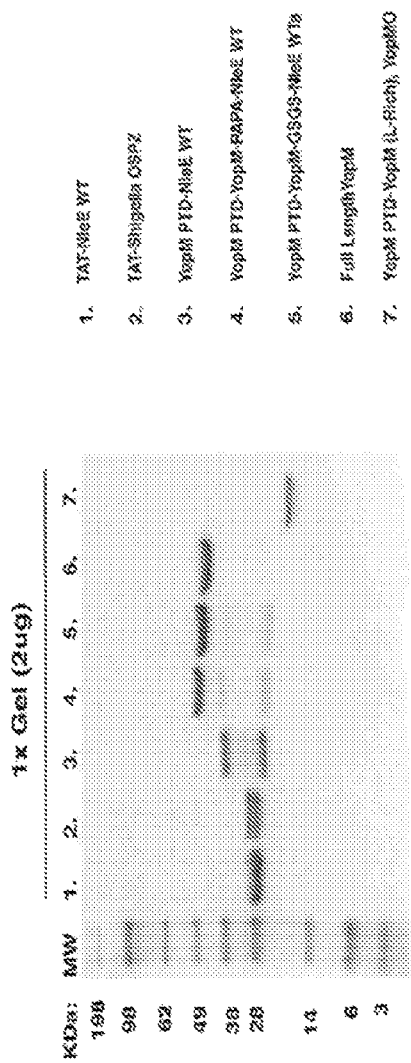
FIG. 7 is an exemplary SDS gel showing purified fusion proteins.

Purified polypeptides were analyzed by SDS-polyacrylamide gel electrophoresis (SDS-PAGE) analysis using known volumes of bovine serum albumin (BSA) as standards. Concentrated samples were aliquoted and stored at −80° C. Proteins were used directly after thawing on ice. An SDS-PAGE analysis of purified recombinant chimeric effector proteins is shown in FIG. 7. Each lane contained 2 µg of protein. Proteins were visualized by Coomassie blue staining.

Example 3: Cytokine Release

The effect of the bacterial effector proteins on cytokine release was analyzed in a cell-based assay using the human monocyte cell line, THP-1. Cytokine release was measured in vitro using the LEGENDplex Multi-Analyte Flow Assay Kit (BioLegend, Cat no. 740118) according to the supplier's directions. For culturing THP-1 cells, RPMI with glutamine and 20% FBS was used. These cells were incubated at 37° C. in humidified air 5% CO2 atmosphere. Finally, cell medium was changed every 2-3 days, and the cells were passaged at 95% confluence. To allow the cells to adapt to their environment, $3\times10^5$ cells were added to a 24-well plate the night before. The next day, protein was added to these cells for a period of 3 hours. The protein was then washed out with PBS. After cells were stimulated overnight with LPS stimulation, a concentration of 1 ug/mL was used. The next day, cells were washed again and cytokine were measured. All 13 inflammatory cytokines were measured using the LEGENDplex Human Inflammation Plane (13-plex) assay from Biolegend.

We analyzed the effect of effector protein constructs on the release of the pro-inflammatory cytokines IL-1beta, TNF-alpha, 11-6, MCP-1, IL 23 and IL-8. The effector protein constructs are shown in the table below:

| Construct name | Protein transduction domain | Effector 1 | Linker | Effector 2 | SEQ ID NO |
|---|---|---|---|---|---|
| YopM Full-length | YopM | YopM | | | 3 |
| TAT-NleE | TAT | EPEC NLeE | — | — | 28 |
| TAT Shigella OSPZ | TAT | Shigella OSPZ | — | — | 34 |
| YopM PTD-NleE | YopM | EPEC NLeE | — | — | 37 |
| YopM PTD-NleE (No linker) | YopM | YopM (L-rich) | — | EPEC NLeE | 10 |
| YopM PTD-NleE (GSGS linker) | YopM | YopM (L-rich) | GSGS | EPEC NLeE | 16 |
| YopM PTD-NleE (PAPA linker) | YopM | YopM (L-rich) | PAPA | EPEC NLeE | 13 |
| YopM PTD-YopM (L-rich) | YopM | YopM (L-rich) | — | — | 7 |
| IpaH 7.8 | | IpaH 7.8 | | | |
| IpaH 9.8 | | IpaH 9.8 | | | |

Figure 8:
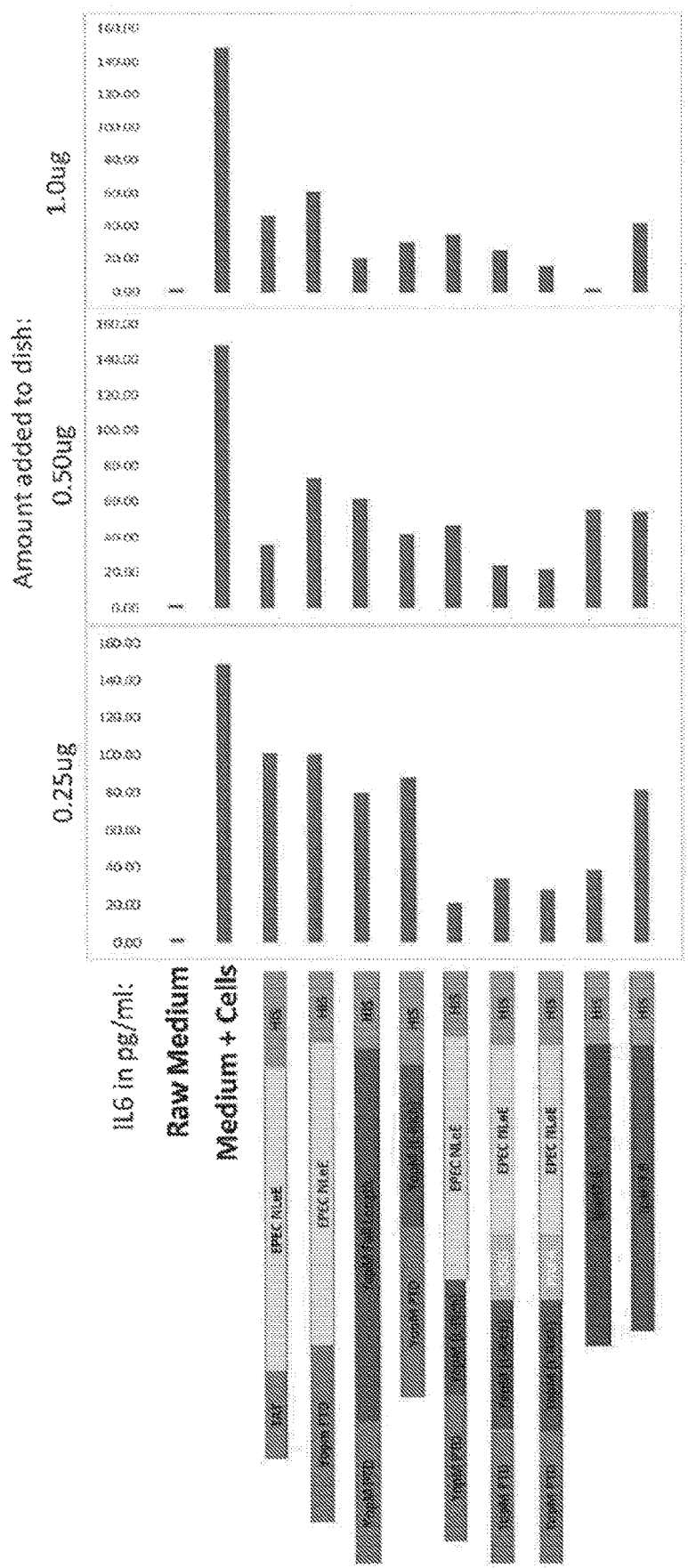
FIG. 8 is a graph showing the results of a dose-response analysis of IL-6 production in cells treated with recombinant purified effector proteins.

The results of these experiments are shown in FIGS. 8, 9, 10, 11 and 12. As shown in FIGS. 8, 9, 10, 11 and 12, the effector proteins reduced the levels of cytokines released into the medium relative to control samples that did not receive effector proteins. This effect was dose-dependent, with higher doses of effector proteins resulting in a steeper reduction in levels of released cytokines. These dose-dependent effects are shown in FIG. 8 with respect to IL-6. Similar dose-dependent effects were observed for IL-1beta, TNF-alpha, 11-6, MCP-1, IL 23, and IL-8.

Figure 9:
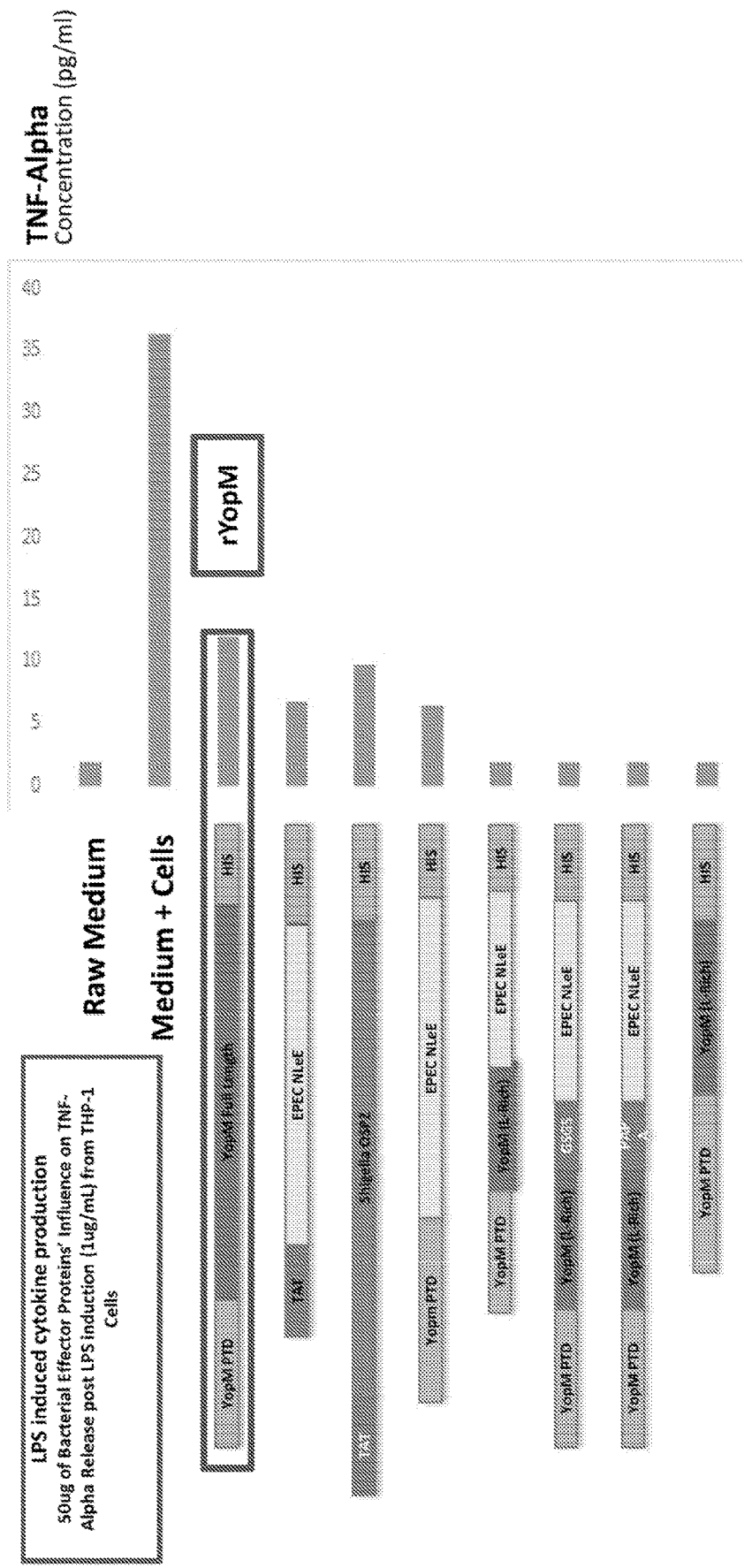
FIG. 9 is a graph showing the results of an analysis of the effect of paired fusion proteins on TNF-alpha.

The effector fusion proteins that included more than one effector protein domain produced a steeper reduction in the level of all released cytokines than did native effector proteins. As shown in FIG. 9, the paired effector fusion proteins YopM PTD-YopM (L-rich)-NLeE; YopM PTD-YopM (L-rich)-GSGS-NLeE; YopM PTD-YopM (L-rich)-PAPA NLeE; and YopM PTD-YopM (L-rich) produced a greater reduction in levels of TNF alpha released into the medium shown than did the full length YopM (rYopM) or Shigella OSPZ. This reduction was observed for effector fusion proteins that did not include a linker sequence and for effector proteins that included either a GSGS or a PAPA linker sequence.

Figure 10:
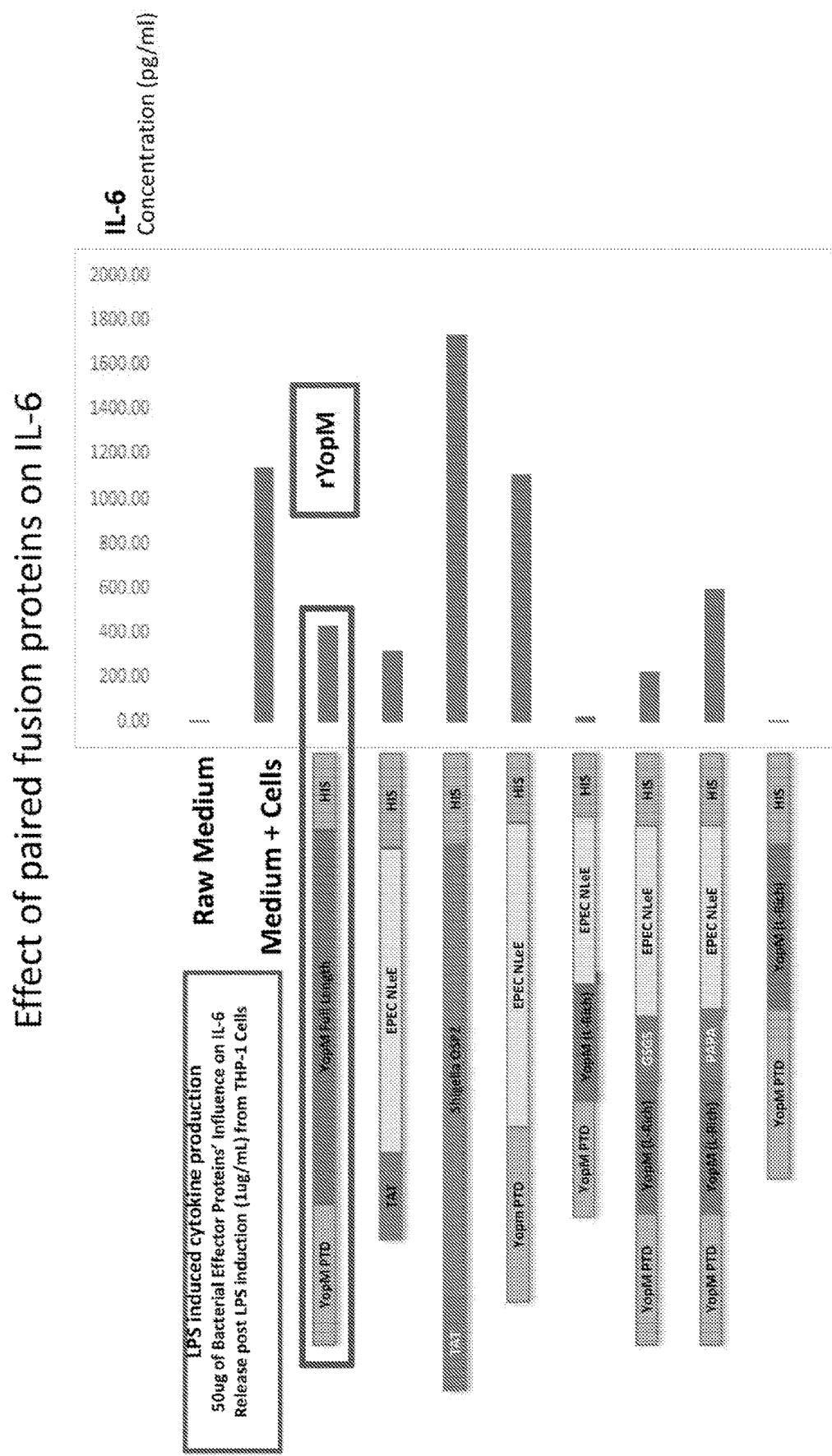
FIG. 10 is a graph showing the results of an analysis of the effect of paired fusion proteins on IL-6.

As shown in FIG. 10, the paired effector fusion proteins YopM PTD-YopM (L-rich)-NLeE; YopM PTD-YopM (L-rich)-GSGS-NLeE; YopM PTD-YopM (L-rich)-PAPA NLeE; and YopM PTD-YopM (L-rich) produced a greater reduction in levels of IL-6 released into the medium shown than did the full length YopM (rYopM) or Shigella OSPZ. This reduction was observed for effector fusion proteins that did not include a linker sequence and for effector proteins that included either a GSGS or a PAPA linker sequence.

Figure 11:
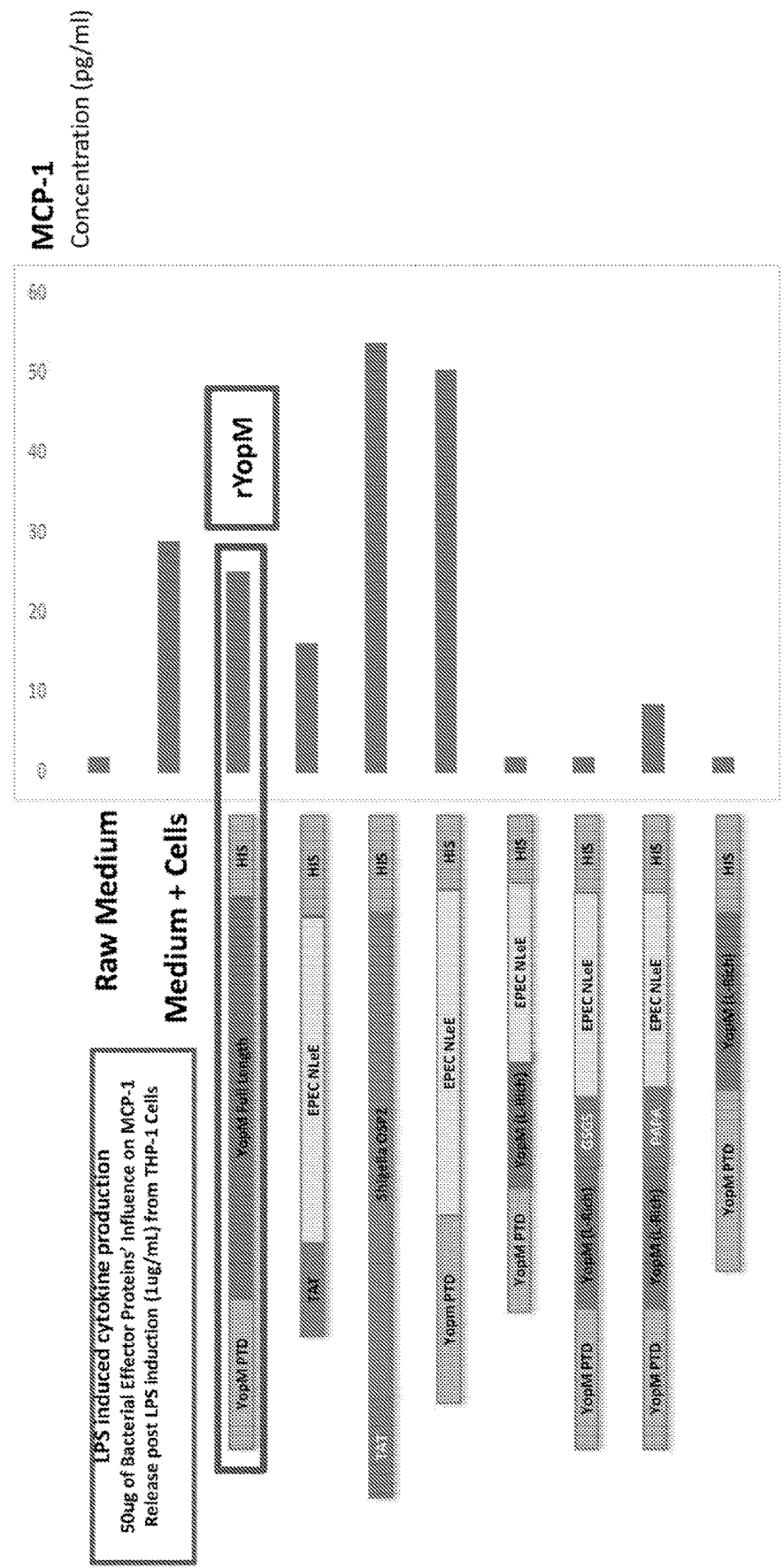
FIG. 11 is a graph showing the results of an analysis of the effect of paired fusion proteins on MCP-1.

As shown in FIG. 11, the paired effector fusion proteins YopM PTD-YopM (L-rich)-NLeE; YopM PTD-YopM (L-rich)-GSGS-NLeE; YopM PTD-YopM (L-rich)-PAPA NLeE; and YopM PTD-YopM (L-rich) produced a greater reduction in levels of MCP-1 released into the medium shown than did the full length YopM (rYopM) or Shigella OSPZ. This reduction was observed for effector fusion proteins that did not include a linker sequence and for effector proteins that included either a GSGS or a PAPA linker sequence.

Figure 12:
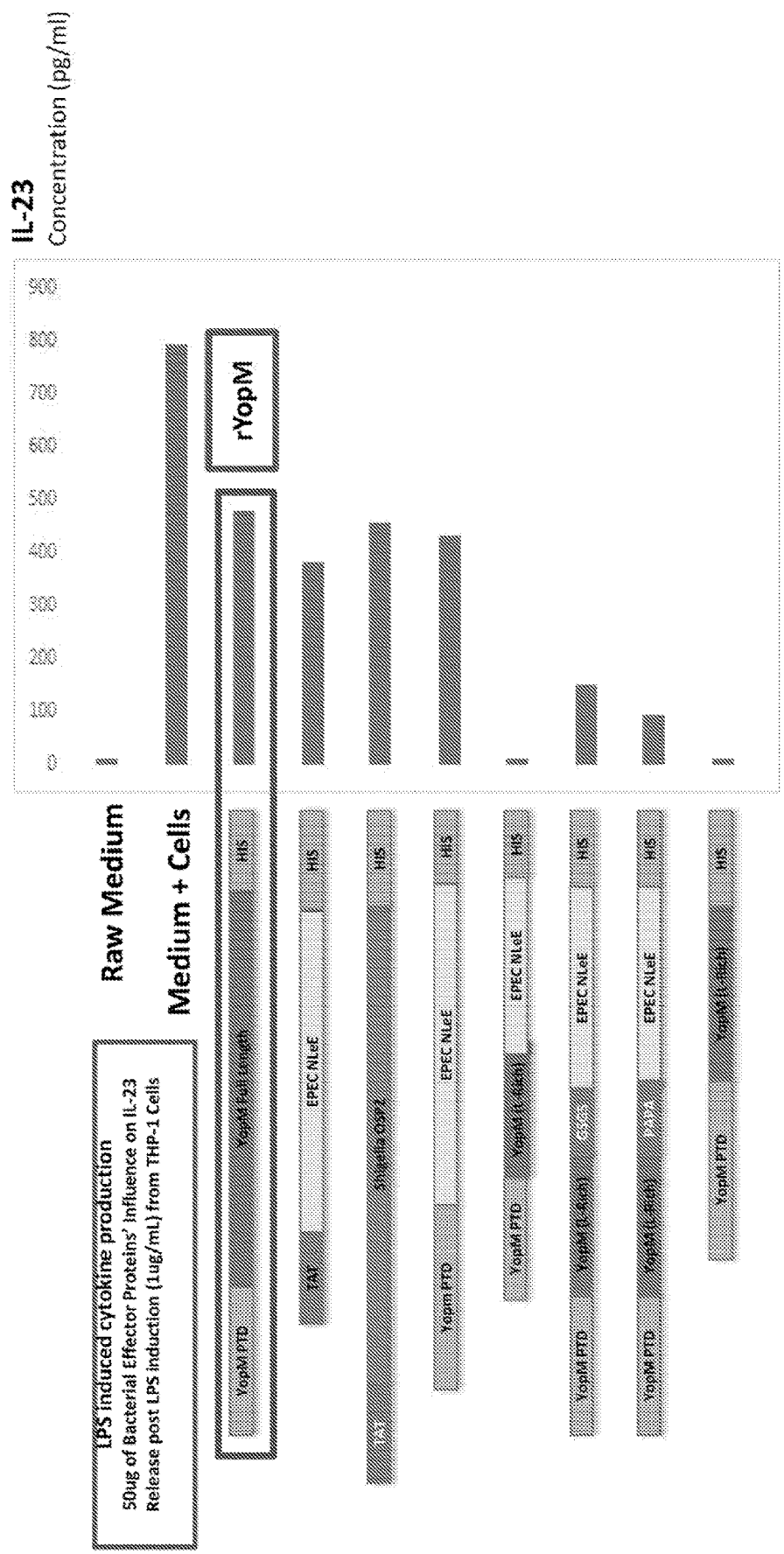
FIG. 12 is a graph showing the results of an analysis of the effect of paired fusion proteins on IL-23.

As shown in FIG. 12, the paired effector fusion proteins YopM PTD-YopM (L-rich)-NLeE; YopM PTD-YopM (L-rich)-GSGS-NLeE; YopM PTD-YopM (L-rich)-PAPA NLeE; and YopM PTD-YopM (L-rich) produced a greater reduction in levels of IL-23 released into the medium shown then did the full length YopM (rYopM) or Shigella OSPZ. This reduction was observed for effector fusion proteins that did not include a linker sequence and for effector proteins that included either a GSGS or a PAPA linker sequence.

Similar results were observed for IL-8. Taken together, the results shown in FIGS. 8, 9, 10, 11, and 12 indicate that fusion proteins that target multiple inflammatory pathways are more effective at reducing an inflammatory response than are proteins that target a single inflammatory pathway.

Example 4: Caspase Activity

The effect of YopM on caspase activity was measured using R&D System's Caspase-1/ICE Colorimetric Assay Kit (K111-100) according to the supplier's instructions. THP-1.cells were incubated with rYopM or a truncated YopM (YopMo) and then stimulated with LPS (lipopolysaccharide) and ATP to induce activation of caspase 1. More specifically, $2\times10^6$ THP-1 cells were seeded in 6-well cell culture plates in triplicate. The cells were incubated for 2 hours with rYopM (25 µg/ml) or a truncated YopM (YopMo) and then LPS was added (1 µg/mL) and the cells were incubated for an additional for 4 hours. Finally, ATP (5 mM) was added and the cells were incubated for 45 minutes. To pellet the cells, centrifugation was carried out at 250×g for 10 min. The cell pellet ($2\times10^6$ cells) was resuspended in 50 µl lysis buffer (Caspase 1/ICE Colorimetric Assay Kit R & D Systems) and incubated on ice for 10 min. Cell debris were pelleted at 10,000×g for 1 min. The colorimetric assay was carried out in 96-well plates. For this purpose, 50 ul cell lysate/well were placed and mixed with 50 ul 2× reaction buffer (Caspase 1/ICE Colorimetric Assay Kit R & D Systems). After addition of 5 µl of the substrate Ac-YVAD-pNA, incubation was carried out at 37° C. for 3 h. Subsequently, the absorbance at 405 nm was measured.

Figure 13:
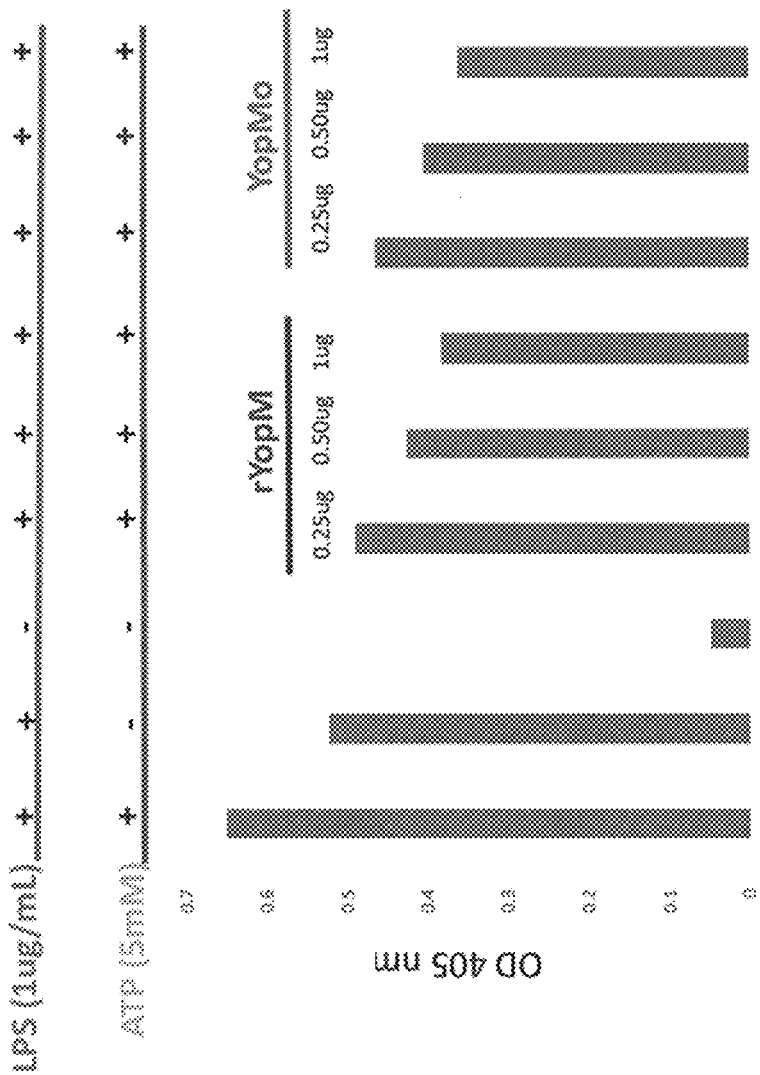
FIG. 13 is 12 is a graph showing the results of a dose response analysis of rYopM and YopMo on caspase 1 activity.

The results of this experiment are shown in FIG. 13. As shown in FIG. 13, a dose-dependent reduction of caspase 1 activity was observed in THP-1 cells that had been treated with rYopM. A dose-dependent reduction of caspase 1 activity was also observed in THP-1 cells that had been treated with the truncated YopM (YopMo). These data showed that the truncated YopM (YopMo) that contained only the L-rich region of the YopM retained the caspase I reducing function of the full length YopM.

Examples 5: Effector Polypeptide Uptake

Confocal microscopy. Cell uptake of effector polypeptides was analyzed using confocal microscopy. We analyzed single cell uptake of the following fusion protein constructs:

| Construct name | Protein transduction domain | Effector 1 | Linker | Effector 2 | SEQ ID NO |
|---|---|---|---|---|---|
| TAT-NleE | TAT | EPEC NleE | — | — | 28 |
| YopM PTD-NleE (No linker) | YopM | YopM (L-rich) | — | EPEC NleE | 10 |
| YopM PTD-NleE (GSGS linker) | YopM | YopM (L-rich) | GSGS | EPEC NleE | 16 |
| YopM PTD-NleE (PAPA linker) | YopM | YopM (L-rich) | PAPA | EPEC NleE | 13 |

Fusion proteins were labeled with FITC using the Sigma-Aldrich FluoroTag™ FITC Conjugation Kit according to the supplier's instructions as follows. Protein and FITC were dissolved in carbonate-bicarbonate buffer. The FITC was slowly added to the protein with stirring, then covered with foil and stirred for two hours at room temperature. The conjugate was separated from free FITC on a G-25 column in the fractions were collected. Fractions containing conjugate were pooled and the F/P ratio of conjugate was determined spectrophotometrically. The labeled protein was stabilized with 1% bovine serum albumin and 0.1% sodium azide and stored at 0-5° C.

HaCat cells were cultured using DMEM High glucose medium with 10% FBS. These cells were incubated at 37° C. in humidified air 5% CO2 atmosphere. Finally, cell medium was changed every 2-3 days, and the cells were passaged at 95% confluence. Cells were grown to appropriate confluency. Next, appropriate coated coverslips were added to well plates and the cells were seeded in the well plates containing the coverslips. For uptake analysis, polypeptides were added to the cells to a final concentration of 50 ug/mL and incubated for two hours. The protein with the cells were incubated and the protein was aspirated after the incubation period was complete. The cells were fixed with 4% formaldehyde and washed once again. The membrane was permeabilized with 0.2% triton-x-100 and washed again. The cells were blocked for 30 minutes and incubated in primary antibody (either Cy5 or Actin) overnight. The antibody was then aspirated, washed, and incubated in appropriate secondary antibody for 30 minutes. The cells were then washed and DAPI solution was applied for 5 minutes. The cells were then washed and mounted using Prolong Gold Anti-Fade Reagent. The mounted cells were allowed to cure overnight and then imaged. The DAPI was imaged using a wavelength of 490 nm. The Cy5 and Actin were imaged using 594 nm wavelength.

Detection of protein from fixed cells was performed using Nikon 80i upright fluorescent microscope. A filter cube specific for the relative green range (~488 nm) was used to detect FITC labelled protein within cells.

Figure 14:
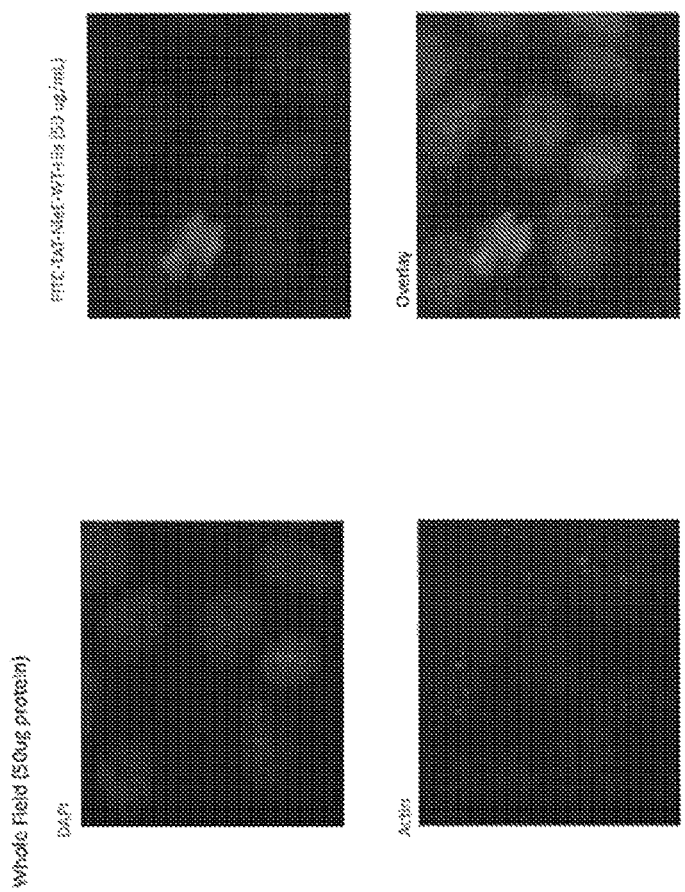
FIG. 14 shows the uptake of FITC-TAT-NleE-WT-His protein by Hacat cells.
Figure 15:
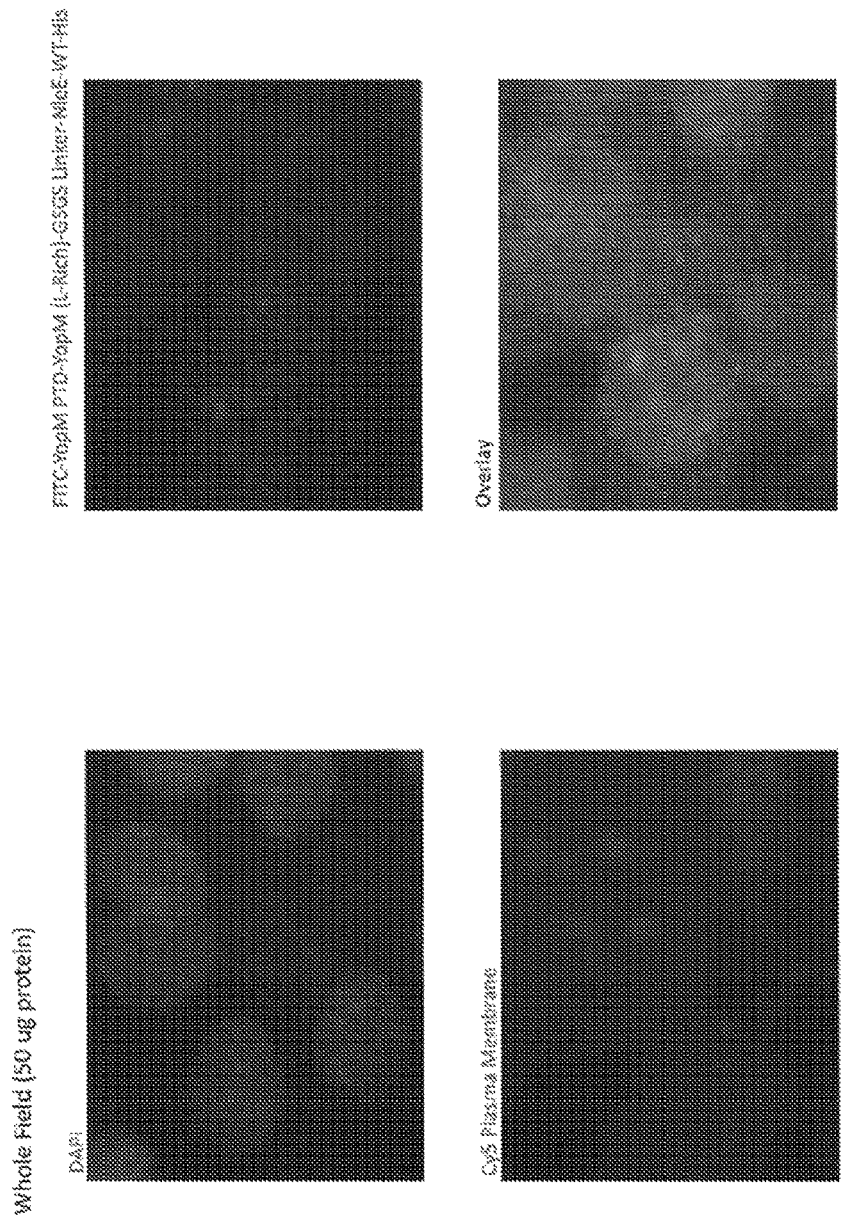
FIG. 15 shows the uptake of FITC-YopM PTD-YopM (L-Rich)-GSGS Linker NleE-WT-His protein by Hacat cells.
Figure 16:
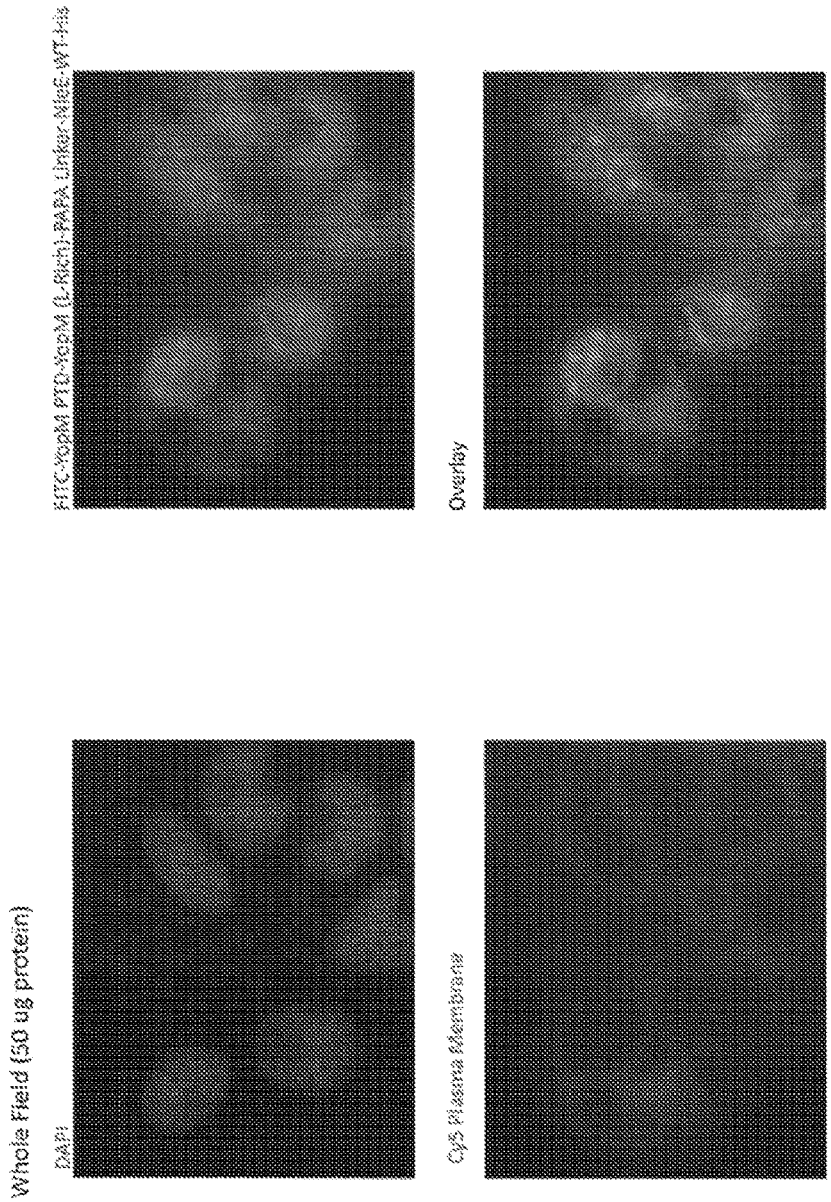
FIG. 16 shows the uptake of FITC-YopM PTD-YopM (L-Rich)-PAPA Linker-NleE-WT-His protein by Hacat cells
Figure 17:
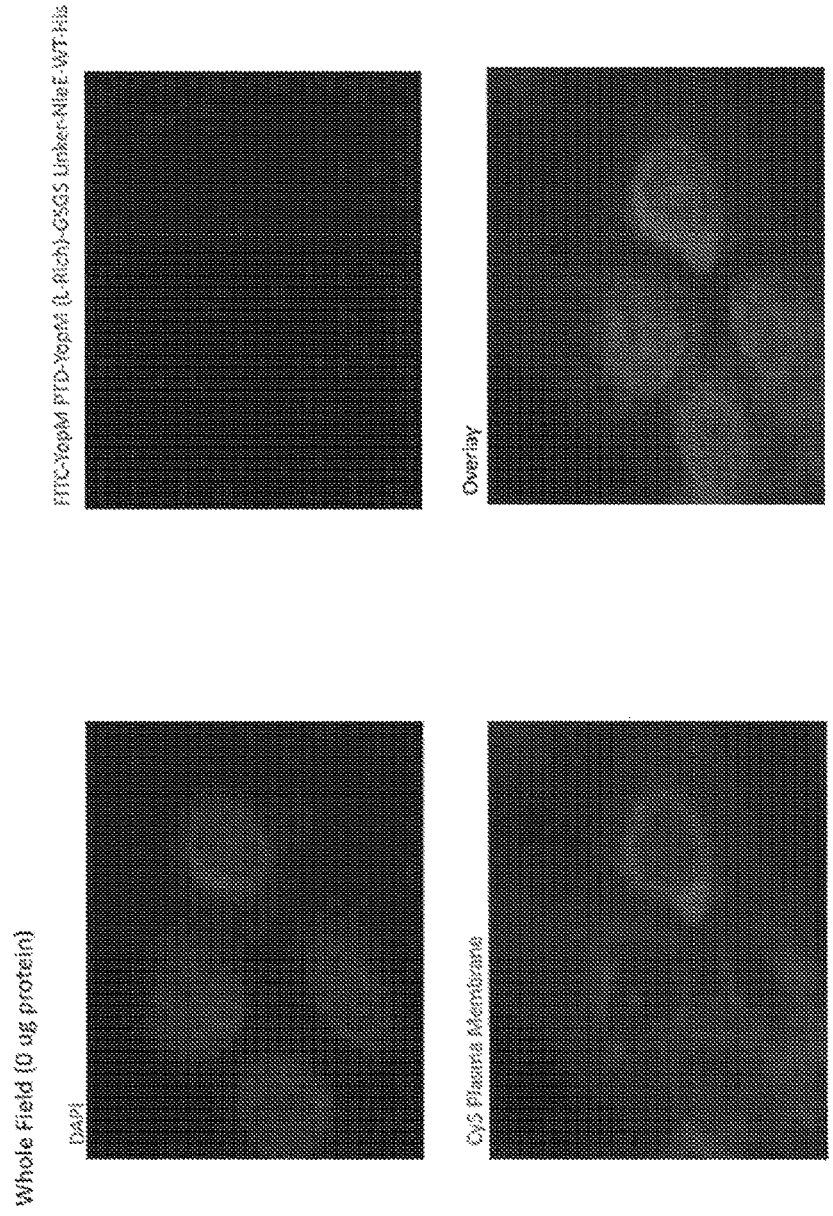
FIG. 17 shows the uptake of FITC-YopM PTD-YopM (L-Rich)-GSGS Linker-NleE-WT-His protein by Hacat cells.

The results of this experiment are shown in FIGS. 14, 15, 16, and 17. As shown in FIG. 14, incubation of cells with QE12-TAT-NleE resulted in nuclear fluorescence. As shown in FIGS. 15 and 16, both QE60-YopM PTD-NleE (GSGS linker) and QE60-YopM PTD-NleE (PAPA linker), respectively, produced punctate cytoplasmic fluorescence that was not observed in untreated control cells (FIG. 17). Taken together, these data show that the fusion polypeptides were taken up by individual cells.

Figure 18:
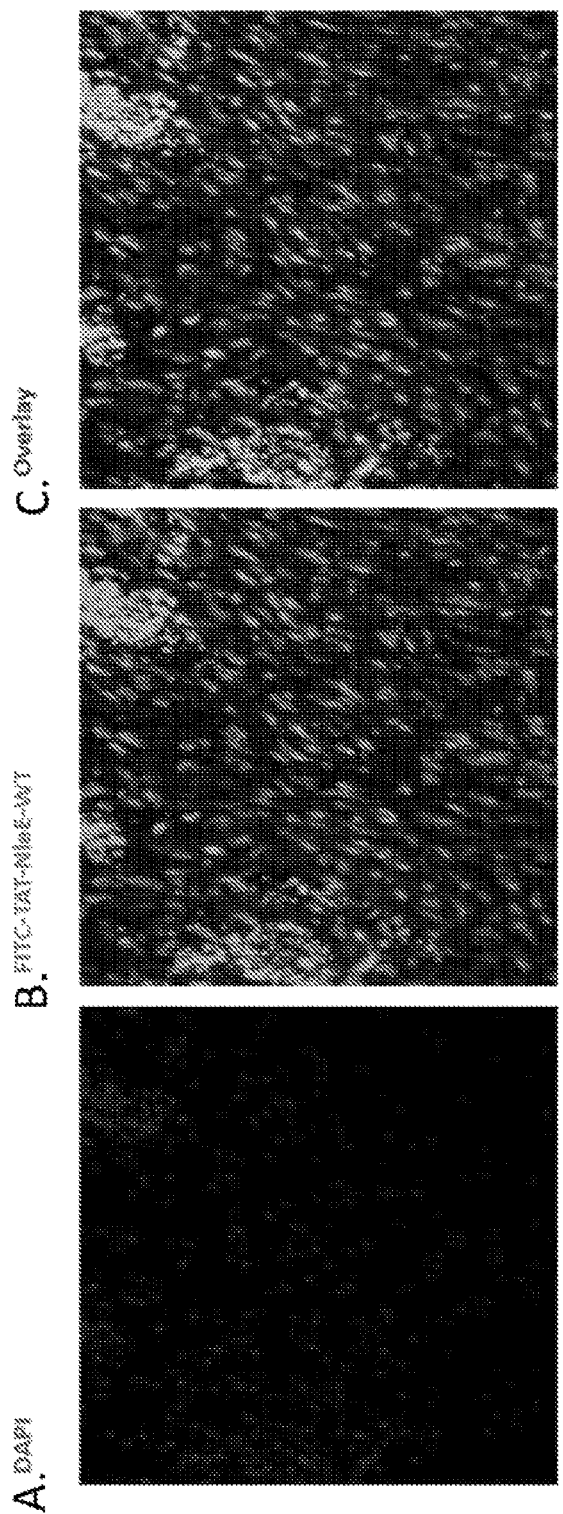
FIG. 18 shows the uptake of TAT-NleE fusion polypeptide into intact mouse skin.

Inverted microscopy. Uptake of QE12-TAT-NleE was analyzed by inverted microscopy as follows. A segment of skin was isolated from a shaved section of a mouse, and the tissue was preserved in a saline solution to maintain the cell viability within the tissue. The tissue was stained with 50 ug of FITC labeled TAT-NleE that was applied to the top of the sample and allowed to diffuse over a 2 hour period. Afterwards, the tissue was fixed with paraformaldehyde and stained with DAPI. The skin segment was then sliced in 10 uM increments, and the top slice was observed in an inverted microscope was used with varying objectives. As shown in FIG. 18, the TAT-NleE fusion polypeptide entered intact mouse skin and penetrated through multiple cell layers.

Two-photon microscopy. Penetration of TAT-NleE- into mouse skin was analyzed by two-photon microscopy. A 1 cm×1 cm segment of mouse skin was stained with. 50 μg of FITC-labeled TAT-NleE for two hours and counter stained with DAPI. the sample was analyzed by two-photon microscopy. More specifically, mouse hair was removed post-euthanasia and a 1 cm×1 cm segment of skin was removed and submerged in 1×PBS pH 7.4 to maintain tissue viability. Afterwards, the PBS was removed, and 50 ug FITC-TAT-NleE was applied to the top of the skin and allowed to incubate at room temperature for two hours. Afterwards, the tissue was washed three times for five minutes each with 1×PBS pH 7.4 to remove all waste. From there the tissue was permeabilized with Triton-x and fixed with 4% PFA. DAPI was then added to solution of PBS at a concentration of 1:1000 and incubated in the tissue for 3-5 minutes. Then the washing period was repeated (three times for five minutes each in 1 ml of PBS). The tissue was then mounted on a dish submerged in PBS ready for 2-photon imaging.

Figure 19:
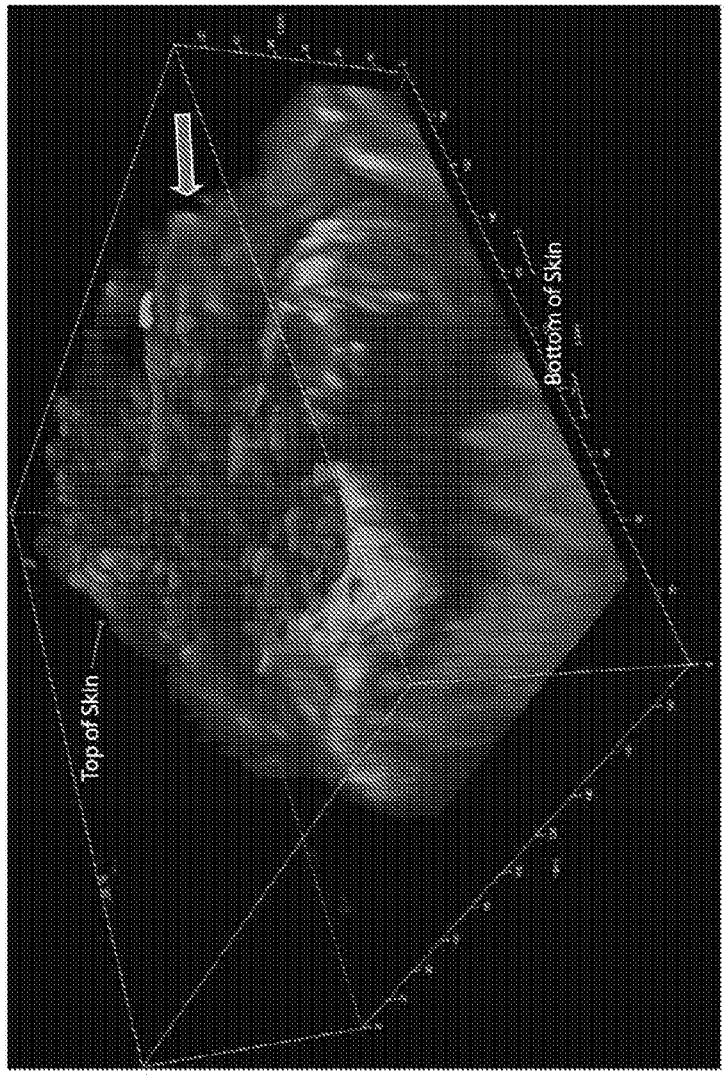
FIG. 19 shows is an two-photon microscopy image of uptake of TAT-NleE fusion polypeptide into intact mouse skin.
Figure 20:
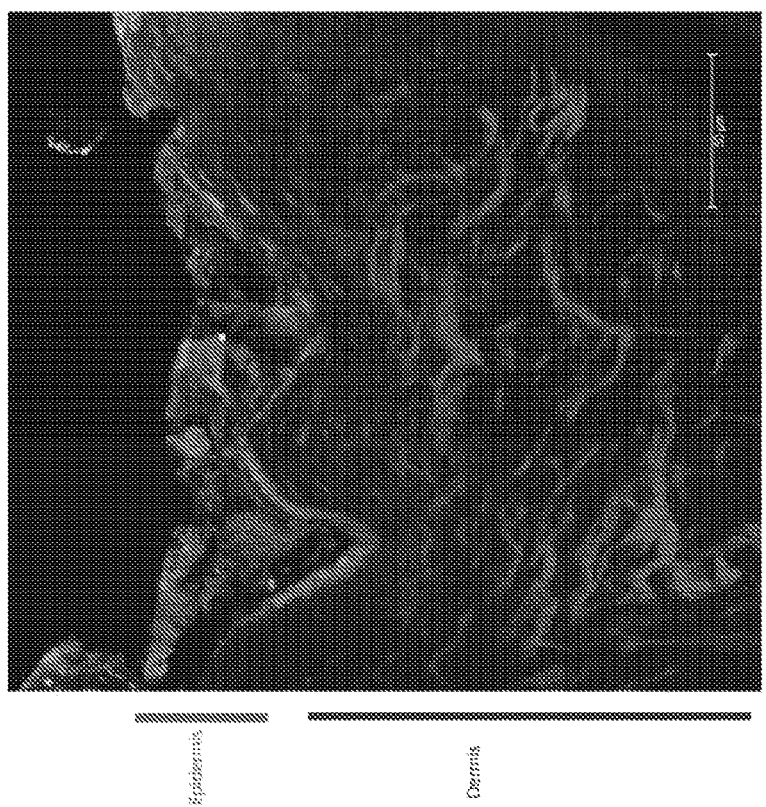
FIG. 20 shows a two-photon microscopy image of a 10 micron slice of mouse skin showing uptake of TAT-NleE fusion polypeptide into intact mouse skin.

A 3 dimensional image is shown in FIG. 19 and a 10 uM slice of the stained tissue is shown in FIG. 20. As shown in FIGS. 19 and 20, the TAT-NleE penetrated the skin into the epidermis, but not the dermis.

Example 6: Methylase Activity

Methylase activity of recombinant proteins that included NleE effectors was analyzed using the MTase glo assay from Promega. We assayed the methylase activity of wild-type NleE, mutant NleE R107A and fusion proteins YopM PTD-NleE (GSGS linker), YopM PTD-NleE (PAPA linker). We also analyzed the methylase activity of NLeE from *Shigella*.

The in vitro methylase assay was developed using as a base, the MTase glo assay from Promega Inc. The primary assay buffer for enzyme activity was (25 mM Tris, pH 8, 50 mM NaCl, 1 mM EDTA, 3 mM MgCL2, 0.1% BSA, 0.005% Tween20, 5 mM DTT). To determine the effect of various vehicles and buffers on NLeE a 40 uL aliquot of vehicle was spiked with 1 uL of 20 mg/mL NLeE (0.5 mg/mL final). After 30 mins, 5 uL of spiked vehicle was diluted into 5000 uL of primary assay buffer—(termed 'SPIKED' in graphs).

To determine the effect of diluted vehicle on NLeE activity, 5 uL of vehicle diluted to 5000 uL of assay buffer was used. 1000 uL was then removed and used for the no enzyme controls. 1 uL of 0.5 mg/mL NLEE was then added to 1000 uL of diluted vehicle and the assay commenced. The methyltransferase assay itself was performed in 4×1:2 serial dilutions of each sample generated above in assay buffer and 2.5 uL added to 384-well assay plate. Reactions were initiated at various time points by the addition of 2.5 uL of 2× MTaseGlo, 1 uM GST-TAB2 protein substrate and 20 uM SAM in assay buffer. After the time course, reactions were terminated by the addition of 5 uL Methyltransferase Detection Reagent and the multiwell plates read for quantitative O.D. using a standard plate reader.

Figure 21:
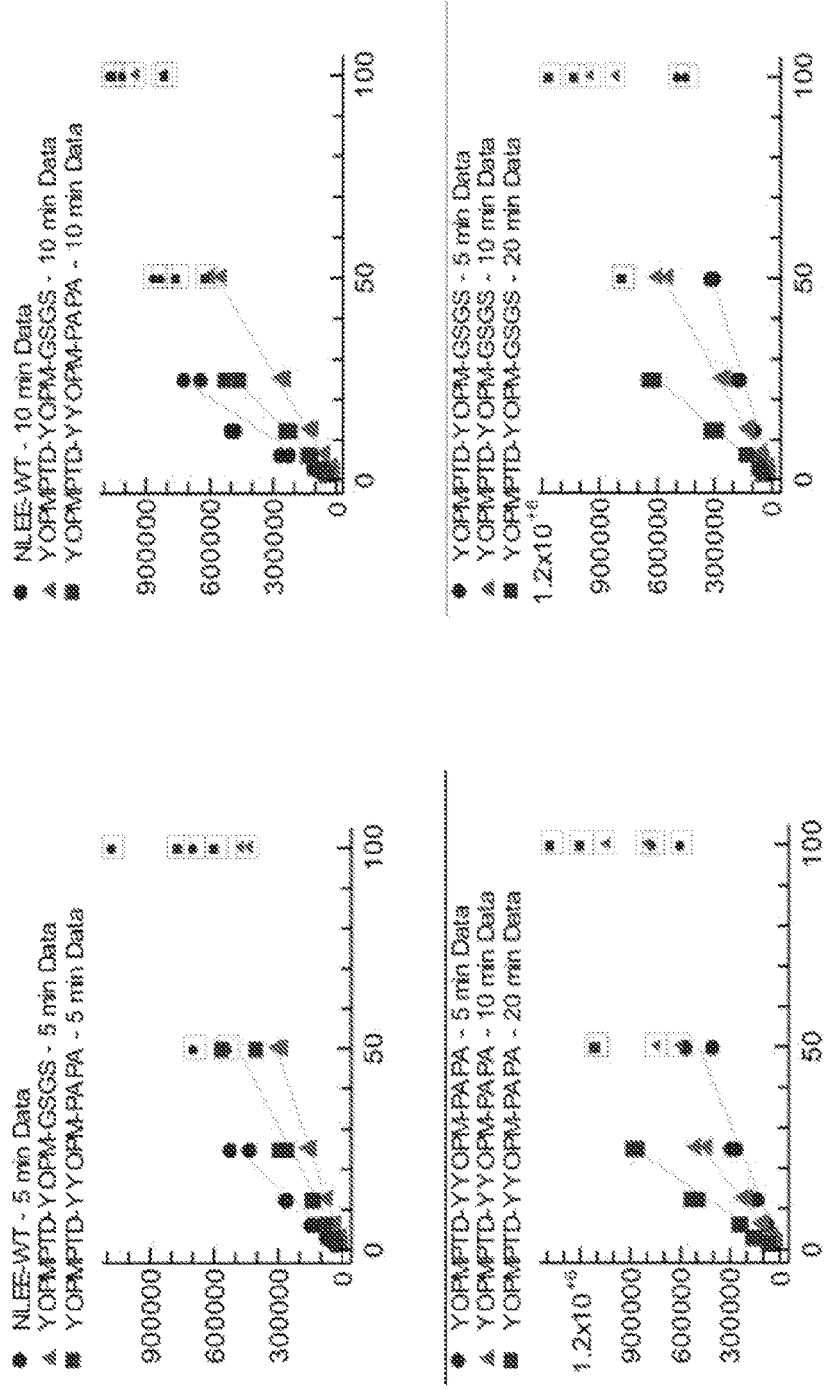
FIG. 21 shows graphs illustrating an analysis of methylase activity of YopM PTD-YopM (L-Rich)-PAPA/GSGS-NleE-WT-His fusion proteins.
Figure 22:
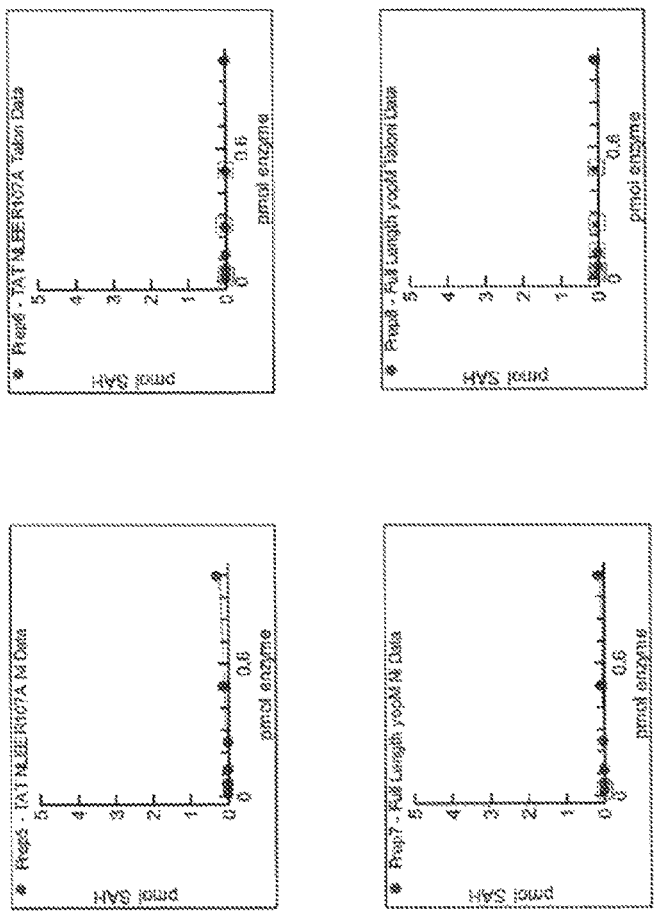
FIG. 22 shows graphs illustrating an analysis of methyltransferase activity NleE-R107A mutant and YopM.
Figure 23:
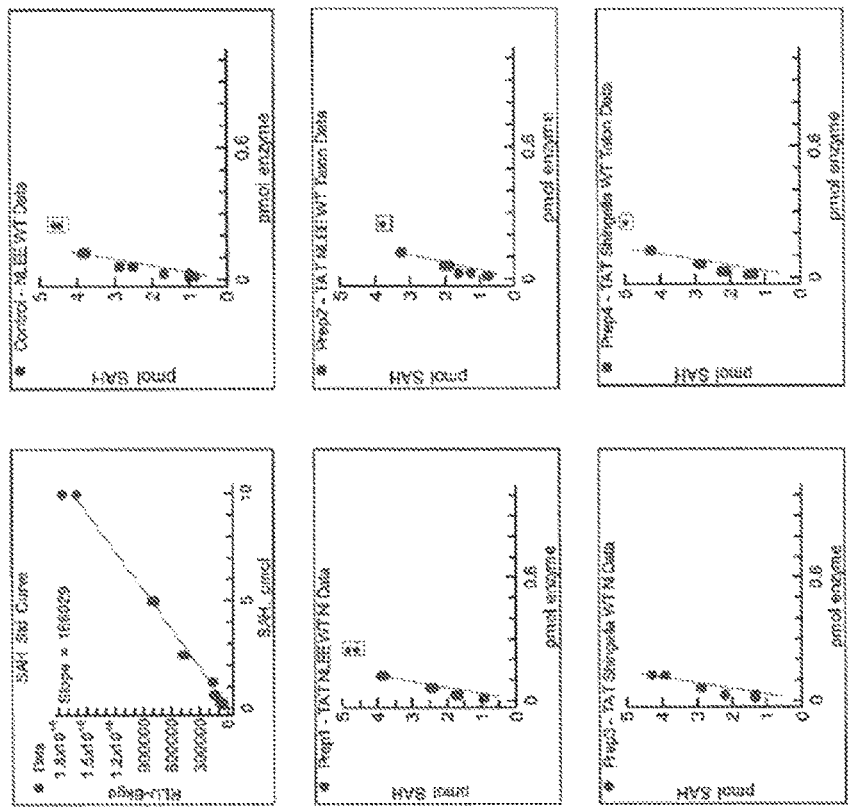
FIG. 23 shows graphs illustrating a NleE and *Shigella* Methyltransferase activity assay.

The results of this analysis are shown in FIGS. 21, 22 and 23. As shown in FIG. 21, both fusion constructs retained the methylase functionality of native NLeE. As shown in FIG. 22, the presence of an R107A mutation in NLeE abolished methylase activity. As shown in FIG. 23, the *Shigella* NleE showed methylase activity at levels comparable to that seen for the EPEC NleE

Example 7: Effect of Formulations on NleE Methylation Activity

Figure 24:
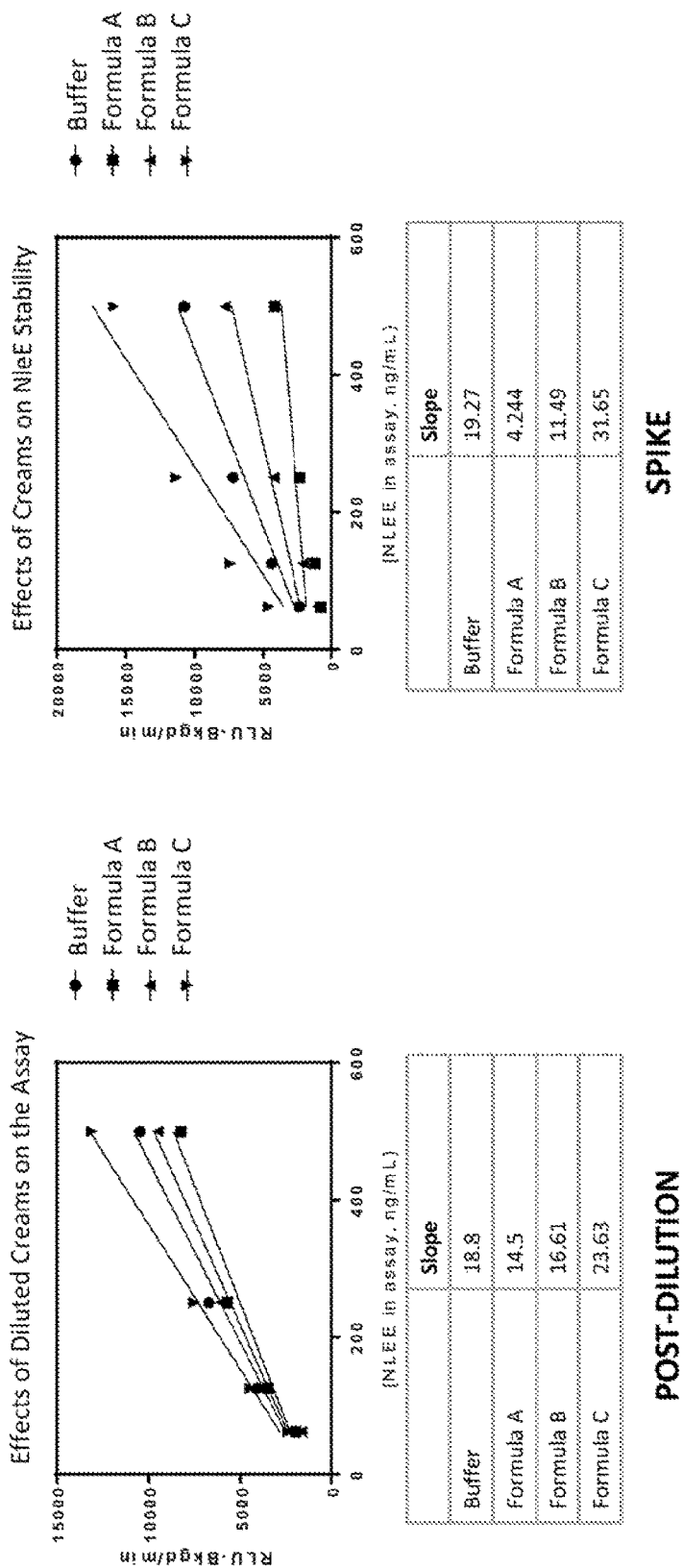
FIG. 24 depicts the results of an experiment comparing the effect of formulations on NleE methylation activity.
Figure 25:
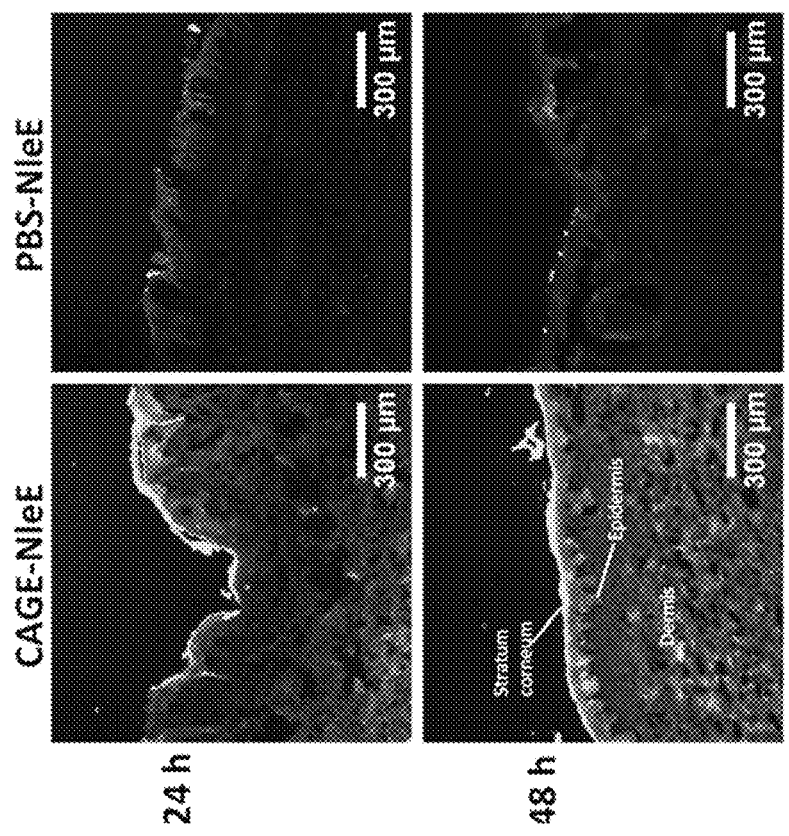
FIG. 25 shows four micrograph panels showing transdermal penetration of CAGE-NleE protein.
Figure 26:
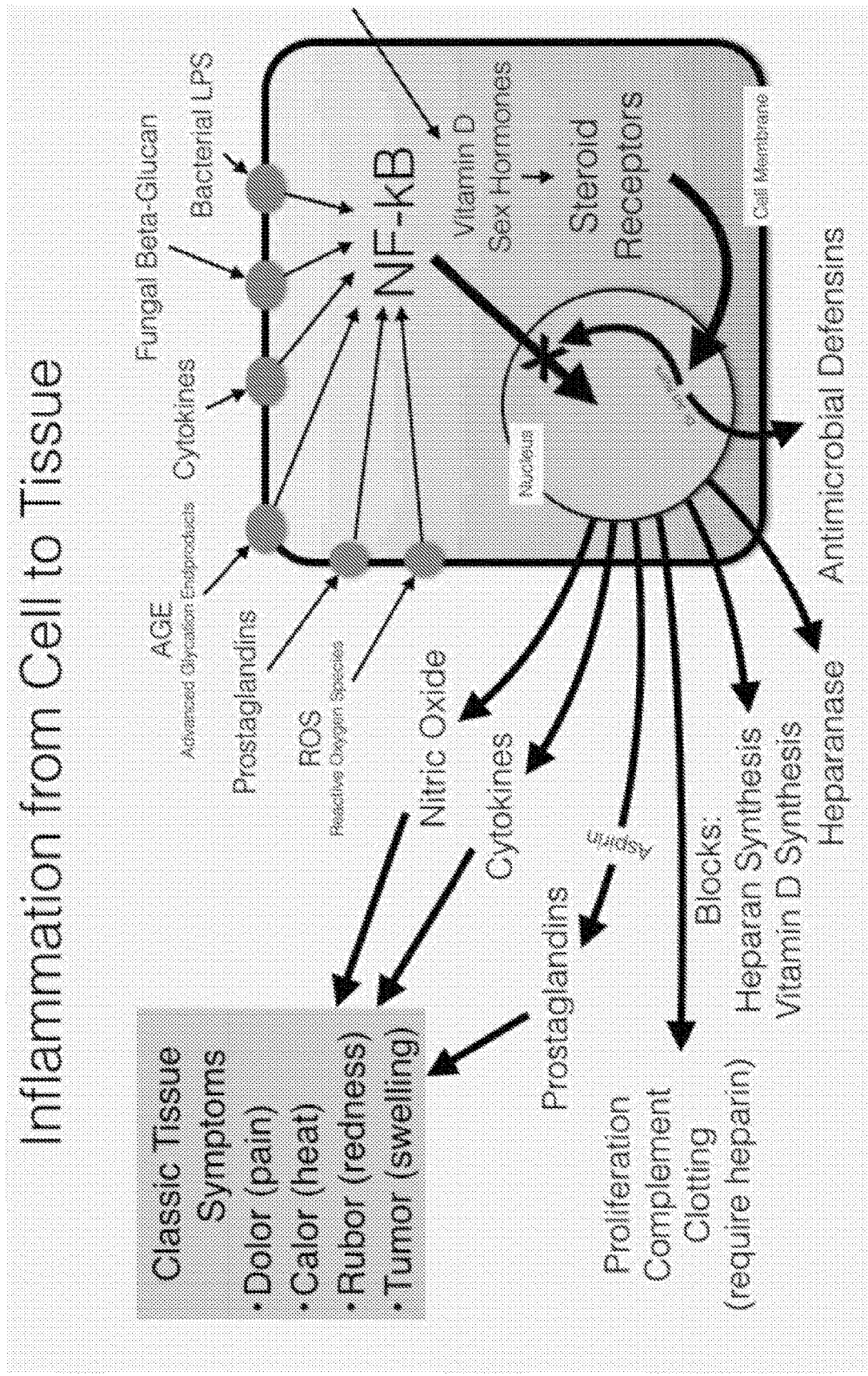
FIG. 26 is a schematic showing how inflammation develops from cell to tissue in the skin.
Figure 27:
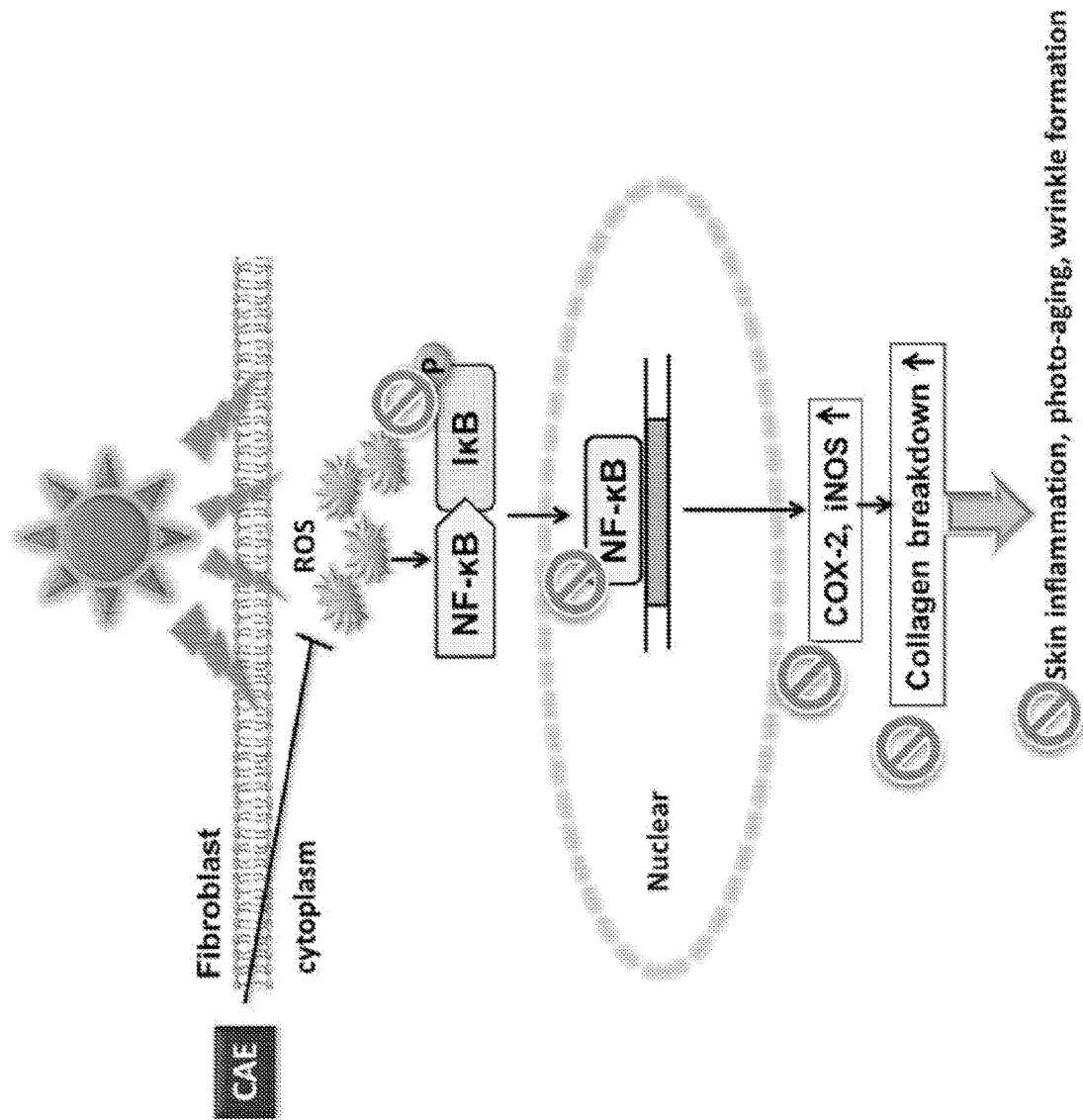
FIG. 27 is a schematic showing the impact of a skin irritant on the NFKB pathways.

We analyzed the effective three different commercial formulations/delivery agents on NleE methylation activity in vitro. These were designated: Formula A, Formula B, and Formula C The experimental setup was exactly as described above except that the buffer controls contained an equivalent amount of Formula A, Formula B or Formula C as controls. The results of this experiment are summarized in FIG. 24. As shown in FIG. 24*a*, NLeE methylase activity was retained in the presence of all three formulations. As shown in FIG. 24*b*, NLeE was stable in the presence of each of the formulations, although the degree of stability varied.

Example 8: How Specific is NleE for Inhibiting NFKB?

We cloned expressed and tested 64 other human C4 ZF containing proteins, among them the sequences identified in the table below. But few of them were modified by NleE. Thus, the specificity of NleE is extremely high.

| | | |
|---|---|---|
| CAN15_HUMAN/7-26 | WsCvr..CtflNpagqrqCsiC | |
| CAN15_HUMAN/48-67 | WpCar..CtfrNflgkeaCevC | |
| CAN15_HUMAN/147-166 | WaCpr..CtlhNtpvassCsvC | |
| CAN15_HUMAN/344-363 | WsCak..CtlrNptvaprCsaC | |
| CAN15_HUMAN/416-435 | WaCpa..CtllNalrakhCaaC | |
| EWS_HUMAN/522-543 | WqCpnpgCgnqNfawrteCnqC | Oncogene RNA Binder |
| FUS_HUMAN/426-447 | WkCpnptCenmNfswrneCnqC | Oncogene Annealing |
| HOIL1_HUMAN/197-216 | WqCpg..CtfiNkptrpgCemC | Binds Ub Chains |
| MDM2_HUMAN/303-322 | WkCts..CnemNpplpshCnrC | P53 regulation |
| MDM4_HUMAN/304-323 | WqCte..CkkfNspskryCfrC | P53 regulation |
| NEIL3_HUMAN/321-340 | WtCvv..CtliNkpsskaCdaC | Endonuclease8 Repair |
| NPL4_HUMAN/584-603 | WaCqh..CtfmNqpgtghCemC | Ub Chaperone Erad |
| NRP1_YEAST/359-378 | WnCps..CgfsNfqrrtaCfrC | Rna Binder No Fcn |
| NRP1_YEAST/585-604 | WkCst..CtyhNfaknvvClrC | |
| NU153_HUMAN/662-681 | WqCdt..CllqNkvtdnkCiaC | NUP153 Nuc Pore |
| NU153_HUMAN/726-745 | WdCdt..ClvqNkpeaikCvaC | |
| NU153_HUMAN/797-816 | WeCsv..CcvsNnaednkCvsC | |
| NU153_HUMAN/855-874 | WdCel..ClvqNkadstkClaC | |
| RBM10_HUMAN/217-236 | WlCnk..CgvqNfkrrekCfkC | RNA Binding |
| RBM5_HUMAN/185-204 | WlCnk..CclnNfrkrlkCfrC | RNA Binding |
| RBP2_HUMAN/1356-1375 | WhCns..CslkNastakkCvsC | RANBP2 Huge Nuc Pore |
| RBP2_HUMAN/1419-1438 | WdCsi..ClvrNeptvsrCiaC | |
| RBP2_HUMAN/1483-1502 | WdCsa..ClvqNegsstkCaaC | |
| RBP2_HUMAN/1547-1566 | WdCss..ClvrNeanatrCvaC | |
| RBP2_HUMAN/1610-1629 | WdCsv.. ClvrNeasatkCiaC | |
| RBP2_HUMAN/1669-1688 | WdCsv..ClvrNeasatkCiaC | |
| RBP2_HUMAN/1728-1747 | WdCsv..ClvrNeasatkCiaC | |
| RBP2_HUMAN/1785-1804 | WdCsv..CcvqNesssslkCvaC | |
| RBP56_HUMAN/358-379 | WvCpnpsCgnmNfarrnsCnqC | |
| RNF31_HUMAN/304-323 | WhCaa..CamlNepwavlCvaC | |
| RNF31_HUMAN/354-373 | WaCqs..CtfeNeaaavlCsiC | |
| RNF31_HUMAN/413-432 | WyCih..CtfcNsspgwvCvmC | |
| RYBP_HUMAN/25-44 | WdCsv..CtfrNsaeafkCsiC | |
| SHRPN_HUMAN/352-371 | WsCps..CtfiNapdrpgCemC | |
| TAB2_HUMAN/668-687 | WnCta..CtflNhpalirCeqC | NFKB pathway |
| TAB3_HUMAN/687-706 | WnCds..CtflNhpalnrCeqC | NFKB pathway |
| TX13A_HUMAN/380-399 | WdCpw..CnavNfsrrdtCfdC | |

A cysteine methylation assay was performed and shows that NleE does not utilize zinc fingers of known highly related zinc fingers. NleE targets NFKB signaling at a key step in TAK1 kinase activation. The CYS-4 Zinc Finger of TAB2 was required to bind free K63 Ub chains to activate TAK1 kinase, which thereby triggers NFKB signaling. The TAB2/3 Cys 4 Zinc-Finger binds K63 linked Ub chains: The metal chelated structure of the ZF required binding. NleE targets NFKB signaling by methylating a single Cysteine in the C4 ZF TAB2 of TAB2 abolishing K63 Ub sensing. Cys 673 in TAB2 is the target of NleE. This highly specific activity of NleE is repurposed in the compositions described herein to shut down the NFKB pathway and reduce inflammation.

Example 9: Penetration of Recombinant NleE into the Skin in an Ex Vivo Pig Skin Model A key claim and potential stumbling block to use of NleE as a skin anti-inflammatory compound is to show that this globular folded protein of MW 38 kDa is able to penetrate the dermis and epidermis in order to access cells in which the NFKB system is aberrantly activated. A recombinant construct was prepared by fusing the amino acid sequence of NleE to an N-terminal histidine, and covalently labelling that peptide with FITC dye, resulting in the peptide His-NleE-FITC. --This construct was mixed with the eutectic, cholinate-based solvent CAGE, as described above at a concentration above at a concentration of 1-10 mg/ml. The amount of peptide in CAGE or PBS was 1 mg/ml. The final CAGE concentration was 90% v/v. The mixture was applied to live pig skin being perfused in a Franz diffusion chamber at 37 degrees C. for 24 or 48 hours. The Franz diffusion chamber is described by Technical Brief 2009 vol. 10, Particle Sciences-Drug Development Services (Bethlehem, PA). After these time periods, skin was harvested, fixed and sections followed by microscopy to visualize the FITC dye. The results (FIG. 25) show that CAGE-solubilized NleE FITC was able to penetrate the stratum corneum, epidermis and dermis and that virtually every cellular compartment of the skin. Up to 20-30 cell layers were contacted.-

In comparison to published reports by Banerjee et. al 2017, particularly FIG. 1 using CAGE to transport the globular proteins ovalbumin and bovine serum albumin, the NleE penetrates as well if not better than these test proteins. NleE solubilized in PBS and applied to the pig skin showed no transduction past the stratum corneum.

In summary, this pre-clinical data provides support that recombinant NleE protein is stable in the eutectic solvent CAGE and can be delivered to multi layers of the skin locally in a topical manner. It also provides support for using NleE protein and the combinations described herein that contain an intrinsic PTD domain which renders the protein capable of penetrating cells and tissues and turning off inflammatory cytokines. The ability of these combinations of proteins to penetrate, in an apparently active form and inhibit production of a multitude of inflammatory cytokines, is reflected in its therapeutic effect on psoriatic lesions in a mouse skin model. These compositions delivered in a cream topically, in therapeutic levels are not anticipated to appreciably enter the regional lymphatics.

These observations strongly support the use of recombinant bacterial effector proteins containing PTDs (Table 1) are useful as a platform for inhibiting various accessible inflammatory disease processes in the body.

Thus, methods and compositions for treating inflammation related to activation of the NFkB, JNK and p38 pathways, e.g., inflammatory conditions of skin, include a composition comprising a first construct comprising a selected immunomodulatory effector protein or functional equivalent thereof that targets a first functional domain; and at least one additional construct comprising a different effector protein or a functional equivalent thereof that targets an additional functional domain. The first construct is optionally linked to a selected protein transduction domain (PTD) or penetrating peptide (CPP) or to a targeting moiety. The additional construct is optionally linked to the same PTD or CPP of the first construct or to an additional PTD or CPP. In one embodiment, a combination of these constructs is provided. In another embodiment the first construct is fused to one or more additional constructs in a single polypeptide. The composition further comprise an optional linker amino acid sequence interposed between each construct and an optional targeting moiety.

Each and every patent, patent application, and publication, including websites cited throughout specification are incorporated herein by reference. Similarly, the SEQ ID NOs which are reference herein and which appear in the appended Sequence Listing are incorporated by reference. While the invention has been described with reference to particular embodiments, it will be appreciated that modifications can be made without departing from the spirit of the invention. Such modifications are intended to fall within the scope of the appended claims.

The invention claimed is:

1. A composition comprising a set of paired peptides, wherein the set of paired peptides is linked to a protein transduction domain, and wherein the set of paired peptides comprises a first bacterial effector polypeptide linked to a second bacterial effector polypeptide, wherein the protein transduction domain is a YopM protein transduction domain, an SspH1 protein transduction domain, or an 1paH protein transduction domain wherein the protein transduction domain and the set of paired peptides comprise a fusion protein and the amino acid sequence of the fusion protein is at least 85% identical to the sequence set forth in SEQ ID NO. 10, 13, 16, 19, 22, or 24.

2. The composition of claim 1, wherein the first bacterial effector polypeptide and second bacterial effector polypeptide are different.

3. The composition of claim 1, wherein a first bacterial effector polypeptide and the second bacterial effector polypeptide are immunomodulatory.

4. The composition of claim 1, wherein the first bacterial effector polypeptide and the second bacterial effector polypeptide recognize a different molecular target or modulate a different inflammatory pathway.

5. The composition of claim 4, wherein the inflammatory pathway is the NFKB pathway, the JNK pathway, the p38 pathway or the STING pathway.

6. The composition of claim 1, wherein a linker is positioned between the first bacterial effector polypeptide and the second bacterial effector polypeptide.

7. The composition of claim 1, wherein the protein transduction domain is a YopM protein transduction domain.

8. The composition of claim 7, wherein the protein transduction domain comprises SEQ ID NO. 5.

9. The composition of claim 1, wherein
   (a) the first bacterial effector polypeptide is a YopM polypeptide or an NLeE polypeptide; or
   (b) the second bacterial effector polypeptide is a YopM polypeptide or an NLeE polypeptide.

10. The composition of claim 1, wherein the first bacterial effector polypeptide is a YopM polypeptide and the second bacterial effector polypeptide is an NLeE polypeptide.

11. A fusion protein comprising a set of paired peptides, wherein the set of paired peptides comprises a first bacterial effector polypeptide linked to a second bacterial effector polypeptide wherein the amino acid sequence of the fusion protein is at least 85% identical to the sequence set forth in SEQ ID NO. 10, 13, 16, 19, 22, or 24.

12. A composition comprising a protein transduction domain polypeptide linked to a first bacterial effector polypeptide and at least one additional bacterial effector polypeptides wherein the first bacterial effector polypeptide is a polypeptide having 90% sequence identity to an amino acid sequence set forth in the group consisting of SEQ ID NOs 3, 89, 42, 44, 46, 48, 50, 52, 54, 56, 58, 60, 62, 64, 66, 68, 70, 72, 74, 76, 78, and 79 and the at least one additional effector polypeptide is a polypeptide having 90% sequence identity to an amino acid sequence set forth in the group consisting of SEQ ID NOs. 3, 89, 42, 44, 46, 48, 50, 52, 54, 56, 58, 60, 62, 64, 66, 68, 70, 72, 74, 76, 78, and 79.

* * * * *